(12) United States Patent
Weitz et al.

(10) Patent No.: US 10,224,485 B2
(45) Date of Patent: Mar. 5, 2019

(54) PROCESS FOR PREPARING A CRYSTALLINE ORGANIC SEMICONDUCTOR MATERIAL

(71) Applicant: BASF SE, Ludwigshafen (DE)

(72) Inventors: Thomas Weitz, Mannheim (DE); Ilja Vladimirov, Mannheim (DE); Tiziana Chiodo, Mannheim (DE); Thomas Seyfried, Ludwigshafen (DE)

(73) Assignee: BASF SE, Ludwigshafen (DE)

( * ) Notice: Subject to any disclaimer, the term of this patent is extended or adjusted under 35 U.S.C. 154(b) by 1 day.

(21) Appl. No.: 15/504,463

(22) PCT Filed: Aug. 17, 2015

(86) PCT No.: PCT/IB2015/056249
§ 371 (c)(1),
(2) Date: Feb. 16, 2017

(87) PCT Pub. No.: WO2016/027218
PCT Pub. Date: Feb. 25, 2016

(65) Prior Publication Data
US 2017/0237005 A1    Aug. 17, 2017

(30) Foreign Application Priority Data
Aug. 18, 2014  (EP) .................................... 14181269

(51) Int. Cl.
| H01L 51/00 | (2006.01) |
| C07D 471/06 | (2006.01) |
| H01L 51/05 | (2006.01) |
| H01L 51/42 | (2006.01) |
| H01L 51/50 | (2006.01) |

(52) U.S. Cl.
CPC ........ H01L 51/0053 (2013.01); C07D 471/06 (2013.01); H01L 51/0004 (2013.01); H01L 51/0005 (2013.01); H01L 51/0007 (2013.01); H01L 51/0035 (2013.01); H01L 51/0074 (2013.01); H01L 51/0558 (2013.01); H01L 51/4253 (2013.01); H01L 51/5012 (2013.01); Y02E 10/549 (2013.01); Y02P 70/521 (2015.11)

(58) Field of Classification Search
CPC .................................................. H01L 51/0005
See application file for complete search history.

(56) References Cited

U.S. PATENT DOCUMENTS

| 4,461,922 | A |  | 7/1984  | Gay et al. |
| 4,539,507 | A |  | 9/1985  | VanSlyke et al. |
| 4,678,608 | A | * | 7/1987  | Dugliss .................. C09K 11/07 252/700 |
| 4,720,432 | A |  | 1/1988  | VauSlyke et al. |
| 4,769,292 | A |  | 9/1988  | Tang et al. |
| 5,324,853 | A |  | 6/1994  | Jones et al. |
| 6,198,091 | B1 |  | 3/2001  | Forrest et al. |
| 6,198,092 | B1 |  | 3/2001  | Bulovic et al. |
| 6,310,235 | B1 |  | 10/2001 | Gick |
| 6,451,415 | B1 |  | 9/2002  | Forrest et al. |
| 6,864,396 | B2 |  | 3/2005  | Smith et al. |
| 7,102,154 | B2 |  | 9/2006  | Hanna et al. |
| 7,569,693 | B2 |  | 8/2009  | Marks et al. |
| 7,638,795 | B2 |  | 12/2009 | Hanna et al. |
| 7,671,202 | B2 |  | 3/2010  | Marks et al. |
| 7,902,363 | B2 |  | 3/2011  | Facchetti et al. |
| 8,758,649 | B2 |  | 6/2014  | James et al. |
| 9,133,193 | B2 |  | 9/2015  | Ichikawa et al. |
| 2003/0100779 | A1 |  | 5/2003  | Vogel et al. |
| 2004/0046182 | A1 |  | 3/2004  | Chen et al. |
| 2005/0098726 | A1 |  | 5/2005  | Peumans et al. |
| 2005/0156161 | A1 |  | 7/2005  | Hanna et al. |
| 2005/0224905 | A1 |  | 10/2005 | Forrest et al. |
| 2006/0166396 | A1 |  | 7/2006  | Hanna et al. |
| 2006/0202195 | A1 |  | 9/2006  | Marks et al. |
| 2010/0193777 | A1 |  | 8/2010  | Takahashi et al. |
| 2010/0319778 | A1 |  | 12/2010 | Kastler et al. |
| 2012/0199824 | A1 | * | 8/2012  | Ichikawa et al. |
| 2014/0042369 | A1 | * | 2/2014  | Huang ................ H01L 51/0053 252/500 |

(Continued)

FOREIGN PATENT DOCUMENTS

| DE | 1 945 359 | 3/1971 |
| DE | 26 12 355 A1 | 10/1977 |
| DE | 11 2013 002 903 T5 | 3/2015 |

(Continued)

OTHER PUBLICATIONS

Lim, J.A., et al. "Ink-jet printing of self-aligned soluble-pentacene crystals for high-performance organic field-effect transistors." (2007), Proc. SPIE 6658, Organic Field-Effect Transistors VI. pp. 1-9.*
T. Uemura et al., "Band-Like Transport in Solution-Crystallized Organic Transistors", Current Applied Physics, 12, (2012), pp. S87-S91.
Hiromi Minemawari et al., "Inkjet Printing of Single-Crystal Films", Nature, vol. 475, Jul. 21, 2011, pp. 364-367.

(Continued)

*Primary Examiner* — Andrew D Kosar
*Assistant Examiner* — John S Kenyon
(74) *Attorney, Agent, or Firm* — Oblon, McClelland, Maier & Neustadt, L.L.P.

(57) ABSTRACT

Provided are a process for preparing a crystalline organic semiconductor material wherein the conditions of crystallization lead to the formation of crystals at the gas liquid interface having advantageous semiconductor properties, the obtained crystalline organic semiconductor material and the use thereof for the production of organic semiconductor devices, in particular organic field effect transistors and organic solar cells.

30 Claims, 9 Drawing Sheets

(56) References Cited

U.S. PATENT DOCUMENTS

2014/0218452 A1  8/2014  Li et al.

FOREIGN PATENT DOCUMENTS

| | | |
|---|---|---|
| EP | 0 387 715 A2 | 9/1990 |
| EP | 0 532 798 A1 | 9/1991 |
| EP | 1 266 882 A1 | 12/2002 |
| EP | 2 077 590 B1 | 6/2013 |
| JP | 2014-139143 A | 7/2014 |
| WO | WO 99/32427 A1 | 7/1999 |
| WO | WO 00/70655 A2 | 11/2000 |
| WO | WO 02/100536 A1 | 12/2002 |
| WO | WO 03/029168 A2 | 4/2003 |
| WO | WO 03/029181 A1 | 4/2003 |
| WO | WO 2004/009526 A1 | 1/2004 |
| WO | WO 2005/019373 A2 | 3/2005 |
| WO | WO 2007/093643 A1 | 8/2007 |
| WO | WO 2007/116001 A2 | 10/2007 |
| WO | WO 2011/023490 | 3/2011 |
| WO | WO 2011/023491 A1 | 3/2011 |
| WO | WO 2011/082991 A2 | 7/2011 |
| WO | WO 2012/090110 A1 | 7/2012 |
| WO | WO 2012/113608 A1 | 8/2012 |
| WO | WO 2012/113609 A1 | 8/2012 |
| WO | WO 2013/168048 A1 | 11/2013 |
| WO | WO 2013/187275 A1 | 12/2013 |
| WO | WO 2014/087300 A1 | 6/2014 |

OTHER PUBLICATIONS

Valery A Postnikov et al., "Molecularly Smooth Single-Crystalline Films of Thiophene-Phenylene Co-Oligomers Grown at the Gas-Liquid Interface", Crystal Growth Design, 2014, 14, pp. 1726-1737.

Min-Min Shi, et al., "Bulky Rigid substitutions: A route to high electron mobility and high solid-state luminescence efficiency of perylene diimide", Organic Electronics, XP028803322, vol. 15 No. 1, 2014, pp. 281-285.

International Search Report dated Dec. 18, 2015 in PCT/IB2015/056249.

* cited by examiner

PROCESS FOR PREPARING A CRYSTALLINE ORGANIC SEMICONDUCTOR MATERIAL

FIELD OF THE INVENTION

The present invention relates to a novel process for the preparation of a crystalline organic semiconductor material wherein the conditions of crystallization lead to the formation of crystals at the gas liquid interface having advantageous semiconductor properties. The invention also relates to the obtained crystalline organic semiconductor material and the use thereof for the production of organic semiconductor devices, in particular organic field effect transistors and organic solar cells.

Organic semiconductors based on low molecular weight molecules or polymeric materials are already used in many sectors of the electronics industry. In many cases, these organic semiconductors have advantages over the classical inorganic semiconductors, for example better substrate compatibility and better processability of the semiconductor components based on them. They allow processing on flexible substrates and enable their orbital energies to be adjusted precisely to the particular application range by the methods of molecular modeling. The significantly reduced costs of such components have brought an upswing to the field of research of organic electronics.

Organic electronics is concerned principally with the development of new materials and manufacturing processes for the production of electronic components based on organic semiconductor layers. These include in particular organic field-effect transistors (OFETs) and organic electroluminescent devices (hereinafter abbreviated as "EL" devices). Great potential for development is ascribed to organic field-effect transistors, for example in storage elements, backplanes and integrated optoelectronic devices. An organic electroluminescent device is a self-emission device utilizing the principle that a fluorescent material emits light by the recombination energy of holes injected from an anode and electrons injected from a cathode when an electric field is applied. EL devices in form of organic light-emitting diodes (OLEDs) are especially of interest as an alternative to cathode ray tubes and liquid-crystal displays for producing flat visual display units. Owing to the very compact design and the intrinsically low power consumption, devices which comprise OLEDs are suitable especially for mobile applications, for example for applications in cell phones, laptops, etc.

Organic photovoltaics is concerned principally with the development of new materials for organic solar cells. A great potential for development is ascribed to materials which have maximum transport widths and high mobilities for light-induced excited states (high exciton diffusion lengths) and are thus advantageously suitable for use as an active material in so-called excitonic solar cells. It is generally possible with solar cells based on such materials to achieve very good quantum yields.

Different types of chemical sensors are known, in particular electronic conductance sensors, mass-sensitive-sensors utilizing a quartz crystal microbalance, surface acoustic-wave sensors and optical sensors. Organic semiconductors with a sufficient crystal size are promising candidates for gas sensors. They are e.g. chemically sensitive to reactive gases and can be oxidized or reduced. Gas sensors have found wide application in various technical fields, e.g. in the field of work safety and environmental protection for detecting toxic or irritant gases or vapors like $CO$ and $NO_2$, as well as in air conditioning in cars, airplanes, houses etc. to ethanol sensors for breath analyzers.

It is still a challenge to provide organic electronic devices, organic solar cells and optoelectronic devices, such as organic thin film transistors (OTFTs), OLEDs, printable circuits, capacitors, sensors etc., that have good performance properties and can be prepared by large-scale standard manufacturing processes. In particular there is still a demand for cost-effective wet-processing techniques that allow the preparation of active components comprising organic semiconductors that good application properties (e.g. high charge carrier mobilities) and are stable under ambient conditions.

Known methods for the fabrication of devices on the basis of solution-processed semiconducting films have several drawbacks. Thus, in many cases the obtained application properties, like charge carrier mobilities, still need to be improved. Further, the solvents employed in such processes have only a limited compatibility with the organic semiconductors or are environmentally harmful.

US 2014042369 A1 describes an organic semiconductor formulation comprising an organic semiconductor in a liquid medium, wherein the liquid medium comprises a first liquid and optionally a second liquid, the first liquid being an aromatic compound having electronic properties complementary to the electronic structure of the organic semiconductor compound, and the second liquid being a solvent or solvent mixture in which the organic semiconductor has a solubility of at least about 0.1 mg/mL. Although this document names a plethora of different semiconductors and solvents the only semiconductor used in the working examples is N,N'-bis(2-ethylhexyl)-(1,7 and 1,6)-dicyanoperylene-3,4:9,10-bis(dicarboximide). The tested solvents are N,N-dimethylaniline, nitrobenzene, 2-methylanisole, xylene, dichlorobenzene and benzonitrile.

Valery A. Postnikov et al. describe in Cryst Growth Des. 2014, 14, 1726-1737, the formation of molecularly smooth single-crystalline films of thiophene-phenylene co-oligomers (TPCOs) grown at the gas-liquid interface. Suitable techniques for the growth of single crystals at the gas-solution interface are solvent-antisolvent crystallization (SAC), isothermal slow solvent evaporation (ISSE) and isochoric cooling (IC). For SAC toluene was used as solvent and ethanol, isopropanol or mixtures thereof were used as antisolvent. For ISSE and IC toluene, hexane and chlorobenzene were employed. By far the most preferred method according to this document is SAC. Thus, it is mentioned on page 1735, right column that remarkably, the SAC results in a higher lateral growth rate as compared to other solution crystal growth methods used for the same TPCOs. The higher lateral growth rate in SAC than in ISSE can be explained by the enhanced crystallization driving force at the gas-solution interface due to the use of an antisolvent. First, the saturation in the near surface layer is facilitated in SAC because of antisolvent condensation. Second, as the antisolvent surface energy is lower than that of the solvent. Consequently, a person skilled in the art would not take into consideration to make use of other gas-liquid interface crystallization techniques than SAC.

H. Minemawari et al. describe in Nature, vol. 475, 21 Jul. 2011, 364-367 a method that combines the technique of antisolvent crystallization with inkjet printing to produce organic semiconducting thin films of high crystallinity. Specifically, it is shown that mixing fine droplets of an antisolvent and a solution of an active semiconducting component within a confined area on an amorphous substrate can trigger the controlled formation of uniform single-crystal or polycrystalline thin films that grow at the liquid-air interface. In all examples 1,2-dichlorobenzene is used as the solvent and N,N-dimethylformamide is used as the antisolvent.

The application properties of semiconductor devices on the basis of crystalline organic semiconductor materials obtained by known crystallization methods still need improvement. In many cases the properties of the obtained crystals is still not sufficient as only good crystals lead to good semiconductor properties. Where it is not possible to obtain single crystals that are large enough for the intended use it is necessary to employ a polycrystalline material with as little defects as possible. Good crystals are characterized generally by a relatively thin crystal layer compared to the lateral size of the crystals. A good method for the provision of a crystalline material is also characterized by the formation of larger crystals without a rise in the number of crystal defects.

Accordingly, there is a need for an improved method for providing crystalline organic semiconductor materials that enable manufacturing of semiconductor devices with good application properties by large-scale standard processes.

It has now surprisingly been found that crystallization of a great number of different organic semiconductors can be effected advantageously by crystallization from an organic solvent or a solvent mixture comprising an organic solvent having a boiling point at 1013.25 mbar of at least 140° C., a viscosity of at least 1.2 mPas at 23° C., and a surface tension of at least 31.5 mN/m at 20° C. Corresponding organic solvents show a good compatibility with a great number of different organic semiconductors and the resulting liquid organic semiconductor formulations are suitable for the production of various crystalline organic semiconductor materials with good application properties. The use of said solvents or solvent mixtures allows the formation of thin crystalline films that exhibit excellent application properties in various field effect devices. The method according to the invention is especially suitable for the formation of organic thin film transistors (OTFTs) by a wet-processing technique under ambient conditions. The semiconductor layers obtained from the liquid compositions according to the invention are characterized by good solid state properties, e.g. a good crystallinity. As a result, field effect devices such as thin film transistors that are fabricated with the semiconductor compositions usually have high performance under ambient conditions, e.g. characterized by one or more of the following properties: large charge mobilities, low threshold voltages, and high current on-off ratios.

SUMMARY OF THE INVENTION

A first object of the present invention relates to a process for preparing a crystalline organic semiconductor material comprising
(a) providing a solution of at least one organic semiconductor A) in a solvent (L1) or in a solvent mixture comprising at least one solvent (L1), wherein the solvent (L1) has
a boiling point at 1013.25 mbar of at least 140° C.,
a viscosity of at least 1.2 mPas at 23° C., and
a surface tension of at least 31.5 mN/m at 20° C.,
(b) applying the solution provided in step (a) to the surface of a substrate to allow evaporation of the solvent or solvent mixture and crystallization of the organic semiconductor A).
It is a special feature of the process according to the invention that the crystallization of the organic semiconductor A) proceeds from the gas liquid interface.

A further object of the invention is a crystalline organic semiconductor material, obtained by the process defined above and in the following.

A further object of the invention is the use of organic semiconductor crystals obtained by a process as defined above and in the following for the production of a semiconductor material, preferably a semiconductor material in organic electronics or in organic photovoltaics.

A further object of the invention is a process for the preparation of an electronic device, optical device or optoelectronic device, comprising:
(a) providing a solution of at least one organic semiconductor A) in a solvent (L1) or in a solvent mixture comprising a solvent (L1), wherein the solvent (L1) has
a boiling point at 1013.25 mbar of at least 140° C.,
a viscosity of at least 1.2 mPas at 23° C., and
a surface tension of at least 31.5 mN/m at 20° C.,
(b) applying the solution provided in step (a) to the surface of a substrate to allow evaporation of the solvent or solvent mixture and crystallization of the organic semiconductor A),
wherein the substrate provided in step b) is the substrate of an electronic device, optical device or optoelectronic device or wherein the crystals formed in step b) are transferred to an electronic device, optical device or optoelectronic device.

DETAILED DESCRIPTION OF THE INVENTION

A method to distinguish good solvents from bad solvents is via the obtained crystal size. Good crystals in the sense of the invention are characterized by a relatively thin crystal layer compared to the lateral size of the crystals. Thus, the obtained crystalline organic semiconductor material should have an area of larger than $10 \times 10$ $\mu m^2$, wherein the average thickness is 0.1 $\mu m$ at the most. A good solvent is also characterized by the formation of larger crystals without a rise in the number of crystal defects.

Without wishing to be bound to any particular theory, it is believed that devices comprising an organic semiconductor component prepared from a composition according to the invention can exhibit improved properties because the liquid component B) is beneficial for the formation of a crystalline organic semiconductor A) and its deposition on a substrate. Inter alia, component B) shows an ideal balance of sufficient solubility with respect to the semiconductors A) and a sufficient low volatility.

In conclusion, component B) allows the formation of crystalline semiconductor layers with excellent properties. This leads to advantageous solid state properties, like the formation of larger crystallites and a reduced number of grain boundaries. An increase in crystal grain size and crystalline domains of semiconductor layers deposited from a composition according to the invention can be detected by optical microscopy (see e.g. FIGS. 4a and 4b). Larger crystallites can contribute, at least in part, to improved charge transport, possibly because of the reduced number of grain boundaries which act as charge trapping sites.

In light of the foregoing, the present teaching provides a method for providing crystalline organic semiconductors that exhibits properties such as tailored compatibility with a given organic semiconductor, preparation of good crystalline materials, low-temperature processability, and large processing versatility. As a result, crystalline organic semiconductors are obtained that lead to field effect devices such as thin film transistors having high performance under ambient conditions, for example, demonstrating one or more of large charge mobilities, low threshold voltages, and high current on-off ratios.

In particular, the process according to the invention has at least one of the following advantages:

The process of the invention using special solvents allows to induce crystal growth that occurs at the gas-liquid interface (i.e. predominantly on top of solution droplets).

As the crystallization does not penetrate the droplets from the contact line to the substrate and the organic semiconductor does predominantly not crystallize on the substrate, the nature of the substrate does not have a direct impact on the morphology of the obtained crystal. The nature of the substrate of course has an influence on the deposition of the crystals on the substrate surface, as mentioned above, and the electrical properties of the electronic device.

In the process of the invention, nucleation sites are formed readily after application of the solution to a substrate, e.g. by casting or printing of the solution; crystal growth from the nucleus occurs at the liquid-air interface.

The process allows solution growth of a large-area thin crystalline material, i.e. a crystalline film of the semiconductor material.

Surprisingly, for solvents (L1) the drying time of the solution seems not to have an impact on the crystal habit. If a solvent (L1) is used, good crystals having large areas of low thickness are obtained. On the other hand, if another solvent is employed even a longer drying time does not lead to crystals having the high quality of those obtained from a solvent (L1).

Advantageously, the use of a viscosity-modifying additive, e.g. a dielectric or semiconducting polymer has no negative impact on the quality of the obtained crystalline semiconductor material. Furthermore, it has been surprisingly found that if a viscosity-modifying additive is used in combination with a solvent that is not a solvent (L1) in the sense of the invention or in combination with a solvent mixture that does not contain a solvent (L1) the obtained crystalline semiconducting material is not improved.

The process according to the invention allows the preparation of various articles, structures, or devices from semiconductors A) by solution-processing, including spin-coating and various printing techniques.

OFETs, in particular OTFTs produced from the semiconductor composition according to the invention are characterized by at least one of the following properties: a high charge transport mobility, a high on/off ratio, low threshold voltages and air stability.

The obtained organic semiconductors have advantageous solid state properties, like the formation of larger crystallites, a reduced number of grain boundaries and therefore to an improved charge transport.

OFETs, in particular OTFTs produced from semiconductors obtained by the method according to the invention are characterized by a greater continuity of the obtained film within the channel region of the organic electronic device.

In the context of the invention the boiling point, viscosity and the surface tension of the solvent (L1) or (L2) or a solvent mixture refers to a single pure solvent or a mixture of pure solvents. Generally a pure solvent in the sense of the invention has a purity of ≥95%, in many cases ≥98%.

The crystalline organic semiconductor material obtained by the method according to the invention may contain or consist of single crystals, polycrystals, liquid crystals or combinations thereof.

In a single crystal or monocrystalline material the crystal lattice of the entire semiconductor material is continuous and unbroken to the edges of the sample, with no grain boundaries. A polycrystalline material is composed of randomly oriented crystalline regions, so-called crystallites. The polycrystalline materials of the invention are characterized by having very few crystal defects. In liquid crystals the matter is in a state that has properties between those of a conventional liquid and those of a solid crystal. In particular, the process of the invention leads to controlled formation of uniform single-crystal or polycrystalline thin films that grow at the liquid-gas interface. In one special embodiment, at least a part of the crystalline organic semiconductor material consists of large continuous crystalline areas.

In the process of the invention the crystal growth proceeds from the gas-liquid interface. Advantageously, a significant amount of the obtained crystalline organic semiconductor material results from the crystallization at the gas liquid interface.

It has been found that the use of a solution of at least one organic semiconductor A) in a solvent (L1) or in a solvent mixture comprising at least one solvent (L1) promotes the formation of crystalline semiconductor material grown at the gas-liquid interface. Surprisingly, a crystalline semiconductor material having large areas of small thickness can be obtained without the use of an antisolvent.

In particular, after providing the solution of the organic semiconductor A) in a solvent (L1) or in a solvent mixture comprising a solvent (L1), no additional component is added to the solution to effect crystallization of the organic semiconductor A).

Especially, after providing the solution of the organic semiconductor A) in a solvent (L1) or in a solvent mixture comprising a solvent (L1), no solvent is added to the solution, wherein the organic semiconductor A) has a solubility at 20° C. of less than 0.01 mg/ml.

The surface of the crystalline semiconductor materials can be examined using scanning probe microscopy (SPM). In particular, high-resolution atomic force microscopy (AFM) or scanning force microscopy (SFM) allows the analysis of certain areas of the semiconductor materials with regard to their thickness. Thus it is possible to identify the crystalline areas that are obtained by crystallization at the gas-liquid interface. SPM data analysis can be effected by known software, e.g. Gwyddion.

Preferably, the obtained crystalline organic semiconductor material has an area of larger than $10 \times 10$ μm$^2$, wherein the average thickness is 0.1 μm at the most, more preferably 0.05 μm at the most, in particular 0.01 μm at the most. In many cases the process of the invention allows the formation of a crystalline organic semiconductor material having an area of larger than $100 \times 100$ μm$^2$, wherein the average thickness is 0.1 μm at the most, preferably 0.05 μm at the most.

The solvent parameters of most pure solvents can be taken from scientific reference works like Knovel Critical Tables (2nd Edition 2008), electronic ISBN: 978-1-59124-550-6 or Handbook of Chemistry and Physics CRC Press, Inc., Boca Raton, Fla., USA. The determination of a boiling point of a solvent at a certain temperature and pressure, the viscosity or surface tension is a standard operation for a person skilled in the art.

The viscosities of the solvents (L1) and (L2) and also of solvents containing viscosity-modifying agents, e.g. thickening polymers, can be measured with a common viscosimeter, e.g a Brookfield DV-II+Pro Viscosimeter at 23° C. temperature at a shear rate of 93 s$^{-1}$ at a rotational speed of 100 rpm using a 13R cup and a 21 Spindle.

The surface tension can be measured with a common tensiometer, e.g. a Tensiometer K100 from Krüss using the Wilhelmy-plate method.

Preferably, the solvent (L1) or the solvent mixture comprising a solvent (L1) employed in step a) has a boiling point at 1013.25 mbar of at least 150° C.

Preferably, the solvent (L1) has a viscosity in the range of 1.3 to 1000 mPas at 20° C.

Preferably, the solvent (L1) has a surface tension in the range of 32 to 65 mN/m, preferably in the range of 32 to 44 mN/m at 20° C.

Preferably, the organic semiconductor A) has a solubility in the solvent (L1) or in the solvent mixture comprising a solvent (L1) employed in step a) at 20° C. of at least 0.01 mg/ml, preferably of at least 0.05 mg/ml.

In one preferred embodiment, the solvent employed to provide the solution the organic semiconductor A) consists only of solvents (L1).

In another preferred embodiment, the solvent employed to provide the solution the organic semiconductor A) is a mixture of at least one solvent (L1) and at least one solvent (L2) different from (L1). Preferably, the amount solvent (L1) in the solvent mixture is in a range of from 1 to 99% by weight, more preferably 2 to 98% by weight, in particular 5 to 95% by weight, based on the total weight of the solvent mixture.

Suitable and preferred solvents (L1) and (L2) are mentioned in the following.

The expression "halogen" denotes in each case fluorine, bromine, chlorine or iodine, particularly chlorine, bromide or iodine.

In the context of the invention, the expression "unsubstituted or substituted alkyl, cycloalkyl, heterocycloalkyl, aryl and hetaryl" represents unsubstituted or substituted alkyl, unsubstituted or substituted cycloalkyl, unsubstituted or substituted heterocycloalkyl, unsubstituted or substituted aryl and unsubstituted or substituted hetaryl.

In the context of the invention, the expression "in each case unsubstituted or substituted linear $C_1$-$C_{30}$-alkyl, branched $C_3$-$C_{30}$-alkyl, linear $C_2$-$C_{30}$-alkenyl, branched $C_3$-$C_{30}$-alkenyl, linear $C_2$-$C_{30}$-alkinyl, branched $C_4$-$C_{30}$-alkinyl, cycloalkyl, aryl and hetaryl," represents unsubstituted or substituted linear $C_1$-$C_{30}$-alkyl, unsubstituted or substituted branched $C_3$-$C_{30}$-alkyl, unsubstituted or substituted linear $C_2$-$C_{30}$-alkenyl, unsubstituted or substituted branched $C_3$-$C_{30}$-alkenyl, unsubstituted or substituted linear $C_2$-$C_3$-alkinyl, unsubstituted or substituted branched $C_4$-$C_{30}$-alkinyl, unsubstituted or substituted cycloalkyl, unsubstituted or substituted aryl and unsubstituted or substituted hetaryl.

In the context of the invention, the expression "in each case unsubstituted or substituted alkyl, cycloalkyl and aryl" represents unsubstituted or substituted alkyl, unsubstituted or substituted cycloalkyl and unsubstituted or substituted aryl.

In the context of the invention, the expression "unsubstituted or substituted alkyl, alkoxy, alkylthio, (monoalkyl)amino, (dialkyl)amino, cycloalkyl, cycloalkoxy, cycloalkylthio, (monocycloalkyl)amino, (dicycloalkyl)amino, heterocycloalkyl, heterocycloalkoxy, heterocycloalkylthio, (monoheterocycloalkyl)amino, (diheterocycloalkyl)amino, aryl, aryloxy, arylthio, (monoaryl)amino, (diaryl)amino, hetaryl, hetaryloxy, hetarylthio, (monohetaryl)amino and (dihetaryl)amino" represents unsubstituted or substituted alkyl, unsubstituted or substituted alkoxy, unsubstituted or substituted alkylthio, unsubstituted or substituted (monoalkyl)amino, unsubstituted or substituted (dialkyl)amino, unsubstituted or substituted cycloalkyl, unsubstituted or substituted cycloalkoxy, unsubstituted or substituted cycloalkylthio, unsubstituted or substituted (monocycloalkyl)amino, unsubstituted or substituted (dicycloalkyl)amino, unsubstituted or substituted heterocycloalkyl, unsubstituted or substituted heterocycloalkoxy, unsubstituted or substituted heterocycloalkylthio, unsubstituted or substituted (monoheterocycloalkyl)amino, unsubstituted or substituted (diheterocycloalkyl)amino, unsubstituted or substituted aryl, unsubstituted or substituted aryloxy, unsubstituted or substituted arylthio, unsubstituted or substituted (monoaryl)amino, unsubstituted or substituted (diaryl)amino, unsubstituted or substituted hetaryl, unsubstituted or substituted hetaryloxy, unsubstituted or substituted hetarylthio, unsubstituted or substituted (monohetaryl)amino and unsubstituted or substituted (dihetaryl)amino.

In the context of the present invention, the expression "alkyl" comprises straight-chain or branched alkyl groups. Alkyl is preferably $C_1$-$C_{30}$-alkyl, more preferably $C_1$-$C_{22}$-alkyl. Short chain alkyl groups are preferably selected from $C_1$-$C_6$-alkyl groups. Long chain alkyl groups are preferably selected from $C_7$-$C_{22}$-alkyl groups. Examples of alkyl groups are especially methyl, ethyl, n-propyl, isopropyl, n-butyl, isobutyl, sec-butyl, tert-butyl, n-pentyl, 1-methylbutyl, 1-ethylpropyl, neo-pentyl, n-hexyl, 1-methylpentyl, 2-methylpentyl, 1-ethylbutyl, 2-ethylbutyl, n-heptyl, 1-methylhexyl, 2-methylhexyl, 1-ethylpentyl, 1-propylbutyl, 2-ethylpentyl, n-octyl, 1-methylheptyl, 2-methylheptyl, 1-ethylhexyl, 2-ethylhexyl, 1-propylpentyl, 2-propylpentyl, n-nonyl, 1-methyloctyl, 2-methyloctyl, 1-ethylheptyl, 2-ethylheptyl, 1-propylhexyl, 2-propylhexyl, 1-butylpentyl, n-decyl, 2-methyldecyl, 1-methylnonyl, 2-methylnonyl, 1-ethyloctyl, 2-ethyloctyl, 1-propylheptyl, 2-propylheptyl, 1-butylhexyl, 2-butylhexyl, n-undecyl, 2-ethylnonyl, 1-propyloctyl, 2-propyloctyl, 1-butylheptyl, 2-butylheptyl, 1-pentylhexyl, n-dodecyl, 2-ethyldecyl, 2-propylnonyl, 1-butyloctyl, 2-butyloctyl, 1-pentylheptyl, 2-pentylheptyl, 2-propyldecyl, n-tridecyl, 1-pentyloctyl, 2-pentyloctyl, 1-hexylheptyl, 2-butylnonyl, n-tetradecyl, 1-hexyloctyl, 2-hexyloctyl, 2-pentylnonyl, 2-hexylnonyl, 2-pentyldecyl, 2-butyldecyl, n-hexadecyl, 1-heptyloctyl, 2-heptylnonyl, 2-hexyldecyl, 2-heptyldecyl, n-octadecyl, 2-octyldecyl, n-eicosyl, 2-nonylundecyl, 2-octylundecyl, 2-heptylundecyl, 2-hexylundecyl, 2-pentylundecyl, 2-butylundecyl, 2-propylundecyl, 2-ethylundecyl, 2-methylundecyl, 2-decyldodecyl, 2-nonyldodecyl, 2-octyldodecyl, 2-heptyldodecyl, 2-hexyldodecyl, 2-pentyldodecyl, 2-butyldodecyl, 2-propyldodecyl, 2-ethyldodecyl, 2-methyldodecyl, 2-undecyttridecyl, 2-decyttridecyl, 2-nonyttridecyl, 2-octyttridecyl, 2-heptyltridecyl, 2-hexyltridecyl, 2-pentyltridecyl, 2-butyltridecyl, 2-propyttridecyl, 2-ethytridecyl, 2-methyltridecyl, 2-undecyltetradecyl, 2-decyltetradecyl, 2-nonyttetradecyl, 2-octyttetradecyl, 2-hetyttetradecyl, 2-hexyttetradecyl, 2-pentyttetradecyl, 2-butyttetradecyl, 2-propyttetradecyl, 2-ethyttetradecyl, 2-methyttetradecyl, 2-tetradecylhexadecyl, 2-tridecylhexadecyl, 2-dodecylhexadecyl, 2-undecylhexadecyl, 2-decylhexadecyl, 2-nonylhexadecyl, 2-octylhexadecyl, 2-heptylhexadecyl, 2-hexylhexadecyl, 2-pentylhexadecyl, 2-butylhexadecyl, 2-propylhexadecyl, 2-ethylhexadecyl, 2-methylhexadecyl, 2-dodecyloctadecyl, 2-undecyloctadecyl, 2-decyloctadecyl, 2-nonyloctadecyl, 2-octyloctadecyl, 2-heptyloctadecyl, 2-hexyloctadecyl, 2-pentyloctadecyl, 2-butyloctadecyl, 2-propyloctadecyl, 2-ethyloctadecyl, 2-methyloctadecyl, 2-decyleicosanyl, 2-nonyleicosanyl, 2-octyleicosanyl, 2-heptyleicosanyl, 2-hexyleicosanyl, 2-pentyleicosanyl, 2-butyleicosanyl, 2-propyleicosanyl, 2-ethyleicosanyl, 2-methyleicosanyl, 2-octadecyldocosanyl, 2-heptadecyldocosanyl, 2-hexadecyldocosanyl, 2-pentadecyldocosanyl, 2-tetradecyldocosanyl, 2-tridecyldocosanyl, 2-undecyldocosanyl, 2-decyldocosanyl, 2-nonyldocosanyl, 2-octyldocosanyl, 2-heptyldocosanyl, 2-hexyldocosanyl, 2-pentyldocosanyl, 2-butyldocosanyl, 2-propyldocosanyl, 2-ethyldocosanyl, 2-methyldocosanyl, 2-docosanyttetracosanyl, 2-hexadecyttetracosanyl, 2-pentadecyttetracosanyl, 2-pentadecyttetracosanyl, 2-tetradecyttetracosanyl, 2-tridecyttetracosanyl, 2-dodecyttetracosanyl, 2-undecyttetracosanyl, 2-decyttetracosanyl, 2-nonyttetracosanyl, 2-octyttetracosanyl, 2-heptyttetracosanyl, 2-hexyttetracosanyl, 2-pentyttetracosanyl, 2-butyttetracosanyl, 2-propyttetracosanyl, 2-ethyttetracosanyl, 2-methyttetracosanyl, 2-dodecyloctacosanyl, 2-undecyloctacosanyl, 2-decyloctacosanyl, 2-nonyloctacosanyl, 2-octyloctacosanyl, 2-heptyloctacosanyl, 2-hexyloctacosanyl, 2-pentyloctacosanyl, 2-butyloctacosanyl, 2-propyloctacosanyl, 2-ethyloctacosanyl and 2-methyloctacosanyl.

The expression alkyl also comprises alkyl radicals whose carbon chains may be interrupted by one or more nonadjacent groups which are selected from —O—, —S—, —NR$^a$—, —C(=O)—, —S(=O)— and/or —S(=O)$_2$—. R$^a$ is preferably hydrogen, alkyl, cycloalkyl, heterocycloalkyl, aryl or hetaryl.

Examples of alkyl groups whose carbon chains are interrupted by one or more nonadjacent groups are especially 2-methoxyethyl, 2-ethoxyethyl, 2-propoxyethyl, 2-isopropoxyethyl, 2-butoxyethyl, 2- and 3-methoxypropyl, 2- and 3-ethoxypropyl, 2- and 3-propoxypropyl, 2- and 3-butoxypropyl, 2- and 4-methoxybutyl, 2- and 4-ethoxybutyl, 2- and 4-propoxybutyl, 3,6-dioxaheptyl, 3,6-dioxaoctyl, 4,8-dioxanonyl, 3,7-dioxaoctyl, 3,7-dioxanonyl, 4,7-dioxaoctyl, 4,7-dioxanonyl, 2- and 4-butoxybutyl, 4,8-dioxadecyl, 3,6,9-trioxadecyl, 3,6,9-trioxaundecyl, 3,6,9-trioxadodecyl, 3,6,9,12-tetraoxatridecyl and 3,6,9,12-tetraoxatetradecyl; 2-methylthioethyl, 2-ethylthioethyl, 2-propylthioethyl, 2-isopropylthioethyl, 2-butylthioethyl, 2- and 3-methylthiopropyl, 2- and 3-ethylthiopropyl, 2- and 3-propylthiopropyl, 2- and 3-butylthiopropyl, 2- and 4-methylthiobutyl, 2- and 4-ethylthiobutyl, 2- and 4-ropylthiobutyl, 3,6-dithiaheptyl, 3,6-dithiaoctyl, 4,8-dithianonyl, 3,7-dithiaoctyl, 3,7-dithianonyl, 2- and 4-butylthiobutyl, 4,8-dithiadecyl, 3,6,9-trithiadecyl, 3,6,9-trithiaundecyl, 3,6,9-trithiadodecyl, 3,6,9,12-tetrathiatridecyl and 3,6,9,12-tetrathiatetradecyl; 2-monomethyl- and 2-monoethylaminoethyl, 2-dimethylaminoethyl, 2- and 3-dimethylaminopropyl, 3-monoisopropylaminopropyl, 2- and 4-monopropylaminobutyl, 2- and 4-dimethylaminobutyl, 6-methyl-3,6-diazaheptyl, 3,6-dimethyl-3,6-diazaheptyl, 3,6-diazaoctyl, 3,6-dimethyl-3,6-diazaoctyl, 9-methyl-3,6,9-triazadecyl, 3,6,9-trimethyl-3,6,9-triazadecyl, 3,6,9-triazaundecyl, 3,6,9-trimethyl-3,6,9-triazaundecyl, 12-methyl-3,6,9,12-tetraazatridecyl and 3,6,9,12-tetramethyl-3,6,9,12-tetraazatridecyl; (1-ethylethylidene)aminoethylene, (1-ethylethylidene)aminopropylene, (1-ethylethylidene)aminobutylene, (1-ethylethylidene)aminodecylene and (1-ethylethylidene)aminododecylene; propan-2-on-1-yl, butan-3-on-1-yl, butan-3-on-2-yl and 2-ethylpentan-3-on-1-yl; 2-methylsulfoxidoethyl, 2-ethylsulfoxidoethyl, 2-propylsulfoxidoethyl, 2-isopropylsulf-oxidoethyl, 2-butylsulfoxidoethyl, 2- and 3-methylsulfoxidopropyl, 2- and 3-ethylsulf-oxidopropyl, 2- and 3-propylsulfoxidopropyl, 2- and 3-butylsulfoxidopropyl, 2- and 4-methylsulfoxidobutyl, 2- and 4-ethylsulfoxidobutyl, 2- and 4-propylsulfoxidobutyl and 4-butylsulfoxidobutyl; 2-methylsulfonylethyl, 2-ethylsulfonylethyl, 2-propylsulfonylethyl, 2-isopropylsulfonylethyl, 2-butylsulfonylethyl, 2- and 3-methylsulfonylpropyl, 2- and 3-ethylsulfonylpropyl, 2- and 3-propylsulfonylpropyl, 2- and 3-butylsulfonylpropyl, 2- and 4-methylsulfonylbutyl, 2- and 4-ethylsulfonylbutyl, 2- and 4-propylsulfonylbutyl and 4-butylsulfonylbutyl.

Substituted alkyl groups may, depending on the length of the alkyl chain, have one or more (e.g. 1, 2, 3, 4, 5 or more than 5) substituents. These are preferably each independently selected from cycloalkyl, heterocycloalkyl, aryl, hetaryl, fluorine, chlorine, bromine, hydroxyl, mercapto, cyano, nitro, nitroso, formyl, acyl, COOH, carboxylate, alkylcarbonyloxy, carbamoyl, SO$_3$H, sulfonate, sulfamino, sulfamide, amidino, NE$^5$E$^6$ where E$^5$ and E$^6$ are each independently hydrogen, alkyl, cycloalkyl, heterocycloalkyl, aryl or hetaryl. Cycloalkyl, heterocycloalkyl, aryl and hetaryl substituents of the alkyl groups may in turn be unsubstituted or substituted; suitable substituents are the substituents mentioned below for these groups. Special embodiments of substituted alkyl groups are perfluoro-C$_1$-C$_{30}$-alkyl, 1H,1H-perfluoro-C$_2$-C$_{30}$-alkyl and 1H,1H,2H,2H-perfluoro-C$_3$-C$_{30}$-alkyl. Examples for those fluorinated alkyl groups are mentioned in the following.

Examples of substituted alkyl groups are especially carboxymethyl, 2-carboxyethyl, 3-carboxypropyl, 4-carboxybutyl, 5-carboxypentyl, 6-carboxyhexyl, 8-carboxyoctyl, 10-carboxydecyl, 12-carboxydodecyl and 14-carboxy-tetradecyl; sulfomethyl, 2-sulfoethyl, 3-sulfopropyl, 4-sulfobutyl, 5-sulfopentyl, 6-sulfohexyl, 8-sulfooctyl, 10-sulfodecyl, 12-sulfododecyl and 14-sulfotetradecyl; 2-hydroxyethyl, 2- and 3-hydroxypropyl, 1-hydroxyprop-2-yl, 3- and 4-hydroxybutyl, 1-hydroxybut-2-yl and 8-hydroxy-4-oxaoctyl; 2-cyanoethyl, 3-cyanopropyl, 3- and 4-cyanobutyl, 2-methyl-3-ethyl-3-cyanopropyl, 7-cyano-7-ethylheptyl and 4,7-dimethyl-7-cyanoheptyl; 2-chloroethyl, 2- and 3-chloropropyl, 2-, 3- and 4-chlorobutyl, 2-bromoethyl, 2- and 3-bromopropyl and 2-, 3- and 4-bromobutyl; 2-nitroethyl, 2- and 3-nitropropyl and 2-, 3- and 4-nitrobutyl.

Carboxylate and sulfonate respectively represent a derivative of a carboxylic acid function and a sulfonic acid function, especially a metal carboxylate or sulfonate, a carboxylic ester or sulfonic ester function or a carboxamide or sulfonamide function. Such derivatives include, for example, esters with C$_1$-C$_4$-alkanols, such as methanol, ethanol, n-propanol, isopropanol, n-butanol, sec-butanol and tert-butanol.

The above remarks regarding alkyl also apply to the alkyl moiety in alkoxy, alkylthio (=alkylsulfanyl), monoalkylamino and dialkylamino.

Examples of alkoxy groups are especially methoxy, ethoxy, propoxy, isopropoxy, butoxy, isobutoxy, sec-butoxy, tert-butoxy, pentoxy, isopentoxy, neopentoxy, tert-pentoxy and hexoxy.

Examples of alkylthio groups are especially methylthio, ethylthio, propylthio, isopropylthio, butylthio, isobutylthio, sec-butythio, tert-butylthio, pentylthio, isopentylthio, neopentythio, tert-pentylthio and hexylthio.

Examples of monoalkylamino groups and dialkylamino groups are especially methylamino, ethylamino, propylamino, isopropylamino, butylamino, isobutylamino, pentylamino, hexylamino, dimethylamino, methylethylamino, diethylamino, dipropylamino, diisopropylamino, dibutylamino, diisobutylamino, dipentylamino, dihexylamino, dicyclopentylamino, dicyclohexylamino, dicycloheptylamino, diphenylamino and dibenzylamino;

Alkylene represents a linear saturated hydrocarbon chain having from 1 to 10 and especially from 1 to 4 carbon atoms, such as ethane-1,2-diyl, propane-1,3-diyl, butane-1,4-diyl, pentane-1,5-diyl or hexane-1,6-diyl.

In the context of the present invention, the term "cycloalkyl" denotes a mono-, bi- or tricyclic hydrocarbon radical having usually from 3 to 20, preferably 3 to 12, more preferably 5 to 12, carbon atoms such as cyclopropyl, cyclobutyl, cyclopentyl, cyclohexyl, cycloheptyl, cyclooctyl, cyclododecyl, cyclopentadecyl, norbornyl, bicyclo[2.2.2]octyl or adamantyl.

Substituted cycloalkyl groups may, depending on the ring size, have one or more (e.g. 1, 2, 3, 4, 5 or more than 5) substituents. These are preferably each independently selected from alkyl, alkoxy, alkylthio, cycloalkyl, heterocycloalkyl, aryl, hetaryl, fluorine, chlorine, bromine, hydroxyl, mercapto, cyano, nitro, nitroso, formyl, acyl, COOH, carboxylate, alkylcarbonyloxy, carbamoyl, $SO_3H$, sulfonate, sulfamino, sulfamide, amidino, $NE^7E^8$ where $E^7$ and $E^8$ are each independently hydrogen, alkyl, cycloalkyl, heterocycloalkyl, aryl or hetaryl. In the case of substitution, the cycloalkyl groups preferably bear one or more, for example one, two, three, four or five, $C_1$-$C_6$-alkyl groups. Examples of substituted cycloalkyl groups are especially 2- and 3-methyl-cyclopentyl, 2- and 3-ethylcyclopentyl, 2-, 3- and 4-methylcyclohexyl, 2-, 3- and 4-ethylcyclohexyl, 2-, 3- and 4-propylcyclohexyl, 2-, 3- and 4-isopropylcyclohexyl, 2-, 3- and 4-butylcyclohexyl, 2-, 3- and 4-sec.-butylcyclohexyl, 2-, 3- and 4-tert-butylcyclohexyl, 2-, 3- and 4-methylcycloheptyl, 2-, 3- and 4-ethylcycloheptyl, 2-, 3- and 4-propylcycloheptyl, 2-, 3- and 4-isopropylcycloheptyl, 2-, 3- and 4-butylcycloheptyl, 2-, 3- and 4-sec-butylcycloheptyl, 2-, 3- and 4-tert-butylcycloheptyl, 2-, 3-, 4- and 5-methyl-cyclooctyl, 2-, 3-, 4- and 5-ethylcyclooctyl, 2-, 3-, 4- and 5-propylcyclooctyl, 3- and 4-hydroxycyclohexyl, 3- and 4-nitrocyclohexyl and 3- and 4-chlorocyclohexyl.

The above remarks regarding cycloalkyl also apply to the cycloalkyl moiety in cycloalkoxy, cycloalkylthio (=cycloalkylsulfanyl), monocycloalkylamino and dicycloalkylamino.

In the context of the present invention, the term "aryl" refers to mono- or polycyclic aromatic hydrocarbon radicals. Aryl usually is an aromatic radical having 6 to 24 carbon atoms, preferably 6 to 20 carbon atoms, especially 6 to 14 carbon atoms as ring members. Aryl is preferably phenyl, naphthyl, indenyl, fluorenyl, anthracenyl, phenanthrenyl, naphthacenyl, chrysenyl, pyrenyl, coronenyl, perylenyl, etc., and more preferably phenyl or naphthyl.

Substituted aryls may, depending on the number and size of their ring systems, have one or more (e.g. 1, 2, 3, 4, 5 or more than 5) substituents. These are preferably each independently selected from alkyl, alkoxy, alkylthio, cycloalkyl, heterocycloalkyl, aryl, hetaryl, fluorine, chlorine, bromine, hydroxyl, mercapto, cyano, nitro, nitroso, formyl, acyl, COOH, carboxylate, alkylcarbonyloxy, carbamoyl, $SO_3H$, sulfonate, sulfamino, sulfamide, amidino, $NE^9E^{10}$ where $E^9$ and $E^{10}$ are each independently hydrogen, alkyl, cycloalkyl, heterocycloalkyl, aryl or hetaryl. The alkyl, alkoxy, alkylamino, alkylthio, cycloalkyl, heterocycloalkyl, aryl and hetaryl substituents on the aryl may in turn be unsubstituted or substituted. Reference is made to the substituents mentioned above for these groups. The substituents on the aryl are preferably selected from alkyl, alkoxy, haloalkyl, haloalkoxy, aryl, fluorine, chlorine, bromine, cyano and nitro. Substituted aryl is more preferably substituted phenyl which generally bears 1, 2, 3, 4 or 5, preferably 1, 2 or 3, substituents.

Substituted aryl is preferably aryl substituted by at least one alkyl group ("alkaryl", also referred to hereinafter as alkylaryl). Alkaryl groups may, depending on the size of the aromatic ring system, have one or more (e.g. 1, 2, 3, 4, 5, 6, 7, 8, 9 or more than 9) alkyl substituents. The alkyl substituents may be unsubstituted or substituted. In this regard, reference is made to the above statements regarding unsubstituted and substituted alkyl. In a preferred embodiment, the alkaryl groups have exclusively unsubstituted alkyl substituents. Alkaryl is preferably phenyl which bears 1, 2, 3, 4 or 5, preferably 1, 2 or 3, more preferably 1 or 2, alkyl substituents.

Aryl which bears one or more radicals is, for example, 2-, 3- and 4-methylphenyl, 2,4-, 2,5-, 3,5- and 2,6-dimethylphenyl, 2,4,6-trimethylphenyl, 2-, 3- and 4-ethylphenyl, 2,4-, 2,5-, 3,5- and 2,6-diethylphenyl, 2,4,6-triethylphenyl, 2-, 3- and 4-propylphenyl, 2,4-, 2,5-, 3,5- and 2,6-dipropylphenyl, 2,4,6-tripropylphenyl, 2-, 3- and 4-isopropylphenyl, 2,4-, 2,5-, 3,5- and 2,6-diisopropylphenyl, 2,4,6-triisopropylphenyl, 2-, 3- and 4-butylphenyl, 2,4-, 2,5-, 3,5- and 2,6-dibutylphenyl, 2,4,6-tributylphenyl, 2-, 3- and 4-isobutylphenyl, 2,4-, 2,5-, 3,5- and 2,6-diisobutylphenyl, 2,4,6-triisobutylphenyl, 2-, 3- and 4-sec-butylphenyl, 2,4-, 2,5-, 3,5- and 2,6-di-sec-butylphenyl, 2,4,6-tri-sec-butylphenyl, 2-, 3- and 4-tert-butylphenyl, 2,4-, 2,5-, 3,5- and 2,6-di-tert-butylphenyl and 2,4,6-tri-tert-butylphenyl; 2-, 3- and 4-methoxyphenyl, 2,4-, 2,5-, 3,5- and 2,6-dimethoxyphenyl, 2,4,6-trimethoxyphenyl, 2-, 3- and 4-ethoxyphenyl, 2,4-, 2,5-, 3,5- and 2,6-diethoxyphenyl, 2,4,6-triethoxyphenyl, 2-, 3- and 4-propoxyphenyl, 2,4-, 2,5-, 3,5- and 2,6-dipropoxyphenyl, 2-, 3- and 4-isopropoxyphenyl, 2,4-, 2,5-, 3,5- and 2,6-diisopropoxyphenyl and 2-, 3- and 4-butoxyphenyl; 2-, 3- and 4-chlorophenyl, (2-chloro-6-methyl)phenyl, (2-chloro-6-ethyl)phenyl, (4-chloro-6-methyl)phenyl, (4-chloro-6-ethyl)phenyl.

The above remarks regarding aryl also apply to the aryl moiety in aryloxy, arylthio (=arylsulfanyl), monoarylamino and diarylamino.

In the context of the present invention, the expression "heterocycloalkyl" comprises nonaromatic, unsaturated or fully saturated, cycloaliphatic groups having generally 5 to 8 ring atoms, preferably 5 or 6 ring atoms. In the heterocycloalkyl groups, compared to the corresponding cycloalkyl groups, 1, 2, 3, 4 or more than 4 of the ring carbon atoms are replaced by heteroatoms or heteroatom-containing groups. The heteroatoms or heteroatom-containing groups are preferably selected from —O—, —S—, —$NR^b$—, —C(=O)—, —S(=O)— and/or —S(=O)$_2$—. $R^b$ is preferably hydrogen, alkyl, cycloalkyl, heterocycloalkyl, aryl or hetaryl. Examples of heterocycloalkyl groups are especially pyrrolidinyl, piperidinyl, 2,2,6,6-tetramethylpiperidinyl, imidazolidinyl, pyrazolidinyl, oxazolidinyl, morpholinyl, thiazolidinyl, isothiazolidinyl, isoxazolidinyl, piperazinyl, tetrahydrothiophenyl, dihydrothien-2-yl, tetrahydrofuranyl, dihydrofuran-2-yl, tetrahydropyranyl, 2-oxazolinyl, 3-oxazolinyl, 4-oxazolinyl and dioxanyl.

Substituted heterocycloalkyl groups may, depending on the ring size, have one or more (e.g. 1, 2, 3, 4, 5 or more than 5) substituents. These are preferably each independently selected from alkyl, alkoxy, alkylthio, cycloalkyl, heterocycloalkyl, aryl, hetaryl, fluorine, chlorine, bromine, hydroxyl, mercapto, cyano, nitro, nitroso, formyl, acyl, COOH, carboxylate, alkylcarbonyloxy, carbamoyl, $SO_3H$, sulfonate, sulfamino, sulfamide, amidino, $NE^{11}E^{12}$ where $E^{11}$ and $E^{12}$ are each independently hydrogen, alkyl, cycloalkyl, heterocycloalkyl, aryl or hetaryl. In the case of substitution, the heterocycloalkyl groups preferably bear one or more, for example one, two, three, four or five, $C_1$-$C_6$-alkyl groups.

The above remarks regarding heterocycloalkyl also apply to the heterocycloalkyl moiety in heterocycloalkoxy, heterocycloalkythio (=heterocycloalkylsulfanyl), monoheterocycloalkylamino and diheterocycloalkylamino.

In the context of the present invention, the expression "hetaryl" (heteroaryl) comprises heteroaromatic, mono- or polycyclic groups. In addition to the ring carbon atoms, these have 1, 2, 3, 4 or more than 4 heteroatoms as ring members. The heteroatoms are preferably selected from oxygen, nitrogen, selenium and sulfur. The hetaryl groups have preferably 5 to 18, e.g. 5, 6, 8, 9, 10, 11, 12, 13 or 14, ring atoms.

Monocyclic hetaryl groups are preferably 5- or 6-membered hetaryl groups, such as 2-furyl (furan-2-yl), 3-furyl (furan-3-yl), 2-thienyl (thiophen-2-yl), 3-thienyl (thiophen-3-yl), selenophen-2-yl, selenophen-3-yl, 1H-pyrrol-2-yl, 1H-pyrrol-3-yl, pyrrol-1-yl, imidazol-2-yl, imidazol-1-yl, imidazol-4-yl, pyrazol-1-yl, pyrazol-3-yl, pyrazol-4-yl, pyrazol-5-yl, 3-isoxazolyl, 4-isoxazolyl, 5-isoxazolyl, 3-isothiazolyl, 4-isothiazolyl, 5-isothiazolyl, 2-oxazolyl, 4-oxazolyl, 5-oxazolyl, 2-thiazolyl, 4-thiazolyl, 5-thiazolyl, 1,2,4-oxadiazol-3-yl, 1,2,4-oxadiazol-5-yl, 1,3,4-oxadiazol-2-yl, 1,2,4-thiadiazol-3-yl, 1,2,4-thiadiazol-5-yl, 1,3,4-thiadiazol-2-yl, 4H-[1,2,4]-triazol-3-yl, 1,3,4-triazol-2-yl, 1,2,3-triazol-1-yl, 1,2,4-triazol-1-yl, pyridin-2-yl, pyridin-3-yl, pyridin-4-yl, 3-pyridazinyl, 4-pyridazinyl, 2-pyrimidinyl, 4-pyrimidinyl, 5-pyrimidinyl, 2-pyrazinyl, 1,3,5-triazin-2-yl and 1,2,4-triazin-3-yl.

Polycyclic hetaryl groups have 2, 3, 4 or more than 4 fused rings. The fused-on rings may be aromatic, saturated or partly unsaturated. Examples of polycyclic hetaryl groups are quinolinyl, isoquinolinyl, indolyl, isoindolyl, indolizinyl, benzofuranyl, isobenzofuranyl, benzothiophenyl, benzoxazolyl, benzisoxazolyl, benzthiazolyl, benzoxadiazolyl, benzothiadiazolyl, benzoxazinyl, benzopyrazolyl, benzimidazolyl, benzotriazolyl, benzotriazinyl, benzoselenophenyl, thienothiophenyl, thienopyrimidyl, thiazolothiazolyl, dibenzopyrrolyl (carbazolyl), dibenzofuranyl, dibenzothiophenyl, naphtho[2,3-b]thiophenyl, naphtha[2,3-b]furyl, dihydroindolyl, dihydroindolizinyl, dihydroisoindolyl, dihydroquinolinyl and dihydroisoquinolinyl.

Substituted hetaryl groups may, depending on the number and size of their ring systems, have one or more (e.g. 1, 2, 3, 4, 5 or more than 5) substituents. These are preferably each independently selected from alkyl, alkoxy, alkylthio, cycloalkyl, heterocycloalkyl, aryl, hetaryl, fluorine, chlorine, bromine, hydroxyl, mercapto, cyano, nitro, nitroso, formyl, acyl, COOH, carboxylate, alkylcarbonyloxy, carbamoyl, $SO_3H$, sulfonate, sulfamino, sulfamide, amidino, $NE^{13}E^{14}$ where $E^{13}$ and $E^{14}$ are each independently hydrogen, alkyl, cycloalkyl, heterocycloalkyl, aryl or hetaryl. Halogen substituents are preferably fluorine, chlorine or bromine. The substituents are preferably selected from $C_1$-$C_6$-alkyl, $C_1$-$C_6$-alkoxy, hydroxyl, carboxyl, halogen and cyano.

The above remarks regarding hetaryl also apply to the hetaryl moiety in hetaryloxy, hetarylthio, monohetarylamino and dihetarylamino.

For the purposes of the present invention, the expression "acyl" refers to alkanoyl or aroyl groups which generally have from 2 to 11, preferably from 2 to 8, carbon atoms, for example the acetyl, propanoyl, butanoyl, pentanoyl, hexanoyl, heptanoyl-, 2-ethyl-hexanoyl, 2-propyiheptanoyl, pivaloyl, benzoyl or naphthoyl group.

The groups $NE^1E^2$, $NE^3E^4$, $NE^5E^6$, $NE^7E^8$, $NE^9E^{10}$, $NE^{11}E^{12}$ and $NE^{13}E^{14}$ are preferably N,N-dimethylamino, N,N-diethylamino, N,N-dipropylamino, N,N-diisopropylamino, N,N-di-n-butylamino, N,N-di-t-butylamino, N,N-dicyclohexylamino or N,N-diphenylamino.

Fused ring systems can comprise alicyclic, aliphatic heterocyclic, aromatic and heteroaromatic rings and combinations thereof, hydroaromatic joined by fusion. Fused ring systems comprise two, three or more (e.g. 4, 5, 6, 7 or 8) rings. Depending on the way in which the rings in fused ring systems are joined, a distinction is made between ortho-fusion, i.e. each ring shares at least one edge or two atoms with each adjacent ring, and peri-fusion in which a carbon atom belongs to more than two rings. Preferred fused ring systems are ortho-fused ring systems.

Component A)

A skilled person will readily appreciate that the compounds (A) may be present in pure form or comprising the respective depicted compound and at least one structural isomer thereof.

In a first preferred embodiment, component A) comprises at least one compound of the formula (II.a)

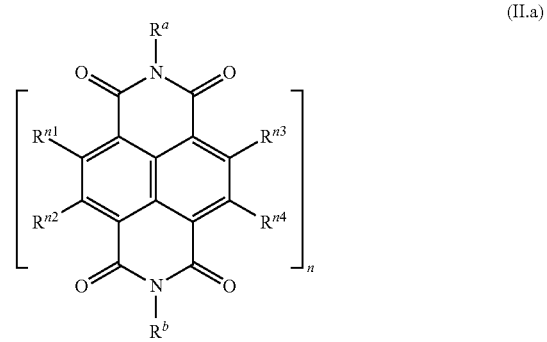

(II.a)

wherein
n is 1, 2, 3 or 4,
$R^a$ and $R^b$ are independently of one another selected from hydrogen and in each case unsubstituted or substituted alkyl, alkenyl, alkadienyl, alkynyl, cycloalkyl, bicycloalkyl, cycloalkenyl, heterocycloalkyl, aryl and heteroaryl,
the $R^{n1}$, $R^{n2}$, $R^{n3}$ and $R^{n4}$ radicals are independently of one another selected from hydrogen, F, Cl, Br, I, CN, hydroxy, mercapto, nitro, cyanato, thiocyanato, formyl, acyl, carboxy, carboxylate, alkylcarbonyloxy, carbamoyl, alkylaminocarbonyl, dialkylaminocarbonyl, sulfo, sulfonate, sulfoamino, sulfamoyl, alkylsulfonyl, arylsulfonyl, amidino, $NE^1E^2$, where $E^1$ and $E^2$ are each independently selected from hydrogen, alkyl, cycloalkyl, heterocycloalkyl, aryl or hetaryl,
in each case unsubstituted or substituted alkyl, alkoxy, alkylthio, (monoalkyl)amino, (dialkyl)amino, cycloalkyl, cycloalkoxy, cycloalkylthio, (monocycloalkyl)amino, (dicycloalkyl)amino, heterocycloalkyl, heterocycloalkoxy, heterocycloalkylthio, (monoheterocycloalkyl)amino, (diheterocycloalkyl)amino, aryl, aryloxy, arylthio, (monoaryl)amino, (diaryl)amino, hetaryl, hetaryloxy, hetarylthio, (monohetaryl)amino and (dihetaryl)amino.

In the compounds of the formula (II.a), n denotes the number of naphthalene units which are bonded in the peri position and form the base skeleton of the inventive rylene compounds. The rylene compounds according to the invention do not only encompass rylene diimides but also the structurally close related naphthalene diimides (n=1). In the individual $R^{n1}$ to $R^{n4}$ radicals, n denotes the particular naphthalene group of the rylene skeleton to which the radicals are bonded. $R^{n1}$ to $R^{n4}$ radicals which are bonded to different naphthalene groups may each have identical or different definitions. Accordingly, the compounds of the general formula I may be naphthalene diimides, perylenediimides, terrylenediimides or quaterrylenediimides of the following formulae:

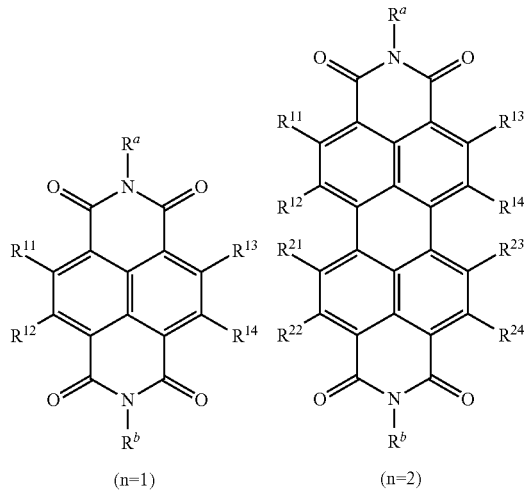

(n=1)     (n=2)

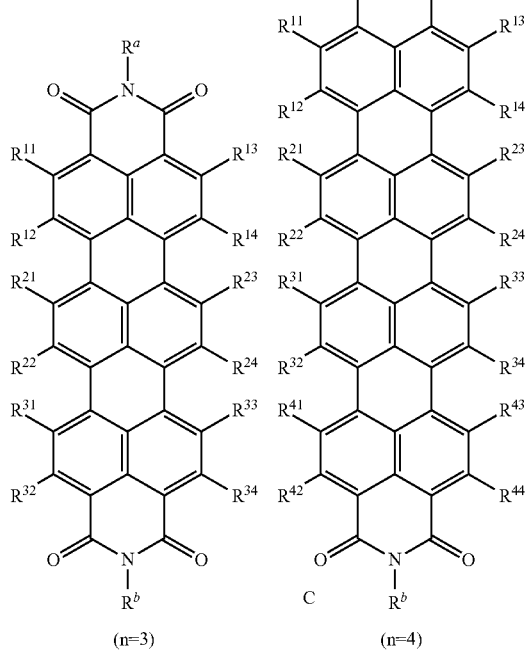

(n=3)     (n=4)

Preferably, in the compounds of the formula (II.a) the radicals $R^a$ and $R^b$ are independently of one another selected from hydrogen, linear $C_1$-$C_{30}$-alkyl, branched $C_3$-$C_{30}$-alkyl, perfluoro-$C_1$-$C_{30}$-alkyl, 1H,1H-perfluoro-$C_2$-$C_{30}$-alkyl, 1H,1H,2H,2H-perfluoro-$C_3$-$C_{30}$-alkyl, a radical of the formula G.1, a radical of the formula G.2 and a radical of the formula G.3

(G.1)

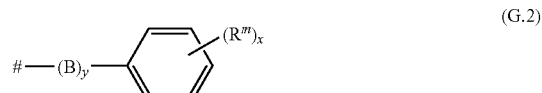

(G.2)

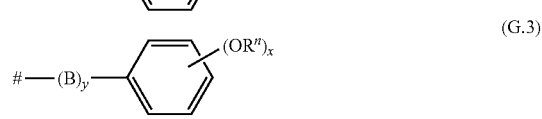

(G.3)

where
# represents the bonding side to a nitrogen atom,
B where present, is a $C_1$-$C_{10}$-alkylene group which may be interrupted by one or more nonadjacent groups which are selected from —O— and —S—,
y is 0 or 1,
$R^m$ is independently of one another selected from $C_1$-$C_{30}$-alkyl, $C_1$-$C_{30}$-fluoroalkyl, fluorine, chlorine, bromine, $NE^3E^4$, nitro and cyano, where $E^3$ and $E^4$, independently of one another, are hydrogen, alkyl, cycloalkyl, heterocycloalkyl, aryl or hetaryl,
$R^n$ is independently of one another selected from $C_1$-$C_3$-alkyl,
x in formulae G.2 and G.3 is 1, 2, 3, 4 or 5.

In a preferred embodiment of the compounds (I), the radicals $R^a$ and $R^b$ are independently selected from radicals of the general formulae (G.1) (G.2) and (G.3). In particular, $R^a$ and $R^b$ have the same meaning and are selected from radicals of the general formulae (G.1) (G.2) and (G.3).

Preferably, in the formula (G.2) the $R^m$ radicals are selected from $C_1$-$C_{12}$-alkyl or $C_1$-$C_{12}$-fluoroalkyl. In particular, in the formula (G.2) the $R^m$ radicals are selected from $C_1$-$C_4$-alkyl or $C_1$-$C_4$-fluoroalkyl.

Preferably, in the formula (G.3) the $R^n$ radicals are selected from $C_1$-$C_{12}$-alkyl.

In a preferred embodiment, in the compounds of the formula (I) $R^a$ and $R^b$ are each independently selected from radicals of the formula (G.2). Preferably, $R^a$ and $R^b$ are each independently selected from phenyl-($C_1$-$C_{30}$)-alkyl groups, wherein the benzene ring of the phenylalkyl group bears 1, 2, 3, 4 or 5 substituents, independently selected from F, Cl, Br, CN, $C_1$-$C_{30}$-alkyl and perfluoro-$C_1$-$C_{30}$-alkyl and the phenylalkyl group is attached to the imide nitrogen atom via the alkyl moiety of the phenylalkyl group.

More preferably, $R^a$ and $R^b$ have the same meaning and are selected from phenyl-($C_1$-$C_{30}$)-alkyl groups, wherein the benzene ring of the phenylalkyl group bears 1, 2, 3, or 5 substituents, independently selected from F, Cl, Br, CN, $C_1$-$C_{30}$-alkyl and perfluoro-$C_1$-$C_{30}$-alkyl. In particular, $R^a$ and $R^b$ have the same meaning and are selected from phenyl-($C_1$-$C_4$)-alkyl groups, wherein the benzene ring of the phenylalkyl group bears 1, 2, 3, 4 or 5 substituents, independently selected from F, Cl, Br, CN, $C_1$-$C_{30}$-alkyl and perfluoro-$C_1$-$C_2$-alkyl.

Examples of preferred radicals of the formula (G.1) are mentioned in the following table 1. In a preferred embodiment, in the compounds of the formula (I) $R^a$ and $R^b$ are each independently selected from radicals of the formula (G.1) mentioned in the following table 1. In particular, $R^a$ and $R^b$ have the same meaning and are selected from radicals of the formula (G.1) mentioned in the following table 1.

TABLE 1

(preferred radicals of the formula G.1):

Examples of preferred radicals of the formula (G.2) are mentioned in the following table 2. In a preferred embodiment, in the compounds of the formula (I) $R^a$ and $R^b$ are each independently selected from radicals of the formula (G.2) mentioned in the following table 2. In particular, $R^a$ and $R^b$ have the same meaning and are selected from radicals of the formula (G.2) mentioned in the following table 2.

TABLE 2

(preferred radicals of the formula G.2):

TABLE 2-continued (preferred radicals of the formula G.2):

In a preferred embodiment, $R^a$ and $R^b$ are each independently selected from linear $C_1$-$C_{30}$-alkyl radicals. In particular, $R^a$ and $R^b$ have the same meaning and are selected from linear $C_1$-$C_{30}$-alkyl radicals. Preferred linear alkyl groups are methyl, ethyl, n-propyl, n-butyl, n-pentyl, n-hexyl, n-heptyl, n-octyl, n-nonyl, n-decyl, n-undecyl, n-dodecyl, n-tridecyl, n-tetradecyl, n-hexadecyl, n-octadecyl and n-eicosyl.

In a preferred embodiment, $R^a$ and $R^b$ are each independently selected from branched $C_3$-$C_{30}$-alkyl radicals. In particular, $R^a$ and $R^b$ have the same meaning and are selected from branched $C_3$-$C_{30}$-alkyl radicals.

Preferably, in the compounds of the formula (II.a) the radicals $R^a$ and $R^b$ are selected from radicals of the general formulae (III.1), (III.2) and (III.3)

$$\#-CH_2-(CH)\diagup^{R^e}_{\diagdown R^f} \quad (III.1)$$

$$\#-(CH)\diagup^{R^g}_{\diagdown R^h} \quad (III.2)$$

$$\#-\underset{R^l}{\overset{R^i}{\underset{|}{C}}}-R^k \quad (III.3)$$

wherein

\# is a bonding site, and in the formula (III.1) $R^e$ and $R^f$ are independently selected from $C_1$- to $C_{27}$-alkyl, where the sum of the carbon atoms of the $R^e$ and $R^f$ radicals is an integer from 2 to 28, in the formula (III.2) $R^g$ and $R^h$ are independently selected from $C_1$- to $C_{28}$-alkyl, where the sum of the carbon atoms of the $R^g$ and $R^h$ radicals is an integer from 2 to 29, in the formula (III.3) $R^i$, $R^k$ and $R^l$ are independently selected from $C_1$- to $C_{27}$-alkyl, where the sum of the carbon atoms of the $R^i$, $R^k$ and $R^l$ radicals is an integer from 3 to 29.

Preferably, in the formula (III.1), $R^e$ and $R^f$ are independently selected from $C_1$- to $C_{20}$-alkyl, especially $C_1$- to $C_{12}$-alkyl.

Preferably, in the formula (III.1), the sum of the carbon atoms of the radicals (III.1) is an integer from 3 to 55, more preferably from 4 to 40, in particular from 5 to 30.

Preferred radicals of the formula (III.1) are:
2-methylpropyl, 2-ethylbutyl, 2-methylbutyl, 2-propylpentyl, 2-ethylpentyl, 2-methylpentyl, 2-butylhexyl, 2-propylhexyl, 2-ethylhexyl, 2-methylhexyl, 2-pentylheptyl, 2-butylheptyl, 2-propylheptyl, 2-ethylheptyl, 2-methylheptyl, 2-hexyloctyl, 2-pentyloctyl, 2-butyloctyl, 2-propyloctyl, 2-ethyloctyl, 2-methyloctyl, 2-heptylnonyl, 2-hexylnonyl, 2-pentylundecyl, 2-butylundecyl, 2-propylundecyl, 2-ethylundecyl, 2-methylundecyl, 2-decyldodecyl, 2-nonyldodecyl, 2-octyldodecyl, 2-heptyldodecyl, 2-hexyldodecyl, 2-pentyldodecyl, 2-butyldodecyl, 2-propyldodecyl, 2-ethyldodecyl, 2-methyldodecyl, 2-undecyltridecyl, 2-decyltridecyl, 2-nonyltridecyl, 2-octyltridecyl, 2-heptyltridecyl, 2-methyltridecyl, 2-undecyltetradecyl, 2-decyltetradecyl, 2-nonyttetradecyl, 2-octyltetradecyl, 2-hetyltetradecyl, 2-hexyttetradecyl, 2-pentyltetradecyl, 2-butyltetradecyl, 2-propyttetradecyl, 2-ethyttetradecyl, 2-methyttetradecyl, 2-tetradecylhexadecyl, 2-tridecylhexadecyl, 2-dodecylhexadecyl, 2-undecylhexadecyl, 2-decylhexadecyl, 2-nonylhexadecyl, 2-octylhexadecyl, 2-heptylhexadecyl, 2-hexylhexadecyl, 2-pentylhexadecyl, 2-butylhexadecyl, 2-propylhexadecyl, 2-ethylhexadecyl, 2-methylhexadecyl, 2-hexadecyloctadecyl, 2-pentadecyloctadecyl, 2-tetradecyloctadecyl, 2-tridecyloctadecyl, 2-dodecyloctadecyl, 2-undecyloctadecyl, 2-decyloctadecyl, 2-nonyloctadecyl, 2 octyloctadecyl, 2-heptyloctadecyl, 2-hexyloctadecyl, 2-pentyloctadecyl, 2-butyloctadecyl, 2-propyloctadecyl, 2-ethyloctadecyl, 2-methyloctadecyl, 2-octadecyleicosanyl, 2-heptadecyleicosanyl, 2-hexadecyleicosanyl, 2-pentadecyleicosanyl, 2-tetradecyleicosanyl, 2-tridecyleicosanyl, 2-dodecyleicosanyl, 2-undecyleicosanyl, 2-decyleicosanyl, 2-nonyleicosanyl, 2-octyleicosanyl, 2-heptyleicosanyl, 2-hexyleicosanyl, 2-pentyleicosanyl, 2-butyleicosanyl, 2-propyleicosanyl, 2-ethyleicosanyl, 2-methyleicosanyl, 2-eicosanyldocosanyl, 2-nonadecyldocosanyl, 2-octadecyldocosanyl, 2-heptadecyldocosanyl, 2-hexadecyldocosanyl, 2-pentadecyldocosanyl, 2-tetradecyldocosanyl, 2-tridecyldocosanyl, 2-undecyldocosanyl, 2-decyldocosanyl, 2-nonyldocosanyl, 2-octyldocosanyl, 2-heptyldocosanyl, 2-hexyldocosanyl, 2-pentyldocosanyl, 2-butyldocosanyl, 2-propyldocosanyl, 2-ethyldocosanyl, 2-methyldocosanyl, 2-docosanyltetracosanyl, 2-nonadecyltetracosanyl, 2-octadecyltetracosanyl, 2-heptadecyltetracosanyl, 2-hexadecyttetracosanyl, 2-pentadecyttetracosanyl, 2-pentadecyttetracosanyl, 2-tetradecyttetracosanyl, 2-tridecyttetracosanyl, 2-dodecyttetracosanyl, 2-undecyttetracosanyl, 2-decyttetracosanyl, 2-nonyttetracosanyl, 2-octyttetracosanyl, 2-heptyttetracosanyl, 2-hexyttetracosanyl, 2-pentyttetracosanyl, 2-butyttetracosanyl, 2-propyttetracosanyl, 2-ethyttetracosanyl, 2-methyttetracosanyl, 2-hexacosanyloctacosanyl, 2-pentacosanyloctacosanyl, 2-tetracosanyloctacosanyl, 2-tricosanyloctacosanyl, 2-docosanyloctacosanyl, 2-nonadecyloctacosanyl, 2-octadecyloctacosanyl, 2-heptadecyloctacosanyl, 2-hexadecyloctacosanyl, 2-hexadecyloctacosanyl, 2-pentadecyloctacosanyl, 2-tetradecyloctacosanyl, 2-tridecyloctacosanyl, 2-dodecyloctacosanyl, 2-undecyloctacosanyl, 2-decyloctacosanyl, 2-nonyloctacosanyl, 2-octyloctacosanyl, 2-heptyloctacosanyl, 2-hexyloctacosanyl, 2-pentyloctacosanyl, 2-butyloctacosanyl, 2-propyloctacosanyl, 2-ethyloctacosanyl, 2-methyloctacosanyl.

Examples of preferred radicals of the formula (III.1) are 2-ethylhexyl, 2-ethylheptyl, 2-ethyloctyl, 2-ethylnonyl and 2-ethyldecyl.

In a preferred embodiment of the compounds (II.a), the radicals $R^a$ and $R^b$ are each independently selected from radicals of the formula (III.2). In particular, $R^a$ and $R^b$ have the same meaning and are selected from radicals of the formula (III.2).

Preferred radicals of the formula (III.2) are:
1-ethylpropyl, 1-methylpropyl, 1-propylbutyl, 1-ethylbutyl, 1-methylbutyl, 1-butylpentyl, 1-propylpentyl, 1-ethylpentyl, 1-methylpentyl, 1-pentylhexyl, 1-butylhexyl, 1-propylhexyl, 1-ethylhexyl, 1-methylhexyl, 1-hexylheptyl, 1-pentylheptyl, 1-butylheptyl, 1-propylheptyl, 1-ethylheptyl, 1-methylheptyl, 1-heptyloctyl, 1-hexyloctyl, 1-pentyloctyl, 1-butyloctyl, 1-propyloctyl, 1-ethyloctyl, 1-methyloctyl, 1-octylnonyl, 1-heptylnonyl, 1-hexylnonyl, 1-pentylnonyl, 1-butylnonyl, 1-propylnonyl, 1-ethylnonyl, 1-methylnonyl, 1-nonyldecyl, 1-octyldecyl, 1-heptyldecyl, 1-hexyldecyl, 1-pentyldecyl, 1-butyldecyl, 1-propyldecyl, 1-ethyldecyl, 1-methyldecyl, 1-decylundecyl, 1-nonylundecyl, 1-octylundecyl, 1-heptylundecyl, 1-hexylundecyl, 1-pentylundecyl, 1-butylundecyl, 1-propylundecyl, 1-ethylundecyl, 1-methylundecyl, 1-undecyldodecyl, 1-decyldodecyl, 1-nonyldodecyl, 1-octyldodecyl, 1-heptyldodecyl, 1-hexyldodecyl, 1-pentyldodecyl, 1-butyldodecyl, 1-propyldodecyl, 1-ethyldodecyl, 1-methyldodecyl, 1-dodecyltridecyl, 1-undecyltridecyl, 1-decyltridecyl, 1-nonyltridecyl, 1-octyltridecyl, 1-heptyltridecyl, 1-hexyltridecyl, 1-pentyltridecyl, 1-butyltridecyl, 1-propyttridecyl, 1-ethyltridecyl, 1-methyltridecyl, 1-tridecyltetradecyl, 1-undecyltetradecyl, 1-decyltetradecyl, 1-nonyttetradecyl, 1-octyttetradecyl, 1-heptyltetradecyl, 1-hexyttetradecyl, 1-pentyttetradecyl, 1-butyttetradecyl, 1-propyttetradecyl, 1-ethyttetradecyl, 1-methyttetradecyl, 1-pentadecylhexadecyl, 1-tetradecylhexadecyl, 1-tridecylhexadecyl, 1-dodecylhexadecyl, 1-undecylhexadecyl, 1-decylhexadecyl, 1-nonylhexadecyl, 1-octylhexadecyl, 1-heptylhexadecyl, 1-hexylhexadecyl, 1-pentylhexadecyl, 1-butylhexadecyl, 1-propylhexadecyl, 1-ethylhexadecyl, 1-methylhexadecyl, 1-hexadecyloctadecyl, 1-pentadecyloctadecyl, 1-tetradecyloctadecyl, 1-tridecyloctadecyl, 1-dodecyloctadecyl, 1-undecyloctadecyl, 1-decyloctadecyl, 1-nonyloctadecyl, 1-octyloctadecyl, 1-heptyloctadecyl, 1-hexyloctadecyl, 1-pentyloctadecyl, 1-butyloctadecyl, 1-propyloctadecyl, 1-ethyloctadecyl, 1-methyloctadecyl, 1-nonadecyleicosanyl, 1-octadecyleicosanyl, 1-heptadecyleicosanyl, 1-hexadecyleicosanyl, 1-pentadecyleicosanyl, 1-tetradecyleicosanyl, 1-tridecyleicosanyl, 1-dodecyleicosanyl, 1-undecyleicosanyl, 1-decyleicosanyl, 1-nonyleicosanyl, 1-octyleicosanyl, 1-heptyleicosanyl, 1-hexyleicosanyl, 1-pentyleicosanyl, 1-butyleicosanyl, 1-propyleicosanyl, 1-ethyleicosanyl, 1-methyleicosanyl, 1-eicosanyldocosanyl, 1-nonadecyldocosanyl, 1-octadecyldocosanyl, 1-heptadecyldocosanyl, 1-hexadecyldocosanyl, 1-pentadecyldocosanyl, 1-tetradecyldocosanyl, 1-tridecyldocosanyl, 1-undecyldocosanyl, 1-decyldocosanyl, 1-nonyldocosanyl, 1-octyldocosanyl, 1-heptyldocosanyl, 1-hexyldocosanyl, 1-pentyldocosanyl, 1-butyldocosanyl, 1-propyldocosanyl, 1-ethyldocosanyl, 1-methyldocosanyl, 1-tricosanytetracosanyl, 1-docosanyttetracosanyl, 1-nonadecyltetracosanyl, 1-octadecyltetracosanyl, 1-heptadecyltetracosanyl, 1-hexadecyttetracosanyl, 1-pentadecyttetracosanyl, 1-pentadecyttetracosanyl, 1-tetradecyttetracosanyl, 1-tridecyttetracosanyl, 1-dodecyttetracosanyl, 1-undecyttetracosanyl, 1-decyttetracosanyl, 1-nonyttetracosanyl, 1-octyttetracosanyl, 1-heptyttetracosanyl, 1-hexyttetracosanyl, 1-pentyttetracosanyl, 1-butyttetracosanyl, 1-propyttetracosanyl, 1-ethyttetracosanyl, 1-methyttetracosanyl, 1-heptacosanyloctacosanyl, 1-hexacosanyloctacosanyl, 1-pentacosanyloctacosanyl, 1-tetracosanyloctacosanyl, 1-tricosanyloctacosanyl, 1-docosanyloctacosanyl, 1-nonadecyloctacosanyl, 1-octadecyloctacosanyl, 1-heptadecyloctacosanyl, 1-hexadecyloctacosanyl, 1-hexadecyloctacosanyl, 1-pentadecyloctacosanyl, 1-tetradecyloctacosanyl, 1-tridecyloctacosanyl, 1-dodecyloctacosanyl, 1-undecyloctacosanyl, 1-decyloctacosanyl, 1-nonyloctacosanyl, 1-octyloctacosanyl, 1-heptyloctacosanyl, 1-hexyloctacosanyl, 1-pentyloctacosanyl, 1-butyloctacosanyl, 1-propyloctacosanyl, 1-ethyloctacosanyl, 1-methyloctacosanyl.

Particularly preferred radicals of the formula (III.2) are: 1-methylethyl, 1-methylpropyl, 1-methylbutyl, 1-methylpentyl, 1-methylhexyl, 1-methylheptyl, 1-methyloctyl, 1-ethylpropyl, 1-ethylbutyl, 1-ethylpentyl, 1-ethylhexyl, 1-ethylheptyl, 1-ethyloctyl, 1-propylbutyl, 1-propylpentyl, 1-propylhexyl, 1-propylheptyl, 1-propyloctyl, 1-butylpentyl, 1-butylhexyl, 1-butylheptyl, 1-butyloctyl, 1-pentylhexyl, 1-pentylheptyl, 1-pentyloctyl, 1-hexylheptyl, 1-hexyloctyl, 1-heptyloctyl.

In a preferred embodiment of the compounds (II.a), the radicals $R^a$ and $R^b$ are each independently selected from radicals of the formula (III.3). In particular, $R^a$ and $R^b$ have the same meaning and are selected from radicals of the formula (III.3).

A particularly preferred radical of the formula (III.3) is tert-butyl.

Preferably at least one of the radicals $R^a$ and $R^b$ is selected from perfluoro-$C_1$-$C_{30}$-alkyl, 1H,1H-perfluoro-$C_2$-$C_{30}$-alkyl or 1H,1H,2H,2H-perfluoro-$C_3$-$C_{30}$-alkyl.

In a preferred embodiment of the compounds (I.a), the radicals $R^a$ and $R^b$ are selected from perfluoro-$C_1$-$C_{30}$-alkyl, 1H,1H-perfluoro-$C_2$-$C_{30}$-alkyl or 1H,1H,2H,2H-perfluoro-$C_3$-$C_{30}$-alkyl.

In a preferred embodiment, at least one of the radicals $R^a$ and $R^b$ is selected from $CF_3$, $C_2F_5$, n-$C_3F_7$, n-$C_4F_9$, n-$C_5F_{11}$, n-$C_6F_{13}$, $CF(CF_3)_2$, $C(CF_3)_3$, $CF_2CF(CF_3)_2$, $CF(CF_3)(C_2F_5)$, $CH_2$—$CF_3$, $CH_2$—$C_2F_5$, $CH_2$—(n-$C_3F_7$), $CH_2$—(n-$C_4F_9$), $CH_2$—(n-$C_5F_{11}$), $CH_2$—(n-$C_6F_{13}$), $CH_2$—$CF(CF_3)_2$, $CH_2$—$C(CF_3)_3$, $CH_2$—$CF_2CF(CF_3)_2$, $CH_2$—$CF(CF_3)(C_2F_5)$, $CH_2$—$CH_2$—$CF_3$, $CH_2$—$CH_2$—$C_2F_5$, $CH_2$—$CH_2$-(n-$C_3F_7$), $CH_2$—$CH_2$-(n-$C_4F_9$), $CH_2$—$CH_2$-(n-$C_5F_{11}$), $CH_2$—$CH_2$-(n-$C_6F_{13}$), $CH_2$—$CH_2$—$CF(CF_3)_2$, $CH_2$—$CH_2$—$C(CF_3)_3$, $CH_2$—$CH_2$—$CF_2CF(CF_3)_2$ and $CH_2$—$CH_2$—$CF(CF_3)(C_2F_5)$. In particular, $R^a$ and $R^b$ have the same meaning and are selected from the afore-mentioned radicals.

It has been found that semiconductors prepared from an enantiomerically enriched mixture or an enantiomerically pure rylene compound of the general formula (I.a) can have advantageous properties. WO 2012/090110 describes enantiomerically enriched mixtures that have unexpected electron-transport efficiency compared to the racemate or either of the enantiomers in optically pure form. The teaching of this document is incorporated herein by reference.

In particular, the substituents $R^a$ and $R^b$ are identical and selected from a branched $C_{4-40}$ alkyl group, a branched $C_{4-40}$ alkenyl group and a branched $C_{4-40}$ haloalkyl group, wherein the branched $C_{4-40}$ alkyl group, the branched $C_{4-40}$ alkenyl group, or the branched $C_{4-40}$ haloalkyl group are selected from:

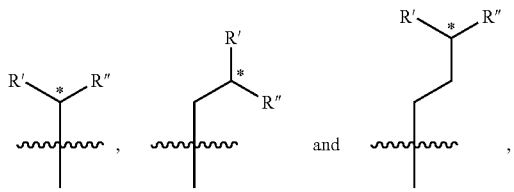

where R' is a $C_{1-20}$ alkyl or haloalkyl group; and R" is different from R' and selected from a $C_{1-20}$ alkyl group, a $C_{2-20}$ alkenyl group, and a $C_{1-20}$ haloalkyl group. The asterisk * denotes a stereogenic center such that $R^a$ and $R^b$ have either an (R)- or an (S)-configuration. In a preferred embodiment, the mixture is enantiomerically enriched, that is, the mixture includes an excess of either the (R,R)-stereoisomer (in which both $R^a$ and $R^b$ have the (R)-configuration) or the (S,S)-stereoisomer (in which both $R^a$ and $R^b$ have the (S)-configuration).

Preferred chiral substituents $R^a$ and $R^b$ are (1S)-1-methylbutyl, (1S)-1-methylpentyl, (1S)-1-methylhexyl, (1S)-1-methylheptyl, (1S)-1-methyloctyl, (1S)-1-ethylpropyl, (1S)-1-ethylbutyl, (1S)-1-ethylpentyl, (1S)-1-propylbutyl, (1S)-1-propylpentyl, (1S)-1-propylhexyl, (1R)-1-methylbutyl, (1R)-1-methylpentyl, (1R)-1-methylhexyl, (1R)-1-methylheptyl, (1R)-1-methyloctyl, (1R)-1-ethylpropyl, (1R)-1-ethylbutyl, (1R)-1-ethylpentyl, (1R)-1-propylbutyl, (1R)-1-propylpentyl, (1R)-1-propylhexyl.

A preferred class of compounds of the formula (II.a) are cyanated or halogenated rylene diimides, more preferably cyanated or halogenated perylene diimides, in particular N,N'-bis-substituted-(1,7 & 1,6)-di-cyano-perylene-3,4:9,10-bis(dicarboximide)s, N,N'-bis-substituted-(1,7 & 1,6)-di-fluoro-perylene-3,4:9,10-bis(dicarboximide)s, N,N'-bis-substituted-(1,7 & 1,6)-di-chloro-perylene-3,4:9,10-bis(dicarboximide)s and N,N'-bis-substituted-(1,7 & 1,6)-di-bromo-perylene-3,4:9,10-bis(dicarboximide)s.

Suitable cyanated or halogenated rylene diimides are described e.g. in U.S. Pat. Nos. 7,671,202, 7,902,363, and 7,569,693, and U.S. Patent Application Publication No. 2010/0319778.

In a further preferred embodiment the compounds of the formula (II.a) are selected from halogenated perylene bisimide derivatives described by R. Schmidt, J. H. Oh, Y.-S. Sun, M. Deppisch, A.-M. Krause, K. Radacki, H. Braunschweig, M. Könemann, P. Erk, Z. Bao and F. Würthner in *J. Am. Chem. Soc* 2009, 131, 6215-6228.

In a further preferred embodiment the compounds of the formula (II.a) are selected from perylenediimides as described in WO 2007/093643 and WO 2007/116001.

Specific examples of compounds of the formula (II.a) include:
N,N'-bis(cyclohexyl)-1,6-dicyano-perylene-3,4:9,10-bis(dicarboximide),
N,N'-bis(cyclohexyl)-1,7-dicyano-perylene-3,4:9,10-bis(dicarboximide),
N,N'-bis(1H,1H-perfluorobutyl)-1,6-dicyano-perylene-3,4:9,10-bis(dicarboximide),
N,N'-bis(1H,1H-perfluorobutyl)-1,7-dicyano-perylene-3,4:9,10-bis(dicarboximide),
N,N'-bis(n-octyl)-1,6-dicyano-perylene-3,4:9,10-bis(dicarboximide),
N,N'-bis(n-octyl)-1,7-dicyano-perylene-3,4:9,10-bis(dicarboximide),
N,N'-bis(2-methylhexyl)-1,6-dicyano-perylene-3,4:9,10-bis(dicarboximide), N,N'-bis(2-methylhexyl)-1,7-dicyano-perylene-3,4:9,10-bis(dicarboximide),
N,N'-bis(2-ethylhexyl)-1,6-dicyano-perylene-3,4:9,10-bis(dicarboximide),
N,N'-bis(2-ethylhexyl)-1,7-dicyano-perylene-3,4:9,10-bis(dicarboximide),
N,N'-bis[(3S)-3,7-dimethyl-6-octenyl]-1,6-dicyano-perylene-3,4:9,10-bis(dicarboximide),
N,N'-bis[(3S)-3,7-dimethyl-6-octenyl]-1,7-dicyano-perylene-3,4:9,10-bis(dicarboximide),
N,N'-bis(4-n-hexylphenyl)-1,6-dicyano-perylene-3,4:9,10-bis(dicarboximide),
N,N'-bis(4-n-hexylphenyl)-1,7-dicyano-perylene-3,4:9,10-bis(dicarboximide),
N,N'-bis(4-n-dodecylphenyl)-1,6-dicyano-perylene-3,4:9,10-bis(dicarboximide),
N,N'-bis(4-n-dodecylphenyl)-1,7-dicyano-perylene-3,4:9,10-bis(dicarboximide),
N,N'-bis(4-[(3S)-3,7-dimethyl-6-octenyl]phenyl)-1,6-dicyano-perylene-3,4:9,10-bis(dicarboximide),
N,N'-bis(4-[(3S)-3,7-dimethyl-6-octenyl]phenyl)-1,7-dicyano-perylene-3,4:9,10-bis(dicarboximide),
N,N'-bis(4-heptyloxyphenyl)-1,6-dicyano-perylene-3,4:9,10-bis(dicarboximide),
N,N'-bis(4-heptyloxyphenyl)-1,7-dicyano-perylene-3,4:9,10-bis(dicarboximide),
N,N'-bis(4-biphenylyl)-1,6-dicyano-perylene-3,4:9,10-bis(dicarboximide),
N,N'-bis(4-biphenylyl)-1,7-dicyano-perylene-3,4:9,10-bis(dicarboximide),
N,N'-bis[4-(4'-n-octylbiphenylyl)]-1,6-dicyano-perylene-3,4:9,10-bis(dicarboximide),
N,N'-bis[4-(4'-n-octylbiphenylyl)]-1,7-dicyano-perylene-3,4:9,10-bis(dicarboximide),
N,N'-bis(4-[4'-((3S)-3,7-dimethyl-6-octenyl]biphenylyl)-1,6-dicyano-perylene-3,4:9,10-bis(dicarboximide),
N,N'-bis(4-[4'-((3S)-3,7-dimethyl-6-octenyl]biphenylyl)-1,7-dicyano-perylene-3,4:9,10-bis(dicarboximide),
N,N'-bis[4-(2',3',4',5',6'-pentafluorobiphenyl)]-1,6-dicyano-perylene-3,4:9,10-bis(dicarboximide),
N,N'-bis[4-(2',3',4',5',6'-pentafluorobiphenyl)]-1,7-dicyano-perylene-3,4:9,10-bis(dicarboximide),
N,N'-bis[4-(4'-n-octyl-2',3',5',6'-tetrafluorobiphenyl)]-1,6-dicyano-perylene-3,4:9,10-bis(dicarboximide),
N,N'-bis[4-(4'-n-octyl-2',3',5',6'-tetrafluorobiphenyl)]-1,7-dicyano-perylene-3,4:9,10-bis(dicarboximide),
N,N'-bis[4-(4'-n-octyl-2,3,5,6-tetrafluorobiphenyl)]-1,6-dicyano-perylene-3,4:9,10-bis(dicarboximide),
N,N'-bis[4-(4'-n-octyl-2,3,5,6-tetrafluorobiphenyl)]-1,7-dicyano-perylene-3,4:9,10-bis(dicarboximide),
N,N'-bis(benzyl)-1,6-dicyano-perylene-3,4:9,10-bis(dicarboximide),
N,N'-bis(benzyl)-1,7-dicyano-perylene-3,4:9,10-bis(dicarboximide),
N,N'-bis(4-n-butylbenzyl)-1,6-dicyano-perylene-3,4:9,10-bis(dicarboximide),
N,N'-bis(4-n-butylbenzyl)-1,7-dicyano-perylene-3,4:9,10-bis(dicarboximide),
N,N'-bis(4-sec-butylphenyl)-1,6-dicyano-perylene-3,4:9,10-bis(dicarboximide),
N,N'-bis(4-sec-butylphenyl)-1,7-dicyano-perylene-3,4:9,10-bis(dicarboximide),
N,N'-bis(4-[(3S)-3,7-dimethyl-6-octenyloxy]benzyl)-1,6-dicyano-perylene-3,4:9,10-bis(dicarboximide),
N,N'-bis(4-[(3S)-3,7-dimethyl-6-octenyloxy]benzyl)-1,7-dicyano-perylene-3,4:9,10-bis(dicarboximide),
N,N'-bis(4-benzylphenyl)-1,6-dicyano-perylene-3,4:9,10-bis(dicarboximide),
N,N'-bis(4-benzylphenyl)-1,7-dicyano-perylene-3,4:9,10-bis(dicarboximide),
N,N'-bis(4-[1-(2-phenylethyl)]phenyl)-1,6-dicyano-perylene-3,4:9,10-bis(dicarboximide),
N,N'-bis(4-[1-(2-phenylethyl)]phenyl)-1,7-dicyano-perylene-3,4:9,10-bis(dicarboximide),
N,N'-bis(4-n-benzoylphenyl)-1,6-dicyano-perylene-3,4:9,10-bis(dicarboximide),
N,N'-bis(4-n-benzoylphenyl)-1,7-dicyano-perylene-3,4:9,10-bis(dicarboximide),
N,N'-bis(1-methylbutyl)-1,6-dicyano-perylene-3,4:9,10-bis(dicarboximide),
N,N'-bis(1-methylbutyl)-1,7-dicyano-perylene-3,4:9,10-bis(dicarboximide),
N,N'-bis(1-methylpentyl)-1,6-dicyano-perylene-3,4:9,10-bis(dicarboximide),
N,N'-bis(1-methylpentyl)-1,7-dicyano-perylene-3,4:9,10-bis(dicarboximide),
N,N'-bis[(1 S)-1-methylpentyl]-1,6-dicyano-perylene-3,4:9,10-bis(dicarboximide)
N,N'-bis[(1 S)-1-methylpentyl]-1,7-dicyano-perylene-3,4:9,10-bis(dicarboximide)
N,N'-bis[(1R)-1-methylpentyl]-1,6-dicyano-perylene-3,4:9,10-bis(dicarboximide)
N,N'-bis[(1R)-1-methylpentyl]-1,7-dicyano-perylene-3,4:9,10-bis(dicarboximide)
N,N'-bis(1-methylhexyl)-1,6-dicyano-perylene-3,4:9,10-bis(dicarboximide),
N,N'-bis(1-methylhexyl)-1,7-dicyano-perylene-3,4:9,10-bis(dicarboximide),
N,N'-bis(1-ethylpropyl)-1,6-dicyano-perylene-3,4:9,10-bis(dicarboximide),
N,N'-bis(1-ethylpropyl)-1,7-dicyano-perylene-3,4:9,10-bis(dicarboximide),
N,N'-bis(1-ethylbutyl)-1,6-dicyano-perylene-3,4:9,10-bis(dicarboximide),
N,N'-bis(1-ethylbutyl)-1,7-dicyano-perylene-3,4:9,10-bis(dicarboximide),
N,N'-bis(1-ethylpentyl)-1,6-dicyano-perylene-3,4:9,10-bis(dicarboximide),
N,N'-bis(1-ethylpentyl)-1,7-dicyano-perylene-3,4:9,10-bis(dicarboximide),
N,N'-bis(1-ethylhexyl)-1,6-dicyano-perylene-3,4:9,10-bis(dicarboximide),
N,N'-bis(1-ethylhexyl)-1,7-dicyano-perylene-3,4:9,10-bis(dicarboximide),
N,N'-bis(1,3-dimethylbutyl)-1,6-dicyano-perylene-3,4:9,10-bis(dicarboximide),
N,N'-bis(1,3-dimethylbutyl)-1,7-dicyano-perylene-3,4:9,10-bis(dicarboximide),
N,N'-bis(cyclohexyl)-1,6-dichloro-perylene-3,4:9,10-bis(dicarboximide),
N,N'-bis(cyclohexyl)-1,7-dichloro-perylene-3,4:9,10-bis(dicarboximide),
N,N'-bis(1H,1H-perfluorobutyl)-1,6-dichloro-perylene-3,4:9,10-bis(dicarboximide),
N,N'-bis(1H,1H-perfluorobutyl)-1,7-dichloro-perylene-3,4:9,10-bis(dicarboximide),
N,N'-bis(n-octyl)-1,6-dichloro-perylene-3,4:9,10-bis(dicarboximide),
N,N'-bis(n-octyl)-1,7-dichloro-perylene-3,4:9,10-bis(dicarboximide),
N,N'-bis(2-methyl hexyl)-1,6-dichloro-perylene-3,4:9,10-bis(dicarboximide), N,N'-bis(2-methyl hexyl)-1,7-dichloro-perylene-3,4:9,10-bis(dicarboximide),
N,N'-bis(2-ethyl hexyl)-1,6-dichloro-perylene-3,4:9,10-bis(dicarboximide),
N,N'-bis(2-ethyl hexyl)-1,7-dichloro-perylene-3,4:9,10-bis(dicarboximide),
N,N'-bis[(3S)-3,7-dimethyl-6-octenyl]-1,6-dichloro-perylene-3,4:9,10-bis(dicarboximide),
N,N'-bis[(3S)-3,7-dimethyl-6-octenyl]-1,7-dichloro-perylene-3,4:9,10-bis(dicarboximide),
N,N'-bis(4-n-hexyl phenyl)-1,6-dichloro-perylene-3,4:9,10-bis(dicarboximide),
N,N'-bis(4-n-hexylphenyl)-1,7-dichloro-perylene-3,4:9,10-bis(dicarboximide),
N,N'-bis(4-n-dodecylphenyl)-1,6-dichloro-perylene-3,4:9,10-bis(dicarboximide),
N,N'-bis(4-n-dodecyl phenyl)-1,7-dichloro-perylene-3,4:9,10-bis(dicarboximide),
N,N'-bis(4-[(3S)-3,7-dimethyl-6-octenyl]phenyl)-1,6-dichloro-perylene-3,4:9,10-bis(dicarboximide),
N,N'-bis(4-[(3S)-3,7-dimethyl-6-octenyl]phenyl)-1,7-dichloro-perylene-3,4:9,10-bis(dicarboximide),
N,N'-bis(4-heptyloxyphenyl)-1,6-dichloro-perylene-3,4:9,10-bis(dicarboximide),
N,N'-bis(4-heptyloxyphenyl)-1,7-dichloro-perylene-3,4:9,10-bis(dicarboximide),
N,N'-bis(4-biphenylyl)-1,6-dichloro-perylene-3,4:9,10-bis(dicarboximide),
N,N'-bis(4-biphenylyl)-1,7-dichloro-perylene-3,4:9,10-bis(dicarboximide),
N,N'-bis[4-(4'-n-octylbiphenylyl)]-1,6-dichloro-perylene-3,4:9,10-bis(dicarboximide),
N,N'-bis[4-(4'-n-octylbiphenylyl)]-1,7-dichloro-perylene-3,4:9,10-bis(dicarboximide),
N,N'-bis(4-[4'-((3S)-3,7-dimethyl-6-octenyl]biphenylyl)-1,6-dichloro-perylene-3,4:9,10-bis(dicarboximide),
N,N'-bis(4-[4'-((3S)-3,7-dimethyl-6-octenyl]biphenylyl)-1,7-dichloro-perylene-3,4:9,10-bis(dicarboximide),
N,N'-bis[4-(2',3',4',5',6'-pentafluorobiphenyl)]-1,6-dichloro-perylene-3,4:9,10-bis(dicarboximide),
N,N'-bis[4-(2',3',4',5',6'-pentafluorobiphenyl)]-1,7-dichloro-perylene-3,4:9,10-bis(dicarboximide),
N,N'-bis[4-(4'-n-octyl-2',3',5',6'-tetrafluorobiphenyl)]-1,6-dichloro-perylene-3,4:9,10-bis(dicarboximide),
N,N'-bis[4-(4'-n-octyl-2',3',5',6'-tetrafluorobiphenyl)]-1,7-dichloro-perylene-3,4:9,10-bis(dicarboximide),
N,N'-bis[4-(4'-n-octyl-2,3,5,6-tetrafluorobiphenyl)]-1,6-dichloro-perylene-3,4:9,10-bis(dicarboximide),
N,N'-bis[4-(4'-n-octyl-2,3,5,6-tetrafluorobiphenyl)]-1,7-dichloro-perylene-3,4:9,10-bis(dicarboximide),
N,N'-bis(benzyl)-1,6-dichloro-perylene-3,4:9,10-bis(dicarboximide),
N,N'-bis(benzyl)-1,7-dichloro-perylene-3,4:9,10-bis(dicarboximide),
N,N'-bis(4-n-butylbenzyl)-1,6-dichloro-perylene-3,4:9,10-bis(dicarboximide),
N,N'-bis(4-n-butylbenzyl)-1,7-dichloro-perylene-3,4:9,10-bis(dicarboximide),
N,N'-bis(4-sec-butylphenyl)-1,6-dichloro-perylene-3,4:9,10-bis(dicarboximide),
N,N'-bis(4-sec-butylphenyl)-1,7-dichloro-perylene-3,4:9,10-bis(dicarboximide),
N,N'-bis(4-[(3S)-3,7-dimethyl-6-octenyloxy]benzyl)-1,6-dichloro-perylene-3,4:9,10-bis(dicarboximide),
N,N'-bis(4-[(3S)-3,7-dimethyl-6-octenyloxy]benzyl)-1,7-dichloro-perylene-3,4:9,10-bis(dicarboximide),
N,N'-bis(4-benzylphenyl)-1,6-dichloro-perylene-3,4:9,10-bis(dicarboximide),
N,N'-bis(4-benzylphenyl)-1,7-dichloro-perylene-3,4:9,10-bis(dicarboximide),
N,N'-bis(4-[1-(2-phenylethyl)]phenyl)-1,6-dichloro-perylene-3,4:9,10-bis(dicarboximide),
N,N'-bis(4-[1-(2-phenylethyl)]phenyl)-1,7-dichloro-perylene-3,4:9,10-bis(dicarboximide),
N,N'-bis(4-n-benzoylphenyl)-1,6-dichloro-perylene-3,4:9,10-bis(dicarboximide),
N,N'-bis(4-n-benzoylphenyl)-1,7-dichloro-perylene-3,4:9,10-bis(dicarboximide),
N,N'-bis(1-methylbutyl)-1,6-dichloro-perylene-3,4:9,10-bis(dicarboximide),
N,N'-bis(1-methylbutyl)-1,7-dichloro-perylene-3,4:9,10-bis(dicarboximide),
N,N'-bis(1-methylpentyl)-1,6-dichloro-perylene-3,4:9,10-bis(dicarboximide),
N,N'-bis(1-methylpentyl)-1,7-dichloro-perylene-3,4:9,10-bis(dicarboximide),
N,N'-bis(1-methylhexyl)-1,6-dichloro-perylene-3,4:9,10-bis(dicarboximide),
N,N'-bis(1-methylhexyl)-1,7-dichloro-perylene-3,4:9,10-bis(dicarboximide),
N,N'-bis(1-ethylpropyl)-1,6-dichloro-perylene-3,4:9,10-bis(dicarboximide),
N,N'-bis(1-ethylpropyl)-1,7-dichloro-perylene-3,4:9,10-bis(dicarboximide),
N,N'-bis(1-ethylbutyl)-1,6-dichloro-perylene-3,4:9,10-bis(dicarboximide),
N,N'-bis(1-ethylbutyl)-1,7-dichloro-perylene-3,4:9,10-bis(dicarboximide),
N,N'-bis(1-ethylpentyl)-1,6-dichloro-perylene-3,4:9,10-bis(dicarboximide),
N,N'-bis(1-ethylpentyl)-1,7-dichloro-perylene-3,4:9,10-bis(dicarboximide),
N,N'-bis(1-ethylhexyl)-1,6-dichloro-perylene-3,4:9,10-bis(dicarboximide),
N,N'-bis(1-ethylhexyl)-1,7-dichloro-perylene-3,4:9,10-bis(dicarboximide),
N,N'-bis(1,3-dimethylbutyl)-1,6-dichloro-perylene-3,4:9,10-bis(dicarboximide),
N,N'-bis(1,3-dimethylbutyl)-1,7-dichloro-perylene-3,4:9,10-bis(dicarboximide),
N,N'-bis(cyclohexyl)-1,6-dibromo-perylene-3,4:9,10-bis(dicarboximide),
N,N'-bis(cyclohexyl)-1,7-dibromo-perylene-3,4:9,10-bis(dicarboximide),
N,N'-bis(1H,1H-perfluorobutyl)-1,6-dibromo-perylene-3,4:9,10-bis(dicarboximide),
N,N'-bis(1H,1H-perfluorobutyl)-1,7-dibromo-perylene-3,4:9,10-bis(dicarboximide),
N,N'-bis(n-octyl)-1,6-dibromo-perylene-3,4:9,10-bis(dicarboximide),
N,N'-bis(n-octyl)-1,7-dibromo-perylene-3,4:9,10-bis(dicarboximide),
N,N'-bis(2-methylhexyl)-1,6-dibromo-perylene-3,4:9,10-bis(dicarboximide),
N,N'-bis(2-methylhexyl)-1,7-dibromo-perylene-3,4:9,10-bis(dicarboximide),
N,N'-bis(2-ethylhexyl)-1,6-dibromo-perylene-3,4:9,10-bis(dicarboximide),
N,N'-bis(2-ethylhexyl)-1,7-dibromo-perylene-3,4:9,10-bis(dicarboximide),
N,N'-bis[(3S)-3,7-dimethyl-6-octenyl]-1,6-dibromo-perylene-3,4:9,10-bis(dicarboximide), N,N'-bis[(3S)-3,7-dimethyl-6-octenyl]-1,7-dibromo-perylene-3,4:9,10-bis(dicarboximide),
N,N'-bis(4-n-hexylphenyl)-1,6-dibromo-perylene-3,4:9,10-bis(dicarboximide),
N,N'-bis(4-n-hexylphenyl)-1,7-dibromo-perylene-3,4:9,10-bis(dicarboximide),
N,N'-bis(4-n-dodecyl phenyl)-1,6-dibromo-perylene-3,4:9,10-bis(dicarboximide),
N,N'-bis(4-n-dodecyl phenyl)-1,7-dibromo-perylene-3,4:9,10-bis(dicarboximide),
N,N'-bis(4-[(3S)-3,7-dimethyl-6-octenyl]phenyl)-1,6-dibromo-perylene-3,4:9,10-bis(dicarboximide),
N,N'-bis(4-[(3S)-3,7-dimethyl-6-octenyl]phenyl)-1,7-dibromo-perylene-3,4:9,10-bis(dicarboximide),
N,N'-bis(4-heptyloxyphenyl)-1,6-dibromo-perylene-3,4:9,10-bis(dicarboximide),
N,N'-bis(4-heptyloxyphenyl)-1,7-dibromo-perylene-3,4:9,10-bis(dicarboximide),
N,N'-bis(4-biphenylyl)-1,6-dibromo-perylene-3,4:9,10-bis(dicarboximide),
N,N'-bis(4-biphenylyl)-1,7-dibromo-perylene-3,4:9,10-bis(dicarboximide),
N,N'-bis[4-(4'-n-octylbiphenylyl)]-1,6-dibromo-perylene-3,4:9,10-bis(dicarboximide),
N,N'-bis[4-(4'-n-octylbiphenylyl)]-1,7-dibromo-perylene-3,4:9,10-bis(dicarboximide),
N,N'-bis(4-[4'-((3S)-3,7-dimethyl-6-octenyl]biphenylyl)-1,6-dibromo-perylene-3,4:9,10-bis(dicarboximide),
N,N'-bis(4-[4'-((3S)-3,7-dimethyl-6-octenyl]biphenylyl)-1,7-dibromo-perylene-3,4:9,10-bis(dicarboximide),
N,N'-bis[4-(2',3',4',5',6'-pentafluorobiphenyl)]-1,6-dibromo-perylene-3,4:9,10-bis(dicarboximide),
N,N'-bis[4-(2',3',4',5',6'-pentafluorobiphenyl)]-1,7-dibromo-perylene-3,4:9,10-bis(dicarboximide),
N,N'-bis[4-(4'-n-octyl-2',3',5',6'-tetrafluorobiphenyl)]-1,6-dibromo-perylene-3,4:9,10-bis(dicarboximide),
N,N'-bis[4-(4'-n-octyl-2',3',5',6'-tetrafluorobiphenyl)]-1,7-dibromo-perylene-3,4:9,10-bis(dicarboximide),
N,N'-bis[4-(4'-n-octyl-2,3,5,6-tetrafluorobiphenyl)]-1,6-dibromo-perylene-3,4:9,10-bis(dicarboximide),
N,N'-bis[4-(4'-n-octyl-2,3,5,6-tetrafluorobiphenyl)]-1,7-dibromo-perylene-3,4:9,10-bis(dicarboximide),
N,N'-bis(benzyl)-1,6-dibromo-perylene-3,4:9,10-bis(dicarboximide),
N,N'-bis(benzyl)-1,7-dibromo-perylene-3,4:9,10-bis(dicarboximide),
N,N'-bis(4-n-butylbenzyl)-1,6-dibromo-perylene-3,4:9,10-bis(dicarboximide),
N,N'-bis(4-n-butylbenzyl)-1,7-dibromo-perylene-3,4:9,10-bis(dicarboximide),
N,N'-bis(4-sec-butylphenyl)-1,6-dibromo-perylene-3,4:9,10-bis(dicarboximide),
N,N'-bis(4-sec-butylphenyl)-1,7-dibromo-perylene-3,4:9,10-bis(dicarboximide),
N,N'-bis(4-[(3S)-3,7-dimethyl-6-octenyloxy]benzyl)-1,6-dibromo-perylene-3,4:9,10-bis(dicarboximide),
N,N'-bis(4-[(3S)-3,7-dimethyl-6-octenyloxy]benzyl)-1,7-dibromo-perylene-3,4:9,10-bis(dicarboximide),
N,N'-bis(4-benzylphenyl)-1,6-dibromo-perylene-3,4:9,10-bis(dicarboximide),
N,N'-bis(4-benzylphenyl)-1,7-dibromo-perylene-3,4:9,10-bis(dicarboximide),
N,N'-bis(4-[1-(2-phenylethyl)]phenyl)-1,6-dibromo-perylene-3,4:9,10-bis(dicarboximide),
N,N'-bis(4-[1-(2-phenylethyl)]phenyl)-1,7-dibromo-perylene-3,4:9,10-bis(dicarboximide), N,N'-bis(4-n-benzoylphenyl)-1,6-dibromo-perylene-3,4:9,10-bis(dicarboximide),
N,N'-bis(4-n-benzoylphenyl)-1,7-dibromo-perylene-3,4:9,10-bis(dicarboximide),
N,N'-bis(1-methylbutyl)-1,6-dibromo-perylene-3,4:9,10-bis(dicarboximide),
N,N'-bis(1-methylbutyl)-1,7-dibromo-perylene-3,4:9,10-bis(dicarboximide),
N,N'-bis(1-methylpentyl)-1,6-dibromo-perylene-3,4:9,10-bis(dicarboximide),
N,N'-bis(1-methylpentyl)-1,7-dibromo-perylene-3,4:9,10-bis(dicarboximide),
N,N'-bis(1-methylhexyl)-1,6-dibromo-perylene-3,4:9,10-bis(dicarboximide),
N,N'-bis(1-methylhexyl)-1,7-dibromo-perylene-3,4:9,10-bis(dicarboximide),
N,N'-bis(1-ethylpropyl)-1,6-dibromo-perylene-3,4:9,10-bis(dicarboximide),
N,N'-bis(1-ethylpropyl)-1,7-dibromo-perylene-3,4:9,10-bis(dicarboximide),
N,N'-bis(1-ethylbutyl)-1,6-dibromo-perylene-3,4:9,10-bis(dicarboximide),
N,N'-bis(1-ethylbutyl)-1,7-dibromo-perylene-3,4:9,10-bis(dicarboximide),
N,N'-bis(1-ethylpentyl)-1,6-dibromo-perylene-3,4:9,10-bis(dicarboximide),
N,N'-bis(1-ethylpentyl)-1,7-dibromo-perylene-3,4:9,10-bis(dicarboximide),
N,N'-bis(1-ethylhexyl)-1,6-dibromo-perylene-3,4:9,10-bis(dicarboximide),
N,N'-bis(1-ethylhexyl)-1,7-dibromo-perylene-3,4:9,10-bis(dicarboximide),
N,N'-bis(1,3-dimethylbutyl)-1,6-dibromo-perylene-3,4:9,10-bis(dicarboximide) and
N,N'-bis(1,3-dimethylbutyl)-1,7-dibromo-perylene-3,4:9,10-bis(dicarboximide).

Some particularly preferred compounds (II.a) are specified below:

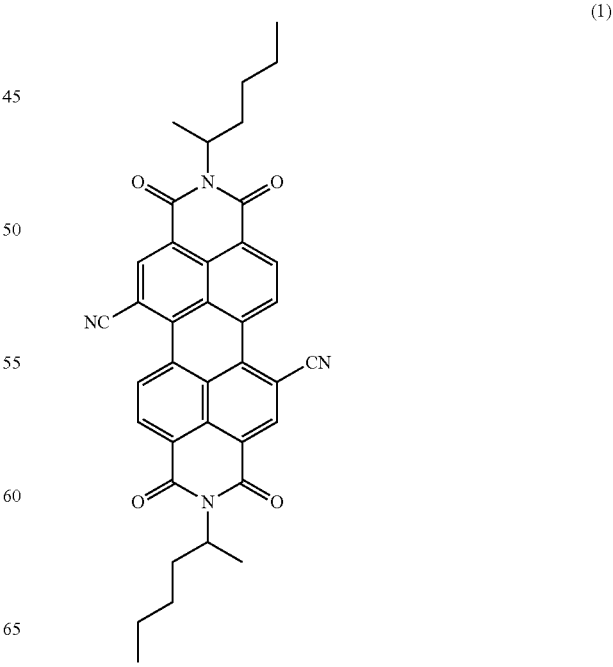

(1)

-continued
(2)
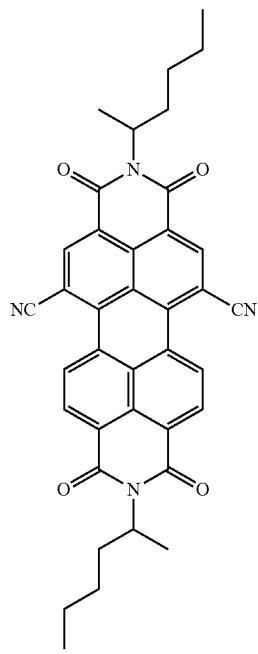
(3)
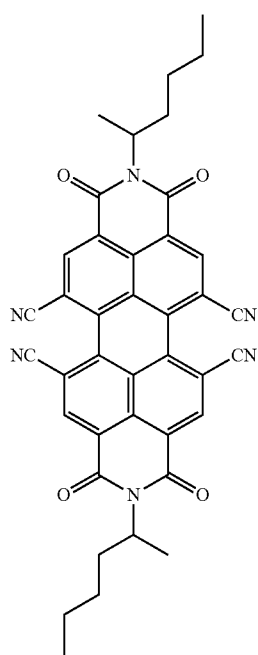
-continued
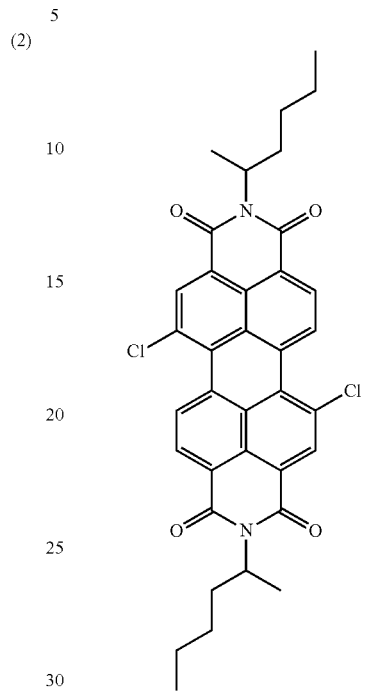
(4)
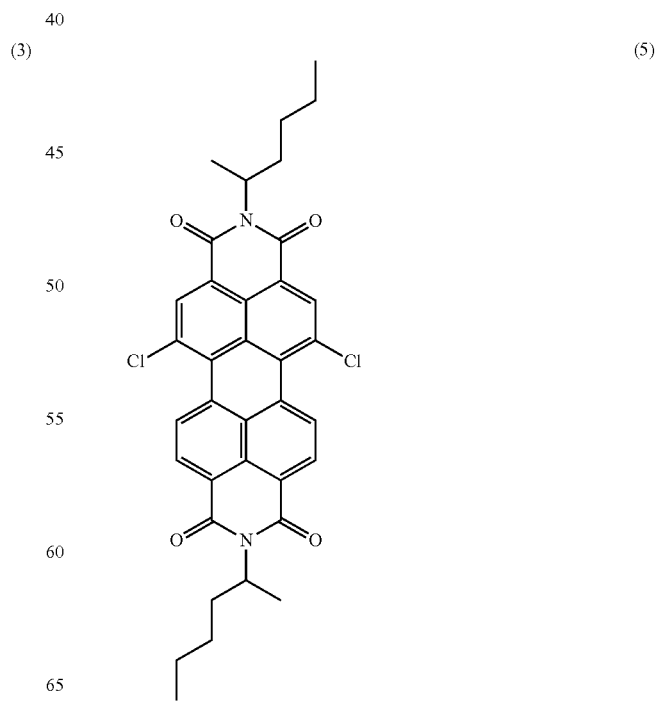
(5)

(6)
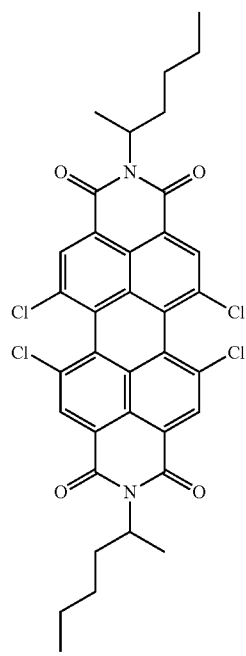
(7)
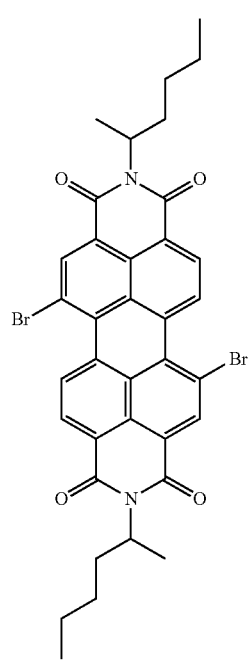
(8)
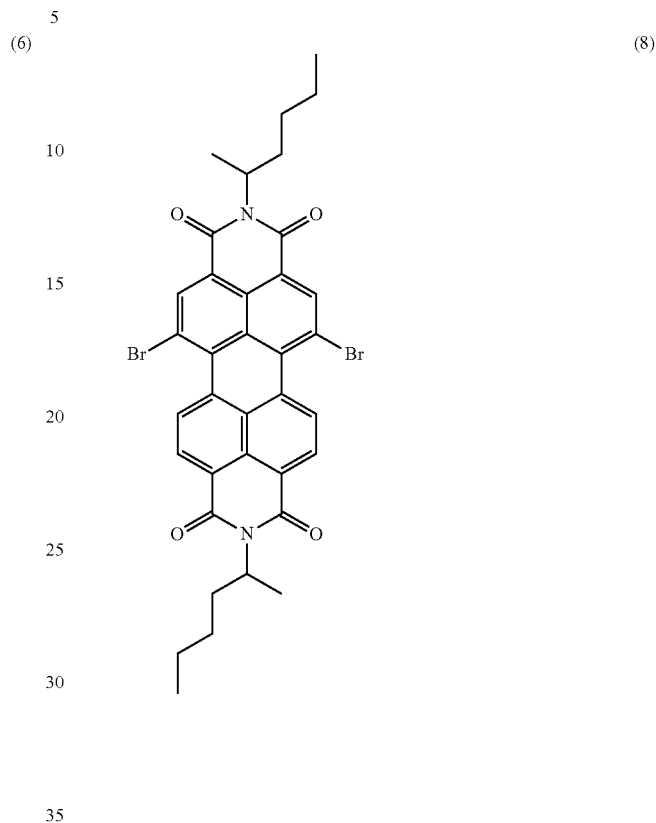
(9)
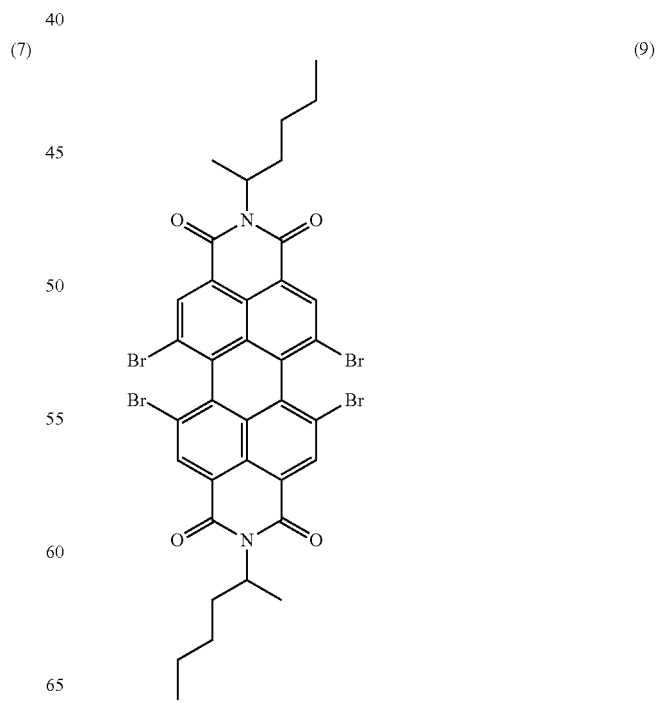

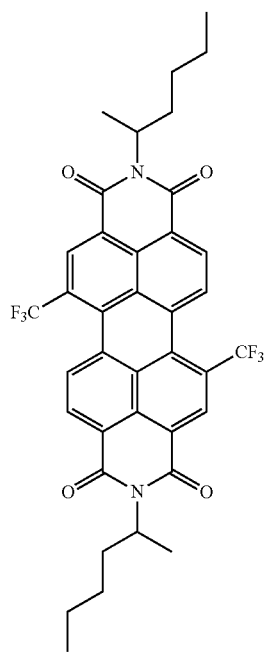
(10)
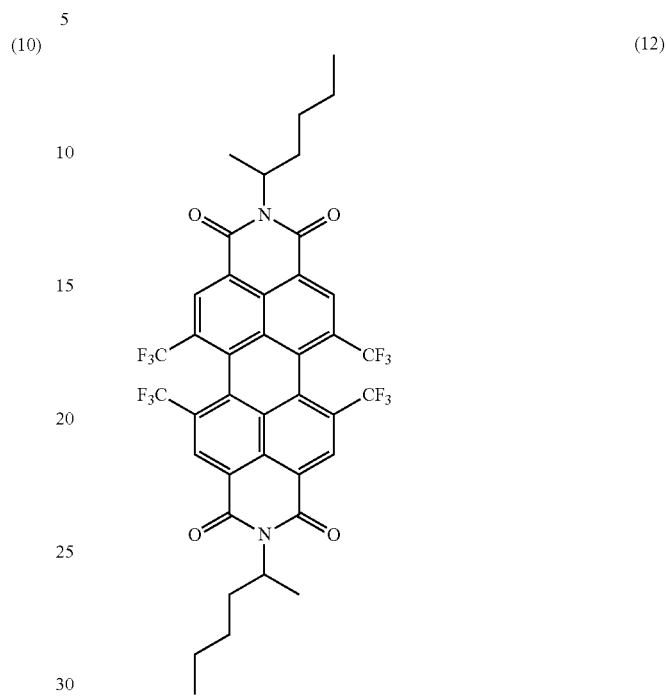
(11)
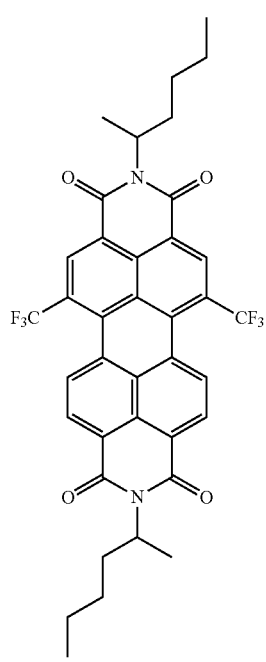
(12)
(13)
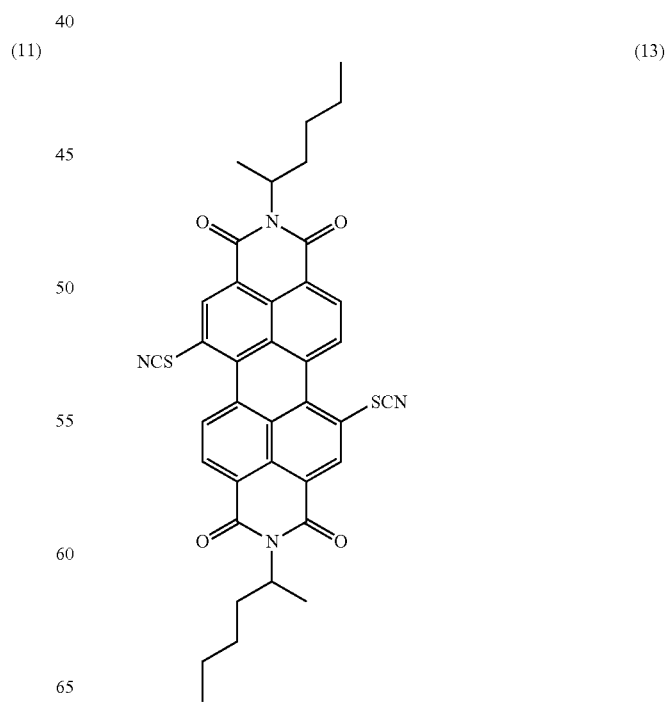

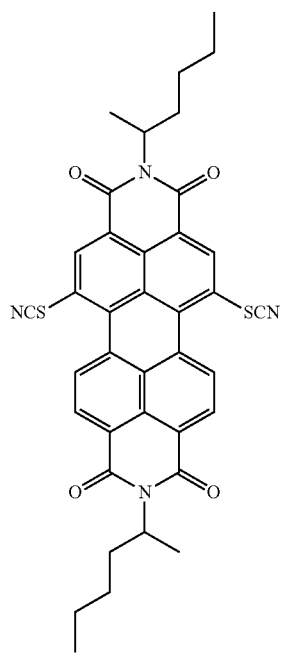
(14)
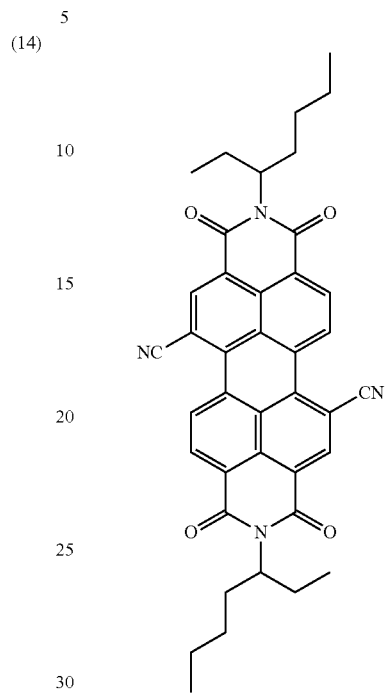
(16)
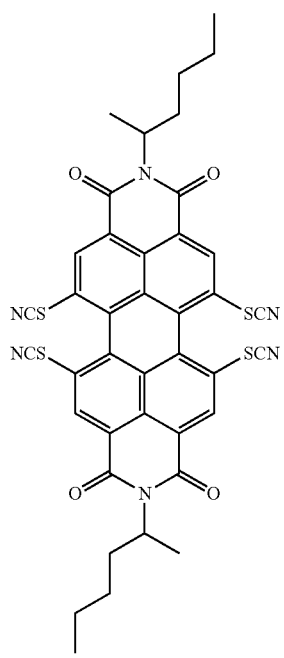
(15)
(17)

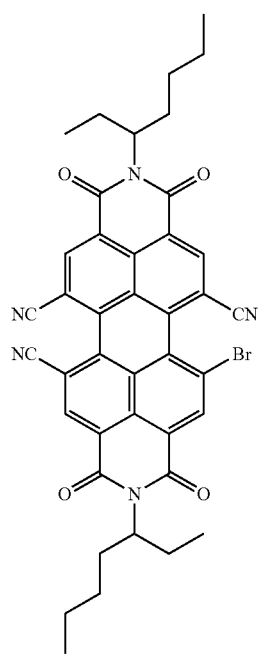
(18)
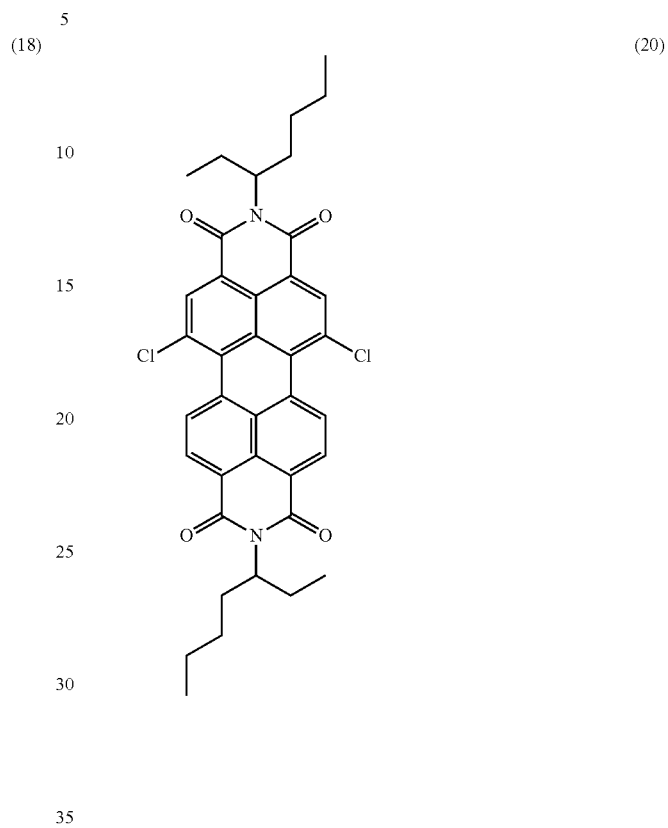
(20)
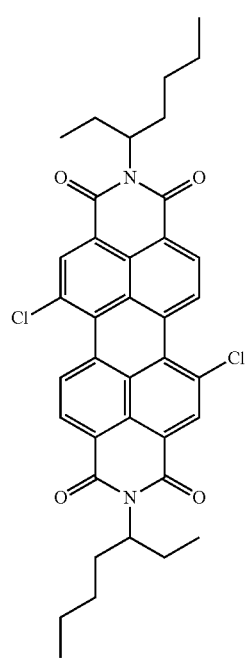
(19)
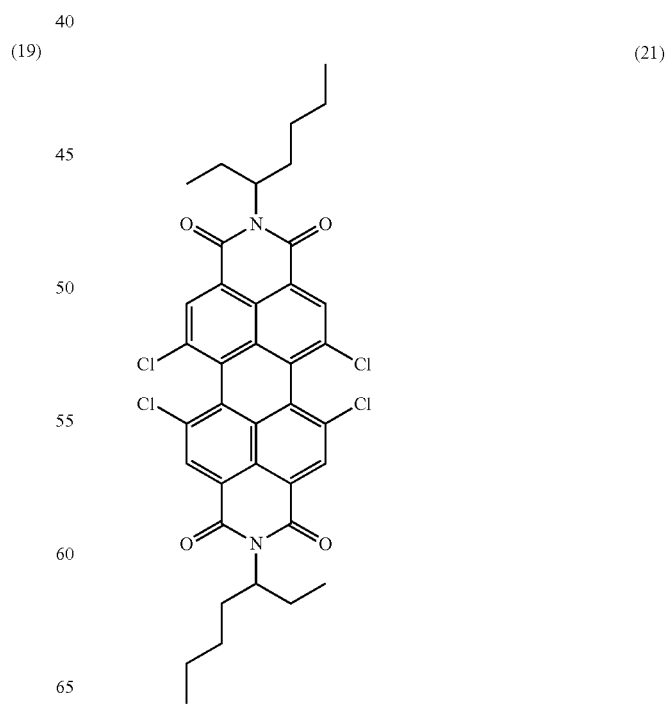
(21)

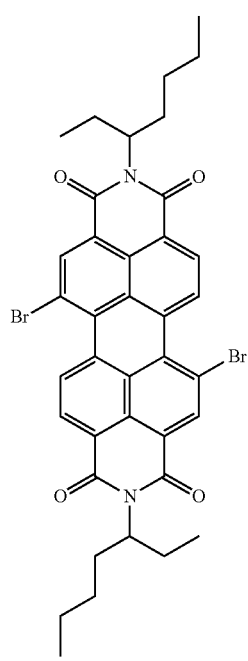
(22)
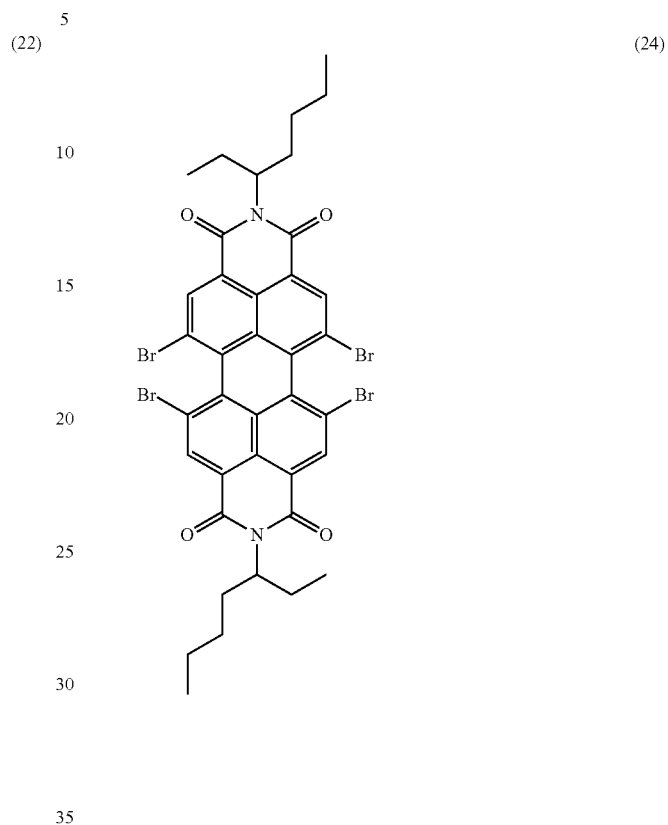
(24)
(23)
(25)
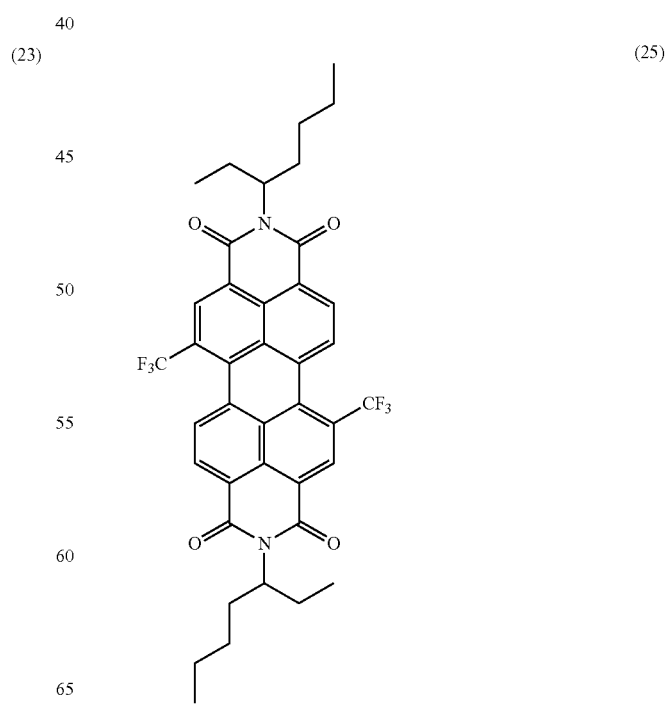

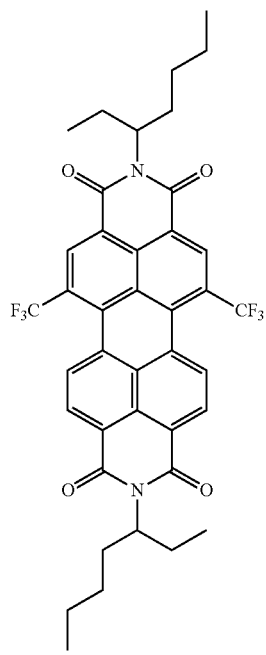
(26)
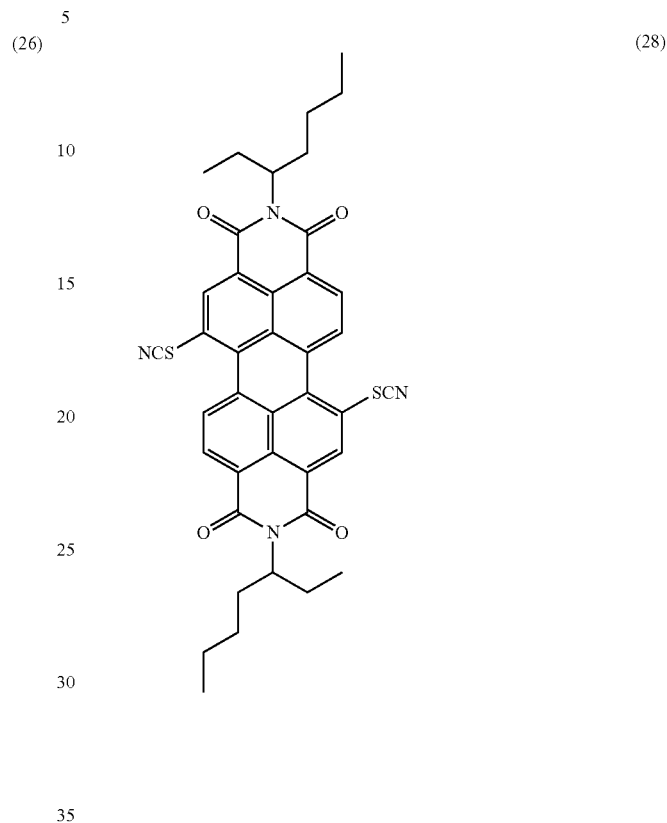
(27)
(28)
(29)
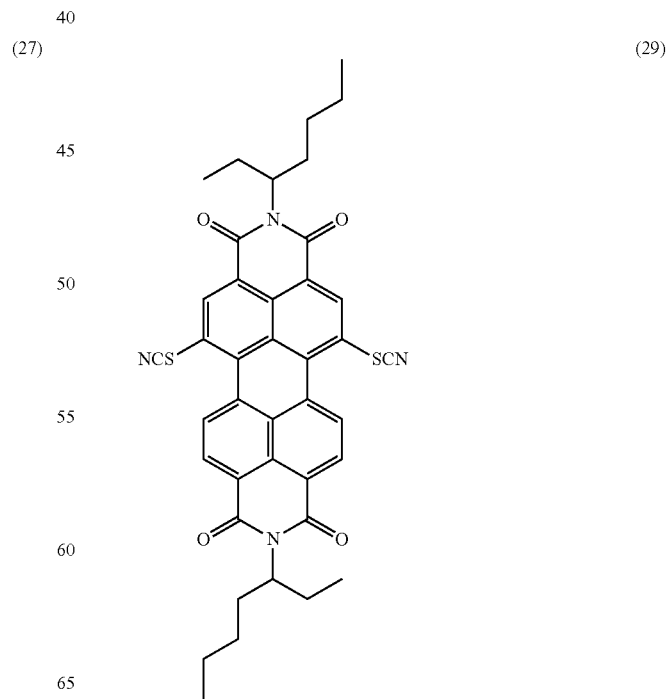

(30)
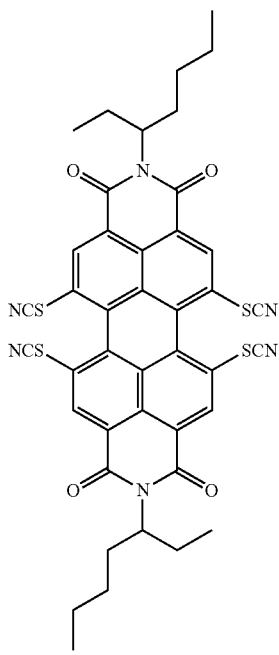
(31)
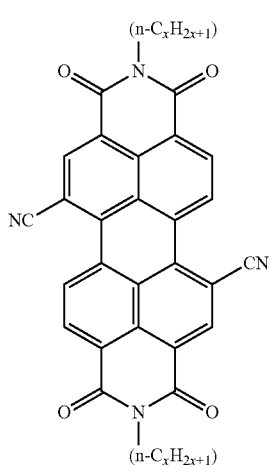
(32)
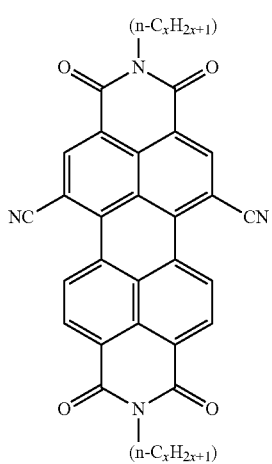
(33)
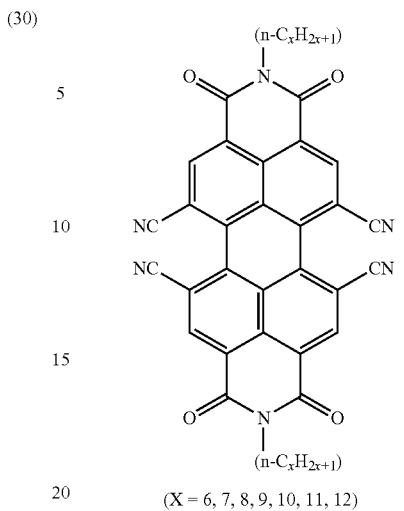
(X = 6, 7, 8, 9, 10, 11, 12)
(34)
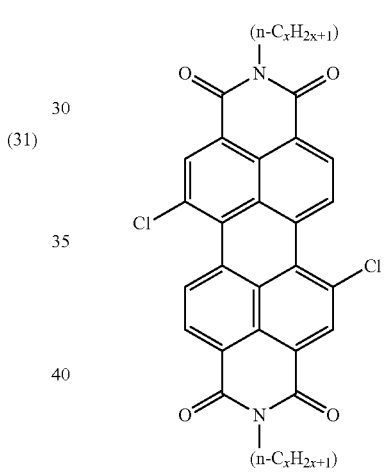
(35)
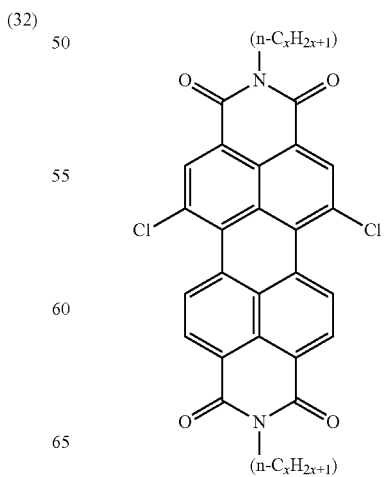

-continued
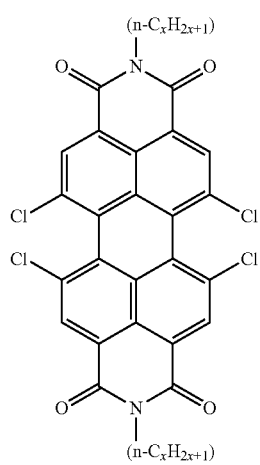
(36)
(X = 6, 7, 8, 9, 10, 11, 12)
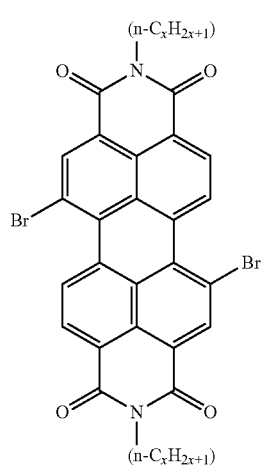
(37)
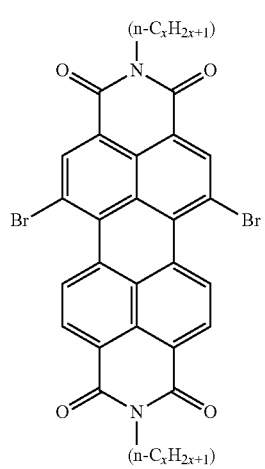
(38)
-continued
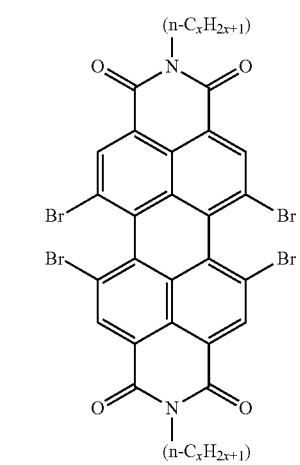
(39)
(X = 6, 7, 8, 9, 10, 11, 12)
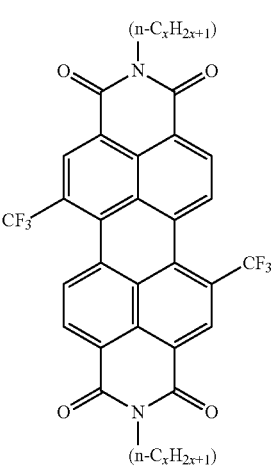
(40)
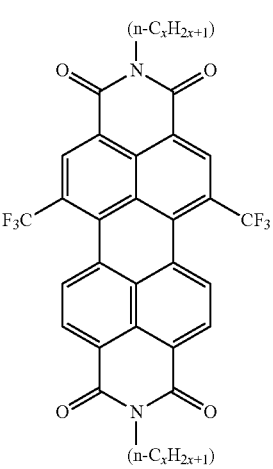
(41)

(42)
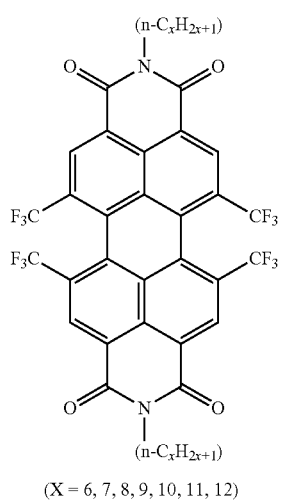
(X = 6, 7, 8, 9, 10, 11, 12)
(43)
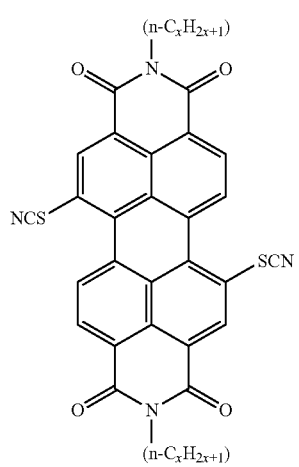
(44)
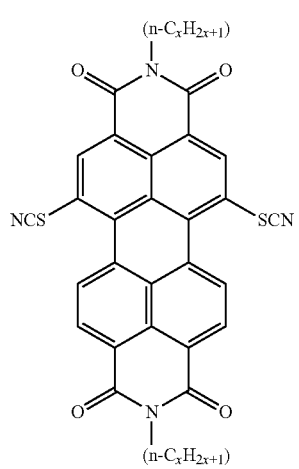
(45)
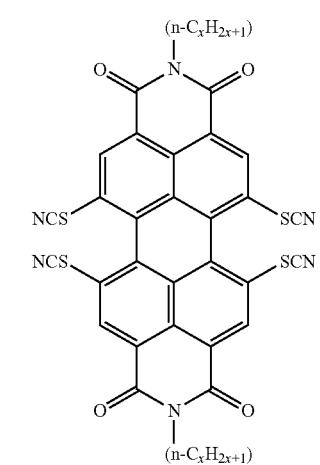
(X = 6, 7, 8, 9, 10, 11, 12)
(46)
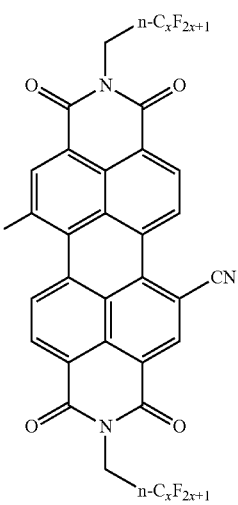
(47)
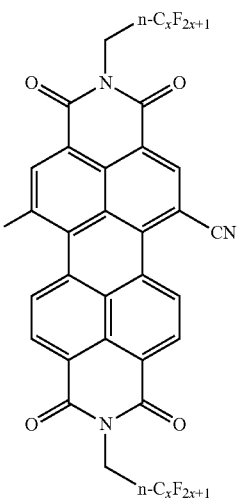

-continued
(48)
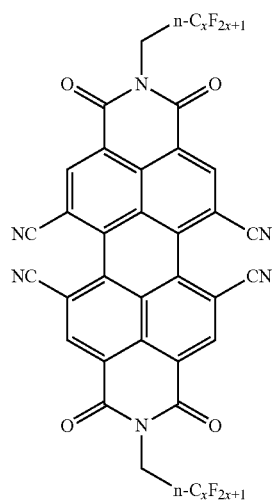
(X = 2, 3, 4)
(49)
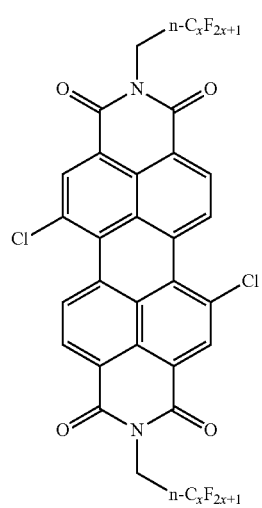
(50)
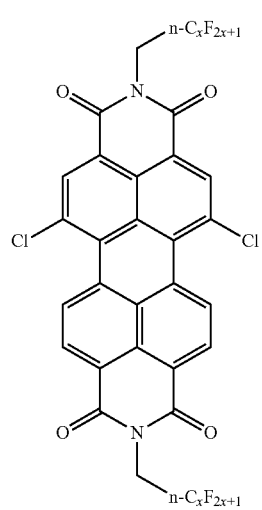
-continued
(51)
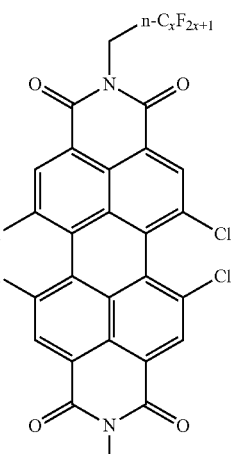
(X = 2, 3, 4)
(52)
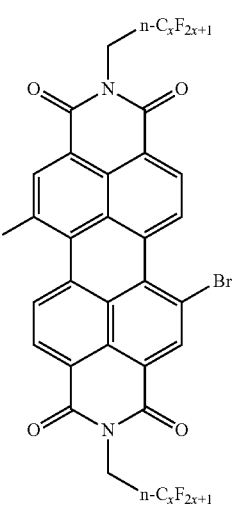
(53)
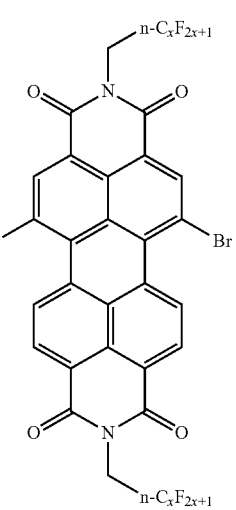

-continued
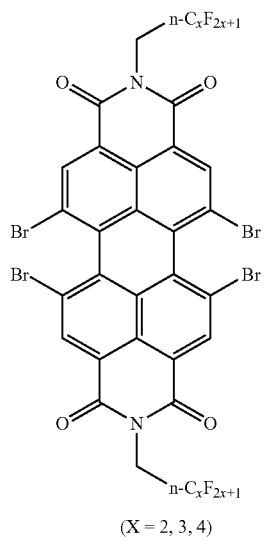
(54)
(X = 2, 3, 4)
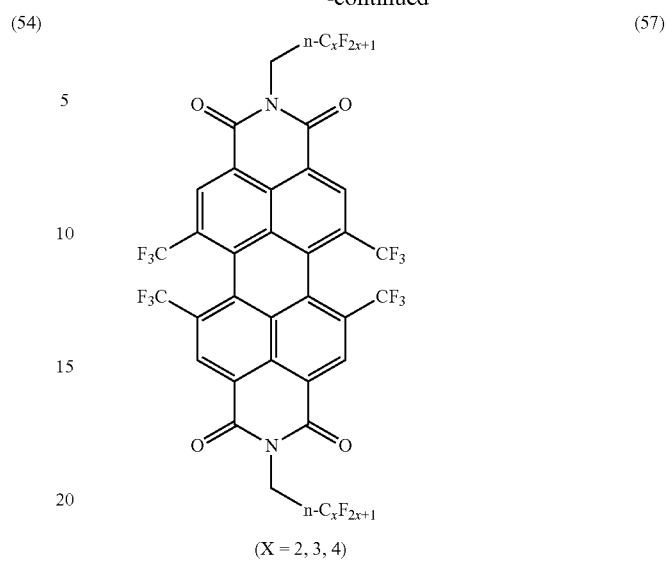
(57)
(X = 2, 3, 4)
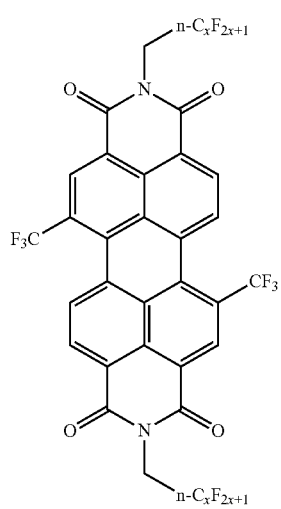
(55)
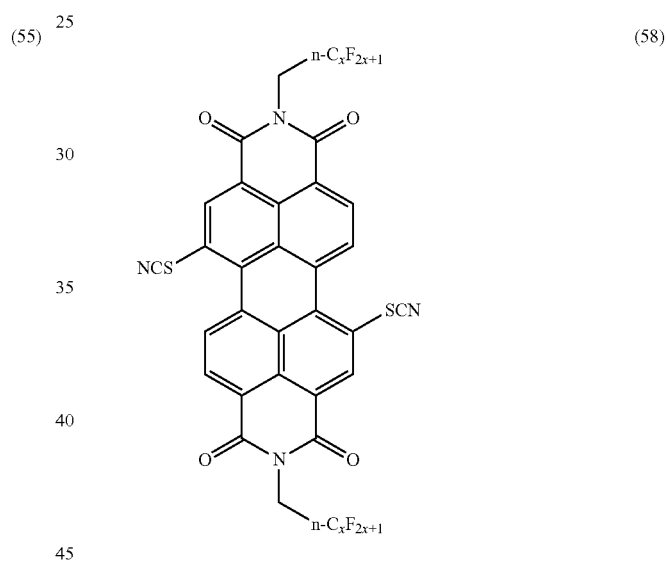
(58)
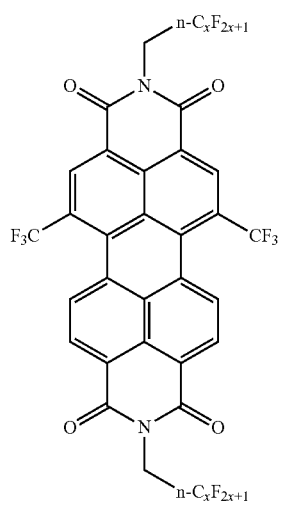
(56)
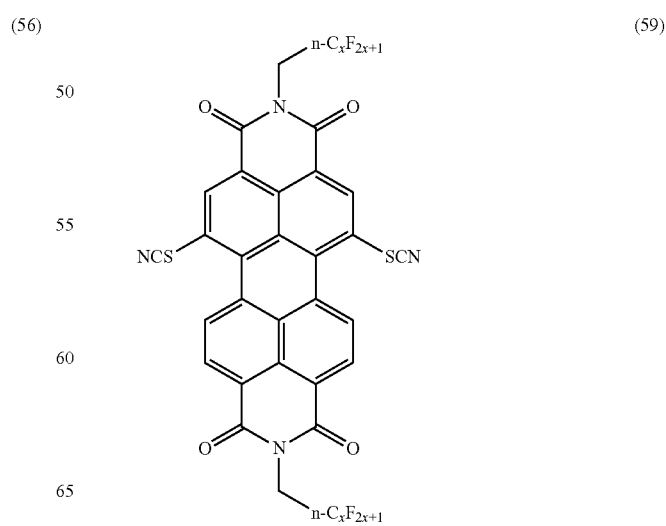
(59)

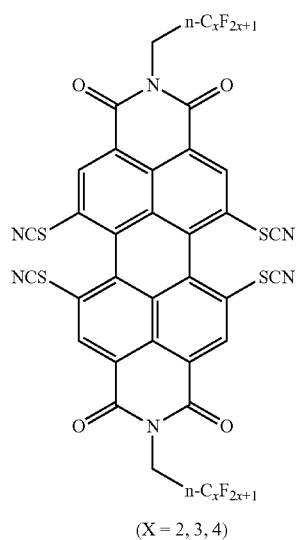
(X = 2, 3, 4)
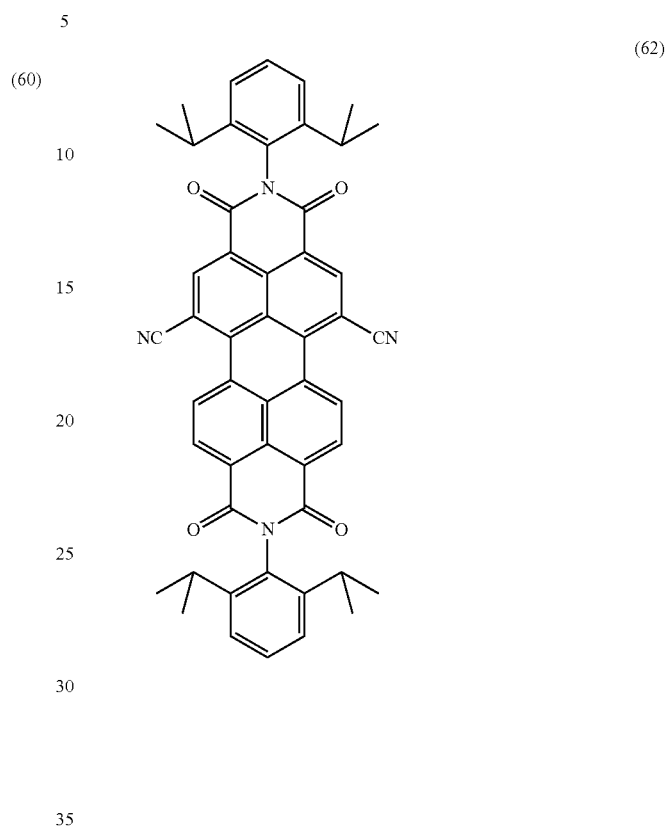
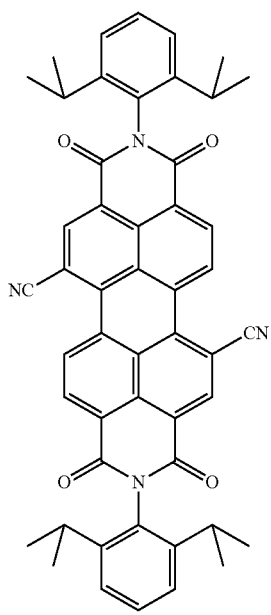
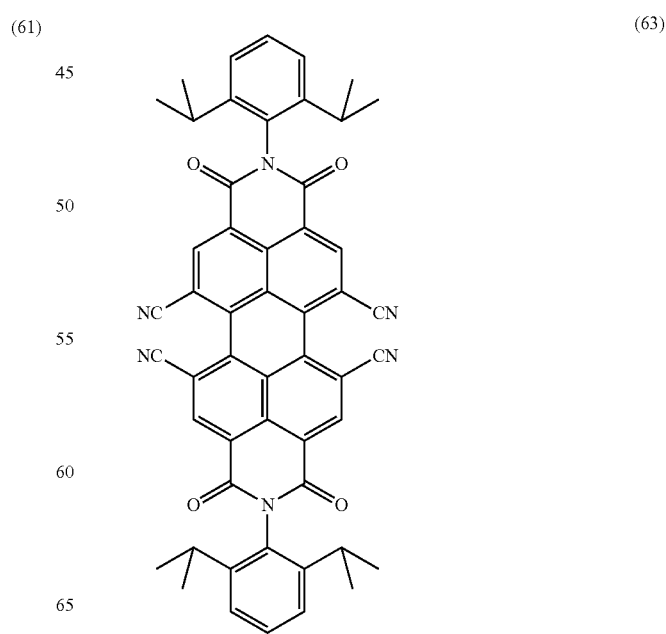

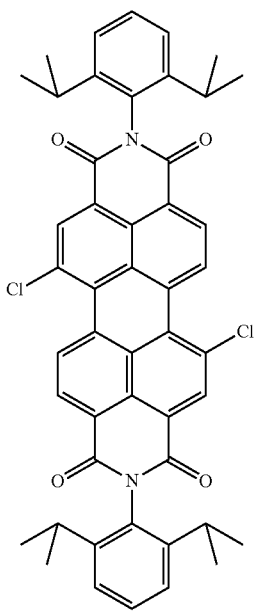
(64)
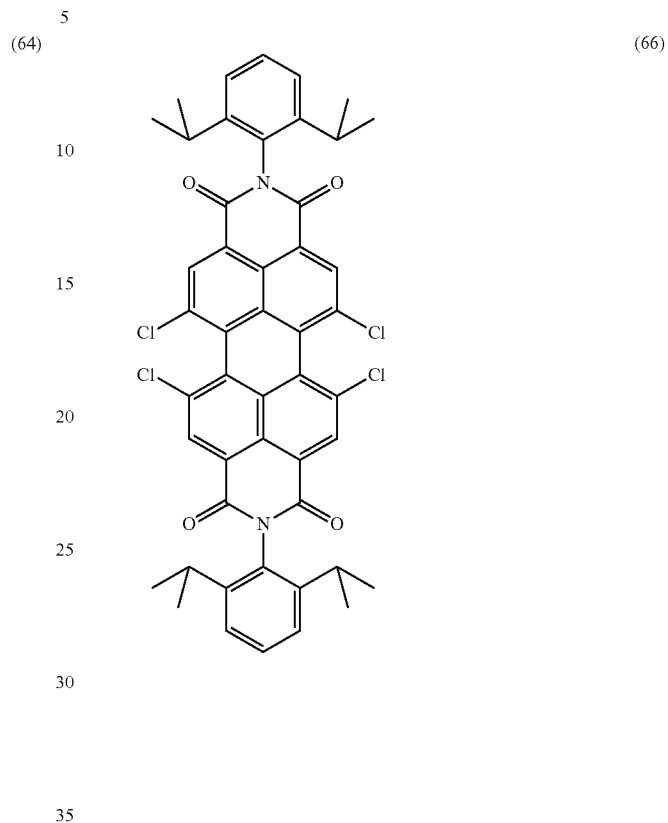
(65)
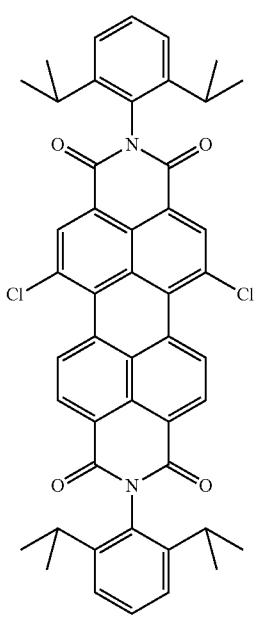
(66)
(67)
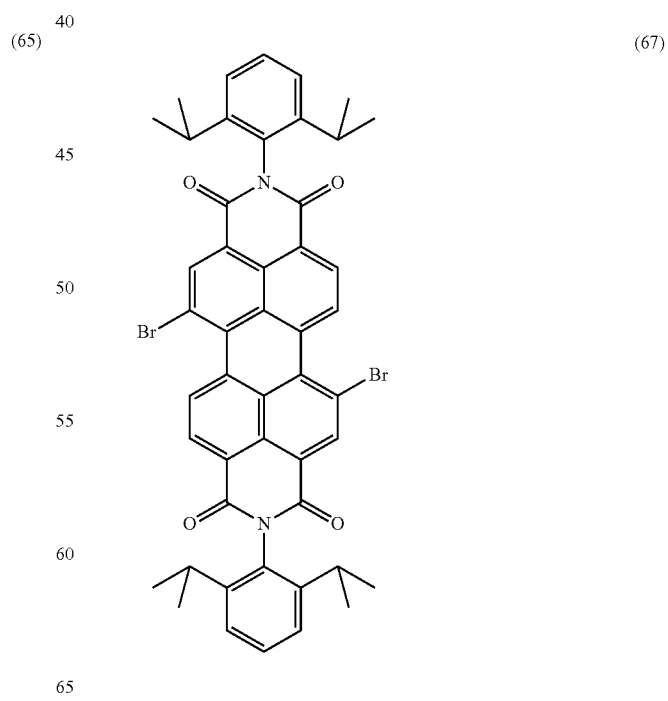

(68)
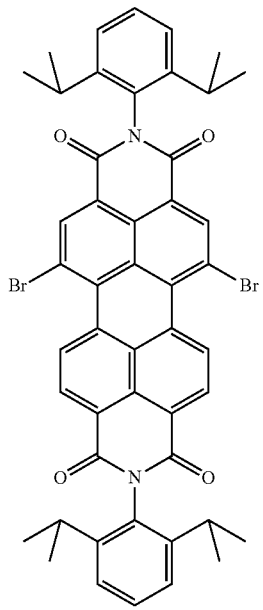
(69)
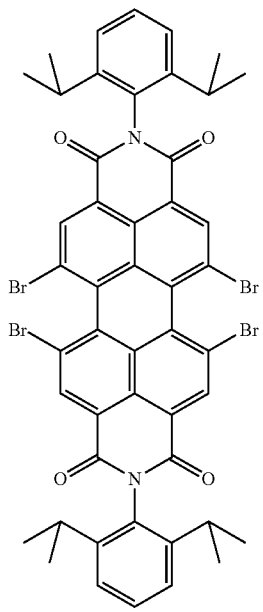
(70)
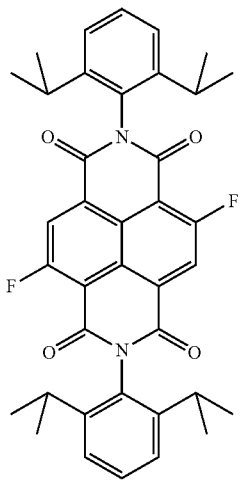
(71)
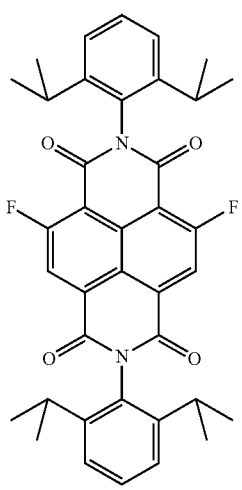
(72)
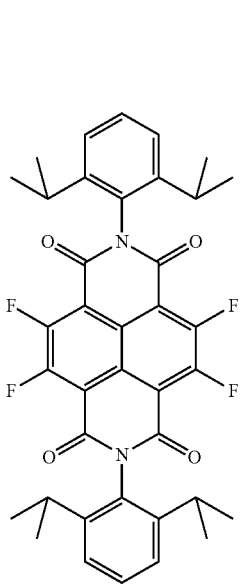

(73)
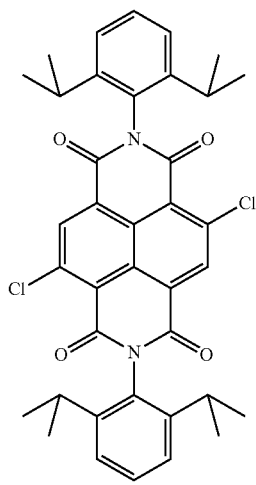
(74)
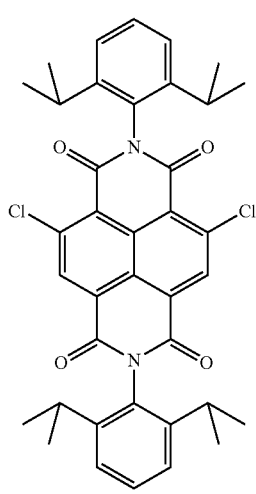
(75)
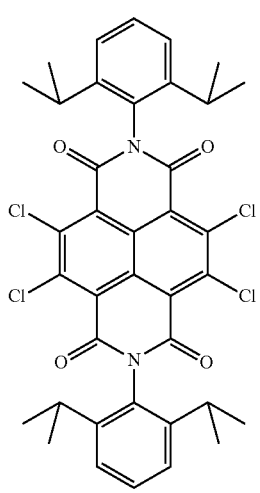
(76)
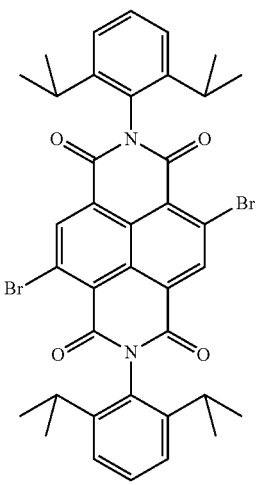
(77)
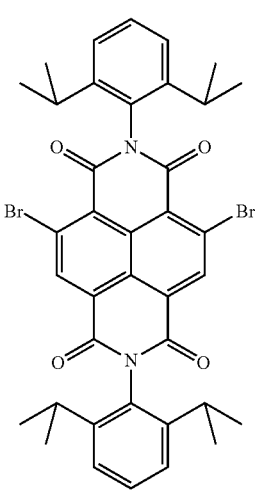
(78)
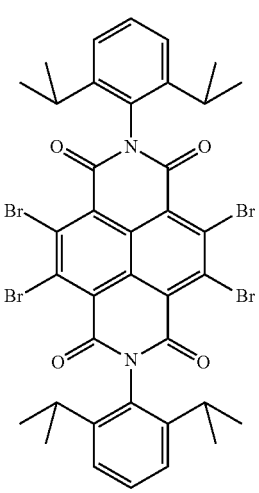

(79)
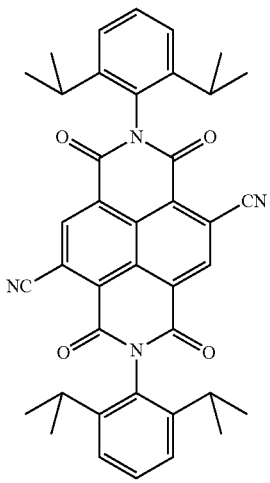
(80)
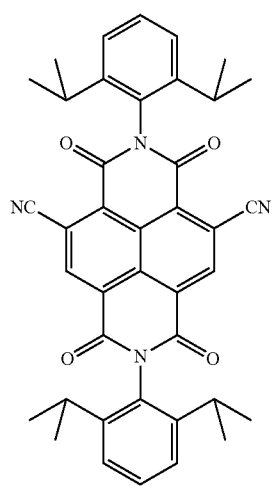
(81)
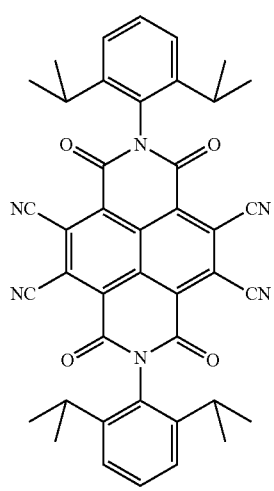
(82)
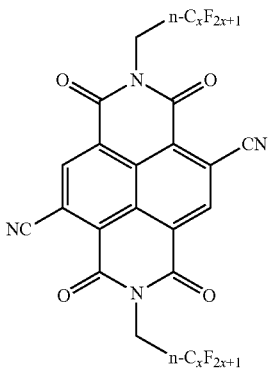
(83)
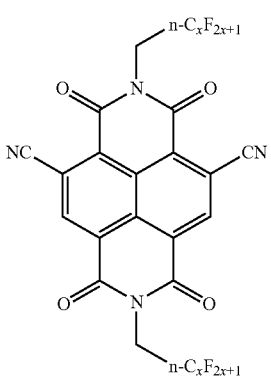
(84)
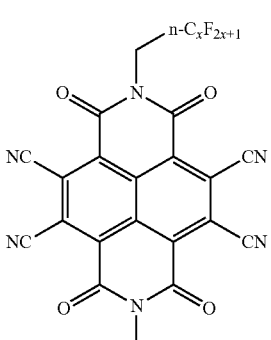
(x = 2, 3, 4)
(85)

-continued
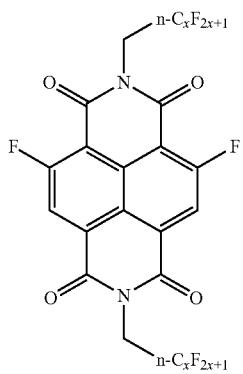
(86)
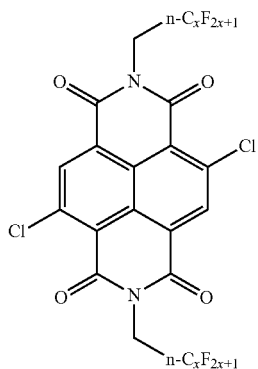
(87)
(x = 2, 3, 4)
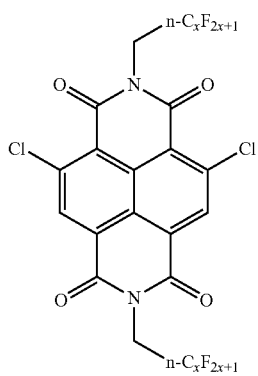
(88)
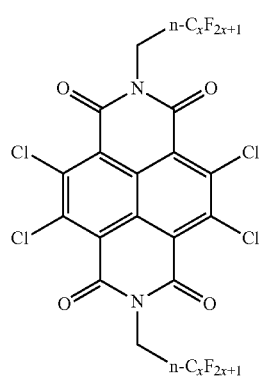
(89)
-continued
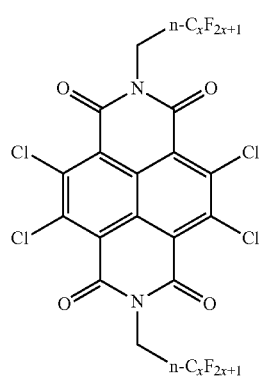
(90)
(x = 2, 3, 4)
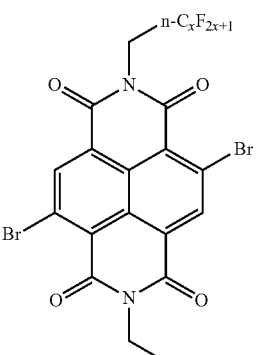
(91)
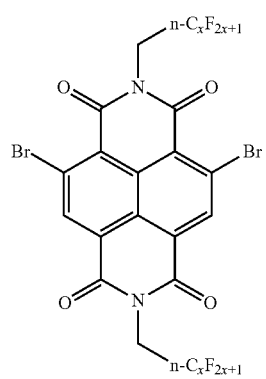
(92)
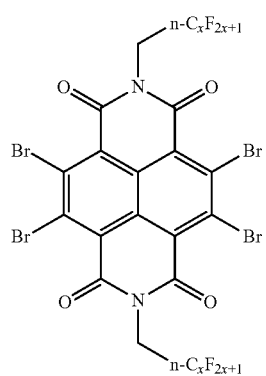
(93)
(x = 2, 3, 4)

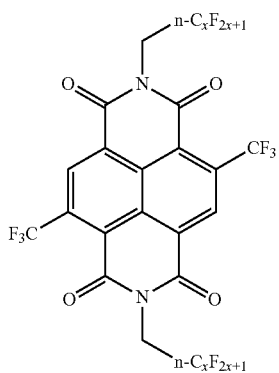
(94)
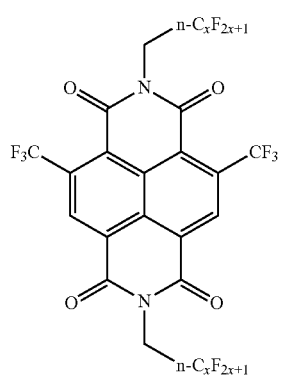
(95)
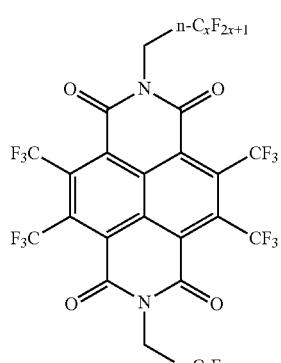
(96)
(x = 2, 3, 4)
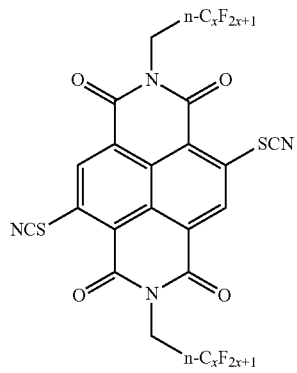
(97)
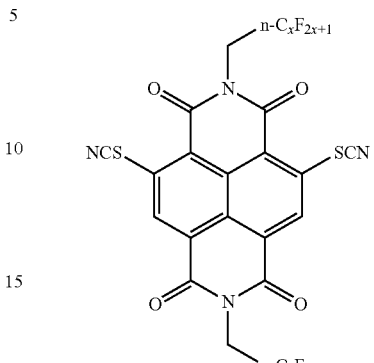
(98)
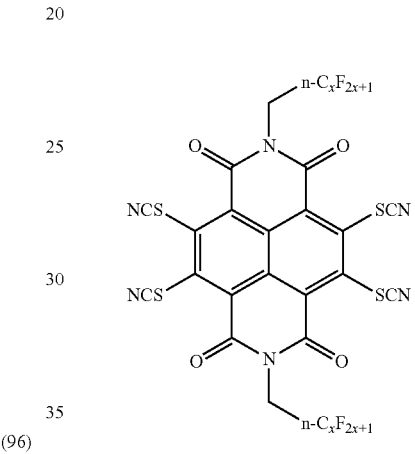
(99)
(x = 2, 3, 4)
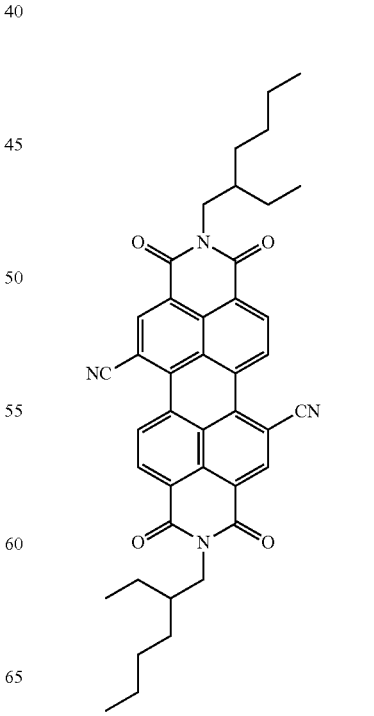
(100)

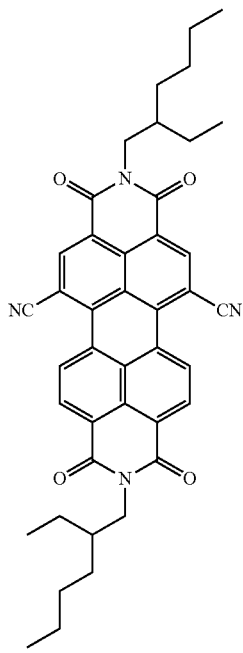
(101)
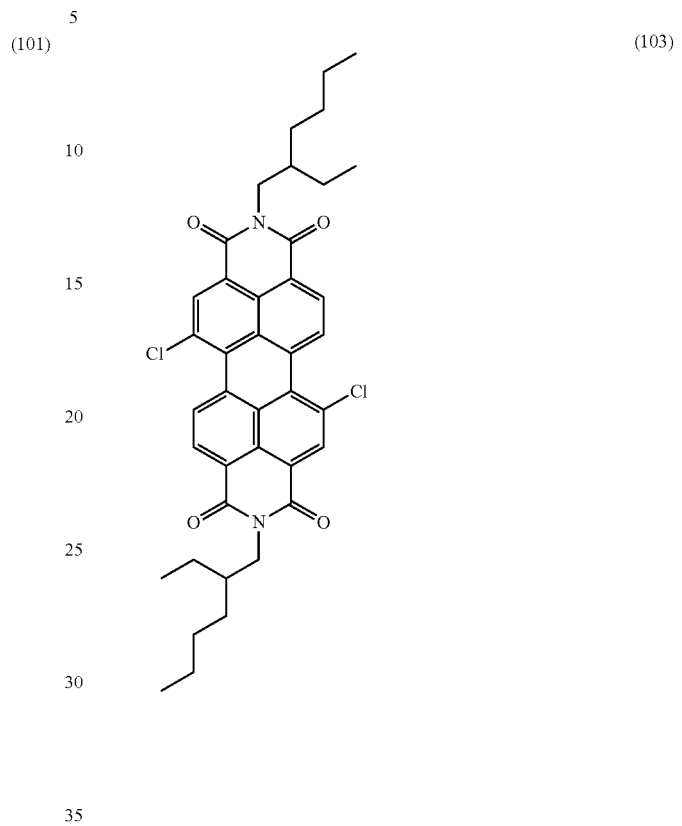
(103)
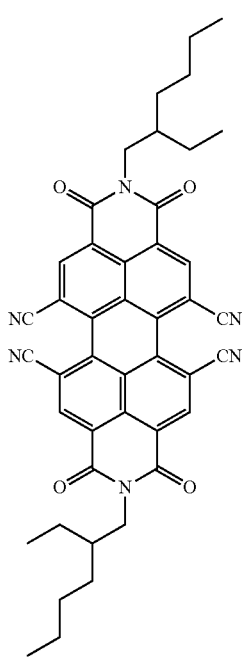
(102)
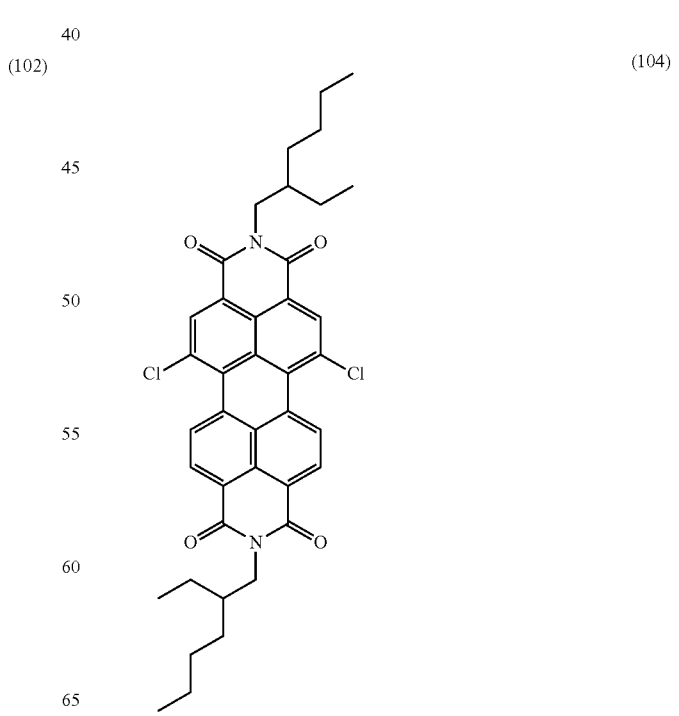
(104)

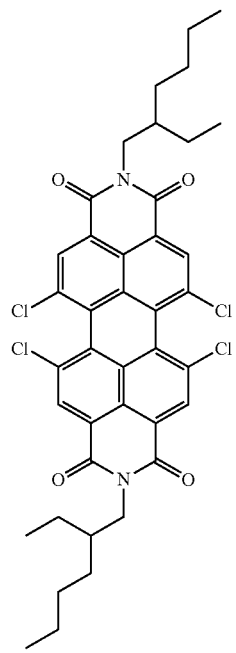
(105)
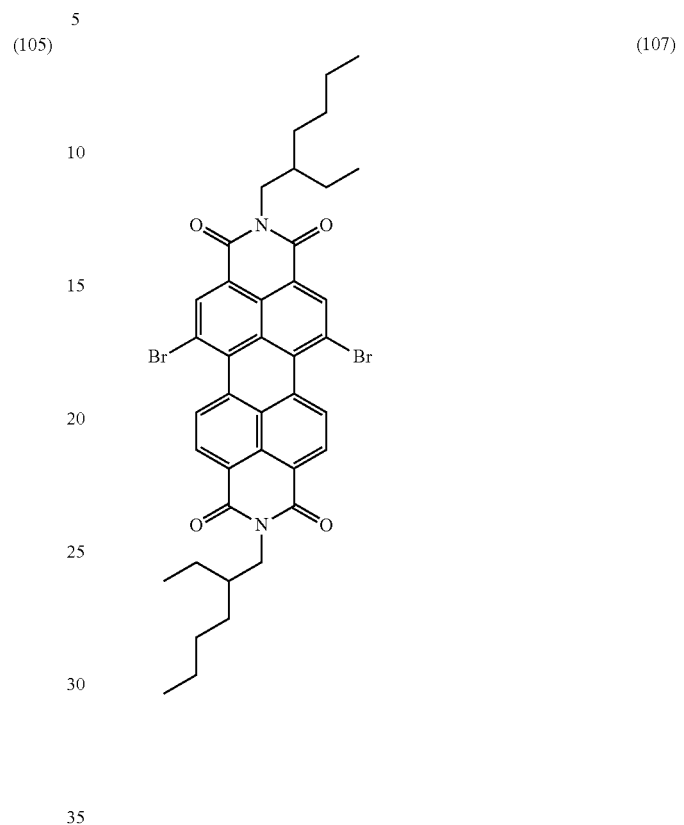
(106)
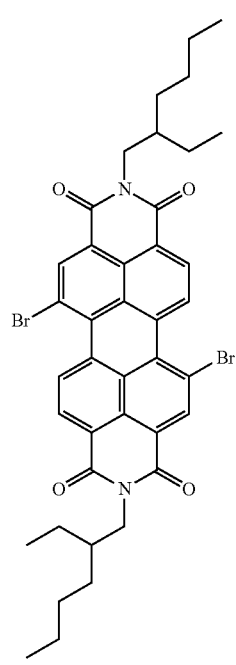
(107)
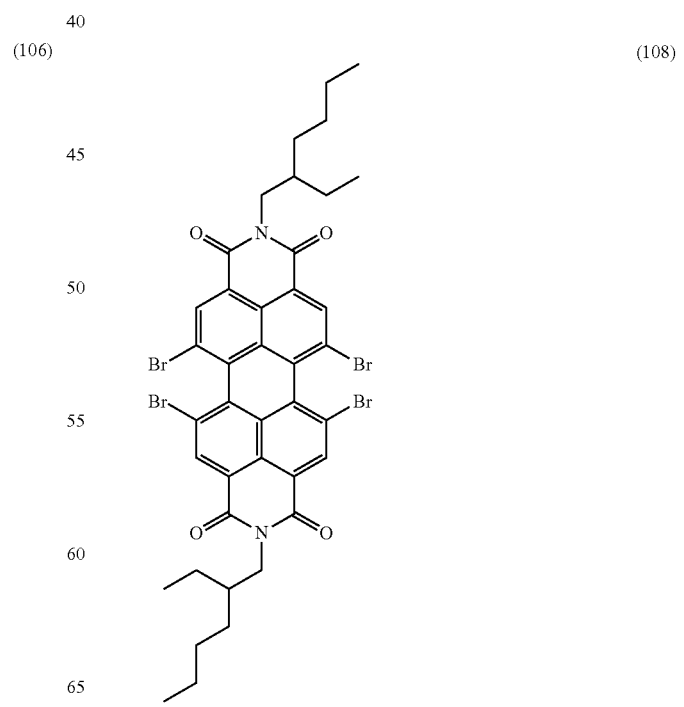
(108)

(109)
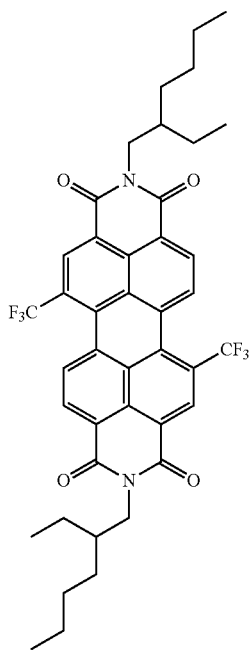
(110)
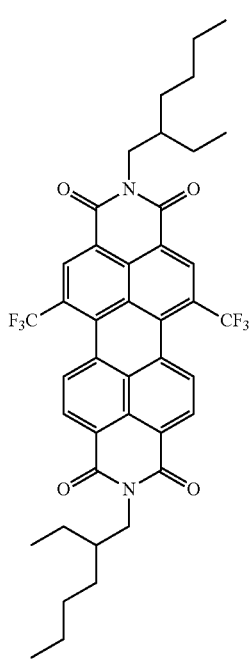
(111)
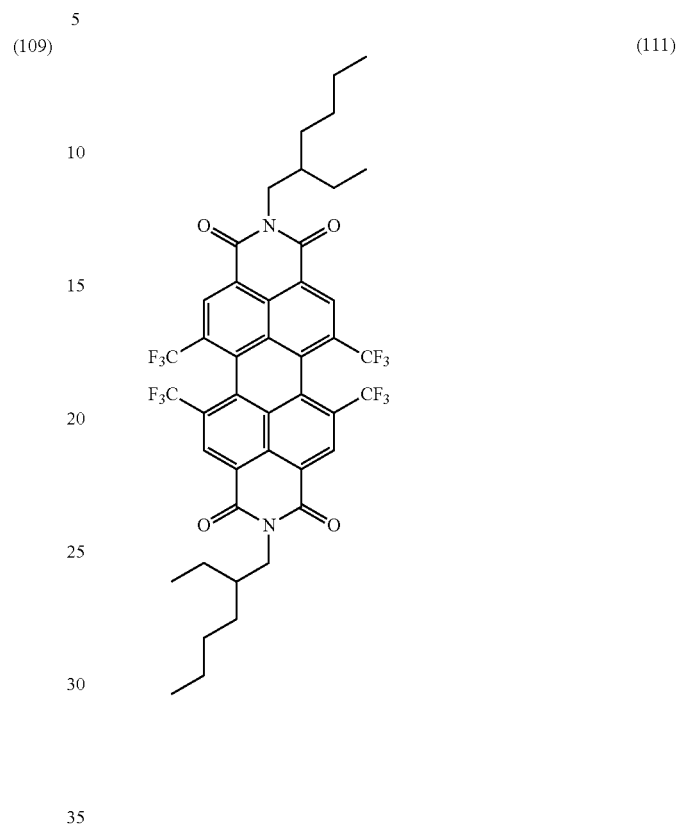
(112)
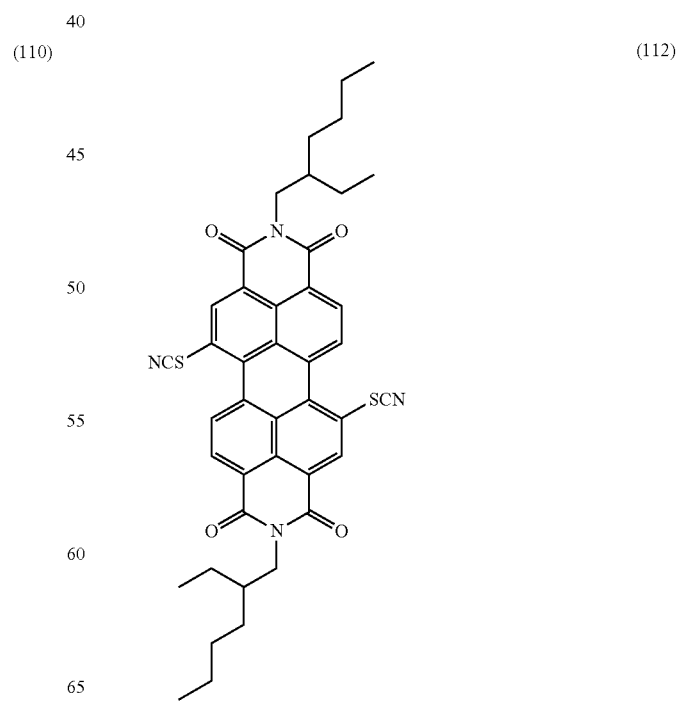

73
-continued
74
-continued
(113)
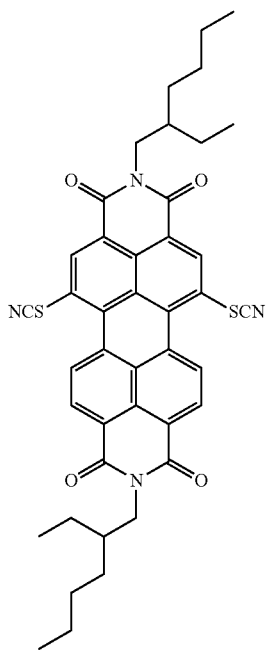
(115)
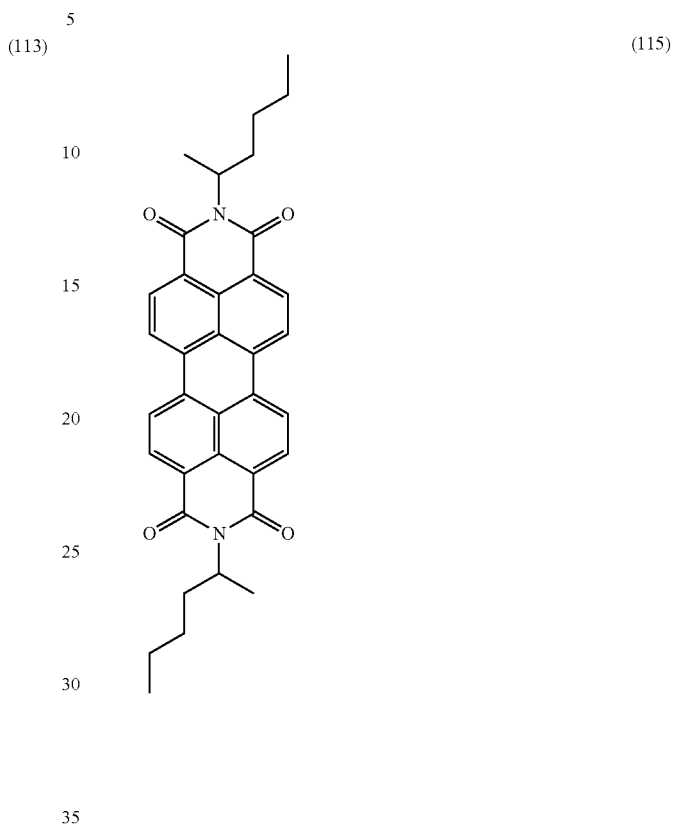
(114)
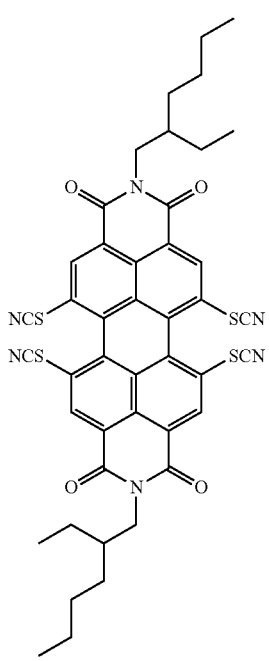
(116)
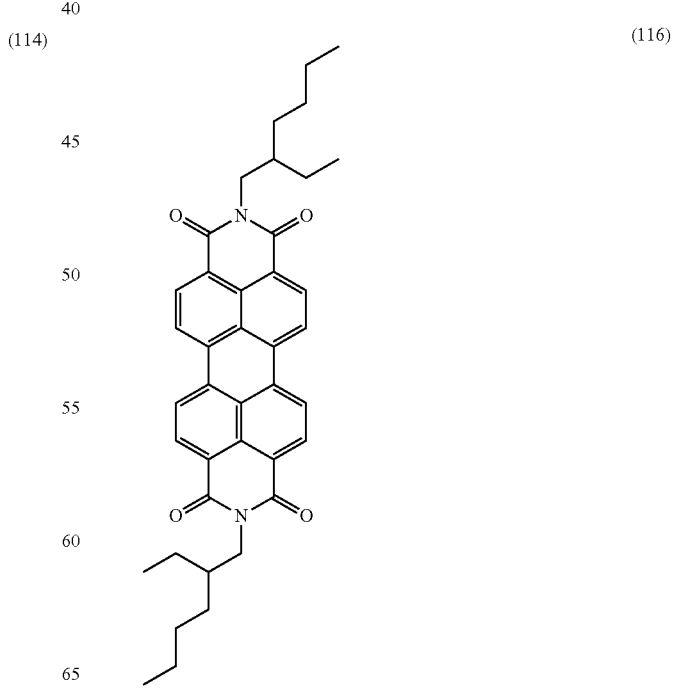

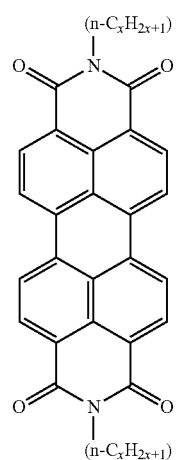
(117)
(x = 6, 7, 8, 9, 10, 11, 12)
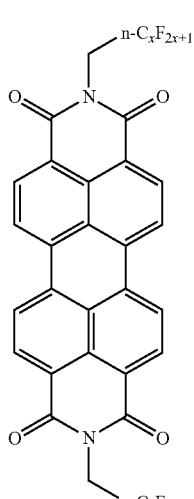
(118)
(X = 2, 3, 4)
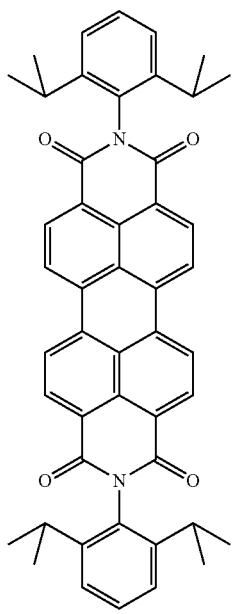
(119)
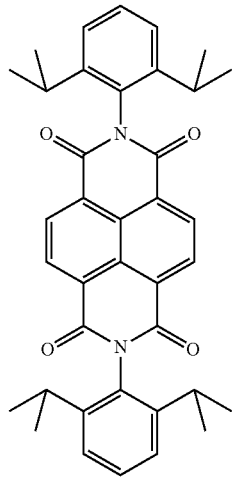
(120)
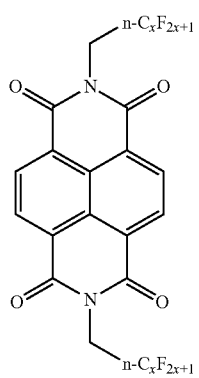
(121)
(X = 2, 3, 4)
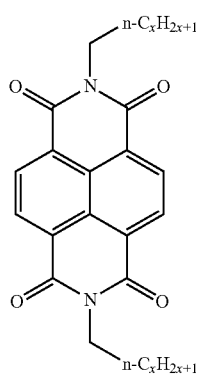
(122)
(X = 2, 3, 4)
In a further preferred embodiment, component A) comprises at least one compound of the formula (II.b)
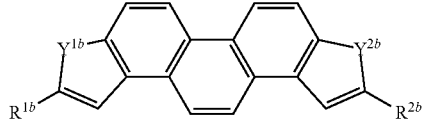
(II.b)

wherein $R^{1b}$ and $R^{2b}$ are independently selected from hydrogen and in each case unsubstituted or substituted linear $C_1$-$C_{30}$-alkyl, branched $C_3$-$C_{30}$-alkyl, linear $C_2$-$C_{30}$-alkenyl, branched $C_3$-$C_{30}$-alkenyl, linear $C_2$-$C_{30}$-alkinyl, branched $C_4$-$C_{30}$-alkinyl, cycloalkyl, aryl and hetaryl, $Y^{1b}$ and $Y^{2b}$ are independently selected from O, S, Se and $NR^{3b}$, where $R^{3b}$ is selected from hydrogen and in each case unsubstituted or substituted alkyl, cycloalkyl and aryl, Suitable compounds of the formula (II.b) and methods for their preparation are described in WO 2013/168048 which is incorporated herein by reference.

Preferably, $R^{1b}$ and $R^{2b}$ are independently selected from hydrogen, unsubstituted linear $C_1$-$C_{30}$-alkyl, unsubstituted branched $C_3$-$C_{30}$-alkyl, halogen substituted linear $C_1$-$C_{30}$-alkyl and halogen substituted branched $C_3$-$C_{30}$-alkyl.

Preferably, $R^{1b}$ and $R^{2b}$ are independently selected from hydrogen, unsubstituted linear $C_1$-$C_{30}$-alkyl, unsubstituted branched $C_3$-$C_{30}$-alkyl, linear $C_1$-$C_{30}$-fluoroalkyl and branched $C_3$-$C_{30}$-fluoroalkyl. In particular, $R^{1b}$ and $R^{2b}$ are independently selected from hydrogen, unsubstituted linear $C_1$-$C_{30}$-alkyl and unsubstituted branched $C_3$-$C_{30}$-alkyl. Preferably, in the compounds of the formula (II.b) $R^{1b}$ and $R^{2b}$ have the same meaning.

In a preferred embodiment, the compounds of the formula (II.b) are selected from compound of the formula (I.b1)

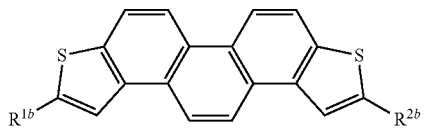

(II.b1)

wherein $R^{1b}$ and $R^{2b}$ are independently selected from linear $C_7$-$C_{22}$-alkyl and branched $C_7$-$C_{22}$-alkyl.

Preferably, in the compounds of the formula (II.b1) $R^{1b}$ and $R^{2b}$ have the same meaning.

In a special embodiment, $R^{1b}$ and $R^{2b}$ have the same meaning and are selected from linear $C_7$-$C_{22}$-alkyl.

In a further preferred embodiment, component A) comprises at least one compound of the formula (II.c)

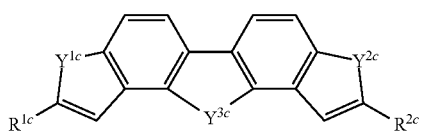

(II.c)

wherein $R^{1c}$ and $R^{2c}$ are independently selected from hydrogen and in each case unsubstituted or substituted linear $C_1$-$C_{30}$-alkyl, branched $C_3$-$C_{30}$-alkyl, linear $C_2$-$C_{30}$-alkenyl, branched $C_3$-$C_{30}$-alkenyl, linear $C_2$-$C_{30}$-alkinyl, branched $C_4$-$C_{30}$-alkinyl, cycloalkyl, aryl and hetaryl, $Y^{1c}$, $Y^{2c}$ and $Y^{3c}$ are independently selected from O, S, Se and $NR^{3c}$, where $R^{3c}$ is selected from hydrogen and in each case unsubstituted or substituted alkyl, cycloalkyl and aryl, Suitable compounds of the formula (II.c) and methods for their preparation are described in PCT/IB2015/051226 which is incorporated herein by reference.

Preferably, $Y^{1c}$, $Y^{2c}$ and $Y^{3c}$ are all S.

Preferably, $R^{1c}$ and $R^{2c}$ are independently selected from hydrogen, unsubstituted linear $C_1$-$C_{30}$-alkyl, unsubstituted branched $C_3$-$C_{30}$-alkyl, halogen substituted linear $C_1$-$C_{30}$-alkyl and halogen substituted branched $C_3$-$C_{30}$-alkyl.

Preferably, $R^{1c}$ and $R^{2c}$ are independently selected from hydrogen, unsubstituted linear $C_1$-$C_{30}$-alkyl, unsubstituted branched $C_3$-$C_{30}$-alkyl, linear $C_1$-$C_{30}$-fluoroalkyl and branched $C_3$-$C_{30}$-fluoroalkyl. In particular, $R^{1c}$ and $R^{2c}$ are independently selected from hydrogen, unsubstituted linear $C_1$-$C_{30}$-alkyl and unsubstituted branched $C_3$-$C_{30}$-alkyl.

In one special embodiment of the compounds of the formula (II.c) $R^{1c}$ is hydrogen and $R^{2c}$ is selected from linear $C_1$-$C_{30}$-alkyl and branched $C_3$-$C_{30}$-alkyl.

In a further special embodiment of the compounds of the formula (II.c) $R^{1c}$ and $R^{2c}$ are both selected from linear $C_1$-$C_{30}$-alkyl and branched $C_3$-$C_{30}$-alkyl.

In a preferred embodiment, the compounds of the formula (II.c) are selected from compound of the formula (II.c1) and (II.c2)

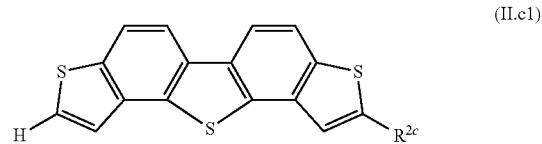

(II.c1)

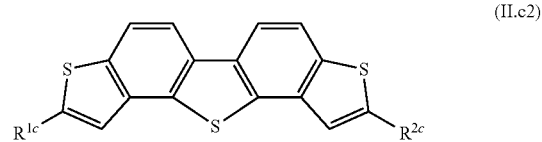

(II.c2)

wherein $R^{1c}$ and $R^{2c}$ are independently selected from linear $C_7$-$C_{22}$-alkyl and branched $C_7$-$C_{22}$-alkyl.

Preferably, in the compounds of the formula (II.c1) $R^{2c}$ is selected from linear $C_7$-$C_{22}$-alkyl.

Preferably, in the compounds of the formula (II.c2) $R^{1c}$ and $R^{2c}$ have the same meaning.

In a special embodiment, $R^{1c}$ and $R^{2c}$ have the same meaning and are selected from linear $C_7$-$C_{22}$-alkyl.

In a further preferred embodiment, component A) comprises at least one compound of the formula (II.d)

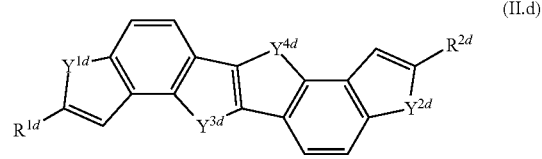

(II.d)

wherein $R^{1d}$ and $R^{2d}$ are independently selected from hydrogen and in each case unsubstituted or substituted linear $C_1$-$C_{30}$-alkyl, branched $C_3$-$C_{30}$-alkyl, linear $C_2$-$C_{30}$-alkenyl, branched $C_3$-$C_{30}$-alkenyl, linear $C_2$-$C_{30}$-alkinyl, branched $C_4$-$C_{30}$-alkinyl, cycloalkyl, aryl and hetaryl, $Y^{1d}$, $Y^{2d}$, $Y^{3d}$ and $Y^{4d}$ are independently selected from O, S, Se and $NR^{3d}$, where $R^{3d}$ is selected from hydrogen and in each case unsubstituted or substituted alkyl, cycloalkyl and aryl.

Suitable compounds of the formula (II.d) and methods for their preparation are described in WO/2014/087300 which is incorporated herein by reference.

Preferably, $Y^{1d}$, $Y^{2d}$, $Y^{3d}$ and $Y^{4d}$ are all S.

Preferably, $R^{1d}$ and $R^{2d}$ are independently selected from hydrogen, unsubstituted linear $C_1$-$C_{30}$-alkyl, unsubstituted branched $C_3$-$C_{30}$-alkyl, halogen substituted linear $C_1$-$C_{30}$-alkyl and halogen substituted branched $C_3$-$C_{30}$-alkyl.

Preferably, $R^{1d}$ and $R^{2d}$ are independently selected from hydrogen, unsubstituted linear $C_1$-$C_{30}$-alkyl, unsubstituted branched $C_3$-$C_{30}$-alkyl, linear $C_1$-$C_{30}$-fluoroalkyl and branched $C_3$-$C_{30}$-fluoroalkyl. In particular, $R^{1d}$ and $R^{2d}$ are independently selected from hydrogen, unsubstituted linear $C_1$-$C_{30}$-alkyl and unsubstituted branched $C_3$-$C_{30}$-alkyl.

In one special embodiment of the compounds of the formula (II.d) $R^{1d}$ is hydrogen and $R^{2d}$ is selected from linear $C_1$-$C_{30}$-alkyl and branched $C_3$-$C_{30}$-alkyl.

In a further special embodiment of the compounds of the formula (II.d) $R^{1d}$ and $R^{2d}$ are both selected from linear $C_1$-$C_{30}$-alkyl and branched $C_3$-$C_{30}$-alkyl.

In a preferred embodiment, the compounds of the formula (II.d) are selected from compound of the formula (II.d1) and (II.d2)

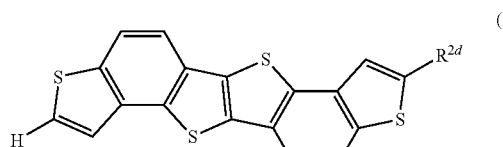
(I.d1)

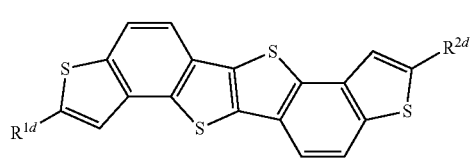
(I.d2)

wherein
$R^{1d}$ and $R^{2d}$ are independently selected from linear $C_7$-$C_{22}$-alkyl and branched $C_7$-$C_{22}$-alkyl.

Preferably, in the compounds of the formula (II.d1) $R^{2d}$ selected from linear $C_7$-$C_{22}$-alkyl.

Preferably, in the compounds of the formula (II.d2) $R^{1d}$ and $R^{2d}$ have the same meaning.

In a special embodiment, $R^{1d}$ and $R^{2d}$ have the same meaning and are selected from linear $C_7$-$C_{22}$-alkyl.

In a further preferred embodiment, component A) comprises at least one compound of the formula (II.e)

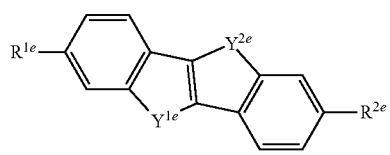
(II.e)

wherein
$R^{1e}$ and $R^{2e}$ are independently selected from hydrogen and in each case unsubstituted or substituted linear $C_1$-$C_{30}$-alkyl, branched $C_3$-$C_{30}$-alkyl, linear $C_2$-$C_{30}$-alkenyl, branched $C_3$-$C_{30}$-alkenyl, linear $C_2$-$C_{30}$-alkinyl, branched $C_4$-$C_{30}$-alkinyl, cycloalkyl, aryl and hetaryl,
$Y^{1e}$ and $Y^{2e}$ are independently selected from O, S, Se and $NR^{3e}$, where $R^{3e}$ is selected from hydrogen and in each case unsubstituted or substituted alkyl, cycloalkyl and aryl.

Suitable compounds of the formula (II.e) and methods for their preparation are described in EP 2 077 590 B1 which is incorporated herein by reference.

Preferably, $Y^{1e}$ and $Y^{2e}$ are both S or are both Se. In particular, $Y^{1e}$ and $Y^{2e}$ are both S.

Preferably, $R^{1e}$ and $R^{2e}$ are independently selected from hydrogen, unsubstituted linear $C_1$-$C_{30}$-alkyl, unsubstituted branched $C_3$-$C_{30}$-alkyl, linear $C_1$-$C_{30}$-fluoroalkyl and branched $C_3$-$C_{30}$-fluoroalkyl. In particular, $R^{1e}$ and $R^{2e}$ are independently selected from hydrogen, unsubstituted linear $C_1$-$C_{30}$-alkyl and unsubstituted branched $C_3$-$C_{30}$-alkyl.

Preferably, $R^{1e}$ is hydrogen and $R^{2e}$ is independently selected from unsubstituted linear $C_1$-$C_{30}$-alkyl, unsubstituted branched $C_3$-$C_{30}$-alkyl, halogen substituted linear $C_1$-$C_{30}$-alkyl and halogen substituted branched $C_3$-$C_{30}$-alkyl.

In a special embodiment of the compounds of the formula (II.e) $R^{1e}$ and $R^{2e}$ are both selected from linear $C_1$-$C_{30}$-alkyl and branched $C_3$-$C_{30}$-alkyl.

In a preferred embodiment, the compounds of the formula (II.e) are selected from compound of the formula (II.e1) and (II.e2)

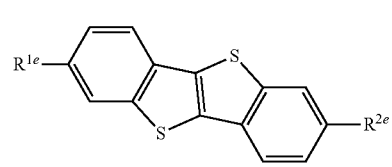
(II.e1)

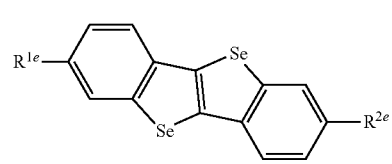
(II.e2)

wherein
$R^{1e}$ and $R^{2e}$ are independently selected from unsubstituted linear $C_7$-$C_{22}$-alkyl and unsubstituted branched $C_7$-$C_{22}$-alkyl.

Preferably, in the compounds of the formulae (II.e1) and (II.e2) $R^{1e}$ and $R^{2e}$ have the same meaning.

Preferably, in the compounds of the formulae (II.e1) and (II.e2) $R^{1e}$ and $R^{2e}$ are selected from linear $C_7$-$C_{22}$-alkyl.

Solvent L1)

In step (a) of the process according to the invention a solution of at least one organic semiconductor A) in a solvent (L1) or in a solvent mixture comprising at least one solvent (L1) is provided, wherein the solvent (L1) has
a boiling point at 1013.25 mbar of at least 140° C.,
a viscosity of at least 1.2 mPas at 23° C., and
a surface tension of at least 31.5 mN/m at 20° C.

In principle, solvents (L1) and cosolvents (L2) can be selected from the same classes of solvents with the proviso that the solvents (L1) mandatory fulfil the afore-mentioned parameters.

The composition according to the invention comprises as component L1) at least one compound, selected from
L1.1) at least one compound that is liquid at 20° C. and 1013 mbar, selected from compounds of the formula (I)

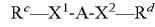
$R^c$—$X^1$-A-$X^2$—$R^d$     (I)

wherein
A is a 5- to 8-membered unsubstituted or substituted, aliphatic or aromatic carbocycle or heterocycle, $X^1$ and $X^2$ are independently selected from *—(C=O)—O—, *—(CH$_2$)$_m$—O— or *—(CH$_2$)$_m$—O—(C=O)—, where * is the point of linkage to the benzene ring, and m has the value 0, 1, or 2; and $R^c$ and $R^d$ are independently selected from unbranched and branched $C_1$-$C_{12}$-alkyl and $C_2$-$C_{12}$-alkenyl, L1.2) alkyl benzoates
L1.3) hydroxybenzoic acid esters,
L1.4) alkylene carbonates,
L1.5) aromatic aliphatic ketones,
L1.6) dimethylsulfoxide (DMSO),
L1.7) N-methylpyrrolidone,
L1.8) polycyclic hydrocarbons containing a cycloaliphatic ring,
L1.9) dichlorobenzenes,
and mixtures thereof.

In a preferred embodiment, the at least one organic semiconductor A) has a solubility in a solvent (L1) or in a mixture consisting only of solvents solvent (L1) at 20° C. of at least 0.01 mg/ml, more preferably of at least 0.05 mg/ml.

If the at least one organic semiconductor A) has a solubility in component L1) or a mixture of components L1) at 20° C. of less than 0.01 mg/ml, an additional cosolvent L2), selected from organic solvents and mixtures of organic solvents different from component L1), can be added. Thus, in a further preferred embodiment the organic semiconductor A) has a solubility in the mixture of components L1) and L2) at 20° C. of at least 0.01 mg/ml, preferably of at least 0.5 mg/ml.

It is of course also possible to employ an additional cosolvent L2) if the at least one organic semiconductor A) has a sufficient solubility in component L1) alone. In this case, the additional cosolvent may be added to provide certain application properties, e.g. a good processability of the composition by a printing process.

Preferably, the component L1) is present in an amount of 1 to 99.9999999 wt.-%, preferably in an amount of 2 to 99.999999 wt.-%, more preferably in an amount of 5 to 99.99999 wt.-%, in particular in an amount of 10 to 99.99999 wt.-%, based on the total weight of the solution.

Preferably, the component L1) is present in an amount of 1 to 99.9999999 wt.-%, preferably in an amount of 2 to 99.999999 wt.-%, more preferably in an amount of 5 to 99.99999 wt.-%, in particular in an amount of 10 to 99.99999 wt.-%, based on the total weight of components A) and L1).

Preferably, the compound of the general formula (L1.1) is selected from compounds of the formulae (I.1), (I.2), (I.3), (I.4) and (I.5)

1.

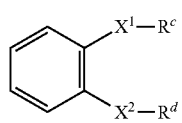

(I.1)

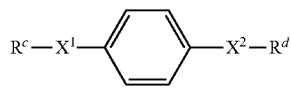

(I.2)

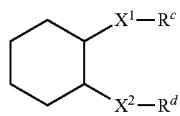

(I.3)

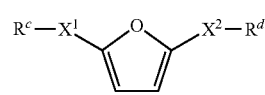

(I.4)

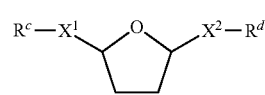

(I.5)

wherein
$X^1$ and $X^2$ are independently selected from *—(C=O)—O—, *—(CH$_2$)$_m$—O— or *—(CH$_2$)$_m$—O—(C=O)—, where * is the point of linkage to the aliphatic or aromatic carbocycle or heterocycle, and m has the value 0, 1, or 2; and $R^c$ and $R^d$ are independently selected from unbranched and branched $C_1$-$C_{12}$-alkyl and $C_2$-$C_{12}$-alkenyl.

It is preferable that the moieties $R^c$ and $R^d$ in the compounds of the formulae (I), (I.1), (I.2), (I.3), (I.4) and (I.5) are independently of each other an unbranched or branched $C_7$-$C_{12}$-alkyl moiety.

Preferably, the moieties $R^c$ and $R^d$ in the compounds of the formulae (I), (I.1), (I.2), (I.3), (I.4) and (I.5) have the same meaning.

Preferably, in the compounds of the formulae (I), (I.1), (I.2), (I.3), (I.4) and (I.5) $R^c$ and $R^d$ are independently selected methyl, ethyl, n-propyl, isopropyl, n-butyl, sec.-butyl, tert.-butyl, isobutyl, n-pentyl, n-hexyl, n-heptyl, n-octyl, 2-ethylhexyl, n-nonyl, isononyl, isodecyl, 2-propylheptyl, n-undecyl and isoundecyl.

Preferably, in the compounds of the formulae (I), (I.1), (I.2), (I.3), (I.4) and (I.5) are both *—(C=O)—O—.

In particular, the compound of the formula I.1 is selected from dimethylphthalate, diethylphthalate, di(n-propyl)phthalate, di(n-butyl)phthalate, diallylphthalate and mixtures thereof.

Suitable compounds of the general formula (I) and of the formulae (I), (I.1), (I.2), (I.3), (I.4) and (I.5) and methods for their production are known to a person skilled in the art. Those compounds have long been known as plasticizers, i.e. additives that are used to achieve desired processing properties or desired performance characteristics in many plastics. Phthalic diesters (I.1) and terephthalic diesters (I.2) with alcohols of different chemical structure have in the past often been used as plasticizers because they have good compatibility with PVC and advantageous performance characteristics. Short-chain phthalates, e.g. dibutyl phthalate (DBP), diisobutyl phthalate (DIBP), etc. are also used as gelling aids ("fast fuser").

Dialkylcyclohexane-1,2-dicarboxylic esters (I.3) can either be purchased or produced by processes known in the prior art. The 1,2-cyclohexanedicarboxylic esters are generally obtained mostly via ring-hydrogenation of the corresponding phthalic esters. The ring-hydrogenation can take place as mentioned above by the process described in WO 99/32427. A particularly suitable ring-hydrogenation process is also described by way of example in WO 2011/082991 A2. 1,2-Cyclohexanedicarboxylic esters can moreover be obtained via esterification of 1,2-cyclohexanedicarboxylic acid or of suitable derivatives thereof with the corresponding alcohols. The esterification can take place by conventional processes known to the person skilled in the art.

The esters of 2,5-furandicarboxylic acid (FDCA=component I.4) are another plasticizer class. R. D.

Sanderson et al. (J. Appl. Pol. Sci., 1994, vol. 53, 1785-1793) describe the synthesis of esters of 2,5-furandicarboxylic acids and their use as plasticizers. WO 2012/113608 describes $C_5$-dialkyl esters of 2,5-furandicarboxylic acid, WO 2012/113609 describes $C_7$-dialkyl esters of 2,5-furandicarboxylic acid, WO 2011/023490 describes $C_9$-dialkyl esters of 2,5-furandicarboxylic acid and WO 2011/023491 describes $C_{10}$-dialkyl esters of 2,5-furandicarboxylic acid.

Preferably, the compounds of the formula (I.2) are selected from dimethylterephthalate, diethylterephthalate, di(n-propyl)terephthalate, di(n-butyl)terephthalate, diallylterephthalate and mixtures thereof.

Preferably, the compounds of the formula (I.3) are selected from dimethyl-1,2-cyclohexanedicarboxylate, diethyl-1,2-cyclohexanedicarboxylate, di(n-propyl)-1,2-cyclohexanedicarboxylate, di(n-butyl)-1,2-cyclohexanedicarboxylate, diallyl-1,2-cyclohexanedicarboxylate and mixtures thereof.

Preferably, the compounds of the formula (I.4) are selected from dimethyl-2,5-furandicarboxylate, diethyl-2,5-furandicarboxylate, di(n-propyl)-2,5-furandicarboxylate, di(n-butyl)-2,5-furandicarboxylate, diallyl-2,5-furandicarboxylate and mixtures thereof.

Preferably, the diesters of 2,5-tetrahydrofurandicarboxylic acid of the formula (I.5)

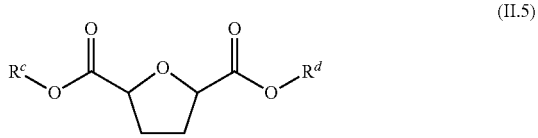
(II.5)

in which
$R^c$ and $R^d$ are independently selected from unbranched and branched $C_1$-$C_{12}$-alkyl and $C_2$-$C_{12}$-alkenyl
are prepared by a method wherein
a) optionally 2,5-furandicarboxylic acid or an anhydride or acyl halide thereof is reacted with a $C_1$-$C_3$-alkanol in the presence of a catalyst to give a di($C_1$-$C_3$-alkyl) 2,5-furandicarboxylate,
b1) 2,5-furandicarboxylic acid or an anhydride or acyl halide thereof, or the di($C_1$-$C_3$-alkyl) 2,5-furandicarboxylate obtained in step a), is reacted with at least one alcohol $R^c$—OH and, if $R^c$ and $R^d$ are different, also with at least one alcohol $R^d$—OH, in the presence of at least one catalyst to give a compound of the formula (II.5a),

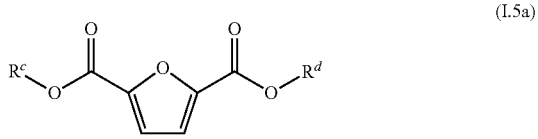
(I.5a)

c1) the compound (I.5a) obtained in step b1) is hydrogenated with hydrogen in the presence of at least one hydrogenation catalyst to give the compound of the general formula (I.5),
or
b2) 2,5-furandicarboxylic acid or the di($C_1$-$C_3$-alkyl) 2,5-furandicarboxylate obtained in step a) is hydrogenated with hydrogen in the presence of at least one hydrogenation catalyst to give a compound of the general formula (I.5b),

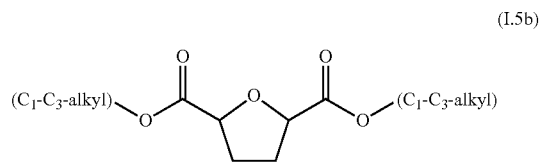
(I.5b)

c2) the compound (I.5b) obtained in step b2) is reacted with at least one alcohol $R^c$—OH and, if $R^c$ and $R^d$ are different, also with at least one alcohol $R^d$—OH, in the presence of a catalyst to give a compound of the formula (I.5).

Preferably, the compounds of the formula (I.5) are selected from dimethyl-2,5-tetrahydrofurandicarboxylate, diethyl-2,5-tetrahydrofurandicarboxylate, di(n-propyl)-2,5-tetrahydrofurandicarboxylate, di(n-butyl)-2,5-tetrahydrofurandicarboxylate, diallyl-2,5-tetrahydrofurandicarboxylate and mixtures thereof.

The afore-mentioned process permits the production of the 2,5-tetrahydrofurandicarboxylic esters of the general formula (I.5) by two different routes (hereinafter termed variant 1 and variant 2).

Examples of $C_1$-$C_3$-alkanols suitable for use in step a) are methanol, ethanol, n-propanol, and mixtures thereof.

In variant 1 of the process of the invention, the 2,5-furandicarboxylic acid or the di($C_1$-$C_3$-alkyl) 2,5-furandicarboxylate obtained in step a) is subjected to esterification or transesterification with at least one alcohol $R^c$—OH and, if $R^c$ and $R^d$ are different, also with at least one alcohol $R^d$—OH, to give the compounds of the formula (I.5a), which are then hydrogenated to give compounds of the general formula (I.5) (step c1)).

In variant 2, the 2,5-furandicarboxylic acid or the 2,5-di($C_1$-$C_3$-alkyl) furandicarboxylate obtained in step a) is first hydrogenated to give 2,5-tetrahydrofurandicarboxylic acid or, respectively, a compound of the general formula (I.1b) (step b2)), and the hydrogenation product is then reacted with at least one alcohol $R^c$—OH and, if R and $R^d$ are different, also with at least one alcohol $R^d$—OH to give the compounds of the general formula (I.5) (step c2)).

Conventional processes known to the person skilled in the art can be used to convert the 2,5-furandicarboxylic acid (FDCA) or the 2,5-tetrahydrofurandicarboxylic acid to the corresponding ester compounds of the general formulae (I.5), (I.5a), and (I.5b). Among these is the reaction of at least one alcohol component selected from $C_1$-$C_3$-alkanols or from the alcohols $R^c$—OH and, respectively, $R^d$—OH with FDCA or a suitable derivative thereof. Examples of suitable derivatives are the acyl halides and anhydrides. A preferred acyl halide is the acyl chloride. Esterification catalysts that can be used are the catalysts conventionally used for this purpose, e.g. mineral acids, such as sulfuric acid and phosphoric acid; organic sulfonic acids, such as methanesulfonic acid and p-toluenesulfonic acid; amphoteric catalysts, in particular titanium compounds, tin(IV) compounds, or zirconium compounds, e.g. tetraalkoxytitanium compounds, e.g. tetrabutoxytitanium, and tin(IV) oxide. The water produced during the reaction can be removed by conventional measures, e.g. by distillation. WO 02/038531 describes a process for producing esters where a) a mixture consisting essentially of the acid component or an anhydride thereof and of the alcohol component is heated to boiling point in the presence of an esterification catalyst in a reaction zone, b) the vapors comprising alcohol and water are fractionated to give an alcohol-rich fraction and a water-rich fraction, c) the alcohol-rich fraction is returned to the reaction zone, and the water-rich fraction is discharged from the process. Esterification catalysts used are the abovementioned catalysts. An effective amount of the esterification catalyst is used and is usually in the range from 0.05 to 10% by weight, preferably from 0.1 to 5% by weight, based on the entirety of acid component (or anhydride) and alcohol component. Other detailed descriptions of the conduct of esterification processes are found by way of example in U.S. Pat. No. 6,310,235, U.S. Pat. No. 5,324,853, DE-A 2612355 (Derwent Abstract No. DW 77-72638 Y) or DE-A 1945359 (Derwent Abstract No. DW 73-27151 U). The entirety of the documents mentioned is incorporated herein by way of reference.

The esterification can generally take place at ambient pressure or at reduced or elevated pressure. It is preferable that the esterification is carried out at ambient pressure or reduced pressure.

The esterification can be carried out in the absence of any added solvent or in the presence of an organic solvent.

If the esterification is carried out in the presence of a solvent, it is preferable that the organic solvent used is inert under the reaction conditions. Among these are by way of example aliphatic hydrocarbons, halogenated aliphatic hydrocarbons, and aromatic and substituted aromatic hydrocarbons and ethers. It is preferable that the solvent is one selected from pentane, hexane, heptane, ligroin, petrol ether, cyclohexane, dichloromethane, trichloromethane, tetrachloromethane, benzene, toluene, xylene, chlorobenzene, dichlorobenzenes, dibutyl ether, THF, dioxane, and mixtures thereof.

The esterification is usually carried out in the temperature range from 50 to 250° C.

If the esterification catalyst is one selected from organic acids or mineral acids, the esterification is usually carried out in the temperature range from 50 to 160° C.

If the esterification catalyst is one selected from amphoteric catalysts, the esterification is usually carried out in the temperature range from 100 to 250° C.

The esterification can take place in the absence of or in the presence of an inert gas.

Conventional processes known to the person skilled in the art can be also used for the reaction, described in steps b1) and c2), of the di($C_1$-$C_3$-alkyl) 2,5-furandicarboxylate and, respectively, the di($C_1$-$C_3$-alkyl) 2,5-tetrahydrofurandicarboxylate to give the corresponding ester compounds II.5a and, respectively, II.5. Among these are the reaction of the di($C_1$-$C_3$)-alkyl esters with at least one $C_7$-$C_{12}$-alkanol or a mixture thereof in the presence of a suitable transesterification catalyst.

Transesterification catalysts that can be used are the conventional catalysts usually used for transesterification reactions, where these are mostly also used in esterification reactions. Among these are by way of example mineral acids, such as sulfuric acid and phosphoric acid; organic sulfonic acids, such as methanesulfonic acid and p-toluenesulfonic acid; and specific metal catalysts from the group of the tin(IV) catalysts, for example dialkyltin dicarboxylates, such as dibutyltin diacetate, trialkyltin alkoxides, monoalkyltin compounds, such as monobutyltin dioxide, tin salts, such as tin acetate, or tin oxides; from the group of the titanium catalysts: monomeric and polymeric titanates and titanium chelates, for example tetraethyl orthotitanate, tetrapropyl orthotitanate, tetrabutyl orthotitanate, triethanolamine titanate; from the group of the zirconium catalysts: zirconates and zirconium chelates, for example tetrapropyl zirconate, tetrabutyl zirconate, triethanolamine zirconate; and also lithium catalysts, such as lithium salts, lithium alkoxides; and aluminum(III) acetylacetonate, chromium (III) acetylacetonate, iron(III) acetylacetonate, cobalt(II) acetylacetonate, nickel(II) acetylacetonate, and zinc(II) acetylacetonate.

The amount of transesterification catalyst used is from 0.001 to 10% by weight, preferably from 0.05 to 5% by weight. The reaction mixture is preferably heated to the boiling point of the reaction mixture, the reaction temperature therefore being from 20° C. to 200° C., depending on the reactants.

The transesterification can take place at ambient pressure or at reduced or elevated pressure. It is preferable that the transesterification is carried out at a pressure of from 0.001 to 200 bar, particularly from 0.01 to 5 bar. The relatively low-boiling-point alcohol eliminated during the transesterification is preferably continuously removed by distillation in order to shift the equilibrium of the transesterification reaction. The distillation column necessary for this purpose generally has direct connection to the transesterification reactor, and it is preferable that said column is a direct attachment thereto. If a plurality of transesterification reactors are used in series, each of said reactors can have a distillation column, or the vaporized alcohol mixture can preferably be introduced into a distillation column from the final tanks of the transesterification reactor cascade by way of one or more collection lines. The relatively high-boiling-point alcohol reclaimed in said distillation is preferably returned to the transesterification.

The transesterification can be carried out in the absence of, or in the presence of, an added organic solvent. It is preferable that the transesterification is carried out in the presence of an inert organic solvent. Suitable organic solvents are those mentioned above for the esterification. Among these are specifically toluene and THF.

The transesterification is preferably carried out in the temperature range from 50 to 200° C.

The transesterification can take place in the absence of or in the presence of an inert gas.

Many processes and catalysts for the hydrogenation of the double bonds of the furan ring carried out in steps c1) and b2) of the invention are available to the person skilled in the art and these by way of example are also used in the hydrogenation of esters of aromatic polycarboxylic acids, examples being phthalates, isophthalates and terephthalates. By way of example, the ring-hydrogenation process described in WO 99/032427 is suitable. This comprises hydrogenation at from 50 to 250° C. and at a pressure of from 20 to 300 bar by means of catalysts which comprise at least one metal of transition group VIII of the Periodic Table of the Elements, for example platinum, rhodium, palladium, cobalt, nickel, or ruthenium, preferably ruthenium, either alone or together with at least one metal from transition group I or VII of the Periodic Table of the Elements, for example copper or ruthenium, deposited on a mesoporous aluminum oxide support material with bimodal pore distribution. The ring-hydrogenation process described in WO 02/100536 is moreover suitable. This comprises hydrogenation with use of a ruthenium catalyst on amorphous silicon dioxide as support. Other suitable processes are described in the following documents: EP-A 1266882—Use of a nickel/magnesium oxide on kieselguhr catalyst, WO 03/029181—Use of a nickel/zinc on silicon dioxide catalyst, WO 03/029168—Use of a palladium/ZnO on $Al_2O_3$ catalyst and of a ruthenium/ZnO on α-$Al_2O_3$ catalyst, or WO 04/09526—Use of a ruthenium on titanium dioxide catalyst. Other suitable catalysts are likewise Raney catalysts, preferably Raney nickel. Other suitable support materials alongside those already mentioned are by way of example zirconium dioxide (ZrO$_2$), sulfated zirconium dioxide, tungsten carbide (WC), titanium dioxide (TiO$_2$), sulfated carbon, activated charcoal, aluminum phosphate, aluminosilicates, or phosphated aluminum oxide, or else a combination thereof.

The hydrogenation can take place by analogy with the known hydrogenation processes for hydrogenating organic compounds which have hydrogenatable groups. To this end, the organic compound in the form of liquid phase or gas phase, preferably in the form of liquid phase, is brought into contact with the catalyst in the presence of hydrogen. The liquid phase can by way of example be passed over a fluidized bed of catalyst (fluidized bed method) or can be passed over a fixed bed of catalyst (fixed bed method).

The hydrogenation generally takes place under elevated hydrogen pressure. Preference is given to hydrogen pressure in the range from 2 to 500 bar, particularly from 10 to 300 bar.

It is preferable that the hydrogenation takes place in the presence of an organic solvent that is inert under the hydrogenation conditions. Suitable solvents are those previously defined for the esterification. Specifically, an ether is used, for example THF, or a dialkylene glycol, or a mono- or diether thereof, for example glyme.

The hydrogenation is preferably carried out at a temperature in the range from 20 to 350° C., particularly preferably from 50 to 300° C.

The amount of hydrogen used for the hydrogenation is generally from 1 to 15 times the stochiometric amount of hydrogen theoretically needed for the complete hydrogenation of the furan ring.

In particular, the compound of the formula (L1) is selected from dimethylphthalate, diethylphthalate, di(n-propyl)phthalate, di(n-butyl)phthalate, diallylphthalate, dimethyl sulfate, ethyl benzoate, ethyl salicylate, acetophenone, propylene carbonate, N-methylpyrrolidone, teralin, 1,2-dichlorobenzene and mixtures thereof.

Preferred alkyl benzoates L1.2) have 1 to 30 carbon atoms, more preferably 1 to 20 carbon atoms, in particular 2 to 10 carbon atoms, especially 2 to 6 carbon atoms in the alkyl chains. In particular, the alkyl benzoates L1.2) are selected from methyl benzoate, ethyl benzoate, n-propyl benzoate and n-butyl benzoate, n-pentyl benzoate, n-hexylbenzoate. Especially preferred is ethyl benzoate.

Suitable hydroxybenzoic acid esters L1.3) are the alkyl esters of o-hydroxybenzoic acid (salicylates), m-hydroxybenzoic acid and p-hydroxybenzoic acid (parabens). Preferred esters L1.3) have 1 to 30 carbon atoms, more preferably 1 to 20 carbon atoms, in particular 2 to 10 carbon atoms, especially 2 to 6 carbon atoms in the alkyl chains. In particular, the esters L1.3) are selected from methyl salicylate, ethyl salicylate, n-propyl salicylate and n-butyl salicylate. Especially preferred is ethyl salicylate.

Preferred alkylene carbonates L1.4) are ethylene carbonate and propylene carbonate. Especially preferred is propylene carbonate.

Preferred aliphatic aromatic ketones L1.5) are acetophenone, 2-acetyltoluene, 3-acetyltoluene, 4-acetyltoluene, propiophenone, butyrophenone, valerophenone and hexanophenone. Especially preferred is acetophenone.

Preferred polycyclic hydrocarbons containing an cycloaliphatic ring L1.8) are tetralin, decalin and indane. Especially preferred is tetralin.

Suitable dichlorobenzenes L1.9) are 1,2-, 1,3- and 1,4-dichlorobenzene. Especially preferred is 1,2-dichlorobenzene.

Solvent L2)

In certain embodiments, the composition according to the invention comprises a cosolvent L2) selected from organic solvents different from component L1) and mixtures of organic solvents different from component L1).

Preferably, the organic semiconductor A) has a solubility in the mixture of components L1) and L2) at 20° C. of at least 0.1 mg/ml.

Preferably, the organic semiconductor A) has a solubility in component L2) alone at 20° C. of at least 0.1 mg/ml.

Preferably, the component L1) is present in an amount of 0.1 to 100 wt.-%, preferably in an amount of 1 to 100 wt.-%, more preferably in an amount of 10 to 100 wt.-%, in particular in an amount of 50 to 100 wt.-%, based on the total weight of components L1) and L2).

Preferably, the component L2) is present in an amount of 0 to 99.9 wt.-%, preferably in an amount of 0 to 99 wt.-%, more preferably in an amount of 0 to 90 wt.-%, in particular in an amount of 0 to 50 wt.-%, based on the total weight of components L1) and L2).

If the composition according to the invention comprises a cosolvent L2), the amount is preferably 0.1 to 99.9 wt.-%, more preferably 1 to 99 wt.-%, in particular 2 to 90 wt.-%, especially 3 to 50 wt.-%, based on the total weight of components L1) and L2).

Preferably, the cosolvent L2) is selected from
aliphatic, cycloaliphatic and aromatic hydrocarbons different from L1.8),
aromatic ethers,
open chain aliphatic ethers, polyethers, ether alcohols and cyclic ethers,
ketones different from L1.5),
esters different from L1.2), L1.3) and L1.4),
aliphatic and cycloaliphatic alcohols,
benzene based alcohols,
halogenated aromatic compounds,
thiophenols and alkylthio-substituted benzenes,
aromatic compounds comprising a phenyl group fused to a 5-, 6-, or 7-membered cycloheteroalkyl group,
5-membered heteroaryl compounds and benzo-fused 5-membered heteroaryl compounds,
aromatic carboxylic acids,
aromatic aldehydes,
trifluoromethyl-substituted benzene compounds,
cyano-substituted or isocyano-substituted benzene compounds,
nitro-substituted benzene compounds,
phenyl sulfones,
6-membered heteroaryl compounds and benzofused 6-membered heteroaryl compounds,
5-membered heteroaryl compounds and benzofused 5-membered heteroaryl compounds,
aprotic polar solvents different from L6) and L7) and mixtures thereof.

Preferred aliphatic, cycloaliphatic and aromatic hydrocarbons L2) are selected from n-pentane, n-hexane, n-heptan, ligroin, cyclohexane, methylcyclohexane, benzene, toluene, o-xylene, m-xylene, p-xylene, cumene, 1,2,3-trimethylbenzene, 1,2,4-trimethylbenzene, 1,3,5-trimethylbenzene, mesitylene, 1-methyl naphthalene, 2-methylnaphtalene, 1-ethyl naphthalene, 2-ethylnaphthalene, indene and mixtures thereof.

Preferred aromatic ethers are anisole (methylphenylether) ethoxybenzene (phenetol), propoxybenzene, isopropoxybenzene, butoxybenzene, 1-methoxynaphthalen, 2-methoxynaphthalen, 2-methylanisole, 3-methylanisole, 4-methylanisole, 2-ethylanisole, 3-ethylanisole, 4-ethylanisole, 2,3-dimethylanisole, 2,4-dimethylanisole, 2,5-dimethylanisole, 2,6-dimethylanisole, 3,4-dimethylanisole, 3,5-dimethylanisole, 1,2-dimethoxybenzene (veratrol), 1,3-dimethoxybenzene, 1,4-dimethoxybenzene, 1-ethoxy-4-methoxybenzene, 1-ethoxy-3-methoxybenzene, 1-ethoxy-2-methoxybenzene, 1,2-diethoxybenzene, 1,3-diethoxybenzene, 1,4-diethoxybenzene, 2,3-dimethoxytoluene, 2,4-dimethoxytoluene, 2,5-dimethoxytoluene, 2,6-dimethoxytoluene, 3,4-dimethoxytoluene, 3,5-dimethoxytoluene, 4-ethoxytoluene, 3-ethoxytoluene, 2-ethoxytoluene, 1-ethoxy-2-ethyl benzene, 1-ethoxy-3-ethylbenzene, 1-ethoxy-4-ethylbenzene, 1-(methoxymethoxy)benzene, (2-methoxyethoxy)benzene, (3-methoxypropoxy)benzene and mixtures thereof. A preferred cosolvent C) is anisole.

Preferred open chain aliphatic ethers, polyethers, ether alcohols and cyclic ethers are diethyl ether, dipropyl ether, diisopropyl ether, methyl tert-butyl ether, ethyleneglycolmonomethylether, ethyleneglycoldimethylether, ethyleneglycolmonoethylether, ethyleneglycoldiethylether, propyleneglycolmonomethylether, propyleneglycoldimethylether, propyleneglycolmonoethylether, propyleneglycoldiethylether, diethylenglycolmonomethylether, diethylenglycoldimethylether, diethylenglycolmonoethylether, diethylenglycoldiethylether, diglyme (=bis(2-methoxyethyl) ether), tetrahydrofuran, tetrahydropyran, 1,4-dioxane, morpholine and mixtures thereof.

Preferred ketones L2) are acetone, methyl ethyl ketone, methyl isobutyl ketone, ethyl n-amyl ketone, diisobutyl ketone, cyclohexanone, pentane-2,4-dione (acetylacetone) and mixtures thereof. Preferred cosolvent L2) are acetylacetone, acetophenone and mixtures thereof.

Preferred esters L2) are ethyl acetate, methyl acetate, ethyl acetoacetate, propyl acetate, isopropyl acetate, n-butyl acetate, sec-butyl acetate, tert-butyl acetate, isobutyl acetate, isoamyl acetate, hexyl acetate, methyl propionate, ethyl butyrate, ethyl lactate, diethyl carbonate, triacetin, phenyl formate, phenyl acetate, o-cresol acetate, p-cresol acetate, m-Cresol acetate, 2-methoxyphenyl acetate, 3-methoxyphenyl acetate, and 4-methoxyphenyl acetate, benzyl benzoate, bis(2-ethylhexyl) adipate, methyl 2-methylbenzoate, methyl 3-methylbenzoate, methyl 4-methylbenzoate, methyl 2-chlorobenzoate, methyl 3-chlorobenzoate, methyl 4-chlorobenzoate, methyl 4-fluorobenzoate, methyl 3-fluorobenzoate, methyl 2-fluorobenzoate, ethyl 2-methylbenzoate, ethyl 3-methylbenzoate, ethyl 4-methylbenzoate, ethyl 4-chlorobenzoate, ethyl 3-chlorobenzoate, ethyl 2-chlorobenzoate, ethyl 2-fluorobenzoate, ethyl 3-fluorobenzoate, ethyl 4-fluorobenzoate, methyl 4-bromobenzoate, methyl 3-bromobenzoate, methyl 2-bromobenzoate and mixtures thereof.

Preferred aliphatic and cycloaliphatic alcohols are methanol, ethanol, n-propanol, isopropanol n-butanol, sec.-butanol, tert.-butanol, n-pentanol, amyl alcohol mixtures, n-hexanol, cyclohexanol, ethanediol, propanediol, ethylene glycol, diethylene glycol and mixtures thereof.

In preferred benzene-based alcohols the phenyl group can be directly substituted with a hydroxyl group, or the phenyl group can be substituted with an alkyl, alkoxy, alkylthio, or amino group, wherein the alkyl, alkoxy, alkylthio, or amino group is substituted with a hydroxyl group. Examples of benzene-based alcohols include phenol; cresol (o-cresol, m-cresol, p-cresol); 2-methoxyphenol, 3-methoxyphenol, 4-methoxyphenol, 4-aminobenzylalcohol; 2-phenoxyethanol; 3-phenoxy-1-propanol; 4-phenoxy-1-butanol; 5-phenoxy-1-heptanol; 6-phenoxy-1-hexanol; 2-(2-methylphenoxy)ethan-1-ol; 2-(3-methylphenoxy)ethan-1-ol; 2-(4-methylphenoxy)ethan-1-ol; phenoxymethanol; 1-phenoxyethanol, 1-phenoxypropanol, 1-phenoxybutanol, 2-(2-methoxyphenoxy)ethan-1-ol, 2-(3-methoxyphenoxy)ethan-1-ol; 2-(4-methoxyphenoxy)ethan-1-ol; 2-(2-methylphenoxy)ethanol, 2-(3-methylphenoxy)ethanol, 2-(4-methylphenoxy)ethanol, 2-(4-methoxyphenoxy)ethanol, 2-(3-methoxyphenoxy)ethan-1-ol, 2-(2-methoxyphenoxy)ethan-1-ol and mixtures thereof.

Preferred halogenated aromatic compounds are selected from chlorobenzene, 1,2-dichlorobenzene, 1,3-dichlorobenzene, 1,2,4-trichlorobenzene, 4-chlorotoluene, 3-chlorobenzene, 2-chlorotoluene, fluorobenzene, 1,2-difluorobenzene, 1,3-difluorobenzene, 1,4-difluorobenzene, 1-chloronaphtalene, 2-chloronaphthalene, 1-fluoronaphthalene, 2-fluoronaphthalene, 2-chloroanisole, 3-chloroanisole, 4-chloroanisole, 4-fluoroanisole, 3-fluoroanisole, 2-fluoroanisole, and mixtures thereof.

Examples of thiophenols include thiophenol, 2-thiocresol, 3-thiocresol, 4-thiocresol, 2-ethyl thiophenol, 3-ethyl thiophenol, 4-ethyl thiophenol, 2,6-dimethylthiophenol, 2,5-dimethylthiophenol, 2,4-dimethylthiophenol, 2,3-dimethylthiophenol, and 2-isopropylthiophenol. Examples of alkylthio-substituted benzenes include thioanisole, (ethylthio)benzene, 2-methylthioanisole, 3-methyl thioanisole, 4-methyl thioanisole, 4-methoxy thioanisole, 3-methoxy thioanisole, 2-methoxy thioanisole.

Suitable aromatic compounds comprising a phenyl group fused to a 5-, 6-, or 7-membered cycloheteroalkyl group include indoline and substituted indolines, such as 7-methylindoline, 5-methylindoline, and 6-methylindoline; 1,2,3,4-tetrahydroquinoline; 6-methyl-3,4-dihydro-2H-1-benzopyran; benzodioxole and substituted benzodioxoles, such as 1,3-benzodioxole, 2-methyl-1,3-benzodioxole, 2-ethyl-1,3-benzodioxole, 5-hydroxy-1,3-benzodioxole, 5-methyl-1,3-benzodioxole, 5-methoxy-1,3-benzodioxole, 5-methyl-1,3-benzodioxole, 5-ethyl-1,3-benzodioxole, 4-hydroxy-1,3-benzodioxole, 4-methyl-1,3-benzodioxole, 4-ethyl-1,3-benzodioxole, 4-methoxy-1,3-benzodioxole, 2,2-dimethyl-1,3-benzodioxole, 3,4-methylenedioxytoluene, and 4-methyl-2H-1,3-benzodioxole; dihydrobenzofuran and substituted dihydrobenzofurans such as 2,3-dihydrobenzofuran, 2,3-dihydro-2-methylbenzofuran, 6-methyl-2,3-dihydrobenzofuran, and 5-methyl-2,3-dihydrobenzofuran; 4H-chromene, chromane, 7-methylchroman, 8-methylchroman, and 2,3-dihydrobenzo[b]thiophene.

Suitable 5-membered heteroaryl compounds and benzo-fused 5-membered heteroaryl compounds are thiophene, 2-methylthiophene, 3-methylthiophene, furan, 3-methylfuran, 2-methylfuran, pyrrole, N-methylpyrrole, N-ethylpyrrole, 1,2-dimethyl-1H-pyrrole, 1,3-dimethyl-1H-pyrrole, 2-methoxyfuran, 3-methoxyfuran, 3-methoxythiophene, 2-methoxythiophene, 2-methylthiofuran, 3-methylthiofuran, 3-methylthiothiophene, 2-methylthiothiophene, 2-N,N-dimethylamino-thiophene, 3-methoxy-1-methyl-1H-pyrrole, 2-methoxy-1-methyl-1H-pyrrole, benzofuran, 6-methylbenzofuran, benzothiophene, and 6-methylbenzothiophene.

Suitable aromatic carboxylic acids are benzoic acid, o-toluic acid, m-toluic acid, p-toluic acid, 4-chlorobenzoic acid, 3-chlorobenzoic acid, 2-chlorobenzoic acid, 2-fluorobenzoic acid, 3-fluorobenzoic acid, 4-fluorobenzoic acid and mixtures thereof.

Suitable aromatic aldehydes are benzaldehyde, 2-methylbenzaldehyde, 3-methylbenzaldehyde, 4-methylbenzaldehyde, 4-ethylbenzaldehyde, 3-ethylbenzaldehyde, 2-ethylbenzaldehyde, 2-chlorobenzaldehyde, 3-chlorobenzaldehyde, 4-chlorobenzaldehyde, 4-fluorobenzaldehyde, 3-fluorobenzaldehyde, 2-fluorobenzaldehyde, 2-bromobenzaldehyde, 3-bromobenzaldehyde, and 4-bromobenzaldehyde.

Suitable trifluoromethyl-substituted benzene compounds are benzotrifluoride, 2-methylbenzotrifluoride, 3-methylbenzotrifluoride, 4-methylbenzotrifluoride, 4-chlorobenzotrifluoride, 3-chlorobenzotrifluoride, 2-chlorobenzotrifluoride, 2-fluorobenzotrifluoride, 3-fluorobenzotrifluoride, 4-fluorobenzotrifluoride, 4-bromobenzotrifluoride, 3-bromobenzotrifluoride, 2-bromobenzotrifluoride, methyl 2-trifluoromethyl benzoate, methyl 3-trifluoromethyl benzoate, methyl 4-trifluoromethylbenzoate, ethyl 2-trifluoromethylbenzoate, ethyl 3-trifluoromethylbenzoate, ethyl 4-trifluoromethylbenzoate and mixtures thereof.

Suitable cyano-substituted or isocyano-substituted benzene compounds are benzonitrile, 2-methylbenzenecarbonitrile, 3-methylbenzenecarbonitrile, 4-methylbenzenecarbonitrile, 4-chlorobenzonitrile, 3-chlorobenzonitrile, 2-chlorobenzonitrile, 2-fluorobenzonitrile, 3-fluorobenzonitrile, 4-fluorobenzonitrile, phenylisocyanide, 2-tolylisocyanide, 3-tolylisocyanide, 4-tolylisocyanide and mixtures thereof.

Suitable nitro-substituted benzene compounds are nitrobenzene, 2-nitrotoluene, 3-nitrotoluene, 4-nitrotoluene, 1-chloro-4-nitrobenzene, 1-chloro-3-nitrobenzene, 1-chloro-2-nitrobenzene, 1-fluoro-2-nitrobenzene, 1-fluoro-3-nitrobenzene, 1-fluoro-4-nitrobenzene and mixtures thereof.

Suitable phenyl sulfones are methyl phenyl sulfone, ethyl phenyl sulfone, (propane-1-sulfonyl)benzene, 1-methanesulfonyl-2-methyl-benzene, 1-methanesulfonyl-3-methylbenzene, and 1-methanesulfonyl-4-methyl-benzene.

Suitable 6-membered heteroaryl compounds or benzo-fused 6-membered heteroaryl compounds are pyridine, 2-methylpyridine, 3-methylpyridine, 4-methylpyridine, 2-chloropyridine, 3-chloropyridine, 4-chloropyridine, 4-fluoropyridine, 3-fluoropyridine, 2-fluoropyridine, 2-bromo-pyridine, 3-bromo-pyridine, 4-bromo-pyridine, 4-(trifluoromethyl)pyridine, 3-(trifluoromethyl)pyridine, 2-(trifluoromethyl)pyridine, 2-cyanopyridine, 3-cyanopyridine, 4-cyanopyridine, 4-nitropyridine, 3-nitropyridine, 2-nitropyridine, 2-picolinic acid methyl ester, 3-picolinic acid methyl ester, and 4-picolinic acid methyl ester; pyrazine and substituted pyrazines, such as methylpyrazine, 2,5-dimethylpyrazine, 2,6-dimethylpyrazine, 2,3-dimethylpyrazine, 2,3,5,6-tetramethyl-pyrazine, 2-chloropyrazine, 2,5-dichloropyrazine, 2,6-dichloropyrazine, 2,3-dichloropyrazine, 2-fluoropyrazine, (trifluoromethyl) pyrazine, 2-pyrazinecarbonitrile, 2-nitro-pyrazine, pyrazine-2-carbaldehyde, 1-pyrazin-2-yl-ethanone, 1-(pyrazin-2-yl)propan-1-one, methyl pyrazine-2-carboxylate, pyrazine 2-carboxylic acid ethyl ester, 2-bromopyrazine, and 2-iodopyrazine; pyridazine and substituted pyridazines, such as 3-methylpyridazine, 4-methylpyridazine, 4,5-dimethylpyridazine, 3,6-dimethylpyridazine, 3-chloropyridazine, 4-chloropyridazine, pyridazine-3-carbonitrile, 4-pyridazinecarbonitrile, 4-(trifluoromethyl)pyridazine, 3-(trifluoromethyl)pyridazine, 3-nitropyridazine, pyridazine-3-carbaldehyde, pyridazine-4-carbaldehyde, 1-(pyridazin-4-yl)ethanone, 3-acetylpyridazine, methylpyridazine-3-carboxylate, and methylpyridazine-4-carboxylate; tetrazine and substituted tetrazines, such as 1,2,4,5-tetrazine, dimethyl-1,2,4,5-tetrazine, and 3,6-dichloro-1,2,4,5-tetrazine; quinoline and substituted quinolones, such as 2-methylquinoline, 3-methylquinoline, 4-methylquinoline, 5-methylquinoline, 6-methylquinoline, 7-methylquinoline, 8-methylquinoline, 2-chloroquinoline, 3-chloroquinoline, 4-chloroquinoline, 5-chloroquinoline, 6-chloroquinoline, 7-chloroquinoline, 8-chloroquinoline, 2-fluoroquinoline, 3-fluoroquinoline, 4-fluoroquinoline, 5-fluoroquinoline, 6-fluoroquinoline, 7-fluoroquinoline, 8-fluoroquinoline, 2-trifluoromethyl quinoline, 3-trifluoromethyl quinoline, 4-trifluoromethyl quinoline, 5-trifluoromethyl quinoline, 6-trifluoromethyl quinoline, 7-trifluoromethyl quinoline, 8-trifluoromethyl quinoline, 2-nitroquinoline, 3-nitroquinoline, 4-nitroquinoline, 5-nitroquinoline, 6-nitroquinoline, 7-nitroquinoline, 8-nitroquinoline, 2-acetylquinoline, 3-acetylquinoline, 4-acetylquinoline, 5-acetylquinoline, 6-acetylquinoline, 7-acetylquinoline, 8-acetylquinoline, 2-cyanoquinoline, 3-cyanoquinoline, 4-cyanoquinoline, 5-cyanoquinoline, 6-cyanoquinoline, 7-cyanoquinoline, 8-cyanoquinoline, methyl 2-quinolinecarboxylate, methyl 3-quinolinecarboxylate, methyl 4-quinolinecarboxylate, methyl 5-quinolinecarboxylate, methyl 6-quinolinecarboxylate, methyl 7-quinolinecarboxylate, ethyl 8-quinolinecarboxylate, ethyl 2-quinolinecarboxylate, ethyl 3-quinolinecarboxylate, ethyl 4-quinolinecarboxylate, ethyl 5 quinolinecarboxylate, ethyl 6-quinolinecarboxylate, ethyl 7-quinolinecarboxylate, ethyl 8-quinolinecarboxylate, 2-quinolinecarboxaldehyde, 3-quinolinecarboxaldehyde, 4-quinolinecarboxaldehyde, 5-quinolinecarboxaldehyde, 6-quinolinecarboxaldehyde, 7-quinolinecarboxaldehyde, 8-quinolinecarboxaldehyde, 1-(2-quinolinyl)-ethanone, 1-(3-quinolinyl)-ethanone, 1-(4-quinolinyl)-ethanone, 1-(5-quinolinyl)-ethanone, 1-(6-quinolinyl)-ethanone, 1-(7-quinolinyl)-ethanone, and 1-(8-quinolinyl)-ethanone; quinoxaline and substituted quinoxalines, such as 2-methylquinoxaline, 5-methylquinoxaline, 6-methylquinoxaline, 2-chloroquinoxaline, 5-chloroquinoxaline, 6-chloroquinoxaline, 2-fluoroquinoxaline, 5-fluoroquinoxaline, 6-fluoroquinoxaline, 2-cyanoquinoxaline, 5-cyanoquinoxaline, 6-cyanoquinoxaline, 2-nitroquinoxaline, 5-nitroquinoxaline, 6-nitroquinoxaline, 2-trifluoromethylquinoxaline, 5-trifluoromethylquinoxaline, 6-trifluoromethyquinoxaline, methyl 2-quinoxalinecarboxylate, methyl 5-quinoxalinecarboxylate, methyl 6-quinoxalinecarboxylate, ethyl 2-quinoxalinecarboxylate, ethyl 5-quinoxalinecarboxylate, ethyl 6-quinoxalinecarboxylate and mixtures thereof.

Suitable 5-membered heteroaryl compounds and benzo-fused 5-membered heteroaryl compounds are thiazole, 2-methylthiazole, 4-methylthiazole, 5-methylthiazole, 2-chlorothiazole, 4-chlorothiazole, 5-chlorothiazole, 2-fluorothiazole, 4-fluorothiazole, 5-fluorothiazole, 2-cyanothiazole, 4-cyanothiazole, 5-cyanothiazole, 2-nitrothiazole, 4-nitrothiazole, 5-nitrothiazole, methyl 1,3-thiazole-2-carboxylate, methyl 1,3-thiazole-5-carboxylate, methyl 1,3-thiazole-6-carboxylate, ethyl 1,3-thiazole-2-carboxylate, ethyl 1,3-thiazole-5-carboxylate, ethyl 1,3-thiazole-6-carboxylate, 2-trifluoromethylthiazole, 4-trifluoromethylthiazole, and 5-trifluoromethylthiazole; imidazole and substituted imidazoles, such as N-methyl imidazole, 2-methylimidazole, 4-methylimidazole, 5-methylimidazole, 2-chloroimidazole, 4-chloroimidazole, 5-chloroimidazole, 2-fluoroimidazole, 4-fluoroimidazole, 5-fluoroimidazole, 2-cyanoimidazole, 4-cyanoimidazole, 5-cyanoimidazole, 2-nitroimidazole, 4-nitroimidazole, 5-nitroimidazole, methyl imidazole-2-carboxylate, methyl imidazole-5-carboxylate, methyl imidazole-5-carboxylate, ethyl imidazole-2-carboxylate, ethyl imidazole-4-carboxylate, ethyl imidazole-5-carboxylate, 2-trifluoromethylimidazole, 4-trifluoromethylimidazole, 5-trifluoromethylimidazole, 2-methyl-N-methyl imidazole, 4-methyl-N-methyl imidazole, 5-methyl-N-methyl imidazole, 2-chloro-N-methyl imidazole, 4-chloro-N-methyl imidazole, 5-chloro-N-methyl imidazole, 2-fluoro-N-methyl imidazole, 4-fluoro-N-methyl imidazole, 5-fluoro-N-methyl imidazole, 2-cyano-N-methyl imidazole, 4-cyano-N-methyl imidazole, 5-cyano-N-methyl imidazole, 2-nitro-N-methyl imidazole, 4-nitro-N-methyl imidazole, 5-nitro-N-methyl imidazole, methyl N-methyl imidazole-2-carboxylate, methyl N-methyl imidazole-4-carboxylate, methyl N-methyl imidazole-5-carboxylate, ethyl N-methyl imidazole-2-carboxylate, ethyl N-methyl imidazole-4-carboxylate, ethyl N-methyl imidazole-5-carboxylate, 2-trifluoromethyl-N-methyl imidazole, 4-trifluoromethyl-N-methyl imidazole, and 5-trifluoromethyl-N-methyl imidazole; triazole and substituted triazoles such as 4-methyl-1,2,3-triazole, 5-methyl-1,2,3-triazole, 4-chloro-1,2,3-triazole, 5-chloro-1,2,3-triazole, 4-fluoro-1,2,3-triazole, 5-fluoro-1,2,3-triazole, 4-cyano-1,2,3-triazole, 5-cyano-1,2,3-triazole, 4-nitro-1,2,3-triazole, 5-nitro-1,2,3-triazole, methyl 1,2,3-triazole-4-carboxylate, methyl 1,2,3-triazole-5-carboxylate, ethyl 1,2,3-triazole-4-carboxylate, ethyl 1,2,3-triazole-5-carboxylate, 4-trifluoromethyl-1,2,3-triazole, 5-trifluoromethyl-1,2,3-triazole, 4-methyl-N-methyl-1,2,3-triazole, 5-methyl-N-methyl-1,2,3-triazole, 4-chloro-N-methyl-1,2,3-triazole, 5-chloro-N-methyl-1,2,3-triazole, 4-fluoro-N-methyl-1,2,3-triazole, 5-fluoro-N-methyl-1,2,3-triazole, 4-cyano-N-methyl-1,2,3-triazole, 5-cyano-N-methyl-1,2,3-triazole, 4-nitro-N-methyl-1,2,3-triazole, 5-nitro-N-methyl-1,2,3-triazole, methyl N-methyl-1,2,3-triazole-4-carboxylate, methyl N-methyl-1,2,3-triazole-5-carboxylate, ethyl N-methyl-1,2,3-triazole-4-carboxylate, ethyl N-methyl-1,2,3-triazole-5-carboxylate, 4-trifluoromethyl-N-methyl-1,2,3-triazole, and 5-trifluoromethyl-N-methyl-1,2,3-triazole; tetrazole and substituted tetrazoles, such as N-methyltetrazole, 5-methyl-tetrazole, 5-methyl-N-methyl-tetrazole, 5-chloro-tetrazole, 5-chloro-N-methyl-tetrazole, 5-fluoro-tetrazole, 5-fluoro-N-methyl-tetrazole, 5-nitro-tetrazole, 5-nitro-N-methyl-tetrazole, 5-cyano-tetrazole, 5-cyano-N-methyl-tetrazole, 5-trifluoromethyl-tetrazole, 5-trifluoromethyl-N-methyl-tetrazole, methyl 1H-1,2,3,4-tetrazole-5-carboxylate, ethyl 1H-1,2,3,4-tetrazole-5-carboxylate, methyl 1-methyl-1,2,3,4-tetrazole-5-carboxylate, ethyl 1-methyl-1,2,3,4-tetrazole-5-carboxylate, tetrazole-5-carboxaldehyde, 1H-tetrazole-5-carboxaldehyde, 1-methyl-1-(1-methyl-1H-1,2,3,4-tetrazol-5-yl)ethan-1-one, 1-(1H-1,2,3,4-tetrazol-5-yl)ethan-1-one; benzothiazole and substituted benzothiazoles, such as 2-methyl-benzothiazole, 4-methyl-benzothiazole, 5-methyl-benzothiazole, 6-methyl-benzothiazole, 7-methyl-benzothiazole, 2-fluoro-benzothiazole, 4-fluoro-benzothiazole, 5-fluoro-benzothiazole, 6-fluoro-benzothiazole, 7-fluoro-benzothiazole, 2-chloro-benzothiazole, 4-chloro-benzothiazole, 5-chloro-benzothiazole, 6-chloro-benzothiazole, 7-chloro-benzothiazole, 2-cyano-benzothiazole, 4-cyano-benzothiazole, 5-cyano-benzothiazole, 6-cyano-benzothiazole, 7-cyano-benzothiazole, 2-nitro-benzothiazole, 4-nitro-benzothiazole, 5-nitro-benzothiazole, 6-nitro-benzothiazole, 7-nitro-benzothiazole, 2-trifluoromethyl-benzothiazole, 4-trifluoromethyl-benzothiazole, 5-trifluoromethyl-benzothiazole, 6-trifluoromethyl-benzothiazole, 7-trifluoromethyl-benzothiazole, 2-benzothiazolecarboxylic acid methyl ester, 4-benzothiazolecarboxylic acid methyl ester, 5-benzothiazolecarboxylic acid methyl ester, 6-benzothiazolecarboxylic acid methyl ester, 7-benzothiazolecarboxylic acid methyl ester, 2-benzothiazolecarboxylic acid ethyl ester, 4-benzothiazolecarboxylic acid ethyl ester, 5-benzothiazolecarboxylic acid ethyl ester, 6-benzothiazolecarboxylic acid ethyl ester, 7-benzothiazolecarboxylic acid ethyl ester, benzothiazole-2-carbaldehyde, benzothiazole-4-carbaldehyde, benzothiazole-5-carbaldehyde, benzothiazole-6-carbaldehyde, benzothiazole-7-carbaldehyde, 2-acetylbenzothiazole, 4-acetylbenzothiazole, 5-Acetylbenzothiazole, 6-acetylbenzothiazole, and 7-acetylbenzothiazole, 3,4-dihydronaphthalen-1 (2H)-one, 8-methyl-3,4-dihydronaphthalen-1(2H)-one, 7-methyl-3,4-dihydronaphthalen-[(2H)-one, 6-methyl-3,4-dihydronaphthalen-1 (2H)-one, 5-methyl-3,4-dihydronaphthalen-1(2H)-one, 2,3-dihydro-1H-inden-1-one, 7-methyl-2,3-dihydro-1H-inden-1-one, 6-methyl-2,3-dihydro-1H-inden-1-one, 57-methyl-2,3-dihydro-1H-inden-1-one, 4-methyl-2,3-dihydro-1H-inden-1-one and mixtures thereof.

Suitable aprotic polar solvents are acetonitrile, formamide, dimethylformamide (DMF), dimethylacetamide, $(CH_3)_2SO$, dimethyl sulfone, sulfolane, cyclic ureas, such as 1,3-dimethyl-3,4,5,6-tetrahydro-2(1H)-pyrimidinone (DMPU), imidazolidin-2-one and mixtures thereof.

In a special embodiment, the composition according to the invention contains a viscosity-modifying additive. Suitable viscosity-modifying additives are dielectric polymers or semiconductive polymers. Suitable dielectric polymers are e.g. polystyrene, polyimides, fluorinated polyimides, polyarylene ether, polyvinylidene fluoride, polytetrafluoroethylene, poly-2-vinyl-naphthalene (P2VN), etc. A preferred viscosity-modifying additive is polystyrene. Preferably, the viscosity-modifying additive has a solubility in component B) at 20° C. of at least 0.01 mg/ml, preferably of at least 0.05 mg/ml. Preferably, the composition according to the invention contains the viscosity-modifying additive in an amount of 0.1 to 30 wt.-%, preferably 0.2 to 20 wt.-%, based on the total weight of component B) and the viscosity-modifying additive.

The composition according to the invention allows the preparation of various articles, structures, or devices from semiconductors A) by solution-processing. As used herein, "solution-processing" refers to various solution-phase processes including spin-coating, printing (e.g., inkjet printing, screen printing, pad printing, offset printing, gravure printing, flexographic printing, lithographic printing, mass-printing and the like), spray coating, electrospray coating, drop casting, dip coating, and blade coating.

Articles that can be advantageously prepared from the composition according to the invention are electronic devices, optical devices and optoelectronic devices. Those include organic field effect transistors (OFETs) (e.g., organic thin film transistors (OTFTs)), organic photovoltaic devices (OPVs), photodetectors, organic light emitting devices such as organic light emitting diodes (OLEDs) and organic light emitting transistors (OLETs), complementary metal oxide semiconductors (CMOSs), complementary inverters, diodes, capacitors, sensors, D flip-flops, rectifiers, and ring oscillators. All of those articles may contain a semiconductor component A) that is deposited from a composition according to the invention.

In step (b) of the process according to the invention, the solution provided in step (a) is applied to the surface of a substrate to allow evaporation of the solvent or solvent mixture and crystallization of the organic semiconductor A).

A further object of the invention is a process for the preparation of an electronic device, optical device or optoelectronic device, comprising:
(a) providing a solution of at least one organic semiconductor A) in a solvent (L1) or in a solvent mixture comprising a solvent (L1), wherein the solvent (L1) has
  a boiling point at 1013.25 mbar of at least 140° C.,
  a viscosity of at least 1.2 mPas at 23° C., and
  a surface tension of at least 31.5 mN/m at 20° C., (b) applying the solution provided in step (a) to the surface of a substrate to allow evaporation of the solvent or solvent mixture and crystallization of the organic semiconductor A), wherein the substrate provided in step b) is the substrate of an electronic device, optical device or optoelectronic device or wherein the crystals formed in step b) are transferred to an electronic device, optical device, optoelectronic device or sensor.

The depositing step b) can be carried out by printing, including inkjet printing and various contact printing techniques (e.g., screen-printing, gravure printing, offset printing, pad printing, lithographic printing, flexographic printing, and microcontact printing). In other embodiments, the depositing step can be carried out by spin coating, drop-casting, zone casting, slot-coating, dip coating, blade coating, or spraying.

Preferably, in step (b) the application of the composition provided in step (a) to at least a portion of the surface of the substrate is performed by printing.

A wide variety of substrates may be used in the method of the present invention. The substrates may be made of virtually any materials which are stable under the process conditions of the method of the invention. Thus, the substrate may include organic and inorganic materials or composite materials. Suitable substrates are in principle all materials known for this purpose. Suitable substrates comprise, for example, oxidic materials, metals, semiconductors, metal alloys, semiconductor alloys, polymers, inorganic solids, paper and combinations thereof.

Suitable substrates are preferably selected from $SiO_2$, inorganic glasses, quartz, ceramics, undoped or doped inorganic semiconductors, metals of groups 8, 9, 10 or 11 of the Periodic Table and metal alloys thereof, polymeric materials, filled polymeric materials and combinations thereof.

Preferred metal and metal alloy substrates comprise Au, Ag, Cu, etc. Preferred undoped or doped inorganic semiconductors are Si, doped Si, Ge and doped Ge. Preferred polymeric materials are selected from acrylics, epoxies, polyamides, polycarbonates, polyimides, polyvinyl chloride, polyolefins, polystyrene homopolymers and copolymers, polyketones, poly(oxy-1,4-phenyleneoxy-1,4-phenylenecarbonyl-1,4-phenylene (sometimes referred to as poly(ether ether ketone) or PEEK), polynorbornenes, polyphenyleneoxides, poly(ethylene naphthalenedicarboxylate) (PEN), poly(ethylene terephthalate) (PET), poly(phenylene sulfide) (PPS), fluoropolymers, polyurethanes, fiber-reinforced plastics (FRP) and combinations thereof.

Especially preferred substrates are selected from Si, $SiO_2$, glass, quartz, ceramics and combinations thereof. The substrate may be flexible or inflexible, and have a curved or planar geometry, depending on the desired use.

In a special embodiment, at least the surface of the substrate comprises or consists of at least one dielectric. Suitable dielectrics are selected from inorganic dielectric materials, polymeric dielectric materials and combinations thereof. Suitable inorganic dielectric materials are $SiO_2$, $Al_2O_3$, $ZrO_2$, $HfO_2$, $TaO_5$, $WO_3SiO_3N_4$, RbBr, LiF, $BaTiO_3$, $PbTiO_3$, and mixtures thereof. Suitable polymeric dielectric materials are polystyrene, poly-α-methylstyrene, polyolefins (such as polypropylene, polyethylene, polyisobutene), polyvinylcarbazole, fluorinated polymers (e.g. Cytop, CYMM), cyanopullulans, polyvinylphenol, poly-p-xylene, polyvinyl chloride, poly(methyl methacrylate)/trimethylolpropane triacrylate copolymers etc., and combinations thereof. Specific dielectrics are "self-assembled nanodielectrics", i.e. polymers which are obtained from monomers comprising SiCl functionalities, for example $Cl_3SiOSiCl_3$, $Cl_3Si$—$(CH_2)_6$—$SiCl_3$, $Cl_3Si$—$(CH_2)_{12}$—$SiCl_3$, and/or which are crosslinked by atmospheric moisture or by addition of water diluted with solvents (see, for example, Facchetti Adv. Mat. 2005, 17, 1705-1725). Instead of water, it is also possible for hydroxyl-containing polymers such as polyvinylphenol or polyvinyl alcohol or copolymers of vinylphenol and styrene to serve as crosslinking components. It is also possible for at least one further polymer to be present during the crosslinking operation, for example polystyrene, which is then also crosslinked (see Facchetti, US patent application 2006/0202195).

Surface Modification

The surface of the substrate and/or the dielectric can be subjected to a modification prior to the deposition of component A). As mentioned before, the nature of the substrate and its surface modification can have an influence on the deposition of the crystals on the substrate surface and the electrical properties of resulting the electronic device.

In a special embodiment, the surface of the substrate and/or the dielectric is subjected to a modification prior to the deposition of compound A) resulting in a self-assembled monolayer (SAM) of the compounds employed for the modification.

In a further modification only parts of the substrate are covered with the self-assembled monolayer (SAM). Those SAMs lead to a change in the surface energy and the wetting properties. Without being bound by a theory this might be advantageous to achieve a lateral structuring of the morphology of the compound A).

The modification of the surface of the substrate and/or the dielectric prior to the deposition of compound A) may e.g. serve to form regions which bind the semiconductor materials and/or regions on which no semiconductor materials can be deposited. Further, the modification of the surface of the substrate and/or the dielectric may have an influence on the properties of the obtained semiconductor, e.g. its charge transport mobility, on/off ratio, etc.

Suitable compounds for the surface modification are:
silanes, such as alkyltrichlorosilanes, e.g. n-octadecyltrichlorosilane (OTS); compounds with trialkoxysilane groups, e.g. alkyltrialkoxysilanes, such as n-octadecyltrimethoxysilane, n-octadecyltriethoxysi lane, n-octadecyltri(n-propyl)oxysilane, n-octadecyltri(isopropyl) oxysilane; trialkoxyaminoalkylsilanes, such as triethoxyaminopropylsilane and N[(3-triethoxysilyl) propyl]ethylenediamine; trialkoxyalkyl 3-glycidyl ether silanes, such as triethoxypropyl 3-glycidyl ether silane; trialkoxyallylsilanes, such as allyltrimethoxysilane; trialkoxy(isocyanatoalkyl)silanes; trialkoxysilyl (meth)acryloyloxyalkanes and trialkoxysilyl(meth) acrylamidoalkanes, such as 1-triethoxysilyl-3-acryloyl-oxypropane,
phosphonic acids, e.g. 4-ethoxyphenylphosphonic acid,
carboxylic acids,
hydroxamic acids,
amines,
phosphines,
sulfur-comprising compounds, especially thiols, and
mixtures thereof.

The compounds for the surface modification are preferably selected from alkyltrichlorosilanes, alkyltrialkoxysilanes, hexaalkyldisilazanes, $C_8$-$C_{30}$-alkylthiols, mercaptocarboxylic acids, mercaptosulfonic acids and mixtures thereof.

In a special embodiment, the compounds for the surface modification are selected from n-octadecyltrichlorosilane (OTS), n-octadecyltrimethoxysilane, n-octadecyltriethoxysilane, hexamethyldisilazane (HMDS), 4-ethoxyphenylphosphonic acid, hexadecanethiol, mercaptoacetic acid, 3-mercaptopropionic acid, mercaptosuccinic acid and 3-mercapto-1-propanesulfonic acid, the alkali metal and ammonium salts of mercaptoacetic acid, 3-mercaptopropionic acid, mercaptosuccinic acid and 3-mercapto-1-propanesulfonic acid and mixtures thereof.

In order to modify the surface of the substrate with a plethora of functional groups it can be activated with acids or bases. Further, the surface of the substrate can be activated by oxidation, irradiation with electron beams or by plasma treatment. Further, the afore-mentioned substances comprising functional groups can be applied to the surface of the substrate, e.g. via deposition from solution, physical vapor deposition (PVD) or chemical vapor deposition (CVD).

The composition according to the invention is advantageously suitable for the fabrication of organic field-effect transistors. They may be used, for example, for the production of integrated circuits (ICs), for which customary n-channel MOSFETs (metal oxide semiconductor field-effect transistors) have been used to date. These are then CMOS-like semiconductor units, for example for microprocessors, microcontrollers, static RAM and other digital logic circuits. OFETs prepared from the composition according to the invention are especially suitable for use in displays (specifically large-surface area and/or flexible displays), RFID tags, smart labels and sensors.

An aspect of the present teaching relates to the fabrication of an organic field-effect transistor that incorporates a semiconductor component prepared from a composition according to the invention. An OFETs generally comprises a substrate having at least one gate structure including a gate electrode and a gate dielectric, a source electrode and a drain electrode and a semiconductor material that is in contact with the source and drain electrode and the gate dielectric.

A specific embodiment is a substrate with a pattern (topography) of organic field-effect transistors, each transistor comprising
- an organic semiconductor disposed on the substrate;
- a gate structure for controlling the conductivity of the conductive channel; and
- conductive source and drain electrodes at the two ends of the channel.

As a buffer layer, any dielectric material is suitable, for example anorganic materials such as LiF, $AlO_x$, $SiO_2$ or silicium nitride or organic materials such as polyimides or polyacrylates, e.g. polymethylmethacrylate (PMMA).

A further specific embodiment is a substrate having a pattern of organic field-effect transistors, each transistor forming an integrated circuit or being part of an integrated circuit and at least some of the transistors are prepared by deposition of an organic semiconductor from a composition according to the invention.

Suitable substrates are those mentioned above. A typical substrate for semiconductor units comprises a matrix (for example a silicon, quartz or polymer matrix) and, optionally, a dielectric top layer. Suitable dielectrics are those mentioned above, wherein $SiO_2$ is especially preferred.

The substrate may additionally have electrodes, such as gate, drain and source electrodes of OFETs, which are normally localized on the substrate (for example deposited onto or embedded into a nonconductive layer on the dielectric). The substrate may additionally comprise conductive gate electrodes of the OFETs, which are typically arranged below the dielectric top layer (i.e. the gate dielectric).

In a specific embodiment, an insulator layer (gate insulating layer) is present on at least part of the substrate surface. The insulator layer comprises at least one insulator which is preferably selected from inorganic insulators, such as $SiO_2$, silicon nitride ($Si_3N_4$), etc., ferroelectric insulators, such as $Al_2O_3$, $Ta_2O_5$, $La_2O_5$, $TiO_2$, $Y_2O_3$, etc., organic insulators such as polyimides, benzocyclobutene (BCB), polyvinyl alcohols, polyacrylates, etc., and combinations thereof.

Suitable materials for source and drain electrodes are in principle electrically conductive materials. These include metals, preferably metals of groups 6, 7, 8, 9, 10 or 11 of the Periodic Table, such as Pd, Au, Ag, Cu, Al, Ni, Cr, etc. Also suitable are conductive polymers, such as PEDOT (=poly (3,4-ethylenedioxythiophene)):PSS (=poly(styrenesulfonate)), polyaniline, surface-modified gold, etc. Preferred electrically conductive materials have a specific resistance of less than $10^{-3}$ ohm×meter, preferably less than $10^{-4}$ ohm×meter, especially less than $10^{-6}$ or $10^{-7}$ ohm×meter.

In a specific embodiment, drain and source electrodes are present at least partly on the organic semiconductor material. It will be appreciated that the substrate may comprise further components as used customarily in semiconductor materials or ICs, such as insulators, resistors, capacitors, conductor tracks, etc.

The electrodes may be applied by customary processes, such as evaporation or sputtering, lithographic processes or another structuring process, such as printing techniques.

The resulting semiconductor layers generally have a thickness which is sufficient for forming a semiconductor channel which is in contact with the source/drain electrodes.

The semiconductor component is preferably deposited on the substrate in a thickness of from 0.5 to 1000 nm, more preferably from 1.5 to 250 nm.

In a preferred embodiment, the inventive field-effect transistor is a thin-film transistor (TFT). In a customary construction, a thin-film transistor has a gate electrode disposed on the substrate or buffer layer (the buffer layer being part of the substrate), a gate insulation layer disposed thereon and on the substrate, a semiconductor layer disposed on the gate insulator layer, an ohmic contact layer on the semiconductor layer, and a source electrode and a drain electrode on the ohmic contact layer.

In a preferred embodiment, the surface of the substrate, before the deposition of at least one compound of the general formula A) is subjected to a modification as mentioned above.

Various semiconductor architectures are conceivable from the composition according to the invention, for example top contact, top gate, bottom contact, bottom gate, or else a vertical construction, for example a VOFET (vertical organic field-effect transistor), as described, for example, in US 2004/0046182.

Preferred semiconductor architectures are the following:
1. substrate, dielectric, organic semiconductor, preferably gate, dielectric, organic semiconductor, source and drain, known as "Bottom Gate Top Contact";
2. substrate, dielectric, organic semiconductor, preferably substrate, gate, dielectric, source and drain, organic semiconductor, known as "Bottom Gate Bottom Contact";
3. substrate, organic semiconductor, dielectric, preferably substrate, source and drain, organic semiconductor, dielectric, gate, known as "Top Gate Bottom Contact";
4. substrate, organic semiconductor, dielectric, preferably substrate, organic semiconductor, source and drain, dielectric, gate, known as "Top Gate Top Contact".

The layer thicknesses are, for example, from 0.5 nm to 5 µm in semiconductors, from 30 nm to 10 µm in the dielectric; the electrodes may, for example, be from 20 nm to 10 µm. The OFETs may also be combined to form other components, such as ring oscillators or inverters.

A further aspect of the invention is the provision of electronic components which comprise a plurality of semiconductor components, which may be n- and/or p-semiconductors. Examples of such components are field-effect transistors (FETs), bipolar junction transistors (BJTs), tunnel diodes, converters, light-emitting components, biological and chemical detectors or sensors, temperature-dependent detectors, photodetectors, such as polarization-sensitive photodetectors, gates, AND, NAND, NOT, OR, TOR and NOR gates, registers, switches, timer units, static or dynamic stores and other dynamic or sequential, logical or other digital components including programmable switches.

A specific semiconductor element is an inverter. In digital logic, the inverter is a gate which inverts an input signal. The inverter is also referred to as a NOT gate. Real inverter switches have an output current which constitutes the opposite of the input current. Typical values are, for example, (0, +5V) for TTL switches. The performance of a digital inverter reproduces the voltage transfer curve (VTC), i.e. the plot of input current against output current. Ideally, it is a staged function and, the closer the real measured curve approximates to such a stage, the better the inverter is.

The composition according to the invention is also particularly suitable for use in organic photovoltaics (OPVs). An aspect of the present teaching relates to the fabrication of organic solar cells, e.g. solar cells which are characterized by diffusion of excited states (exciton diffusion). In this case, one or both of the semiconductor materials utilized is notable for a diffusion of excited states (exciton mobility). Organic solar cells generally have a layer structure and generally comprise at least the following layers: anode, photoactive layer and cathode. These layers are generally applied to a substrate suitable for this purpose. The structure of organic solar cells is described, for example, in US 2005/0098726 and US 2005/0224905.

A representative organic solar cell comprises a substrate with at least one cathode and at least one anode and at least one photoactive region comprising a semiconductor material. A photoactive region may comprise two layers, each of which has a homogeneous composition and forms a flat donor-acceptor heterojunction. A photoactive region may also comprise a mixed layer and form a donor-acceptor heterojunction in the form of a donor-acceptor bulk heterojunction.

Suitable substrates for organic solar cells are those mentioned above, for example, oxidic materials, polymers and combinations thereof. Preferred oxidic materials are selected from glass, ceramic, $SiO_2$, quartz, etc. Preferred polymers are selected from polyethylene terephthalates, polyolefins (such as polyethylene and polypropylene), polyesters, fluoropolymers, polyamides, polyurethanes, polyalkyl (meth) acrylates, polystyrenes, polyvinyl chlorides and mixtures and composites.

Suitable electrodes (cathode, anode) are in principle metals, semiconductors, metal alloys, semiconductor alloys, nanowire thereof and combinations thereof. Preferred metals are those of groups 2, 8, 9, 10, 11 or 13 of the periodic table, e.g. Pt, Au, Ag, Cu, Al, In, Mg or Ca. Preferred semiconductors are, for example, doped Si, doped Ge, indium tin oxide (ITO), fluorinated tin oxide (FTO), gallium indium tin oxide (GITO), zinc indium tin oxide (ZITO), poly(3,4-ethylenedioxythiophene) poly(styrenesulfonate) (PEDOT-PSS), etc. Preferred metal alloys are, for example, alloys based on Pt, Au, Ag, Cu, etc. A specific embodiment is Mg/Ag alloys.

The material used for the electrode facing the light (the anode in a normal structure, the cathode in an inverse structure) is preferably a material at least partly transparent to the incident light. This preferably includes electrodes which have glass and/or a transparent polymer as a carrier material. Transparent polymers suitable as carriers are those mentioned above, such as polyethylene terephthalate. The electrical contact connection is generally effected by means of metal layers and/or transparent conductive oxides (TCOs). These preferably include ITO, doped ITO, FTO (fluorine doped tin oxide), AZO (aluminum doped tin oxide), ZnO, $TiO_2$, Ag, Au, Pt or graphene or multi layer graphene or carbon nanotubes. Particular preference is given to ITO for contact connection. For electrical contact connection, it is also possible to use a conductive polymer, for example a poly-3,4-alkylenedioxythiophene, e.g. poly-3,4-ethyleneoxythiophene poly(styrenesulfonate) (PEDOT).

The electrode facing the light is configured such that it is sufficiently thin to bring about only minimal light absorption but thick enough to enable good charge transport of the extracted charge carriers. The thickness of the electrode layer (without carrier material) is preferably within a range from 20 to 200 nm.

In a specific embodiment, the material used for the electrode facing away from the light (the cathode in a normal structure, the anode in an inverse structure) is a material which at least partly reflects the incident light. This includes metal films, preferably of Ag, Au, Al, Ca, Mg, In, and mixtures thereof. Preferred mixtures are Mg/Al. The thickness of the electrode layer is preferably within a range from 20 to 300 nm.

The photoactive region comprises or consists of at least one layer which comprises an organic semiconductor A). In addition to the photoactive layer there may be one or more further layer(s). These are, for example, selected from
- layers with electron-conducting properties (electron transport layer, ETL),
- layers which comprise a hole-conducting material (hole transport layer, HTL), which need not absorb any radiation,
- exciton- and hole-blocking layers (e.g. EBLs), which must not absorb, and
- multiplication layers.

Suitable materials for these layers are described in detail hereinafter.

Suitable exciton- and hole-blocking layers are described, for example, in U.S. Pat. No. 6,451,415.

Suitable materials for exciton-blocking layers are, for example, bathocuproin (BCP), 4,4',4''-tris[3-methylphenyl-N-phenylamino]triphenylamine (m-MTDATA).

The solar cells preferably comprise at least one photoactive donor-acceptor heterojunction. Optical excitation of an organic material generates excitons. In order that a photocurrent occurs, the electron-hole pair has to be separated, typically at a donor-acceptor interface between two unlike contact materials. At such an interface, the donor material forms a heterojunction with an acceptor material. When the charges are not separated, they can recombine in a process also known as "quenching", either radioactively by the emission of light of a lower energy than the incident light or nonradiatively by generation of heat. Both processes are undesired.

If at least one compound of the general formula (I) is used as an n-semiconductor (electron conductor, acceptor) it is employed as the ETM (electron transport material) of the solar cell. It can then be combined with an appropriate p-semiconductor (electron donor material) that is employed as the HTM (hole transport material) of the solar cell. Hole-conducting materials preferably comprise at least one material with high ionization energy. The materials may be organic or inorganic materials.

Suitable HTMs are, for example,
N,N'-Bis(naphthalen-1-yl)-N,N'-bis(phenyl)-9,9-dimethyl-fluoren,
N,N'-Bis(3-methylphenyl)-N,N'-bis(phenyl)-9,9-diphenyl-fluoren,
N,N'-Bis(naphthalen-1-yl)-N,N'-bis(phenyl)-9,9-diphenyl-fluoren,
N,N'-Bis(naphthalen-1-yl)-N,N'-bis(phenyl)-2,2-dimethyl-benzidin,
N,N'-Bis(3-methylphenyl)-N,N'-bis(phenyl)-9,9-spirobif-luoren,
2,2',7,7'-Tetrakis(N, N-diphenylamino)-9,9'-spirobifluoren,
N,N'-Bis(naphthalen-1-yl)-N,N'-bis(phenyl)-benzidin,
N,N'-Bis(naphthalen-2-yl)-N,N'-bis(phenyl)-benzidin,
N,N'-Bis(3-methylphenyl)-N,N'-bis(phenyl)-benzidin,
N,N'-Bis(3-methylphenyl)-N,N'-bis(phenyl)-9,9-dimethyl-fluoren,
N,N'-Bis(naphthalen-1-yl)-N,N'-bis(phenyl)-9,9-spirobif-luoren,
Di-[4-(N,N-ditolyl-amino)-phenyl]cyclohexan,
2,2',7,7'-tetra(N,N-di-tolyl)amino-spirobifluoren,
9,9-Bis[4-(N,N-bis-biphenyl-4-yl-amino)phenyl]-9H-fluoren,
2,2',7,7'-Tetrakis[N-naphthalenyl(phenyl)-amino]-9,9-spiro-bifluoren,
2,7-Bis[N,N-bis(9,9-spiro-bifluorene-2-yl)-amino]-9,9-spi-robifluoren,
2,2'-Bis[N,N-bis(biphenyl-4-yl)amino]-9,9-spirobifluoren,
N,N'-bis(phenanthren-9-yl)-N,N'-bis(phenyl)-benzidin,
N,N,N',N'-tetra-naphthalen-2-yl-benzidin,
2,2'-Bis(N,N-di-phenyl-amino)-9,9-spirobifluoren,
9,9-Bis[4-(N,N-bis-naphthalen-2-yl-amino)phenyl]-9H-fluoren,
9,9-Bis[4-(N,N'-bis-naphthalen-2-yl-N,N'-bis-phenyl-amino)phenyl]-9H-fluoren,
Titanium oxide phthalocyanin, Copper phthalocyanin,
2,3,5,6-Tetrafluoro-7,7,8,8,-tetracyano-quinodimethan,
4,4',4"-Tris(N-3-methylphenyl-N-phenyl-amino)triph-enylamin,
4,4',4"-Tris(N-(2-naphthyl)-N-phenyl-amino)triph-enylamin,
4,4',4"-Tris(N-(1-naphthyl)-N-phenyl-amino)triph-enylamin,
4,4',4"-Tris(N,N-diphenyl-amino)triphenylamin,
Pyrazino[2,3-f][1,10]phenanthroline-2,3-dicarbonitril
N,N,N',N'-Tetrakis(4-methoxyphenyl)benzidin,
2,7-Bis[N,N-bis(4-methoxy-phenyl)amino]-9,9-spirobifluo-ren,
2,2'-Bis[N,N-bis(4-methoxy-phenyl)amino]-9,9-spirobif-luoren,
N,N'-di(naphthalen-2-yl)-N,N'-diphenylbenzene-1,4-di-amin,
N,N'-di-phenyl-N,N'-di-[4-(N,N-di-tolyl-amino)phenyl] benzidin,
N,N'-di-phenyl-N,N'-di-[4-(N,N-di-phenyl-amino)phenyl] benzidin.

Examples of polymeric hole transport materials, are PEDOT (poly (3,4-ethylenedioxythiophene), polyvinylcar-bazole (PVK), poly(N,N'-bis (4-butylphenyl)-N,N'-bis(phe-nyl) benzidine (PTPD), polyaniline (PANI) and poly (3-hex-ylthiophene (P3HT).

In a first embodiment, the heterojunction has a flat configuration (see: Two layer organic photovoltaic cell, C. W. Tang, Appl. Phys. Lett., 48 (2), 183-185 (1986) or N. Karl, A. Bauer, J. Holzäpfel, J. Marktanner, M. Möbus, F. Stölzle, Mol. Cryst. Liq. Cryst., 252, 243-258 (1994).).

In a second preferred embodiment, the heterojunction is configured as a bulk (mixed) heterojunction, also referred to as an interpenetrating donor-acceptor network. Organic photovoltaic cells with a bulk heterojunction are described, for example, by C. J. Brabec, N. S. Sariciftci, J. C. Hummelen in Adv. Funct. Mater., 11 (1), 15 (2001) or by J. Xue, B. P. Rand, S. Uchida and S. R. Forrest in J. Appl. Phys. 98, 124903 (2005). Bulk heterojunctions are discussed in detail hereinafter.

The composition according to the invention can be used for the fabrication of the photoactive material in cells with MiM, pin, pn, Mip or Min structure (M=metal, p=p-doped organic or inorganic semiconductor, n=n-doped organic or inorganic semiconductor, i=intrinsically conductive system of organic layers; see, for example, J. Drechsel et al., Org. Electron., 5 (4), 175 (2004) or Maennig et al., Appl. Phys. A 79, 1-14 (2004)).

The composition according to the invention can also be used for the fabrication of the photoactive material in tandem cells. Suitable tandem cells are described, for example, by P. Peumans, A. Yakimov, S. R. Forrest in J. Appl. Phys., 93 (7), 3693-3723 (2003) (see also U.S. Pat. No. 4,461,922, U.S. Pat. No. 6,198,091 and U.S. Pat. No. 6,198,092) and are described in detail hereinafter.

The composition according to the invention can also be used for the fabrication of the photoactive material in tandem cells which are constructed from two or more than two stacked MiM, pin, Mip or Min structures (see DE 103 13 232.5 and J. Drechsel et al., Thin Solid Films, 451452, 515-517 (2004)).

The layer thickness of the M, n, i and p layers is typically within a range from 10 to 1000 nm, more preferably from 10 to 400 nm. The other layers which form the solar cell can be produced by customary processes known to those skilled in the art. These include vapor deposition under reduced pressure or in an inert gas atmosphere, laser-ablation or solution or dispersion processing methods such as spincoating, knife-coating, casting methods, spray application, dipcoating or printing (e.g. inkjet, flexographic, offset, gravure; intaglio, nanoimprinting). In a specific embodiment, the entire solar cell is produced by solution processing.

In a suitable embodiment, the solar cells are present as an individual cell with flat heterojunction and normal structure. In a specific embodiment, the cell has the following structure:

an at least partly transparent conductive layer (top electrode, anode) (11)
a hole-conducting layer (12)
a layer which comprises a donor material (13)
a layer which comprises an acceptor material (14)
an exciton-blocking and/or electron-conducting layer (15)
a second conductive layer (back electrode, cathode) (16)

The essentially transparent conductive layer (11) (anode) comprises a carrier, such as glass or a polymer (e.g. polyethylene terephthalate) and a conductive material, as described above. Examples include ITO, doped ITO, FTO, ZnO, AZO, etc. The anode material can be subjected to a surface treatment, for example with UV light, ozone, oxygen plasma, $Br_2$, etc. The layer (11) should be sufficiently thin to enable maximum light absorption, but also sufficiently thick to ensure good charge transport. The layer thickness of the transparent conductive layer (11) is preferably within a range from 20 to 200 nm.

Solar cells with normal structure optionally have a hole-conducting layer (=layer 12). This layer comprises at least one hole-conducting material (hole transport material, HTM). Hole-conducting materials (HTM) suitable for forming layers with hole-conducting properties (HTL) preferably comprise at least one material with high ionization energy. The ionization energy is preferably at least 5.0 eV, more preferably at least 5.5 eV. The materials may be organic or inorganic materials. Organic materials suitable for use in a layer with hole-conducting properties are preferably selected from poly(3,4-ethylenedioxythiophene) poly(styrenesulfonate) (PEDOT-PSS), Ir-DPBIC (tris-N,N'-diphenyl-benzimidazol-2-ylideneiridium(III)), N,N'-diphenyl-N,N'-bis(3-methylphenyl)-1,1'-diphenyl-4,4'-diamine (α-NPD), 2,2',7,7'-tetrakis(N,N-di-p-methoxyphenylamine)-9,9'-spirobifluorene (spiro-MeOTAD), etc. and mixtures thereof. The organic materials may, if desired, be doped with a p-dopant which has a LUMO within the same range as or lower than the HOMO of the hole-conducting material.

Suitable dopants are, for example, 2,3,5,6-tetrafluoro-7,7,8,8-tetracyanoquino-dimethane ($F_4TCNQ$), $WO_3$, $MoO_3$, etc. Inorganic materials suitable for use in a layer with hole-conducting properties are preferably selected from $WO_3$, $MoO_3$, etc.

If present, the thickness of the layers with hole-conducting properties is preferably within a range from 5 to 200 nm, more preferably 10 to 100 nm.

Layer (13) comprises at least one donor material. The thickness of the layer should be sufficient to absorb a maximum amount of light, but thin enough to enable effective dissipation of the charge. The thickness of the layer (13) is preferably within a range from 5 nm to 1 μm, more preferably from 5 to 100 nm.

Layer (14) comprises at least acceptor material. The thickness of the layer should be sufficient to absorb a maximum amount of light, but thin enough to enable effective dissipation of the charge. The thickness of the layer (14) is preferably within a range from 5 nm to 1 μm, more preferably from 5 to 80 nm.

Suitable donor and acceptor materials are in principle organic semiconductors, wherein at least one is a semiconductor A) deposited fro a composition according to the invention.

Solar cells with normal structure optionally comprise an exciton-blocking and/or electron-conducting layer (15) (EBL/ETL). Suitable materials for exciton-blocking layers generally have a greater band gap than the materials of layer (13) and/or (14). They are firstly capable of reflecting excitons and secondly enable good electron transport through the layer. The materials for the layer (15) may comprise organic or inorganic materials. Suitable organic materials are preferably selected from 2,9-dimethyl-4,7-diphenyl-1, 10-phenanthroline (BCP), 4,7-diphenyl-1,10-phenanthroline (Bphen), 1,3-bis[2-(2,2'-bipyridin-6-yl)-1,3,4-oxadiazo-5-yl]benzene (BPY-OXD), etc. The organic materials may, if desired, be doped with an n-dopant which has a HOMO within the same range as or lower than the LUMO of the electron-conducting material. Suitable dopants are, for example, $Cs_2CO_3$, Pyronin B (PyB), Rhodamine B, cobaltocenes, etc. Inorganic materials suitable for use in a layer with electron-conducting properties are preferably selected from ZnO, etc. If present, the thickness of the layer (15) is preferably within a range from 5 to 500 nm, more preferably 10 to 100 nm.

Layer 16 is the cathode and preferably comprises at least one compound with low work function, more preferably a metal, such as Ag, Al, Mg, Ca, etc. The thickness of the layer (16) is preferably within a range from about 10 nm to 10 μm, e.g. 10 nm to 60 nm.

In a further suitable embodiment, the inventive solar cells are present as an individual cell with a flat heterojunction and inverse structure.

In a specific embodiment, the cell has the following structure:
- an at least partly transparent conductive layer (cathode) (11)
- an exciton-blocking and/or electron-conducting layer (12)
- a layer which comprises an acceptor material (13)
- a layer which comprises a donor material (14)
- a hole-conducting layer (15)
- a second conductive layer (back electrode, anode) (16)

With regard to suitable and preferred materials for the layers (11) to (16), reference is made to the above remarks regarding the corresponding layers in solar cells with normal structure.

In a suitable embodiment, the inventive solar cell is a tandem cell.

A tandem cell consists of two or more than two (e.g. 3, 4, 5, etc.) subcells. A single subcell, some of the subcells or all subcells may have photoactive donor-acceptor heterojunctions. Each donor-acceptor heterojunction may be in the form of a flat heterojunction or in the form of a bulk heterojunction. According to the invention, the photoactive layer of at least one subcell is prepared from a composition according to the invention. The subcells which form the tandem cell may be connected in parallel or in series. The subcells which form the tandem cell are preferably connected in series. There is preferably an additional recombination layer in each case between the individual subcells. The individual subcells have the same polarity, i.e. generally either only cells with normal structure or only cells with inverse structure are combined with one another.

"Subcell" refers here to a cell as defined above without cathode and anode. The subcells may, for example, either all have polymorph 2 in the photoactive layer or have other combinations of semiconductor materials, for example C60 with zinc phthalocyanine, C60 with oligothiophene (such as DCV5T). In addition, individual subcells may also be configured as dye-sensitized solar cells or polymer cells.

In addition to the compounds of the general formula (I.a) and (I.b) the following semiconductor materials are suitable for use in organic photovoltaics:

Acenes, such as anthracene, tetracene, pentacene and substituted acenes. Substituted acenes comprise at least one substituent selected from electron-donating substituents (e.g. alkyl, alkoxy, ester, carboxylate or thioalkoxy), electron-withdrawing substituents (e.g. halogen, nitro or cyano) and combinations thereof. These include 2,9-dialkylpentacenes and 2,10-dialkylpentacenes, 2,10-dialkoxypentacenes, 1,4,8,11-tetraalkoxypentacenes and rubrene (5,6,11,12-tetraphenylnaphthacene). Suitable substituted pentacenes are described in US 2003/0100779 and U.S. Pat. No. 6,864,396. A preferred acene is rubrene (5,6,11,12-tetraphenylnaphthacene).

Phthalocyanines, such as hexadecachlorophthalocyanines and hexadecafluorophthalocyanines, metal-free phthalocyanine and phthalocyanine comprising divalent metals, especially those of titanyloxy, vanadyloxy, iron, copper, zinc, especially copper phthalocyanine, zinc phthalocyanine and metal-free phthalocyanine, copper hexadecachlorophthalocyanine, zinc hexadecachlorophthalocyanine, metal-free hexadecachlorophthalocyanine, copper hexadecafluorophthalocyanine, hexadecafluorophthalocyanine or metal-free hexadecafluorophthalocyanine.

Porphyrins, for example 5,10,15,20-tetra(3-pyridyl)porphyrin (TpyP).

Liquid-crystalline (LC) materials, for example hexabenzocoronene (HBC-PhC12) or other coronenes, coronenediimides, or triphenylenes, such as 2,3,6,7,10,11-hexahexylthiotriphenylene (HTT6) or 2,3,6,7,10,11-hexakis(4-n-nonylphenyl)triphenylene (PTP9), 2,3,6,7,10,11-hexakis(undecyloxy)triphenylene (HAT11). Particular preference is given to LCs which are discotic.

Thiophenes, oligothiophenes and substituted derivatives thereof. Suitable oligothiophenes are quaterthiophenes, quinquethiophenes, sexithiophenes, $\alpha,\omega$-di($C_1$-$C_8$)alkyloligothiophenes such as $\alpha,\omega$-dihexylquaterthiophenes, $\alpha,\omega$-dihexylquinquethiophenes and $\alpha,\omega$-dihexylsexithiophenes, poly(alkylthiophenes) such as poly(3-hexylthiophene), bis(dithienothiophenes), anthradithiophenes and dialkylanthradithiophenes such as dihexylanthradithiophene, phenylene-thiophene (P-T) oligomers and derivatives thereof, especially $\alpha,\omega$-alkyl-substituted phenylene-thiophene oligomers.

Preferred thiophenes, oligothiophenes and substituted derivatives thereof, are poly-3-hexylthiophene (P3HT) or compounds of the $\alpha$ $\alpha'$-bis(2,2-dicyanovinyl)quin-quethiophene (DCV5T) type, poly(3-(4-octylphenyl)-2,2'-bithiophene) (PTOPT), poly(3-(4'-(1",4",7"-trioxaoctyl)phenyl) thiophene) (PEOPT), poly(3-(2'-methoxy-5'-octylphenyl) thiophenes) (POMeOPTs), poly(3-octylthiophene) (P3OT), pyridine-containing polymers such as poly(pyridopyrazine vinylene), poly(pyridopyrazine vinylene) modified with alkyl groups e.g. EHH-PpyPz, PTPTB copolymers, polybenzimidazobenzophenanthroline (BBL), poly(9,9-dioctyl-fluorene-co-bis-N,N'-(4-methoxyphenyl)-bis-N,N'-phenyl-1,4-phenylenediamine) (PFMO); see Brabec C., Adv. Mater., 2996, 18, 2884. (PCPDTBT) poly[2,6-(4,4-bis(2-ethylhexyl)-4H-cyclopenta[2,1-b;3,4-b']-dithiophene)-4,7-(2,1,3-benzothiadiazoles)].

Paraphenylenevinylene and paraphenylenevinylene-comprising oligomers and polymers, for example polyparaphenylenevinylene (PPV), MEH-PPV (poly(2-methoxy-5-(2'-ethylhexyloxy)-1,4-phenylenevinylene)), MDMO-PPV (poly(2-methoxy-5-(3',7'-dimethyloctyloxy)-1,4-phenylenevinylene)), cyano-paraphenylenevinylene (CN-PPV), CN-PPV modified with alkoxy groups.

PPE-PPV hybrid polymers (phenylene-ethynylene/phenylene-vinylene hybrid polymers).

Polyfluorenes and alternating polyfluorene copolymers, for example with 4,7-dithien-2'-yl-2,1,3-benzothiadiazoles, and also poly(9,9'-dioctylfluorene-co-benzothiadiazole) ($F_8BT$), poly(9,9'-dioctylfluorene-co-bis-N,N'-(4-butylphenyl)-bis-N,N'-phenyl-1,4-phenylenediamine) (PFB).

Polycarbazoles, i.e. carbazole-comprising oligomers and polymers, such as (2,7) and (3,6).

Polyanilines, i.e. aniline-comprising oligomers and polymers.

Triarylamines, polytriarylamines, polycyclopentadienes, polypyrroles, polyfuran, polysilols, polyphospholes, N,N'-Bis-(3-methylphenyl)-N,N'-bis-(phenyl)-benzidine (TPD), 4,4'-bis(carbazol-9-yl) biphenyl (CBP), 2,2',7,7'-tetrakis-(N,N-di-p-methoxyphenyl-amine)-9,9'-spirobifluorene (spiro-MeOTAD).

Fullerenes, especially C60 and derivatives thereof such as PCBM (=[6,6]-phenyl-$C_{61}$-butyric acid methyl ester). In such cases, the fullerene derivative would be a hole conductor.

Copper(I) iodide, copper(I) thiocyanate.

p-n-Mixed materials, i.e. donor and acceptor in one material, polymer, block copolymers, polymers with C60s, C60 azo dyes, trimeric mixed material which comprises compounds of the carotenoid type, porphyrin type and quinoid liquid-crystalline compounds as donor/acceptor systems, as described by Kelly in S. Adv. Mater. 2006, 18, 1754.

An aspect of the present teaching relates to the fabrication of an electroluminescent (EL) arrangement comprising an upper electrode, a lower electrode, wherein at least one of said electrodes is transparent, an electroluminescent layer and optionally an auxiliary layer, wherein the electroluminescent arrangement comprises a semiconductor component prepared fro a composition according to the invention. An EL arrangement is characterized by the fact that it emits light when an electrical voltage is applied with flow of current. Such arrangements have been known for a long time in industry and technology as light-emitting diodes (LEDs). Light is emitted on account of the fact that positive charges (holes) and negative charges (electrons) combine with the emission of light. In the sense of this application the terms electroluminescing arrangement and organic light-emitting diode (OLEDs) are used synonymously. As a rule, EL arrangements are constructed from several layers. At least on of those layers contains one or more organic charge transport compounds. The layer structure is in principle as follows:

1. Carrier, substrate
2. Base electrode (anode)
3. Hole-injecting layer
4. Hole-transporting layer
5. Light-emitting layer
6. Electron-transporting layer
7. Electron-injecting layer
8. Top electrode (cathode)
9. Contacts
10. Covering, encapsulation This structure represents the most general case and can be simplified by omitting individual layers, so that one layer performs several tasks. In the simplest case an EL arrangement consists of two electrodes between which an organic layer is arranged, which fulfills all functions, including emission of light. The structure of organic light-emitting diodes and processes for their production are known in principle to those skilled in the art, for example from WO 2005/019373. Suitable materials for the individual layers of OLEDs are disclosed, for example, in WO 00/70655. Reference is made here to the disclosure of these documents. In principle OLEDs according to the invention can be produced by methods known to those skilled in the art. The OLED can be produced by successive deposition of the individual layers onto a suitable substrate. In a suitable embodiment, all layers are prepared by solution processing. In an alternative embodiment, at least one layer that does not contain the semiconductor A) may be coated by vapour phase deposition techniques known to those skilled in the art.

Suitable as substrate 1 are transparent carriers, such as glass or plastics films (for example polyesters, such as polyethylene terephthalate or polyethylene naphthalate, polycarbonate, polyacrylate, polysulphone, polyimide foil). Suitable as transparent and conducting materials are a) metal oxide, for example indium-tin oxide (ITO), tin oxide (NESA), etc. and b) semi-transparent metal films, for example Au, Pt, Ag, Cu, etc.

At least one semiconductor A) serves as a charge transport material (electron conductor). Thus, at least one of the following layers: the electron-injecting layer, the electron transporting layer or part of the transparent electrode incorporates a semiconductor component prepared from a composition according to the invention.

In the EL applications according to the invention low molecular weight or oligomeric as well as polymeric materials may be used as light-emitting layer 5. The substances are characterized by the fact that they are photoluminescing. Accordingly, suitable substances are for example fluorescent dyes and fluorescent products that are forming oligomers or are incorporated into polymers. Examples of such materials are coumarins, perylenes, anthracenes, phenanthrenes, stilbenes, distyryls, methines or metal complexes such as $Alq_3$ (tris(8-hydroxyquinolinato)aluminium), etc. Suitable polymers include optionally substituted phenylenes, phenylene vinylenes or polymers with fluorescing segments in the polymer side chain or in the polymer backbone. A detailed list is given in EP-A-532 798. Preferably, in order to increase the luminance, electron-injecting or hole-injecting layers (3 and/or 7) can be incorporated into the EL arrangements. A large number of organic compounds that transport charges (holes and/or electrons) are described in the literature. Mainly low molecular weight substances are used, which are suitable for solution processing. A comprehensive survey of the classes of substances and their use is given for example in the following publications: EP-A 387 715, U.S. Pat. No. 4,539,507, U.S. Pat. No. 4,720,432 and U.S. Pat. No. 4,769,292. A preferred material is PEDOT (poly-(3,4-ethylenedioxythiophene)) which can also be employed in the transparent electrode of the OLEDs.

As a result of the use of the composition according to the invention it is possible to obtain OLEDs with high efficiency. Those OLEDs can be used in all devices in which electroluminescence is useful. Suitable devices are preferably selected from stationary and mobile visual display units. Stationary visual display units are, for example, visual display units of computers, televisions, visual display units in printers, kitchen appliances and advertising panels, illuminations and information panels. Mobile visual display units are, for example, visual display units in cell phones, laptops, digital cameras, vehicles and destination displays on buses and trains. Moreover, the composition according to the invention may be used for the fabrication of OLEDs with inverse structure. The structure of inverse OLEDs and the materials typically used therein are known to those skilled in the art.

The following figures and examples serve to illustrate the invention and should not be interpreted as limiting.

The following compounds (A) were used:

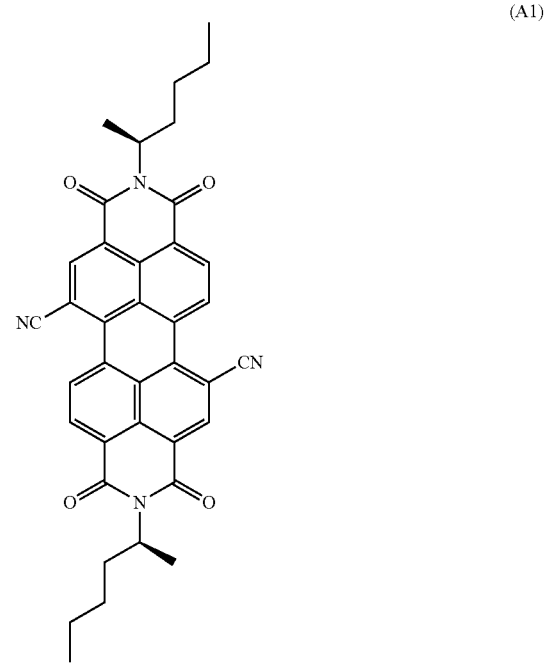

(A1)

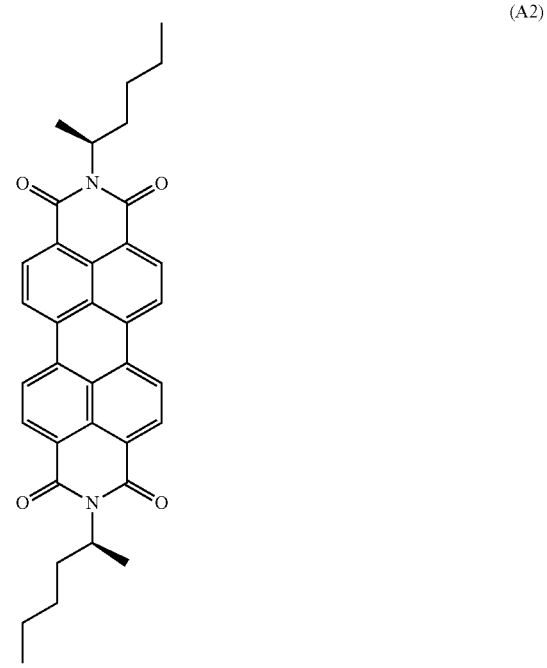

(A2)

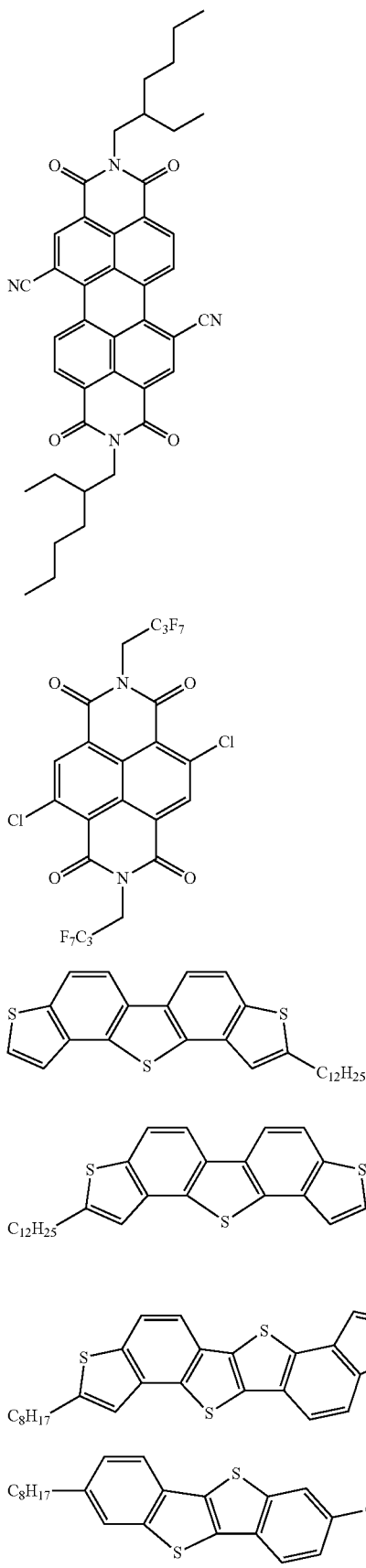

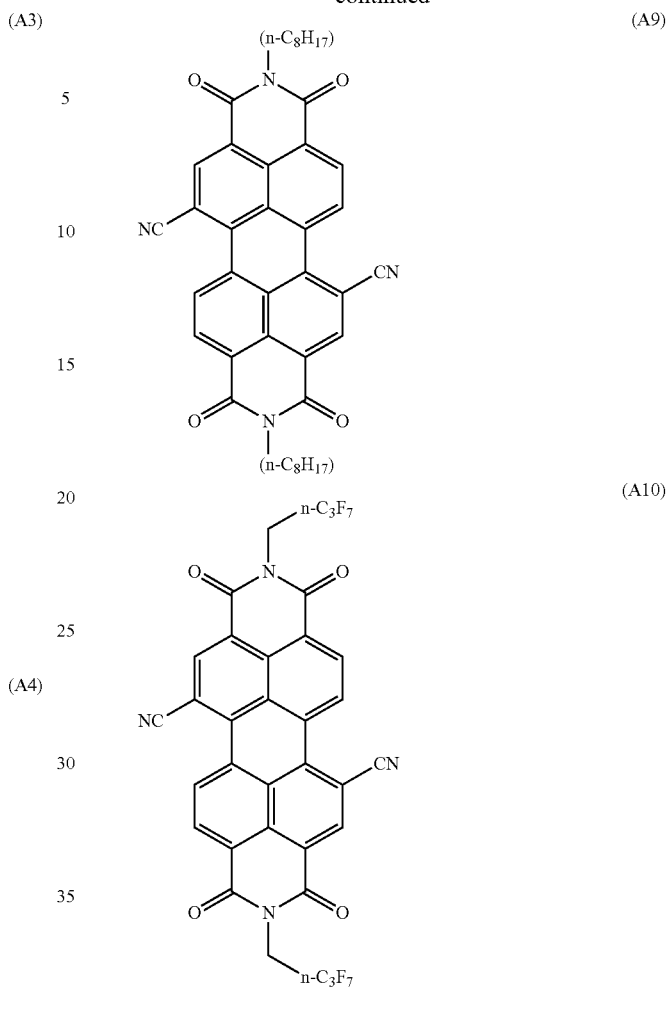

EXAMPLES

Figure 1:
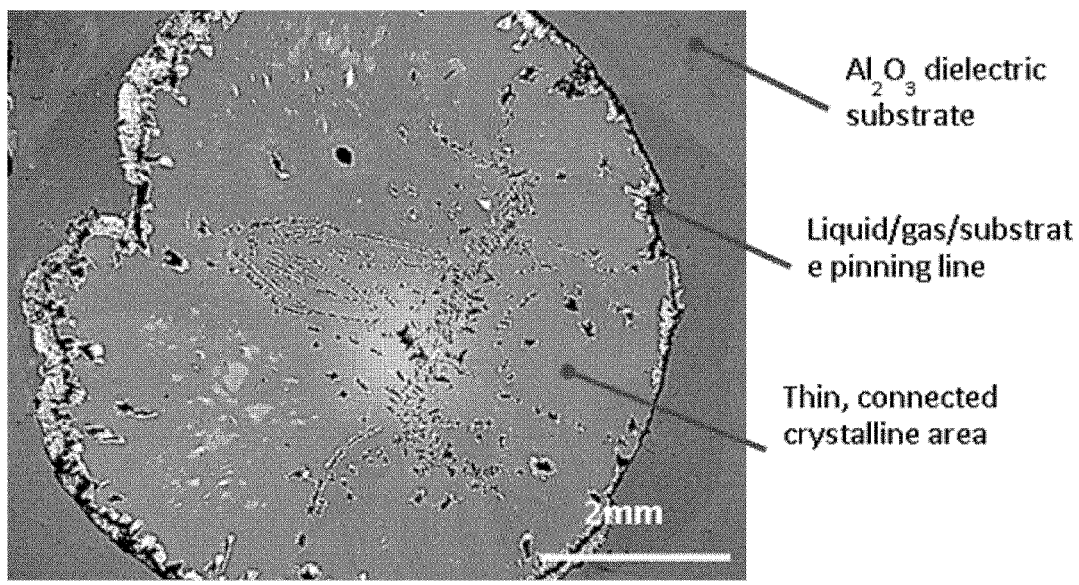
FIG. 1 shows the polarized optical micrograph of the crystalline organic film obtained by drop-casting of compound A1) from a mixture of DMP:Toluene (1:3) (example 1).

Sample Preparation 1 (Mainly Used for the Characterization of the Various Semiconductors):

Degenerately doped silicon wafers (wafers from WRS Materials heavily p-doped with boron, 550-600 μm thickness) coated with a 240 nm thermally grown silicon dioxide were used as substrate. They were subjected to 2 min oxygen plasma treatment (100 W, 20 standard cubic centimeters per minute (sccm) gas flow) and subsequently immersed into a 0.2 vol % solution of octadecyltrichlorosilane (OTS) in toluene for 17 minutes at room temperature. Subsequently the sample was removed from the solution, rinsed with toluene and baked for 30 min at 90° C. Subsequently a 0.5-1 mm thick layer of polydimethylsiloxane (PDMS) comprising holes with a diameter of 7.3 mm was placed onto the hydrophobic substrate that was subsequently subjected to a 5 minutes treatment with air plasma. This plasma burns away the hydrophobic monolayer in the locations of the holes of the PDMS layer exposing the bare, more hydrophilic $SiO_2$ surface.

The respective solvents were either used pure or a mixture of the respective solvents was prepared initially. 0.1 wt % of semiconductor powder was dissolved in the respective solvent or solvent mixture and filtered through a 0.2 μm polytetrafluoroethylene (PTFE) filter. The substrate was placed on a hotplate (temperature for all solvents 70° C. except toluene, here 30° C. was used for drying) and 1 μL of the organic semiconductor solution was drop casted with a pipette onto the hydrophilic areas. Substrates were removed once the solution had dried. Optical images were recorded under a polarized microscope in reflection mode.

Sample Preparation 2 (Used to Make the Experiments with the Solvent Mixture and to Fabricate Transistors):

Degenerately doped silicon wafers coated with $Al_2O_3$ (30 nm thick, grown via atomic layer deposition) were subjected to a 2 minutes treatment with oxygen plasma (100 W, 20 sccm gas flow) and subsequently immersed into a 1.5 mM solution of tetradecyl phosphonic acid (TDPA) in isopropanol for 1 hour at room temperature. Subsequently the sample was removed from the solution and baked for 5 min at 120° C. This procedure yields a hydrophobic self-assembled monolayer (SAM) on the $Al_2O_3$ surface with a surface energy of 22 mN/m (surface energy determined via contact angle measurement). Subsequently a layer of PDMS having a thickness of 0.5-1 mm and comprising holes with a diameter of 7.3 mm was placed onto the hydrophobic substrate that was subsequently subjected to a 5 minutes treatment with air plasma. This plasma burns away the hydrophobic monolayer in the locations of the holes of the PDMS layer exposing the bare, more hydrophilic $Al_2O_3$ surface. The resulting plasma-treated hydrophilic areas of the substrate were then treated with 4-ethoxyphenylphosphonic acid (EPPA) in the same manner as described above for the TDPA SAM. This process yields a hydrophilic EPPA SAM in the circular regions that had been subjected to the second plasma treatment step. The surface energy of the EPPA-treated areas was determined to be 36 mN/m.

0.1 wt % of semiconductor powder was dissolved in the respective solvent for 1 h at 80° C. under constant shaking. After cooling the solution to room temperature it was filtered through a 0.2 µm PTFE filter. In the case that solvent mixtures were used, first the semiconductor was dissolved in the respective individual solvent, subjected to shaking at 80° C. for 1 h, filtered and subsequently mixed to the respective solvent ratios. 1 µL of the organic semiconductor solution was drop casted with a pipette onto the hydrophilic EPPA areas at an elevated substrate temperature (70° C., substrate placed on hotplate). After several hours to 2 days of drying at 70° C. the samples were transferred to a vacuum oven and heated to 60° C. to 90° C. for additional 3 hours to completely remove residual solvent. Optical images were recorded under a polarized microscope in reflection mode.

Sample Preparation Method 3:

A given amount of polystyrene (PS), molecular weight 2,000,000 (obtained from Alfa Aesar; PS-Lot: K05Y052) was dissolved in the respective solvents at room temperature and stirred until all polymer was dissolved. Then 0.1 wt % of the organic semiconductor was dissolved in the mixture. Microscopy cover glass-slides were used as substrates and were thoroughly rinsed with acetone first. The solution was then dropcast onto a microscopy cover glass slide that had been heated to 70° C. on a hotplate. In an alternative experiment the solution was applied via a wire-bar coater (4 µm) onto a heated (70° C.) glass slide. Microscopy images were obtained with an optical microscope.

Transistor Fabrication and Electrical Measurement:

Gold contacts (Umicore, 99.99%) were deposited at a base pressure of $6 \times 10^{-6}$ mbar through a kapton shadow mask via thermal evaporation yielding a channel width (W) of 200 µm and channel length (L) of 100 µm. Electrical characterization was conducted in a Lakeshore CRX—6.5K probe station in vacuum ($<10^{-6}$ mbar) using an Agilent 4145C Semiconductor Parameter Analyzer.

Viscosity Measurement of the Solvents, Solvent Mixtures or Polymer-Solvent Mixtures:

The viscosities were measured using a Brookfield DV-II+ Pro Viscosimeter at 23° C. temperature at a shear rate of 93 s-1 at a rotational speed of 100 rpm using a 13R cup and a 21 Spindle.

Process Description of Surface Tension Measurement of the Solvents and Solvent Mixtures:

The surface tension was measured on a Tensiometer K100 from Kriss using the Wilhelmy-plate method.

Example 1

According to the afore-mentioned sample preparation method 2 a crystalline material of semiconductor (A1) was prepared using a solvent mixture of DMP and toluene (wt. ratio 1:3). The solids content of the semiconductor solution was 0.1 wt. % and drying was performed at 70° C. on a hotplate. FIG. 1 shows the polarized optical micrograph of the obtained crystalline organic film. The combination of DMP as a solvent (L1) in the sense of the invention with toluene as a solvent (L2) leads to a semiconductor material having a large area of thin connected continuous crystals.

Example 2 (Comparative)

Figure 2:
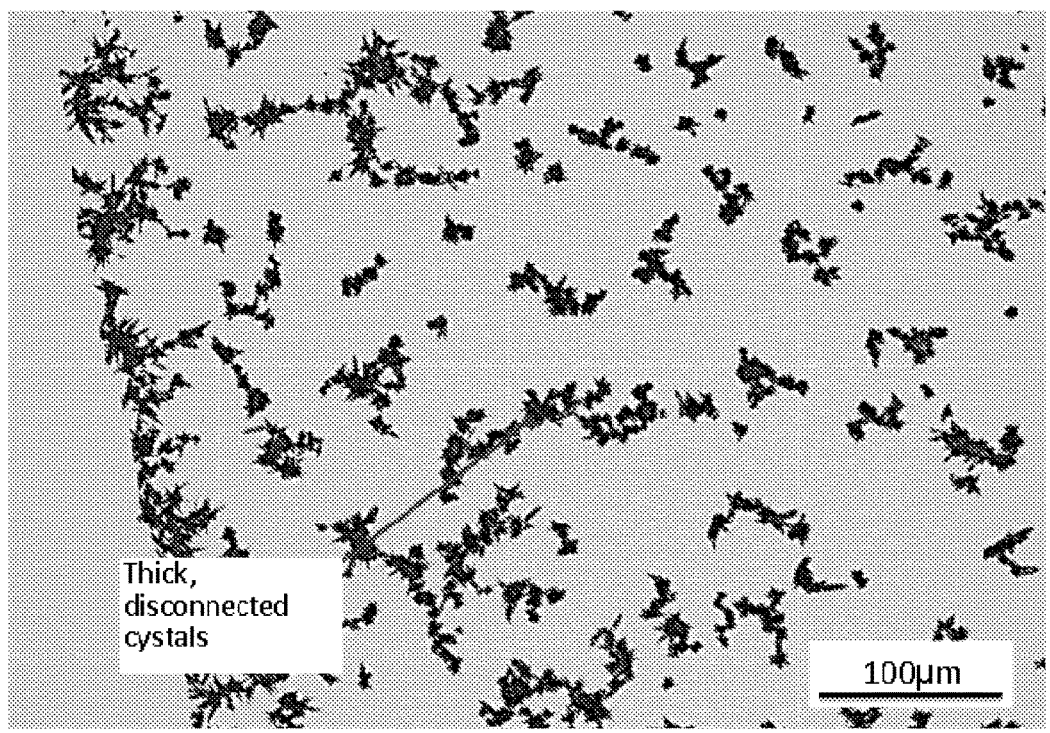
FIG. 2 shows the polarized optical micrograph of the crystalline organic film obtained by drop-casting of compound A1) from acetylacetone (comparative example 2).

According to the afore-mentioned sample preparation method 2 a crystalline material of semiconductor (A1) was prepared using acetylacetone as solvent. The solids content of the semiconductor solution was 0.1 wt.-% and drying was performed at 70° C. on a hotplate. FIG. 2 shows the polarized optical micrograph of the obtained crystalline organic film. The use of a solvent that is not a solvent (L1) in the sense of the invention leads to a semiconductor material having thick disconnected polycrystalline agglomerates.

Example 3 (Comparative)

Figure 3:
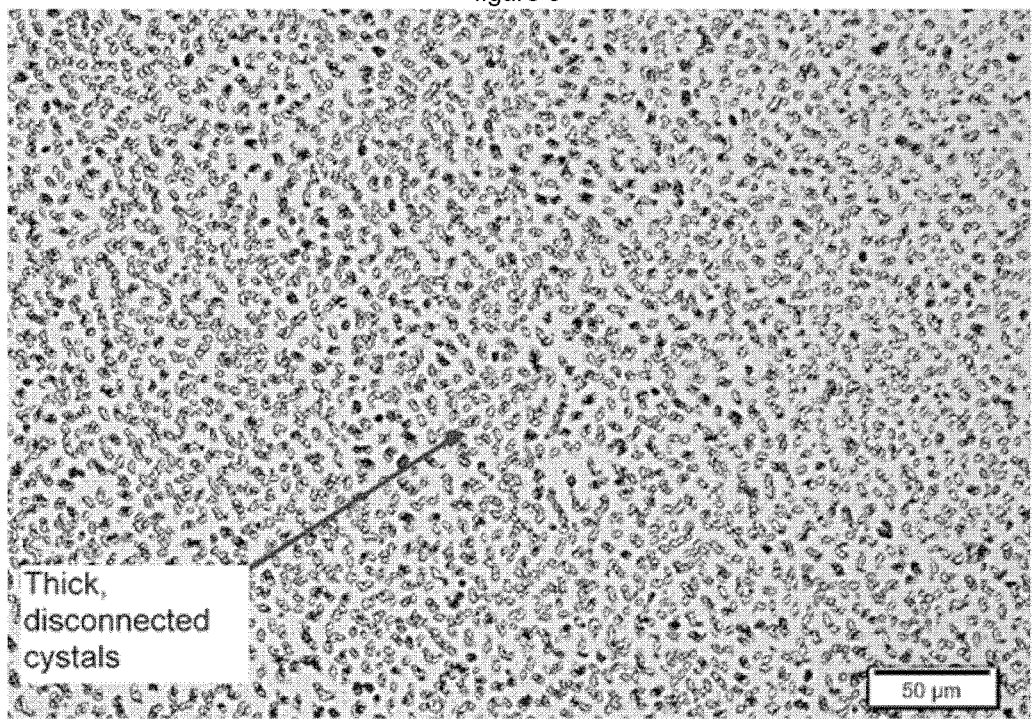
FIG. 3 shows the polarized optical micrograph of the crystalline organic film obtained by drop-casting of compound A1) from toluene (comparative example 3).

According to the afore-mentioned sample preparation method 2 a crystalline material of semiconductor (A1) was prepared using toluene as solvent. The solids content of the semiconductor solution was 0.1 wt.-% and drying was performed at 30° C. on a hotplate. FIG. 3 shows the polarized optical micrograph of the obtained crystalline organic film. The use of toluene alone, being a solvent that is not a solvent (L1) in the sense of the invention, leads to a semiconductor material having thick disconnected polycrystalline agglomerates.

Examples 4 to 22

According to the afore-mentioned sample preparation method 2 a crystalline material of semiconductor (A1) was prepared using a pure solvent according to table 1 as solvent. The solids content of the semiconductor solution was 0.1 wt. % and drying was performed at 70° C. (except toluene, where 30° C. was used for drying) on a hotplate. The obtained crystalline semiconductor materials were examined by polarized optical microscopy. The results are shown in table 1. With the solvents (L1) in the sense of the invention in each case semiconductor materials having a large area of thin connected crystals were obtained. The use of solvents different from the solvents (L1) leads to semiconductor materials having thick polycrystalline agglomerates.

TABLE 1

List of pure solvents tested:

| example no. | solvent | boiling point [° C.] | viscosity [mPa s] @20° C. | surface tension [mN/m] @ 20° C. | polarized optical microscopy[#] |
|---|---|---|---|---|---|
| 4 | Dimethyl Phthalate (DMP) | 283 | 14.4 | 41.9 | (+) |
| 5 | Di-ethyl Phthalate (DEP) | 295 | 10.6 | 37.5 | (+) |
| 6 | Di-allyl Phthalate (DAP) | 165 | 8.5 | 39.0 | (+) |
| 7 | DMSO | 189 | 4.0 | 43.5 | (+) |
| 8 | Ethyl Benzoate | 211 | 2.2 | 34.6 | (+) |
| 9 | Ethyl Salicylate | 222 | 1.8 | 39.1 | (+) |
| 10 | Acetophenone | 202 | 1.7 | 39.0 | (+) |
| 11 | Propylene Carbonate | 242 | 1.7 | 41.1 | (+) |
| 12 | NMP | 202 | 1.7 | 40.8 | (+) |
| 13 | THN | 207 | 1.4 | 32.6 | (+) |
| 14 | 1,2-DCB | 180 | 1.3 | 36.6 | (+) |
| 15 | Amyl Acetate | 149 | 0.9 | 25.1 | (−) |
| 16 | Acetyl Acetone (Acac) | 140 | 0.8 | 31.2 | (−) |
| 17 | Chlorobenzene | 131 | 0.8 | 33.6 | (−) |
| 18 | Butyl Acetate | 126 | 0.7 | 25.1 | (−) |
| 19 | Nitroethane | 112 | 0.6 | 32.0 | (−) |
| 20 | Toluene | 111 | 0.6 | 28.6 | (−) |
| 21 | Trichloromethane | 61 | 0.5 | 27.5 | (−) |
| 22 | Ethyl Acetate (Ethac) | 77 | 0.4 | 23.2 | (−) |

[#](+) = a thin crystalline film is formed, (−) = thick disconnected polycrystalline agglomerates are formed The solvent parameters of the pure solvents were taken from Knovel Critical Tables (2nd Edition 2008), electronic ISBN: 978-1-59124-550-6.

Examples 23 to 40

According to the afore-mentioned sample preparation method 2 for solvent mixtures and sample preparation method 3 for solvent-polymer mixtures a crystalline material of semiconductor (A1) was prepared using a solvent mixture or solvent-polymer mixture according to table 2. All solutions were deposited by drop casting unless noted otherwise. The solids content of the semiconductor solution was 0.1 wt.-% and drying was performed at 70° C. (except for pure toluene that was dried at 30° C. on a hotplate. The obtained crystalline semiconductor materials were examined by polarized optical microscopy. The results are shown in table 2. With solvent mixtures containing a solvent (L1) in the sense of the invention in each case semiconductor materials having a large area of thin connected crystals were obtained. If toluene is used as solvent, an increase in the viscosity of the solution by using polystyrene (PS) as thickener does not lead to an improvement in the quality of the obtained semiconductor material. The use of toluene-polymer mixtures leads to semiconductor materials having thick disconnected crystals. In other words it is not enough to artificially increase the viscosity of a low viscous solvents such as toluene by adding a thickener in order to obtain a preferable crystallization of the semiconductor as in the case that solvents according to the present invention are contained in a solution.

TABLE 2

List of solvent mixtures and solvent-polymer mixtures tested

| example no. | solvent mixture, polymer-solvent mixture | Viscosity [mPas] | Surface tension [mN/m] | crystal form |
|---|---|---|---|---|
| 23 | DMP | 14.4 | 41.9 | thin |
| 24 | Toluene | 0.6 | 28.6 | thick |
| 25 | Toluene: PS (6.6 mg PS/1 g toluene) | 3.5 | not measured | thick |
| 26 | Toluene: PS (9.8 mg PS/1 g toluene) | 5.3 | not measured | thick |
| 27 | Toluene: PS (13.2 mg PS/1 g toluene) | 8 | not measured | thick |
| 28 | DMP: PS (1.5 mg PS/1 g DMP) | 20 | not measured | thin |
| 29 | DEP: PS (2.3 mg PS/1 g DEP) | 19 | not measured | thin |
| 30 | DMP: PS (wire-bar coated) (1.5 mg PS/1 g DMP) | 20 | not measured | thin |
| 31 | DEP: PS (wire-bar coated) (2.3 mg PS/1 g DEP) | 19 | not measured | thin |
| 32 | DMP:Toluene (1:3) | 0.75 | not measured | thin |
| 33 | DMP:Toluene (1:9) | 0.5 | 27.29 | thin |
| 34 | DMP:Acetylacetone (1:3) | 1 | 32.67 | thin |
| 35 | DMP:Acetylacetone (1:9) | 0.5 | 29.65 | thin |
| 36 | DMP:Nitroethane (1:3) | Not measured | Not measured | thin |
| 37 | DMP:1,2-DCB (1:3) | Not measured | Not measured | thin |
| 38 | DMP:Amylacetate (1:3) | Not measured | Not measured | thin |

TABLE 2-continued

List of solvent mixtures and solvent-polymer mixtures tested

| example no. | solvent mixture, polymer-solvent mixture | Viscosity [mPas] | Surface tension [mN/m] | crystal form |
|---|---|---|---|---|
| 39 | DAP:Acetylacetone (1:3) | Not measured | Not measured | thin |
| 40 | DAP:Acetylacetone (1:3) | Not measured | Not measured | thin |

Examples 41 to 47

According to the afore-mentioned sample preparation method 1 a crystalline material of semiconductors according to table 3 was prepared using a solvent mixture or solvent-polymer mixture according to table 3. All solutions were deposited by drop casting unless noted otherwise. The solids content of the semiconductor solution was 0.1 wt. % and drying was performed at 70° C. (except toluene, where 30° C. was used for drying) on a hotplate. The obtained crystalline semiconductor materials were examined by polarized optical microscopy. The results are shown in table 3.

TABLE 3

List of semiconductors tested (sample preparation method 1):

| | | solvent | | | |
|---|---|---|---|---|---|
| example no. | semiconductor | DMP thin layers | DMP:Toluene(1:3) thin layers | Acetophenone thin layers | Toluene thin layers |
| 41 | A4 | yes | not measured | yes | no |
| 42 | A1 | Yes | Yes | Yes | no |
| 43 | A3 | yes | yes | yes | no |
| 44 | A5 | yes | yes | yes | no |
| 45 | A6 | yes | yes | yes | no |
| 46 | A7 | yes | yes | yes | no |
| 47 | A8 | yes | yes | yes | not measured |

Example 48: Drop-Casting of Semiconductor A9)

Figure 4A:
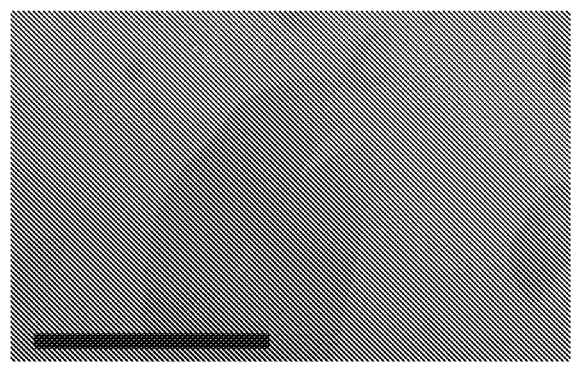
FIG. 4a shows the polarized optical micrograph of the crystalline organic film obtained by drop-casting of compound A9) from DMP (example 48.1). The black bar at the left bottom of the image shows a distance of 50 μm.
Figure 4B:
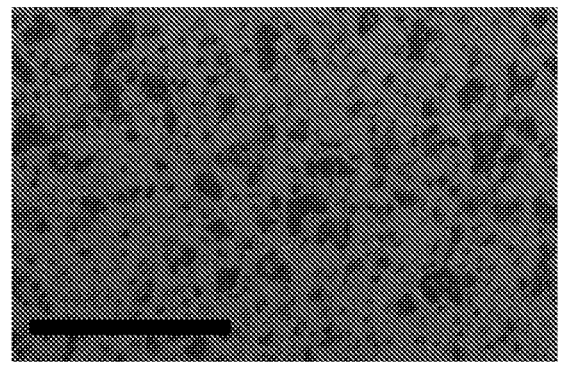
FIG. 4b shows the polarized optical micrograph of the crystalline organic film obtained by drop-casting of compound A9) from EthAc (comparative example 48.4). The black bar at the left bottom of the image shows a distance of 50 μm.

A 0.1 wt. % solution of A9) in a solvent according to table 1 is applied to a SiO$_2$ substrate and the solvent allowed to evaporate. For the preparation of the solutions of A9) in the phthalates the semiconductor is stirred in the phthalate at 80° C. for 60 minutes. FIG. 4a shows the polarized optical micrograph of the crystalline organic film obtained by drop-casting of compound A9) from DMP and FIG. 4b shows the micrograph of film obtained by drop-casting of compound A9) from EthAc. As can be seen, the crystals obtained from the compositions of the invention show remarkably larger crystalline areas.

TABLE 4

| example | solvent | crystal length [μm] | crystal width [μm] |
|---|---|---|---|
| 48.1 | DMP | 50 | 5 |
| 48.2 | DEP | 100 | 30 |
| 48.3 | DAP | 100 | 20 |
| C48.4[+)] | ethylacetate | 3[#] | 0.5[#] |

[+)]comparative,
[#]small polycrystalline to amorphous disconnected agglomerates Example 49: Drop-Casting of Semiconductor A10)

A 0.1 wt. % solution of A10) in a solvent according to table 1 is applied to a SiO$_2$ substrate and the solvent allowed to evaporate. For the preparation of the solutions of A10) in the phthalates the semiconductor is stirred in the phthalate at 80° C. for 60 minutes. In the polarized optical micrograph the crystals obtained from the compositions of the invention show remarkably larger crystalline areas.

TABLE 5

| example | solvent | crystal length [μm] | crystal width [μm] |
|---|---|---|---|
| 49.1 | DMP | 35 | 5 |
| 49.2 | DEP | 100 | 50 |
| 49.3 | DAP | 60 | 50 |
| C49.4[+)] | ethylacetate | 20[#] | 10[#] |

[+)]comparative,
[#]small polycrystalline to amorphous disconnected agglomerates Example 50: Drop-Casting of Semiconductor A3)

A 0.1 wt. % solution of A3) in a solvent according to table 1 is applied to a SiO$_2$ substrate and the solvent allowed to evaporate. For the preparation of the solutions of A3) in the phthalates the semiconductor is stirred in the phthalate at 80° C. for 60 minutes. In the polarized optical micrograph the crystals obtained from the compositions of the invention show remarkably larger crystalline areas.

TABLE 6

| example | solvent | crystal length [μm] | crystal width [μm] |
|---|---|---|---|
| 50.1 | DAP | 200 | 250 |
| C50.2[+)] | ethylacetate | 20 | 3 |
| C50.3[+)] | acetylacetone | 20[#] | 3[#] |

[+)]comparative,
[#]small polycrystalline to amorphous disconnected agglomerates Example 51: Drop-Casting of Semiconductor A1)

A 0.1 wt. % solution of A1) in a solvent according to table 1 is applied to a SiO$_2$ substrate and the solvent allowed to evaporate. For the preparation of the solutions of A1) in the phthalates the semiconductor is stirred in the phthalate at 80° C. for 60 minutes. In the polarized optical micrograph the crystals obtained from the compositions of the invention show remarkably larger crystalline areas.

TABLE 7

| example | solvent | crystal length [μm] | crystal width [μm] |
|---|---|---|---|
| 51.1 | DMP | 500 | 200 |
| 51.2 | DEP | 1200 | 650 |
| 51.3 | DAP | 250 | 150 |
| C51.3[+)] | ethylacetate | 3[#] | 2[#] |

[+)]comparative,
[#]small polycrystalline to amorphous disconnected agglomerates Preparation and Electrical Characterization of OFET Devices

Example 52: Drop-Casting of A1) from DMP Solution on a SiO$_2$ Wafer

A 0.1 wt.-% solution of the semiconductor material A1) was prepared by dissolution in dimethyl phthalate for 1 h at 80° C. and then stirred for further 30 minutes. The solution was allowed to cool to ambient temperature and was filtered through a 0.2 μm PTFE filter. Si/SiO$_2$ wafers from WRS Materials heavily p-doped with boron (550 to 600 μm thickness, 100 nm insulating dielectric layer of thermally oxidized silicon) were used as back gate substrate. 1 to 10 μL of solution was deposited onto the wafer on a hotplate at 60 to 90° C. in a flow box. After complete evaporation of solvent the sample was put in a vacuum oven for 1 h at 70° C. to eliminate residual solvent trapped in the film. Gold contacts (Umicore, 99.99%) were deposited at a base pressure of 6×10$^{-6}$ mbar through a kapton shadow mask via thermal evaporation yielding a channel width (W) of 200 μm and channel length (L) of 100 μm. Electrical characterization was conducted in a dark box under ambient conditions using an Agilent 4145C Semiconductor Parameter Analyzer.

Figure 5A:
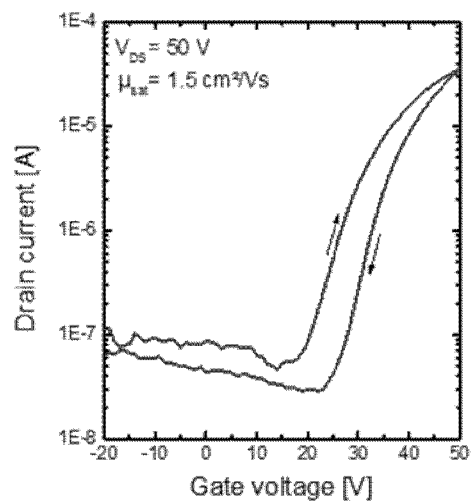
FIG. 5a shows the transfer characteristics of the semiconductor obtained by drop casting of compound A1) from a DMP solution (example 52) with $U_{GS}=-20$ V to $+50$ V with $U_{DS}=50$ V
Figure 5B:
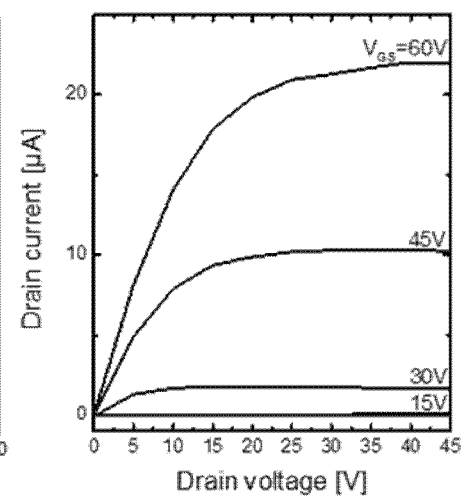
FIG. 5b shows the output characteristics of the semiconductor obtained by drop casting of compound A1) from a DMP solution (example 52) with $U_{DS}$=0 V to +45V with $U_{GS}$=15, 30, 45 and 60V.

The measurement results are depicted in FIGS. 5a and 5b, respectively.

Example 53: Drop-Casting of A1) from DMP:Acac (1:9) Solution on a SiO$_2$ Wafer A 0.1 wt.-% solution of the semiconductor material A1) was prepared by dissolution in a 1:9 mixture of dimethyl phthalate and acetylacetone for 1 h at 80° C. and then stirred for further 30 minutes. The solution was allowed to cool to ambient temperature and was filtered through a 0.2 μm PTFE filter. Si/SiO$_2$ wafers from WRS Materials heavily p-doped with boron (550 to 600 μm thickness, 100 nm insulating dielectric layer of thermally oxidized silicon) were used as back gate substrate. 1 to 10 μL of solution was deposited onto the wafer on a hotplate at 60 to 90° C. in a flow box. After complete evaporation of solvent the sample was put in a vacuum oven for 1 h at 70° C. to eliminate residual solvent trapped in the film. Gold contacts (Umicore, 99.99%) were deposited at a base pressure of 6×10$^{-6}$ mbar through a kapton shadow mask via thermal evaporation yielding a channel width (W) of 200 μm and channel length (L) of 100 μm. Electrical characterization was conducted in a dark box under ambient conditions using an Agilent 4145C Semiconductor Parameter Analyzer.

Figure 6A:
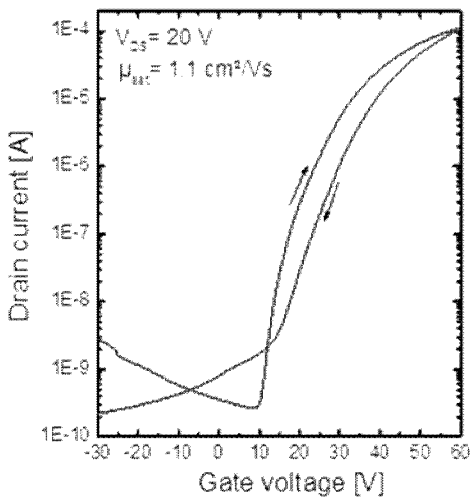
FIG. 6a shows the transfer characteristics of the semiconductor obtained by drop casting of compound A1) from a DMP:Acac (1:9) solution (example 53) with $U_{GS}$=−30 V to +60 V with $U_{DS}$=20 V
Figure 6B:
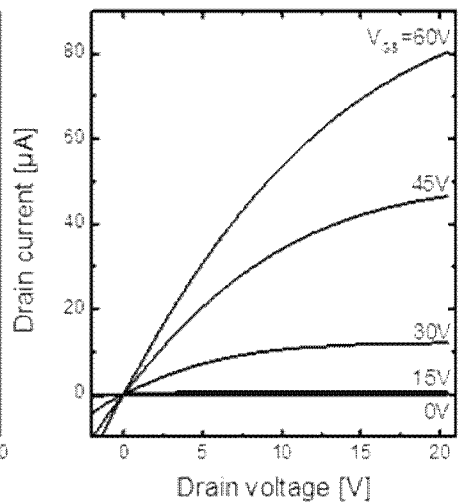
FIG. 6b shows the output characteristics of the semiconductor obtained by drop casting of compound A1) from a DMP:Acac (1:9) solution (example 53) with $U_{DS}$=0 V to +20 V with $U_{GS}$=0, 15, 30, 45 and 60V.

The measurement results are depicted in FIGS. 6a and 6b, respectively.

Example 54: Drop-Casting of A1) from a DMP Solution on an Al$_2$O$_3$ Layer A 0.1 wt.-% solution of the semiconductor material A1) was prepared by dissolution in dimethyl phthalate for 1 h at 80° C. and then stirred for further 30 minutes. The solution was allowed to cool to ambient temperature and was filtered through a 0.2 μm PTFE filter. Si/SiO$_2$ wafers from WRS Materials heavily p-doped with boron (550 to 600 μm thickness, 30 nm insulating dielectric layer of Al$_2$O$_3$) were used as back gate substrate. 1 to 10 μL of solution was deposited onto the wafer on a hotplate at 60 to 90° C. in a flow box. After complete evaporation of solvent the sample was put in a vacuum oven for 1 h at 70° C. to eliminate residual solvent trapped in the film. Gold contacts (Umicore, 99.99%) were deposited at a base pressure of 6×10$^{-6}$ mbar through a kapton shadow mask via thermal evaporation yielding a channel width (W) of 200 μm and channel length (L) of 100 μm. Electrical characterization was conducted in a dark box under ambient conditions using an Agilent 4145C Semiconductor Parameter Analyzer.

Figure 7A:
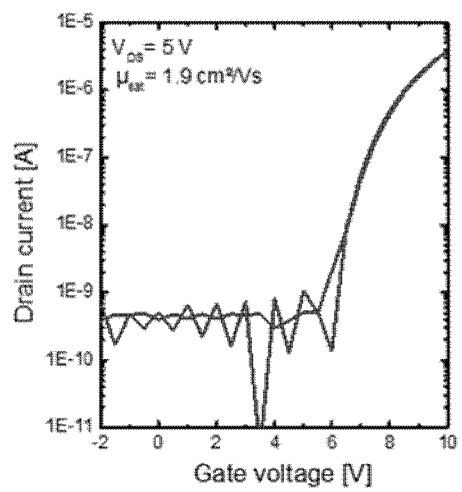
FIG. 7a shows the transfer characteristics of the semiconductor obtained by drop casting of compound A1) from a DMP solution onto a wafer with a 30 nm insulating dielectric layer of $Al_2O_3$ (example 54) with $U_{GS}$=−2 V to +10 V with $U_{DS}$=5 V.
Figure 7B:
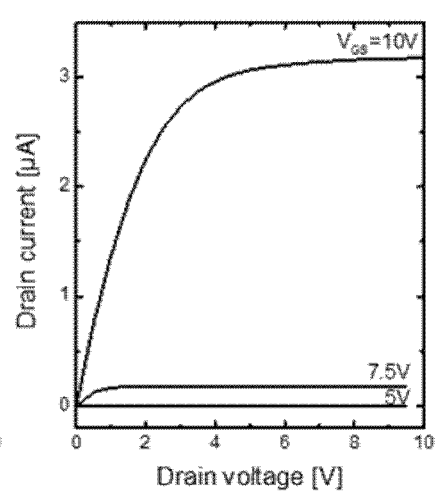
FIG. 7b shows the output characteristics of the semiconductor obtained by drop casting of compound A1) from a DMP solution onto a wafer with a 30 nm insulating dielectric layer of $Al_2O_3$ (example 54) with $U_{DS}$=0 V to +10 V with $U_{GS}$=5, 7.5 and 10 V.

The measurement results are depicted in FIGS. 7a and 7b, respectively.

Example 55: Drop-Casting of A1) from a DM P Solution on Al$_2$O$_3$ after Surface Modification A 0.1 wt.-% solution of the semiconductor material A1) was prepared by dissolution in dimethyl phthalate for 1 h at 80° C. and then stirred for further 30 minutes. The solution was allowed to cool to ambient temperature and was filtered through a 0.2 μm PTFE filter. Si/SiO$_2$ wafers from WRS Materials heavily p-doped with boron (550 to 600 μm thickness, 30 nm insulating dielectric layer of Al$_2$O$_3$) were used as back gate substrate.

Prior to material deposition, a surface treatment was conducted; the substrate was exposed to O$_2$ plasma for 300 seconds. 4-Ethoxyphenylphosphonic acid (CAS 69387-02-6) was dissolved in isopropanol at a concentration of 2 mMol (typically 4 mg/10 ml) and stirred at room temperature for 20 minutes. The substrate was immersed in the solution for 1 hour in a covered petri dish. After subsequent rinsing with isopropanol and drying under N$_2$, the substrates were baked at 150° C. on a hotplate. 1 to 10 μL of solution was deposited onto the wafer on a hotplate at 60 to 90° C. in a flow box. After complete evaporation of solvent the sample was put in a vacuum oven for 1 h at 70° C. to eliminate residual solvent trapped in the film. Gold contacts (Umicore, 99.99%) were deposited at a base pressure of 6×10$^{-6}$ mbar through a kapton shadow mask via thermal evaporation yielding a channel width (W) of 200 μm and channel length (L) of 100 μm. Electrical characterization was conducted in a dark box under ambient conditions using an Agilent 4145C Semiconductor Parameter Analyzer.

Figure 8A:
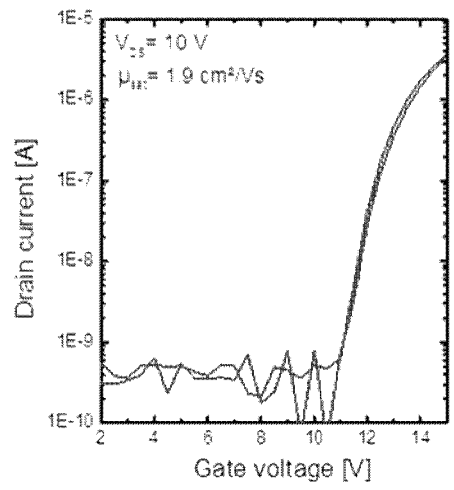
FIG. 8a shows the transfer characteristics of the semiconductor obtained by drop casting of compound A1) from a DMP solution onto a wafer after surface modification with 4-ethoxyphenylphosphonic acid (example 55) with $U_{GS}$=+2 V to +15 V with $U_{DS}$=10V
Figure 8B:
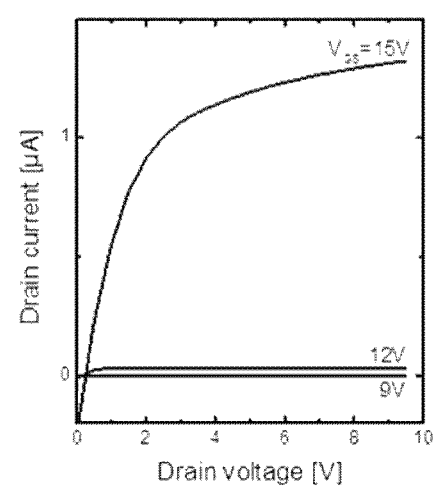
FIG. 8b shows the output characteristics of the semiconductor obtained by drop casting of compound A1) from a DMP solution onto a wafer after surface modification with 4-ethoxyphenylphosphonic acid (example 55) with $U_{DS}$=0 V to +10 V with $U_{GS}$=9, 12 and 15 V.

The measurement results are depicted in FIGS. 8a and 8b, respectively.

Example 56: Drop-Casting of A1) from a DMP Solution on a PET Substrate, Production of a Bottom-Contact Top-Gate Field Effect Transistor Using a PVCH/PMMA Top Gate A 0.1 wt.-% solution of the semiconductor material A1) was prepared by dissolution in dimethyl phthalate for 1 h at 80° C. and then stirred for further 30 minutes. The solution was allowed to cool to ambient temperature and was filtered through a 0.2 μm PTFE filter. A polyethylene terephthalate (PET) foil (Hostaphan 4600GN 175 from Mitsubishi Polyester Film) was used as substrate. Gold contacts (Umicore, 99.99%) were deposited at a base pressure of 6×10$^{-6}$ mbar through a kapton shadow mask via thermal evaporation yielding a channel width (W) of 500 μm and channel length (L) of 50 μm. 1 to 10 μL of solution was deposited onto the substrate on a hotplate at 60 to 90° C. in a flow box. After complete evaporation of the solvent the sample was put in a vacuum oven at 70° C. for 1 h to eliminate residual solvent. Polyvinylcyclohexane (PVCH) (0.4 wt % in cyclohexane) was spin-coated (4000 RPM, 30 seconds) and dried for 5 minutes at 90° C. Polymethylmethacrylate (PMMA) (4 to 7 wt.-% in butylacetate/ethyl-lactate [4:6]) was spin-coated (2000 RPM/60 seconds) and dried for 120 seconds at 90° C. The PVCH/PMMA dielectric thickness was 420 nm ($\varepsilon_r$=4). Electrical characterization was conducted in a dark box under ambient conditions using an Agilent 4145C Semiconductor Parameter Analyzer.

Figure 9A:
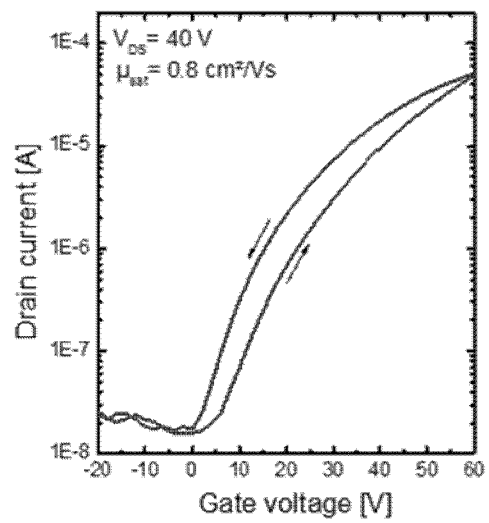
FIG. 9a shows the transfer characteristics of the semiconductor obtained by drop casting of compound A1) from a DMP solution onto a polyethylene terephthalate foil as substrate (example 56) with $U_{GS}$=−20 V to +60 V with $U_{DS}$=40 V.
Figure 9B:
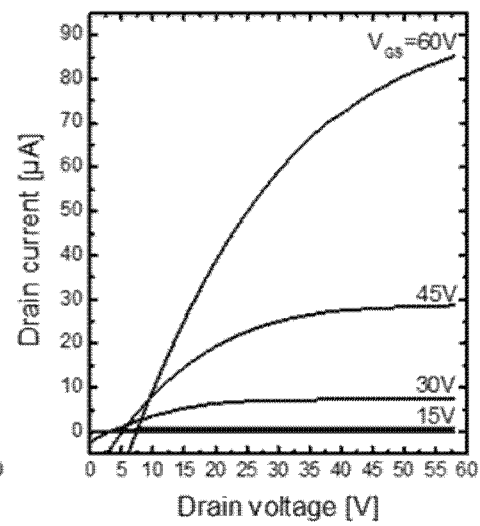
FIG. 9b shows the output characteristics of the semiconductor obtained by drop casting of compound A1) from a DMP solution onto a polyethylene terephthalate foil as substrate (example 56) with $U_{DS}$=0 V to +60 V with $U_{GS}$=15, 30, 45 and 60 V.

The measurement results are depicted in FIGS. 9a and 9b, respectively.

Example 57: Inkjet Printing of A1) from DMP Solution on a SiO$_2$ Wafer

A 0.1 wt.-% solution of the semiconductor material A1) was prepared by dissolution in dimethyl phthalate for 1 h at 80° C. and then stirred for further 30 minutes. The solution was allowed to cool to ambient temperature and was filtered through a 0.2 μm PTFE filter. Si/SiO$_2$ wafers from WRS Materials heavily p-doped with boron (550 to 600 μm thickness, 100 nm insulating dielectric layer of thermally oxidized silicon) were used as back gate substrate. The ink was printed with a Dimatix DMP2831 printer at a drop space of 20 μm with the nozzle at 35° C. and the printing plate at room temperature. The printed substrates were dried 5 h at 60° C. in ambient air followed by a second drying step for one hour at 110° C. in a vacuum oven (about 5 mbar pressure). After complete evaporation of solvent the sample was put in a vacuum oven for 1 h at 70° C. to eliminate residual solvent trapped in the film. Gold contacts (Umicore, 99.99%) were deposited at a base pressure of $6\times10^{-6}$ mbar through a kapton shadow mask via thermal evaporation yielding a channel width (W) of 200 μm and channel length (L) of 100 μm. Electrical characterization was conducted in a dark box under ambient conditions using an Agilent 4145C Semiconductor Parameter Analyzer.

Figure 10A:
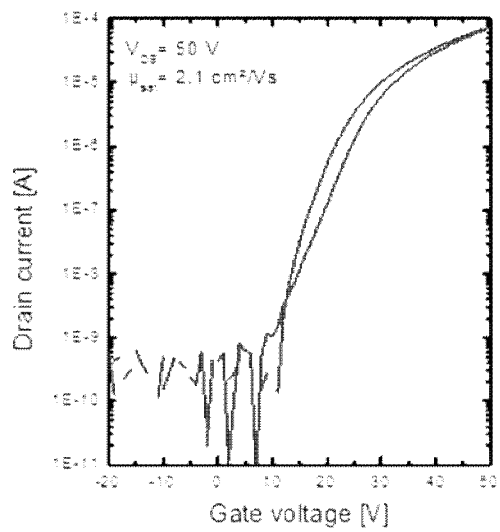
FIG. 10a shows the transfer characteristics of the semiconductor obtained by inkjet printing of compound A1) from a DMP solution onto a $SiO_2$ wafer (example 57) with $U_{GS}$=−20 V to +50 V with $U_{DS}$=50 V.
Figure 10B:
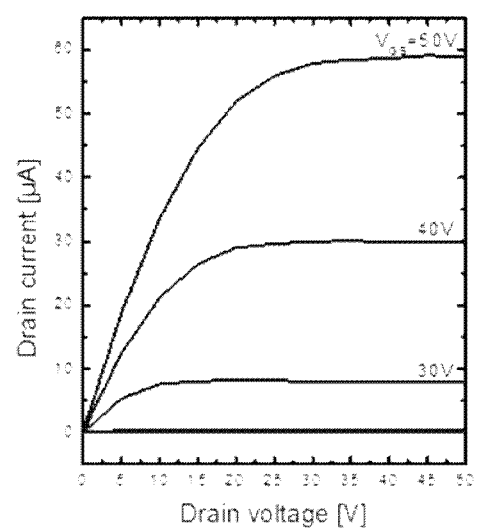
FIG. 10b shows the output characteristics of the semiconductor obtained by inkjet printing of compound A1) from a DMP solution onto a $SiO_2$ wafer (example 57) with $U_{DS}$=0 V to +50 V with $U_{GS}$=20, 30, 40 and 50 V.

The measurement results are depicted in FIGS. 10a and 10b, respectively.

Example 58: Inkjet Printing of A1) from a DMP Solution on Al$_2$O$_3$ after Surface Modification A 0.1 wt.-% solution of the semiconductor material A1) was prepared by dissolution in dimethyl phthalate for 1 h at 80° C. and then stirred for further 30 minutes. The solution was allowed to cool to ambient temperature and was filtered through a 0.2 μm PTFE filter. Si/SiO$_2$ wafers from WRS Materials heavily p-doped with boron (550 to 600 μm thickness, 30 nm insulating dielectric layer of Al$_2$O$_3$) were used as back gate substrate. Prior to material deposition, a surface treatment was conducted; the substrate was exposed to O$_2$ plasma for 300 seconds. 4-Ethoxyphenylphosphonic acid, (CAS 69387-02-6) was dissolved in isopropanol at a concentration of 2 mMol (typically 4 mg/10 ml) and stirred at room temperature for 20 minutes. The substrate was immersed in the solution for 1 hour in a covered petri dish. After subsequent rinsing with isopropanol and drying under N2, the substrates were baked at 150° C. on a hotplate. The ink was printed with a Dimatix DMP2831 printer at a drop space of 20 μm with the nozzle at 35° C. and the printing plate at room temperature. The printed substrates were dried 5 h at 60° C. in ambient air followed by a second drying step for one hour at 110° C. in a vacuum oven (about 5 mbar pressure). After complete evaporation of solvent the sample was put in a vacuum oven for 1 h at 70° C. to eliminate residual solvent trapped in the film. Gold contacts (Umicore, 99.99%) were deposited at a base pressure of 6E-6 mbar through a kapton shadow mask via thermal evaporation yielding a typical channel W/L of 200 μm/100 μm. Electrical characterization was conducted in a dark box under ambient conditions using an Agilent 4145C Semiconductor Parameter Analyzer.

Figure 11A:
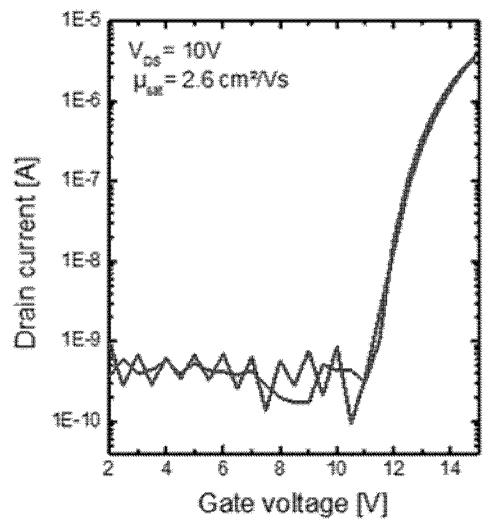
FIG. 11a shows the transfer characteristics of the semiconductor obtained by inkjet printing of compound A1) from a DMP solution onto an $Al_2O_3$ wafer after surface modification (example 58) with $U_{GS}$=+2 V to +15 V with $U_{DS}$=10 V.
Figure 11B:
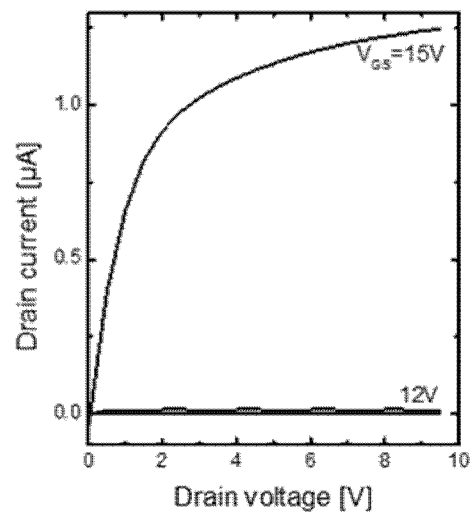
FIG. 11b shows the output characteristics of the semiconductor obtained by inkjet printing of compound A1) from a DMP solution onto an $Al_2O_3$ wafer after surface modification (example 58) with $U_{DS}$=0 V to +10 V with $U_{GS}$=12 and 15 V.

The measurement results are depicted in FIGS. 11a and 11b, respectively.

Example 59: Drop-Casting of A1) from a DMP Solution on a SiO$_2$ Wafer Using a Poly(Methyl Methacrylate)/Trimethylolpropane Triacrylate Bottom-Gate Dielectric A 0.1 wt.-% solution of the semiconductor material A1) was prepared by dissolution in dimethyl phthalate for 1 h at 80° C. and then stirred for further 30 minutes. The solution was allowed to cool to ambient temperature and was filtered through a 0.2 μm PTFE filter. Si/SiO$_2$ wafers from WRS Materials heavily p-doped with boron (550 to 600 μm thickness, 100 nm insulating dielectric layer of thermally oxidized silicon) with a UV-crosslinked polymer dielectric were used as backgate substrate. The dielectric properties are summarized in the table below.

| UV polymer | spin-coating RPM(time) | drying | crosslinking | $\varepsilon_r$ | film thickness |
|---|---|---|---|---|---|
| TMPTA/ PMMA | 2000/10000 (60 seconds) | 10 min 90° C. | 10 × 10 LEDs UV meter 53" 23 mW/cm$^2$ | 3.5 | 328 nm |

$\varepsilon_r$ = relative permittivity (dielectric constant)

1 to 10 μL of solution was deposited onto the wafer on a hotplate at 60 to 90° C. in a flow box. After complete evaporation of solvent the sample was put in a vacuum oven for 1 h at 70° C. to eliminate residual solvent trapped in the film. Gold contacts (Umicore, 99.99%) were deposited at a base pressure of $6\times10^{-6}$ mbar through a kapton shadow mask via thermal evaporation yielding a typical channel W/L of 200 μm/100 μm. Electrical characterization was conducted in a dark box under ambient conditions. Electrical characterization was conducted in a dark box under ambient conditions using an Agilent 4145C Semiconductor Parameter Analyzer.

Figure 12A:
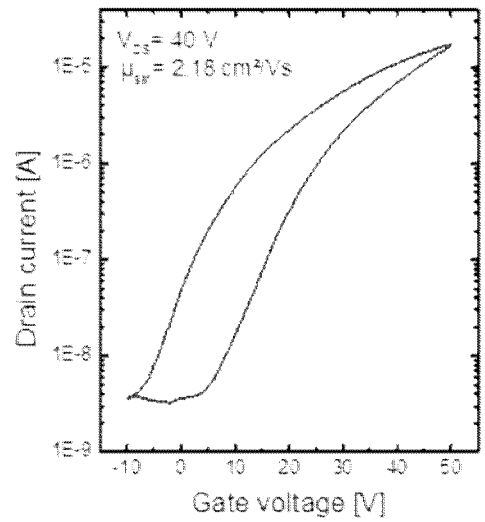
FIG. 12a shows the transfer characteristics of the semiconductor obtained by drop casting of compound A1) from a DMP solution onto a $SiO_2$ wafer using a poly(methyl methacrylate)/trimethylolpropane triacrylate bottom gate dielectric (example 59) with $U_{GS}$=−10 V to +50 V with $U_{DS}$=40 V.
Figure 12B:
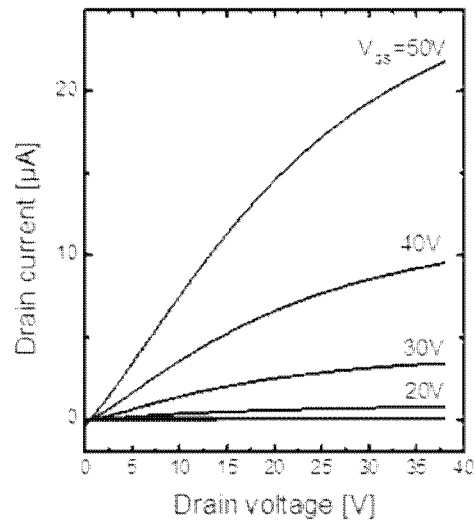
FIG. 12b shows the output characteristics of the semiconductor obtained by drop casting of compound A1) from a DMP solution onto a $SiO_2$ wafer using a poly(methyl methacrylate)/trimethylolpropane triacrylate bottom gate dielectric (example 59) with $U_{DS}$=0 V to +40 V with $U_{GS}$=10, 20, 30, 40 and 50 V.

The measurement results are depicted in FIGS. 12a and 12b, respectively.

Example 60: Inkjet Printing of A3) from DMP Solution on Al$_2$O$_3$

A 0.1 wt.-% solution of the semiconductor material A3) was prepared by dissolution in dimethyl phthalate for 1 h at 80° C. and then stirred for further 30 minutes. The solution was allowed to cool to ambient temperature and was filtered through a 0.2 μm PTFE filter. Si/SiO$_2$ wafers from WRS Materials heavily p-doped with boron (550 to 600 μm thickness, 30 nm insulating dielectric layer of Al$_2$O$_3$) were used as back gate substrate. The ink was printed with a Dimatix DMP2831 printer at a drop space of 20 μm with the nozzle at 35° C. and the printing plate at room temperature. The printed substrates were dried 5 h at 60° C. in ambient air followed by a second drying step for one hour at 110° C.

in a vacuum oven (about 5 mbar pressure). After complete evaporation of solvent the sample was put in a vacuum oven for 1 h at 70° C. to eliminate residual solvent trapped in the film. Gold contacts (Umicore, 99.99%) were deposited at a base pressure of 6×10$^{-6}$ mbar through a kapton shadow mask via thermal evaporation yielding a channel width (W) of 200 µm and channel length (L) of 100 µm. Electrical characterization was conducted in a dark box under ambient conditions using an Agilent 4145C Semiconductor Parameter Analyzer.

Figure 13A:
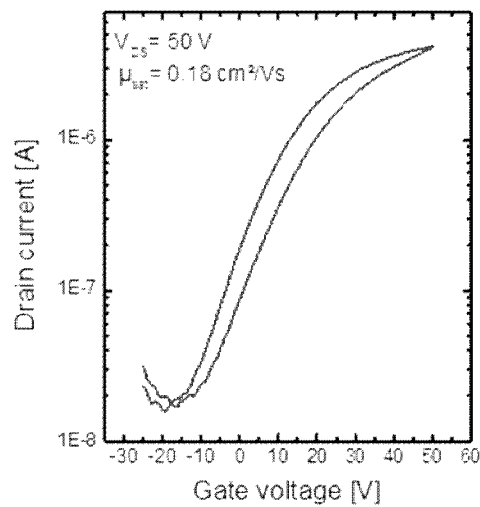
FIG. 13a shows the transfer characteristics of the semiconductor obtained by inkjet printing of compound A3) from a DMP solution onto a wafer with a 30 nm insulating dielectric layer of $Al_2O_3$ (example 60) with $U_{GS}$=−30 V to +60 V with $U_{DS}$=50 V.
Figure 13B:
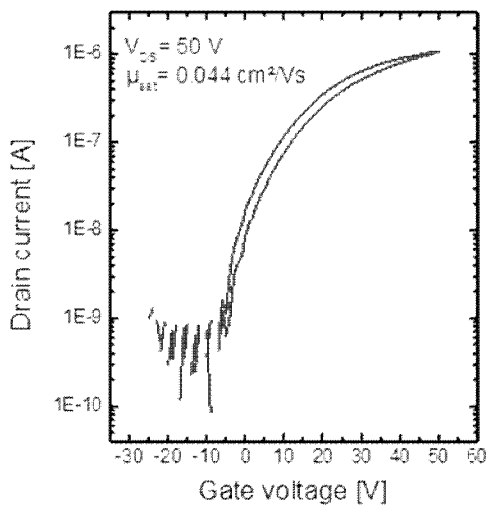
FIG. 13b shows the transfer characteristics of the semiconductor obtained by inkjet printing of compound A3) from a DMP solution onto a wafer with a 30 nm insulating dielectric layer of $Al_2O_3$ (example 60) with $U_{GS}$=−30 V to +60 V with $U_{DS}$=50 V.

The measurement results are depicted in FIGS. 13a and 13b, respectively.

Examples 61 and 62: (Impact of the Drying Time of the Droplets on the Crystal Form)

Example 61

According to the procedure listed under sample preparation 1 a mixture of semiconductor (A1) with a mixture of DM P/Acac (1:3) was prepared, applied by drop-casting onto a glass microscopy cover slide and dried at 70° C. substrate temperature. During drying the cyrstalization was observed in-situ in transmission polarized microscopy setup. Immediately after the liquid was placed on the cover slide the crystallization started in the form of thin crystals that floated on the DMP/Acac mixture.

Comparative Example 62

0.1 weight percent of semiconductor (A1) was dissolved in toluene and a 10 µm droplet applied by drop-casting on a silicon dioxide coated silicon wafer held at room temperature. Subsequently a petri dish was placed over the silicon wafer thus also enclosing the droplet. The drying time therefore was significantly prolonged (>30 min). After drying of the liquid disconnected large crystals comparable to those shown in FIG. 3 were observed.

Example 61 and comparative example 62 show that the drying time of the solution does not have an impact on the crystal habit. With a solvent (L1) according to the invention a good semiconductor material is obtained even if the drying time is significantly shorter than in a comparison with a solvent that is not a solvent (L1) according to the invention.

Example 63: (Drop-Casting of A1) from a DMP:Toluene (1:3) Mixture on Al$_2$O$_3$ after Surface Modification)

A 0.1 wt.-% solution of the semiconductor material A1) was prepared by dissolution in dimethyl phthalate for 1 h at 80° C. and then stirred for further 30 minutes. A second 0.1 wt.-% solution of the semiconductor material A1) was prepared by dissolution in toluene for 1 h at 80° C. and then stirred for further 30 minutes. The two solutions were mixed at a ratio of 1 (DMP) to 3 (toluene). The solution was allowed to cool to ambient temperature and was filtered through a 0.2 µm PTFE filter. Silicon wafers from WRS Materials (heavily p-doped with boron, 550 to 600 µm thickness) coated with Al$_2$O$_3$ (30 nm thick, grown via atomic layer deposition) were subjected to a 2 minutes treatment with oxygen plasma (100 W, 20 sccm gas flow) and subsequently immersed into a 1.5 mM solution of tetradecyl phosphonic acid (TDPA) in isopropanol for 1 hour at room temperature. Subsequently the sample was removed from the solution, rinsed with isopropanol and baked for 5 min at 120° C. on a hotplate. This procedure yields a hydrophobic self-assembled monolayer (SAM) on the Al$_2$O$_3$ surface with a surface energy of 22 mN/m (surface energy determined via water contact angle measurement). Subsequently a layer of PDMS having a thickness of 0.5-1 mm and comprising holes with a diameter of 7.3 mm was placed onto the hydrophobic substrate that was subsequently subjected to a 2 minutes treatment with air plasma (100 W, 20 sccm gas flow). This plasma burns away the hydrophobic monolayer in the locations of the holes of the PDMS layer exposing the bare, more hydrophilic Al$_2$O$_3$ surface. 1 to 10 µL of solution was deposited onto the wafer on a hotplate at 70° C. in a flow box. After complete evaporation of solvent the sample was put in a vacuum oven for 1 h at 90° C. to eliminate residual solvent trapped in the film. Gold contacts (Umicore, 99.99%) were deposited at a base pressure of 6×10$^{-6}$ mbar through a kapton shadow mask via thermal evaporation yielding a channel width (W) of 200 m and channel length (L) of 50 m. The degenerately doped silicon wafers were used as back gate substrate for electrical characterization, conducted in a dark box under ambient conditions using an Agilent 4145C Semiconductor Parameter Analyzer.

Figure 14A:
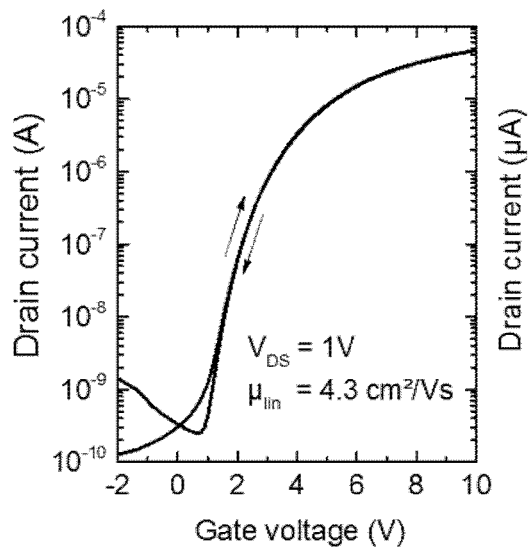
FIG. 14a shows the transfer characteristics of the semiconductor obtained by drop casting of compound A1) from a DMP:Toluene (1:3) solution (example 63) with $U_{GS}$=−2 V to +10V with $U_{DS}$=3 V.
Figure 14B:
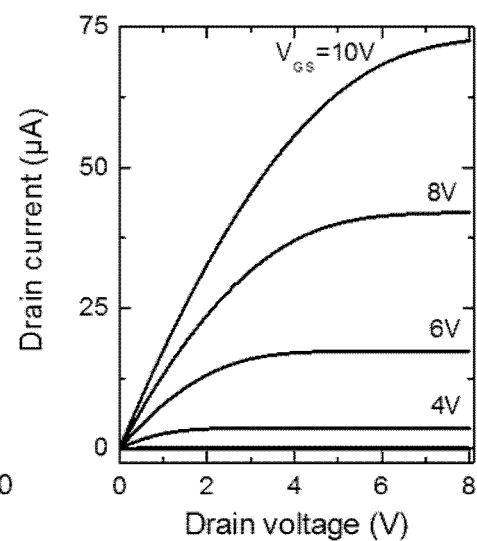
FIG. 14b shows the output characteristics of the semiconductor obtained by drop casting of compound A1) from a DMP:Toluene (1:3) solution (example 63) with $U_{DS}$=0 V to +8 V with $U_{GS}$=2, 4, 6, 8 and 10V.

The measurement results are depicted in FIGS. 14a and 14b, respectively.

The invention claimed is:
1. A process for preparing a crystalline organic semiconductor material, the process comprising:
(a) providing a solution comprising an organic semiconductor A) in a solvent (L1) or in a solvent mixture comprising a solvent (L1) and a solvent (L2), which is different from the solvent (L1),
wherein the solvent (L1) has
a boiling point at 1013.25 mbar of at least 140° C.,
a viscosity of at least 1.2 mPas at 23° C., and
a surface tension of at least 31.5 mN/m at 20° C.; and
(b) applying dig solution to a surface of a substrate, evaporating of the solvent (L1) or die solvent mixture comprising the solvent (L1) and the solvent (L2), and crystallizing the organic semiconductor A),
wherein the organic semiconductor A) is at least one selected from the group consisting of:
a rylene compound of formula (II.a):

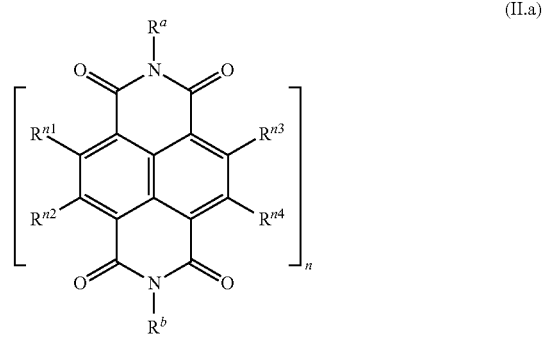

(II.a)

wherein:
n is 1, 2, 3, or 4;
R$^a$ and R$^b$ are independently hydrogen, an optionally substituted alkyl, an optionally substituted alkenyl, an optionally substituted alkadienyl an optionally substituted alkynyl, an optionally substituted cycloalkyl, an optionally substituted bicycloalkyl, an optionally substituted cycloalkenyl, an optionally substituted heterocycloalkyl, an optionally substituted aryl, or an optionally substituted heteroaryl; and $R^{n1}$, $R^{n2}$, $R^{n3}$ and $R^{n4}$ are independently hydrogen, F, Cl, Br, I, CN, hydroxy, mercapto, nitro, cyanato, thiocyanato, formyl, acyl, carboxy, carboxylate, alkylcarbonyloxy, carbamoyl, alkylaminocarbonyl, dialkylaminocarbonyl, sulfo, sulfonate, sulfoamino, sulfamoyl, alkylsulfonyl, arylsulfonyl, amidino, $NE^1E^2$:

where $E^1$ and $E^2$ are each independently hydrogen, alkyl, cycloalkyl, heterocycloalkyl, aryl, or hetaryl, an optionally substituted alkyl, an optionally substituted alkoxy, an optionally substituted alkylthio, an optionally substituted (monoalkyl)amino, an optionally substituted (dialkyl)amino, an optionally substituted cycloalkyl, an optionally substituted cycloalkoxy, an optionally substituted cycloalkylthio, an optionally substituted (monocycloalkyl)amino, an optionally substituted (dicycloalkyl)amino, an optionally substituted heterocycloalkyl, an optionally substituted heterocycloalkoxy, an optionally substituted heterocycloalkylthio, an optionally substituted (monoheterocycloalkyl)amino, an optionally substituted (diheterocycloalkyl)amino, an optionally substituted aryl, an optionally substituted aryloxy, an optionally substituted arylthio, an optionally substituted (monoaryl)amino, an optionally substituted (diaryl)amino, an optionally substituted hetaryl, an optionally substituted hetaryloxy, an optionally substituted hetarylthio, an optionally substituted (monohetaryl)amino, or an optionally substituted (dihetaryl)amino;

a compound of formula (II.b)

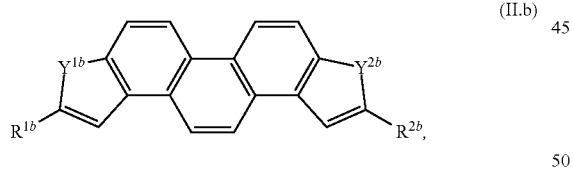

(II.b)

wherein:

$R^{1b}$ and $R^{2b}$ are independently hydrogen, an optionally substituted linear $C_1$-$C_{30}$-alkyl, an optionally substituted branched $C_3$-$C_{30}$-alkyl, an optionally substituted linear $C_2$-$C_{30}$-alkenyl, an optionally substituted branched $C_3$-$C_{30}$-alkenyl, an optionally substituted linear $C_2$-$C_{30}$-alkynyl, an optionally substituted branched $C_4$-$C_{30}$-alkynyl, an optionally substituted cycloalkyl, an optionally substituted aryl, or an optionally substituted hetaryl; and $Y^{1b}$ and $Y^{2b}$ are independently O, S, Se, or $NR^{3b}$, where $R^{3b}$ is independently hydrogen, an optionally substituted alkyl, an optionally substituted cycloalkyl, or an optionally substituted aryl;

a compound of formula (II.c):

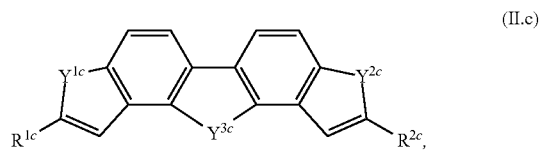

(II.c)

wherein:

$R^{1c}$ and $R^{2c}$ are independently hydrogen, an optionally substituted linear $C_1$-$C_{30}$-alkyl, an optionally substituted branched $C_3$-$C_{30}$-alkyl, an optionally substituted linear $C_2$-$C_{30}$-alkenyl, an optionally substituted branched $C_3$-$C_{30}$-alkenyl, an optionally substituted linear $C_2$-$C_{30}$-alkynyl, an optionally substituted branched $C_4$-$C_{30}$-alkynyl, an optionally substituted cycloalkyl, an optionally substituted aryl, or an optionally substituted hetaryl; and $Y^{1c}$, $Y^{2c}$ and $Y^{3c}$ are independently O, S, Se, or $NR^{3c}$, where $R^{3c}$ is independently hydrogen, an optionally substituted alkyl, an optionally substituted cycloalkyl, or an optionally substituted aryl;

a compound of formula (II.d):

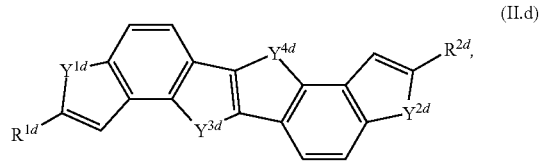

(II.d)

wherein:

$R^{1d}$ and $R^{2d}$ are independently hydrogen, an optionally substituted linear $C_1$-$C_{30}$-alkyl, an optionally substituted branched $C_3$-$C_{30}$-alkyl, an optionally substituted linear $C_2$-$C_{30}$-alkenyl, an optionally substituted branched $C_3$-$C_{30}$-alkenyl, an optionally substituted linear $C_2$-$C_{30}$-alkynyl, an optionally substituted branched $C_4$-$C_{30}$-alkynyl, an optionally substituted cycloalkyl, an optionally substituted aryl, or an optionally substituted hetaryl; and $Y^{1d}$, $Y^{2d}$, $Y^{3d}$ and $Y^{4d}$ are independently O, S, Se, or $NR^{3d}$, where $R^{3d}$ is independently hydrogen, an optionally substituted alkyl, an optionally substituted cycloalkyl, or an optionally substituted aryl; and a compound of formula (II.e):

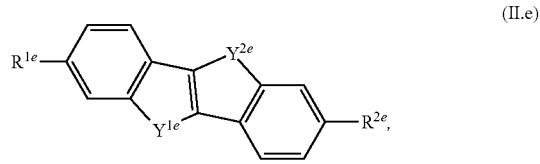

(II.e)

wherein:

$R^{1e}$ and $R^{2e}$ are independently hydrogen, an optionally substituted linear $C_1$-$C_{30}$-alkyl, an optionally substituted branched $C_3$-$C_{30}$-alkyl, an optionally substituted linear $C_2$-$C_{30}$-alkenyl, an optionally substituted branched $C_3$-$C_{30}$-alkenyl, an optionally substituted linear $C_2$-$C_{30}$-alkynyl, an optionally substituted branched $C_4$-$C_{30}$-alkynyl, an optionally substituted cycloalkyl, an optionally substituted aryl, or an optionally substituted hetaryl; and $Y^{1e}$ and $Y^{2e}$ are independently O, S, Se or $NR^{3e}$, where $R^{3e}$ is independently hydrogen, an optionally substituted alkyl, an optionally substituted cycloalkyl, or an optionally substituted aryl, wherein the solvent (L1) is at least one selected from the group consisting of a hydroxybenzoic ester, a compound of formula (I.1), a compound of formula (I.2), a compound of formula (I.3), a compound of formula (I.4), and a compound of formula (I.5):

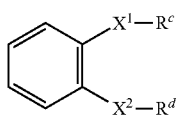  (I.1)

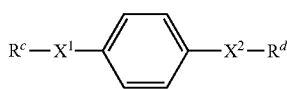  (I.2)

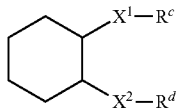  (I.3)

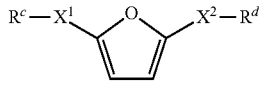  (I.4)

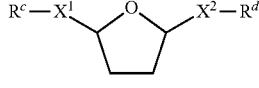  (I.5)

wherein:

$X^1$ and $X^2$ are independently *—(C=O)—O—, *—$(CH_2)_m$—O—, or *—$(CH_2)_m$—O—(C=O)—, where * is a point of linkage to the aliphatic or aromatic carbocycle or heterocycle, and m is 0, 1, or 2; and $R^c$ and $R^d$ are independently unbranched or branched $C_1$-$C_{12}$-alkyl or $C_2$-$C_{12}$-alkenyl, and wherein the solvent (L2) is at least one compound selected from the group consisting of:

an aliphatic, a cycloaliphatic, or an aromatic hydrocarbon other than a polycyclic hydrocarbon comprising a cycloaliphatic ring;

an aromatic ether;

an open chain aliphatic ether, a polyether, an ether alcohol, or a cyclic ether;

a ketone other than an aromatic aliphatic ketone;

an ester other than an alkyl benzoate, a hydroxybenzoic acid ester, and an alkylene carbonate;

an aliphatic or a cycloaliphatic alcohol;

a benzene based alcohol;

a halogenated aromatic compound;

a thiophenol or an alkylthio-substituted benzene;

an aromatic compound comprising a phenyl group fused to a 5-, 6-, or 7-membered cycloheteroalkyl group;

a 5-membered heteroaryl compound or a benzo-fused 5-membered heteroaryl compound;

an aromatic carboxylic acid;

an aromatic aldehyde;

a trifluoromethyl-substituted benzene compound;

a cyano-substituted or isocyano-substituted benzene compound;

a nitro-substituted benzene compound;

a phenyl sulfone;

a 6-membered heteroaryl compound or a benzofused 6-membered heteroaryl compound;

a 5-membered heteroaryl compound or a benzofused 5-membered heteroaryl compound; and an aprotic polar solvent other than dimethylsulfoxide and N-methylpyrrolidone.

2. The process according to claim 1, wherein the crystallization of the organic semiconductor A) proceeds from a gas liquid interface.

3. The process according to claim 1, wherein after (a), no additional component is added to the solution to effect crystallization of the organic semiconductor A).

4. The process according to claim 1, wherein a crystalline organic semiconductor material obtained in (b) has an area of larger than 10×10 μm² and an average thickness of at most 0.1 μm.

5. The process according to claim 1, wherein the solvent (L1) or the solvent mixture comprising the solvent (L1) and the solvent (L2) in (a) has a boiling point at 1013.25 mbar of at least 150° C.

6. The process according to claim 1, wherein the solvent (L1) has a viscosity in the range of 1.3 to 1000 mPas at 23° C.

7. The process according to claim 1, wherein the solvent (L1) has a surface tension in the range of 32 to 65 mN/m at 20° C.

8. The process according to claim 1, wherein the organic semiconductor A) has a solubility in the solvent (L1) or in the solvent mixture comprising the solvent (L1) and the solvent (L2) in (a) at 20° C. of at least 0.01 mg/ml.

9. The process according to claim 1, wherein the solvent in the solution in (a) consists of the solvent (L1).

10. The process according to claim 1, wherein the solvent mixture is used in (a).

11. The process according to claim 10, wherein an amount of the solvent (L1) in the solvent mixture is in a range of from 1 to 99% by weight based on a total weight of the solvent mixture.

12. The process according to claim 1, wherein the solvent (L1) is a hydroxybenzoic acid ester selected from the group consisting of an alkyl ester of o-hydroxybenzoic acid, an alkyl ester of m-hydroxybenzoic acid, and an alkyl ester of p-hydroxybenzoic acid.

13. The process according to claim 1, wherein the solvent (L1) is selected from the group consisting of the compound of formula (I.1), the compound of formula (I.2), the compound of formula (I.3), the compound of formula (I.4), and the compound of formula (I.5)

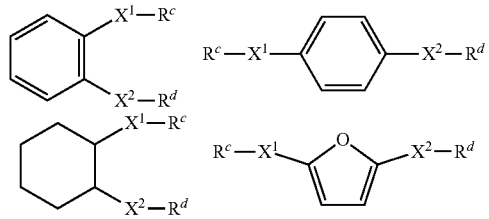

-continued

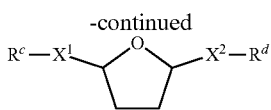

14. The process according to claim 13, wherein, in the formulae (I.1), (I.2), (I.3), (I.4), and (I.5), $R^c$ and $R^d$ are independently methyl, ethyl, n-propyl, isopropyl, n-butyl, sec.-butyl, tert.-butyl, isobutyl, n-pentyl, n-hexyl, n-heptyl, n-octyl, 2-ethylhexyl, n-nonyl, isononyl, isodecyl, 2-propylheptyl, n-undecyl, or isoundecyl.

15. The process according to claim 13, wherein, in the formulae (I.1), (I.2), (I.3), (I.4), and (I.5), $X^1$ and $X^2$ are both *—(C=O)—O—.

16. The process according to claim 1, wherein the solvent (L1) is selected from the group consisting of dimethylphthalate, diethylphthalate, di(n-propyl)phthalate, di(n-butyl)phthalate, diallylphthalate, and ethyl salicylate.

17. The process according to claim 10, wherein the solvent (L2) is at least one selected from the group consisting of:
   at least one aliphatic, cycloaliphatic, or aromatic hydrocarbon selected from the group consisting of n-pentane, n-hexane, n-heptan, heroin, cyclohexane, methylcyclohexane, benzene, toluene, o-xylene, m-xylene, p-xylene, cumene, 1,2,3-trimethylbenzene, 1,2,4-trimethylbenzene, 1,3,5-trimethylbenzene, mesitylene, 1-methyl naphthalene, 2-methylnapthalene, 1-ethyl naphthalene, 2-ethylnapthalene, and indene;
   at least one aromatic ether selected from the group consisting of anisole (methylphenylether) ethoxybenzene (phenetol), propoxybenzene, isopropoxybenzene, butoxybenzene, 1-methoxynaphthalin, 2-methoxynaphthalin, 2-methylanisole, 3-methylanisole, 4-methylanisole, 2-ethylanisole, 3-ethylanisole, 4-ethylanisole, 2,3-dimethylanisole, 2,4-dimethylanisole, 2,5-dimethylanisole, 2,6-dimethylanisole, 3,4-dimethylanisole, 3,5-dimethylanisole, 1,2-dimethoxybenzene, 1,3-dimethoxybenzene, 1,4-di methoxybenzene, 1-ethoxy-4-methoxybenzene, 1-ethoxy-3-methoxybenzene, 1-ethoxy-2-methoxybenzene, 1,2-diethoxy benzene, 1,3-diethoxy benzene, 1,4-diethoxybenzene, 2,3-dimethoxytoluene, 2,4-dimethoxytoluene, 2,5-dimethoxytoluene, 2,6-dimethoxytoluene, 3,4-dimethoxytoluene, 3,5-dimethoxytoluene, 4-ethoxytoluene, 3-ethoxytoluene, 2-ethoxytoluene, 1-ethoxy-2-ethylbenzene, 1-ethoxy-3-ethylbenzene, 1-ethoxy-4-ethylbenzene, 1-(methoxymethoxy)benzene, (2-methoxyethoxy)benzene, and (3-methoxypropoxy)benzene;
   at least one open chain aliphatic ether, polyether, ether alcohol, or cyclic ether selected from the group consisting of diethyl ether, dipropyl ether, diisopropyl ether, methyl tert-butyl ether, ethyleneglycolmonomethylether, ethyleneglycoldimethylether, ethyleneglycolmonoethylether, ethyleneglycoldiethylether, propyleneglycolmonomethylether, propyleneglycoldimethylether, propyleneglycolmonoethylether, propyleneglycoldiethylether, diethylenglycolmonomethylether, diethylenglycoldimethylether, diethylenglycolmonoethylether, diethylenglycoldiethylether, diglyme, tetrahydrofuran, tetrahydropyran, 1,4-dioxane, and morpholine;
   at least one ketone selected from the group consisting of acetone, methyl ethyl ketone, methyl isobutyl ketone, ethyl n-amyl ketone, diisobutyl ketone, cyclohexanone, and pentane-2,4-dione;
   at least one ester selected from the group consisting of ethyl acetate, methyl acetate, ethyl acetoacetate, propyl acetate, isopropyl acetate, n-butyl acetate, sec-butyl acetate, tert-butyl acetate, isobutyl acetate, isoamyl acetate, hexyl acetate, methyl propionate, ethyl butyrate, ethyl lactate, diethyl carbonate, triacetin, phenyl formate, phenyl acetate, o-cresol acetate, p-cresol acetate, m-Cresol acetate, 2-methoxyphenyl acetate, 3-methoxyphenyl acetate, 4-methoxyphenyl acetate, benzyl benzoate, bis(2-ethylhexyl) adipate, methyl 2-methylbenzoate, methyl 3-methylbenzoate, methyl 4-methylbenzoate, methyl 2-chlorobenzoate, methyl 3-chlorobenzoate, methyl 4-chlorobenzoate, methyl 4-fluorobenzoate, methyl 3-fluorobenzoate, methyl 2-fluorobenzoate, ethyl 2-methylbenzoate, ethyl 3-methylbenzoate, ethyl 4-methylbenzoate, ethyl 4-chlorobenzoate, ethyl 3-chlorobenzoate, ethyl 2-chlorobenzoate, ethyl 2-fluorobenzoate, ethyl 3-fluorobenzoate, ethyl 4-fluorobenzoate, methyl 4-bromobenzoate, methyl 3-bromobenzoate, and methyl 2-bromobenzoate;
   at least one aliphatic or cycloaliphatic alcohol selected from the group consisting of methanol, ethanol, n-propanol, isopropanol n-butanol, sec-butanol, tert-butanol, n-pentanol, amyl alcohol mixtures, n-hexanol, cyclohexanol, ethanediol, propanediol, ethylene glycol, and diethylene glycol;
   at least one benzene based alcohol selected from the group consisting of phenol, o-cresol, m-cresol, p-cresol, 2-methoxyphenol, 3-methoxy phenol, 4-methoxyphenol, 4-aminobenzylalcohol, 2-phenoxyethanol, 3-phenoxy-1-propanol, 4-phenoxy-1-butanol, 5-phenoxy-1-heptanol, 6-phenoxy-1-hexanol, 2-(2-methylphenoxy)ethan-1-ol, 2-(3-methylphenoxy)ethan-1-ol, 2-(4-methylphenoxy)ethan-1-ol, phenoxymethanol, 1-phenoxyethanol, 1-phenoxypropanol, 1-phenoxybutanol, 2-(2-methoxyphenoxy)ethan-1-ol, 2-(3-methoxyphenoxy)ethan-1-ol, 2-(4-methoxy phenoxy Methan-1-ol, 2-(2-methylphenoxy)ethanol, 2-(3-methylphenoxy)ethanol, 2-(4-methylphenoxy)ethanol, 2-(4-methoxyphenoxy)ethanol, 2-(3-methoxyphenoxy)ethan-1-ol, and 2-(2-methoxyphenoxy)ethan-1-ol;
   at least one halogenated aromatic compound selected from the group consisting of chlorobenzene, 1,2-dichlorobenzene, 1,3-dichlorobenzene, 1,2,4-trichlorobenzene, 4-chlorotoluene, 3-chlorobenzene, 2-chlorotoluene, fluorobenzene, 1,2-difluorobenzene, 1,3-difluorobenzene, 1,4-difluorobenzene, 1-chloronaphthalene, 2-chloronaphthalene, 1-fluoronaphthalene, 2-fluoronaphthalene, 2-chloroanisole, 3-chloroanisole, 4-chloroanisole, 4-fluoroanisole, 3-fluoroanisole, and 2-fluoroanisole;
   at least one thiophenol or an alkylthio-substituted benzene selected from the group consisting of thiophenol, 2-thiocresol, 3-thiocresol, 4-thiocresol, 2-ethyl thiophenol, 3-ethyl thiophenol, 4-ethyl thiophenol, 2,6-dimethylthiophenol, 2,5-dimethylthiophenol, 2,4-dimethylthiophenol, 2,3-dimethylthiophenol, 2-isopropylthiophenol, thioanisole, (ethylthio)benzene, 2-methylthioanisole, 3-methyl thioanisole, 4-methyl thioanisole, 4-methoxy thioanisole, 3-methoxy thioanisole, and 2-methoxy thioanisole;
   at least one aromatic compound comprising a phenyl group fused to a 5-, 6-, or 7-membered cycloheteroalkyl group selected from the group consisting of indoline, 7-methylindoline, 5-methylindoline, 6-methylindoline, 1,2,3,4-tetrahydroquinoline, 6-methyl-3,4- dihydro-2H-1-benzopyran, benzodioxole, 1,3-benzodioxole, 2-methyl-1,3-benzodioxole, 2-ethyl-1,3-benzodioxole, 5-hydroxy-1,3-benzodioxole, 5-methyl-1,3-benzodioxole, 5-methoxy-1,3-benzodioxole, 5-methyl-1,3-benzodioxole, 5-ethyl-1,3-benzodioxole, 4-hydroxy-1,3-benzodioxole, 4-methyl-1,3-benzodioxole, 4-ethyl-1,3-benzodioxole, 4-methoxy-1,3-benzodioxole, 2,2-dimethyl-1,3-benzodioxole, 3,4-methylenedioxytoluene, 4-methyl-2H-1,3-benzodioxole, dihydrobenzofuran, 2,3-dihydrobenzofuran, 2,3-dihydro-2-methylbenzofuran, 6-methyl-2,3-dihydrobenzofuran, 5-methyl-2,3-dihydrobenzofuran, 4H-chromene, chromane, 7-methylchroman, 8-methylchroman, and 2,3-dihydrobenzo[b]thiophene;

at least one 5-membered heteroaryl compound or a benzofused 5-membered heteroaryl compound selected from the group consisting of thiophene, 2-methylthiophene, 3-methylthiophene, furan, 3-methylfuran, 2-methylfuran, pyrrole, N-methylpyrrole, N-ethylpyrrole, 1,2-dimethyl-1H-pyrrole, 1,3-dimethyl-1H-pyrrole, 2-methoxyfuran, 3-methoxyfuran, 3-methoxythiophene, 2-methoxythiophene, 2-methylthiofuran, 3-methylthiofuran, 3-methylthiothiophene, 2-methylthiothiophene, 2-N,N-dimethylamino-thiophene, 3-methoxy-1-methyl-1H-pyrrole, 2-methoxy-1-methyl-1H-pyrrole, benzofuran, 6-methylbenzofuran, benzothiophene, and 6-methylbenzothiophene;

at least one aromatic carboxylic acid selected from the group consisting of benzoic acid, o-toluic acid, m-toluic acid, p-toluic acid, 4-chlorobenzoic acid, 3-chlorobenzoic acid, 2-chlorobenzoic acid, 2-fluorobenzoic acid, 3-fluorobenzoic acid, and 4-fluorobenzoic acid;

at least one aromatic aldehyde selected from the group consisting of benzaldehyde, 2-methylbenzaldehyde, 3-methylbenzaldehyde, 4-methylbenzaldehyde, 4-ethylbenzaldehyde, 3-ethylbenzaldehyde, 2-ethylbenzaldehyde, 2-chlorobenzaldehyde, 3-chlorobenzaldehyde, 4-chlorobenzaldehyde, 4-fluorobenzaldehyde, 3-fluorobenzaldehyde, 2-fluorobenzaldehyde, 2-bromobenzaldehyde, 3-bromobenzaldehyde, and 4-bromobenzaldehyde;

at least one trifluoromethyl-substituted benzene compound selected from the group consisting of benzotrifluoride, 2-methylbenzotrifluoride, 3-methylbenzotrifluoride, 4-methylbenzotrifluoride, 4-chlorobenzotrifluoride, 3-chlorobenzotrifluoride, 2-chlorobenzotrifluoride, 2-fluorobenzotrifluoride, 3-fluorobenzotrifluoride, 4-fluorobenzotrifluoride, 4-bromobenzotrifluoride, 3-bromobenzotrifluoride, 2-bromobenzotrifluoride, methyl 2-trifluoromethylbenzoate, methyl 3-trifluoromethylbenzoate, methyl 4-trifluoromethylbenzoate, ethyl 2-trifluoromethylbenzoate, ethyl 3-trifluoromethylbenzoate, and ethyl 4-trifluoromethylbenzoate;

at least on cyano-substituted or isocyano-substituted benzene compound selected from the group consisting of benzonitrile, 2-methylbenzenecarbonitrile, 3-methylbenzenecarbonitrile, 4-methylbenzenecarbonitrile, 4-chlorobenzonitrile, 3-chlorobenzonitrile, 2-chlorobenzonitrile, 2-fluorobenzonitrile, 3-fluorobenzonitrile, 4-fluorobenzonitrile, phenylisocyanide, 2-tolylisocyanide, 3-tolylisocyanide, and 4-tolylisocyanide;

at least one nitro-substituted benzene compound selected from the group consisting of nitrobenzene, 2-nitrotoluene, 3-nitrotoluene, 4-nitrotoluene, 1-chloro-4-nitrobenzene, 1-chloro-3-nitrobenzene, 1-chloro-2-nitrobenzene, 1-fluoro-2-nitrobenzene, 1-fluoro-3-nitrobenzene, and 1-fluoro-4-nitrobenzene;

at least one phenyl sulfone selected from the group consisting of methyl phenyl sulfone, ethyl phenyl sulfone, (propane-1-sulfonyl)benzene, 1-methanesulfonyl-2-methyl-benzene, 1-methanesulfonyl-3-methyl-benzene, and 1-methanesulfonyl-4-methyl-benzene;

at least one 6-membered heteroaryl compound or a benzofused 6-membered heteroaryl compound selected from the group consisting of pyridine, 2-methylpyridine, 3-methylpyridine, 4-methylpyridine, 2-chloropyridine, 3-chloropyridine, 4-chloropyridine, 4-fluoropyridine, 3-fluoropyridine, 2-fluoropyridine, 2-bromopyridine, 3-bromo-pyridine, 4-bromo-pyridine, 4-(trifluoromethyl)pyridine, 3-(trifluoromethyl)pyridine, 2-(trifluoromethyl)pyridine, 2-cyanopyridine, 3-cyanopyridine, 4-cyanopyridine, 4-nitropyridine, 3-nitropyridine, 2-nitropyridine, 2-picolinic acid methyl ester, 3-picolinic acid methyl ester, 4-picolinic acid methyl ester, pyrazine, methylpyrazine, 2,5-dimethylpyrazine, 2,6-dimethylpyrazine, 2,3-dimethylpyrazine, 2,3,5,6-tetramethyl-pyrazine, 2-chloropyrazine, 2,5-dichloropyrazine, 2,6-dichloropyrazine, 2,3-dichloropyrazine, 2-fluoropyrazine, (trifluoromethyl)pyrazine, 2-pyrazinecarbonitrile, 2-nitro-pyrazine, pyrazine-2-carbaldehyde, 1-pyrazin-2-yl-ethanone, 1-(pyrazin-2-yl)propan-1-one, methylpyrazine-2-carboxylate, pyrazine 2-carboxylic acid ethyl ester, 2-bromopyrazine, 2-iodopyrazine, pyridazine, 3-methylpyridazine, 4-methylpyridazine, 4,5-dimethylpyridazine, 3,6-dimethylpyridazine, 3-chloropyridazine, 4-chloropyridazine, pyridazine-3-carbonitrile, 4-pyridazinecarbonitrile, 4-(trifluoromethyl)pyridazine, 3-(trifluoromethyl)pyridazine, 3-nitropyridazine, pyridazine-3-carbaldehyde, pyridazine-4-carbaldehyde, 1-(pyridazin-4-yl)ethanone, 3-acetylpyridazine, methylpyridazine-3-carboxylate, methylpyridazine-4-carboxylate, tetrazine, 1,2,4,5-tetrazine, dimethyl-1,2,4,5-tetrazine, 3,6-dichloro-1,2,4,5-tetrazine, quinoline, 2-methylquinoline, 3-methylquinoline, 4-methylquinoline, 5-methylquinoline, 6-methylquinoline, 7-methylquinoline, 8-methylquinoline, 2-chloroquinoline, 3-chloroquinoline, 4-chloroquinoline, 5-chloroquinoline, 6-chloroquinoline, 7-chloroquinoline, 8-chloroquinoline, 2-fluoroquinoline, 3-fluoroquinoline, 4-fluoroquinoline, 5-fluoroquinoline, 6-fluoroquinoline, 7-fluoroquinoline, 8-fluoroquinoline, 2-trifluoromethyl quinoline, 3-trifluoromethyl quinoline, 4-trifluoromethyl quinoline, 5-trifluoromethyl quinoline, 6-trifluoromethyl quinoline, 7-trifluoromethyl quinoline, 8-trifluoromethyl quinoline, 2-nitroquinoline, 3-nitroquinoline, 4-nitroquinoline, 5-nitroquinoline, 6-nitroquinoline, 7-nitroquinoline, 8-nitroquinoline, 2-acetylquinoline, 3-acetylquinoline, 4-acetylquinoline, 5-acetylquinoline, 6-acetylquinoline, 7-acetylquinoline, 8-acetylquinoline, 2-cyanoquinoline, 3-cyanoquinoline, 4-cyanoquinoline, 5-cyanoquinoline, 6-cyanoquinoline, 7-cyanoquinoline, 8-cyanoquinoline, methyl 2-quinolinecarboxylate, methyl 3-quinolinecarboxylate, methyl 4-quinolinecarboxylate, methyl 5-quinolinecarboxylate, methyl 6-quinolinecarboxylate, methyl 7-quinolinecarboxylate, ethyl 8-quinolinecarboxylate, ethyl 2-quinolinecarboxylate, ethyl 3-quinolinecarboxylate, ethyl 4-quinolinecarboxylate, ethyl 5 quinolinecarboxylate, ethyl 6-quinolinecarboxylate, ethyl 7-quinolinecarboxylate, ethyl 8-quinolinecarboxylate, 2-quinolinecarboxaldehyde, 3-quinolinecarboxaldehyde, 4-quinolinecarboxaldehyde, 5-quinolinecarboxaldehyde, 6-quinolinecarboxaldehyde, 7-quinolinecarboxaldehyde, 8-quinolinecarboxaldehyde, 1-(2-quinolinyl)-ethanone, 1-(3-quinolinyl)-ethanone, 1-(4-quinolinyl)-ethanone, 1-(5-quinolinyl)-ethanone, 1-(6-quinolinyl)-ethanone, 1-(7-quinolinyl)-ethanone, 1-(8-quinolinyl)-ethanone, quinoxaline, 2-methylquinoxaline, 5-methylquinoxaline, 6-methylquinoxaline, 2-chloroquinoxaline, 5-chloroquinoxaline, 6-chloroquinoxaline, 2-fluoroquinoxaline, 5-fluoroquinoxaline, 6-fluoroquinoxaline, 2-cyanoquinoxaline, 5-cyanoquinoxaline, 6-cyanoquinoxaline, 2-nitroquinoxaline, 5-nitroquinoxaline, 6-nitroquinoxaline, 2-trifluoromethylquinoxaline, 5-trifluoromethylquinoxaline, 6-trifluoromethyquinoxaline, methyl 2-quinoxalinecarboxylate, methyl 5-quinoxalinecarboxylate, methyl 6-quinoxalinecarboxylate, ethyl 2-quinoxalinecarboxylate, ethyl 5-quinoxalinecarboxylate, and ethyl 6-quinoxalinecarboxylate;

at least one 5-membered heteroaryl compound or a benzofused 5-membered heteroaryl compound selected from the group consisting of thiazole, 2-methylthiazole, 4-methylthiazole, 5-methylthiazole, 2-chlorothiazole, 4-chlorothiazole, 5-chlorothiazole, 2-fluorothiazole, 4-fluorothiazole, 5-fluorothiazole, 2-cyanothiazole, 4-cyanothiazole, 5-cyanothiazole, 2-nitrothiazole, 4-nitrothiazole, 5-nitrothiazole, methyl 1,3-thiazole-2-carboxylate, methyl 1,3-thiazole-5-carboxylate, methyl 1,3-thiazole-6-carboxylate, ethyl 1,3-thiazole-2-carboxylate, ethyl 1,3-thiazole-5-carboxylate, ethyl 1,3-thiazole-6-carboxylate, 2-trifluoromethylthiazole, 4-trifluoromethylthiazole, 5-trifluoromethylthiazole, imidazole, N-methyl imidazole, 2-methylimidazole, 4-methylimidazole, 5-methylimidazole, 2-chloroimidazole, 4-chloroimidazole, 5-chloroimidazole, 2-fluoroimidazole, 4-fluoroimidazole, 5-fluoroimidazole, 2-cyanoimidazole, 4-cyanoimidazole, 5-cyanoimidazole, 2-nitroimidazole, 4-nitroimidazole, 5-nitroimidazole, methyl imidazole-2-carboxylate, methyl imidazole-5-carboxylate, methyl imidazole-5-carboxylate, ethyl imidazole-2-carbaoxylate, ethyl imidazole-4-carboxylate, ethyl imidazole-5-carboxylate, 2-trifluoromethylimidazole, 4-trifluoromethylimidazole, 5-trifluoromethylimidazole, 2-methyl-N-methyl imidazole, 4-methyl-N-methyl imidazole, 5-methyl-N-methyl imidazole, 2-chloro-N-methyl imidazole, 4-chloro-N-methyl imidazole, 5-chloro-N-methyl imidazole, 2-fluoro-N-methyl imidazole, 4-fluoro-N-methyl imidazole, 5-fluoro-N-methyl imidazole, 2-cyano-N-methyl imidazole, 4-cyano-N-methyl imidazole, 5-cyano-N-methyl imidazole, 2-nitro-N-methyl imidazole, 4-nitro-N-methyl imidazole, 5-nitro-N-methyl imidazole, methyl N-methyl imidazole-2-carboxylate, methyl N-methyl imidazole-4-carboxylate, methyl N-methyl imidazole-5-carboxylate, ethyl N-methyl imidazole-2-carboxylate, ethyl N-methyl imidazole-4-carboxylate, ethyl N-methyl imidazole-5-carboxylate, 2-trifluoromethyl-N-methyl imidazole, 4-trifluoromethyl-N-methyl imidazole, 5-trifluoromethyl-N-methyl imidazole, triazole, 4-methyl-1,2,3-triazole, 5-methyl-1,2,3-triazole, 4-chloro-1,2,3-triazole, 5-chloro-1,2,3-triazole, 4-fluoro-1,2,3-triazole, 5-fluoro-1,2,3-triazole, 4-cyano-1,2,3-triazole, 5-cyano-1,2,3-triazole, 4-nitro-1,2,3-triazole, 5-nitro-1,2,3-triazole, methyl 1,2,3-triazole-4-carboxylate, methyl 1,2,3-triazole-5-carboxylate, ethyl 1,2,3-triazole-4-carboxylate, ethyl 1,2,3-triazole-5-carboxylate, 4-trifluoromethyl-1,2,3-triazole, 5-trifluoromethyl-1,2,3-triazole, 4-methyl-N-methyl-1,2,3-triazole, 5-methyl-N-methyl-1,2,3-triazole, 4-chloro-N-methyl-1,2,3-triazole, 5-chloro-N-methyl-1,2,3-triazole, 4-fluoro-N-methyl-1,2,3-triazole, 5-fluoro-N-methyl-1,2,3-triazole, 4-cyano-N-methyl-1,2,3-triazole, 5-cyano-N-methyl-1,2,3-triazole, 4-nitro-N-methyl-1,2,3-triazole, 5-nitro-N-methyl-1,2,3-triazole, methyl N-methyl-1,2,3-triazole-4-carboxylate, methyl N-methyl-1,2,3-triazole-5-carboxylate, ethyl N-methyl-1,2,3-triazole-4-carboxylate, ethyl N-methyl-1,2,3-triazole-5-carboxylate, 4-trifluoromethyl-N-methyl-1,2,3-triazole, 5-trifluoromethyl-N-methyl-1,2,3-triazole, tetrazole, N-methyltetrazole, 5-methyl-tetrazole, 5-methyl-N-methyl-tetrazole, 5-chloro-tetrazole, 5-chloro-N-methyl-tetrazole, 5-fluoro-tetrazole, 5-fluoro-N-methyl-tetrazole, 5-nitro-tetrazole, 5-nitro-N-methyl-tetrazole, 5-cyano-tetrazole, 5-cyano-N-methyl-tetrazole, 5-trifluoromethyl-tetrazole, 5-trifluoromethyl-N-methyl-tetrazole, methyl 1H-1,2,3,4-tetrazole-5-carboxylate, ethyl 1H-1,2,3,4-tetrazole-5-carboxylate, methyl 1-methyl-1,2,3,4-tetrazole-5-carboxylate, ethyl 1-methyl-1,2,3,4-tetrazole-5-carboxylate, tetrazole-5-carboxaldehyde, 1H-tetrazole-5-carboxaldehyde, 1-methyl-1-(1-methyl-1H-1,2,3,4-tetrazol-5-yl)ethan-1-one, 1-(1H-1,2,3,4-tetrazol-5-yl)ethan-1-one, benzothiazole, 2-methyl-benzothiazole, 4-methyl-benzothiazole, 5-methyl-benzothiazole, 6-methyl-benzothiazole, 7-methyl-benzothiazole, 2-fluoro-benzothiazole, 4-fluoro-benzothiazole, 5-fluoro-benzothiazole, 6-fluoro-benzothiazole, 7-fluoro-benzothiazole, 2-chloro-benzothiazole, 4-chloro-benzothiazole, 5-chloro-benzothiazole, 6-chloro-benzothiazole, 7-chloro-benzothiazole, 2-cyano-benzothiazole, 4-cyano-benzothiazole, 5-cyano-benzothiazole, 6-cyano-benzothiazole, 7-cyano-benzothiazole, 2-nitro-benzothiazole, 4-nitro-benzothiazole, 5-nitro-benzothiazole, 6-nitro-benzothiazole, 7-nitro-benzothiazole, 2-trifluoromethyl-benzothiazole, 4-trifluoromethyl-benzothiazole, 5-trifluoromethyl-benzothiazole, 6-trifluoromethyl-benzothiazole, 7-trifluoromethyl-benzothiazole, 2-benzothiazolecarboxylic acid methyl ester, 4-benzothiazolecarboxylic acid methyl ester, 5-benzothiazolecarboxylic acid methyl ester, 6-benzothiazolecarboxylic acid methyl ester, 7-benzothiazolecarboxylic acid methyl ester, 2-benzothiazolecarboxylic acid ethyl ester, 4-benzothiazolecarboxylic acid ethyl ester, 5-benzothiazolecarboxylic acid ethyl ester, 6-benzothiazolecarboxylic acid ethyl ester, 7-benzothiazolecarboxylic acid ethyl ester, benzothiazole-2-carbaldehyde, benzothiazole-4-carbaldehyde, benzothiazole-5-carbaldehyde, benzothiazole-6-carbaldehyde, benzothiazole-7-carbaldehyde, 2-acetylbenzothiazole, 4-acetylbenzothiazole, 5-Acetylbenzothiazole, 6-acetylbenzothiazole, 7-acetylbenzothiazole, 3,4-dihydronaphthalen-1 (2H)-one, 8-methyl-3,4-dihydronaphthalen-1(2H)-one, 7-methyl-3,4-dihydronaphthalen-1(2H)-one, 6-methyl-3,4-dihydronaphthalen-1 (2H)-one, 5-methyl-3,4-dihydronaphthalen-1(2H)-one, 2,3-dihydro-1H-inden-1-one, 7-methyl-2,3-dihydro-1H-inden-1-one, 6-methyl-2,3-dihydro-1H-inden-1-one, 57-methyl-2,3-dihydro-1H-inden-1-one, and 4-methyl-2,3-dihydro-1H-inden-1-one; and at least one aprotic polar solvent selected from the group consisting of acetonitrile, formamide, dimethylformamide, dimethylacetamide, $(CH_3)_2SO$, dimethyl sulfone, sulfolane, 1,3-dimethyl-3,4,5,6-tetrahydro-2 (1H)-pyrimidinone, and imidazolidin-2-one.

18. The process according to claim 1, wherein the organic semiconductor A) is a rylene compound of the formula (II.a), and wherein, in formula (II.a), $R^a$ and $R^b$ are independently hydrogen, linear $C_1$-$C_{30}$-alkyl, branched $C_3$-$C_{30}$-alkyl, perfluoro-$C_1$-$C_{30}$-alkyl, 1H,1H-perfluoro-$C_2$-$C_{30}$-alkyl, 1H,1H,2H,2H-perfluoro-$C_3$-$C_{30}$-alkyl, a radical of the formula G.1, a radical of formula G.2, or a radical of formula G.3

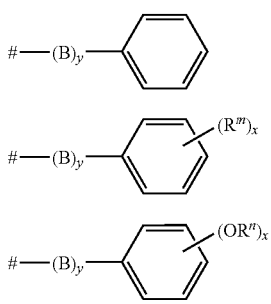

wherein:

\# represents a bonding side to a nitrogen atom;

B where present, is $C_1$-$C_{10}$-alkylene group which is optionally interrupted by one or more nonadjacent groups which are —O— or —S—;

y is 0 or 1;

$R^m$ is independently $C_1$-$C_{30}$-alkyl, $C_1$-$C_{30}$-fluoroalkyl, fluorine, chlorine, bromine, $NE^3E^4$, nitro or cyano, where $E^3$ and $E^4$ are independently hydrogen, alkyl, cycloalkyl, heterocycloalkyl, aryl or hetaryl;

$R^n$ is independently a $C_1$-$C_{30}$-alkyl; and x in formulae G.2 and G.3 is 1,2, 3, 4 or 5.

19. The process according to claim 1, wherein the organic semiconductor A) is a rylene compound of the formula (II.a), and wherein, in formula (II.a), $R^a$ and $R^b$ are independently a radical of formula (III.1), (III.2), or (III.3)

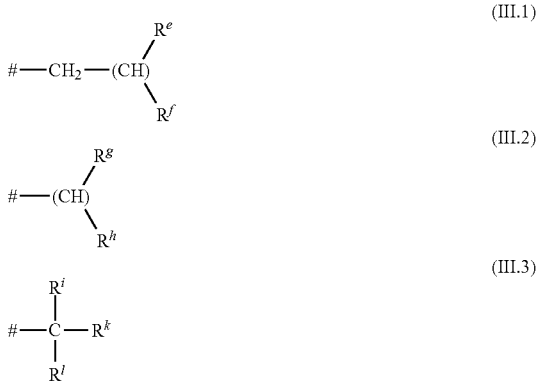

wherein:

\# is a bonding sited; and in the formula (III.1) $R^e$ and $R^f$ are independently $C_1$- to $C_{27}$-alkyl, where a sum of carbon atoms of $R^e$ and $R^f$ is an integer of from 2 to 28, in the formula (III.2) $R^g$ and $R^h$ are independently $C_1$- to $C_{28}$-alkyl, where a sum of carbon atoms of $R^g$ and $R^h$ is an integer of from 2 to 29, in the formula (III.3) $R^i$, $R^k$ and $R^l$ are independently $C_1$- to $C_{27}$-alkyl, where a sum of carbon atoms of $R^i$, $R^k$ and $R^l$ is an integer of from 3 to 29.

20. The process according to claim 1, wherein the organic semiconductor A) is a rylene compound of the formula (II.a), and wherein, in formula (II.a), $R^a$ and $R^b$ are the same.

21. The process according to claim 1, wherein the organic semiconductor A) is a compound of formula (I.a2):

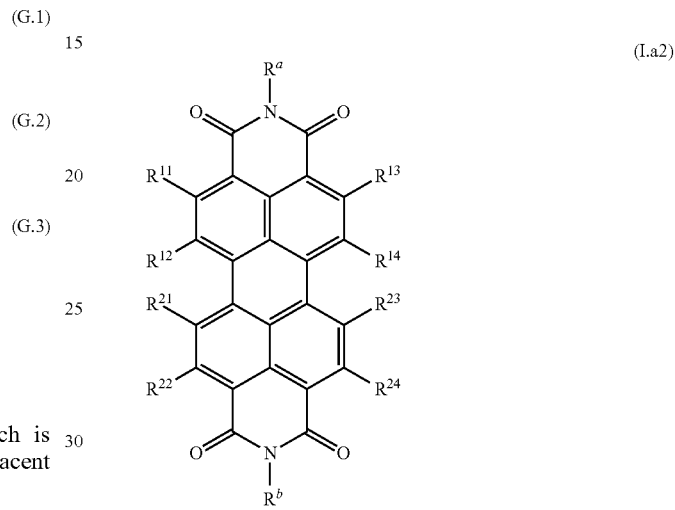

wherein:

$R^a$ and $R^b$ are independently hydrogen, or an unsubstituted or a substituted alkyl, alkenyl, alkadienyl, alkynyl, cycloalkyl, bicycloalkyl, cycloalkenyl, heterocycloalkyl, aryl or heteroaryl;

$R^{12}$ and $R^{23}$ are independently F, Cl, Br, or CN; and $R^{11}$, $R^{13}$, $R^{14}$, $R^{21}$, $R^{22}$ and $R^{24}$ are hydrogen.

22. A process for preparing a device or a sensor, the process comprising:

(a) providing a solution comprising an organic semiconductor A) in a solvent (L1) or in a solvent mixture comprising a solvent (L1) and a solvent (L2), which is different from the solvent (L1), wherein the solvent (L1) has a boiling point at 1013.25 mbar of at least 140° C., a viscosity of at least 1.2 mPas at 23° C., and a surface tension of at least 31.5 mN/m at 20° C.; and (b) applying the solution to a surface of a substrate, evaporating the solvent (L1) or the solvent mixture comprising the solvent (L1) and the solvent (L2), and crystallizing the organic semiconductor A), wherein the substrate in (b) is a substrate of the device, or wherein crystals of the organic semiconductor A) obtained in (b) are transferred to the device or the sensor, wherein the device is an electronic device, an optical device, or an optoelectronic device, wherein the organic semiconductor A) is at least one selected from the group consisting of:

a rylene compound of formula (II.a):

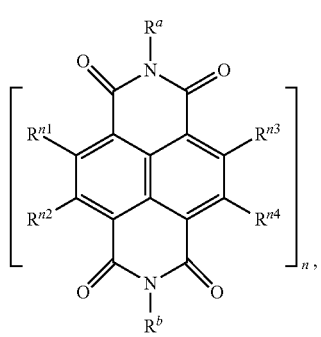

wherein:

n is 1, 2, 3, or 4;

R$^a$ and R$^b$ are independently hydrogen, an optionally substituted alkyl, an optionally substituted alkenyl, an optionally substituted alkadienyl an optionally substituted alkynyl, an optionally substituted cycloalkyl, an optionally substituted bicycloalkyl, an optionally substituted cycloalkenyl, an optionally substituted heterocycloalkyl, an optionally substituted aryl, or an optionally substituted heteroaryl; and R$^{n1}$, R$^{n2}$, R$^{n3}$ and R$^{n4}$ are independently hydrogen, F, Cl, Br, I, CN, hydroxy, mercapto, nitro, cyanato, thiocyanato, formyl, acyl, carboxy, carboxylate, alkylcarbonyloxy, carbamoyl, alkylaminocarbonyl, dialkylaminocarbonyl, sulfo, sulfonate, sulfoamino, sulfamoyl, alkylsulfonyl, arylsulfonyl, amidino,

NE$^1$E$^2$:

where E$^1$ and E$^2$ are each independently hydrogen, alkyl, cycloalkyl, heterocycloalkyl, and, or hetaryl, an optionally substituted alkyl, an optionally substituted alkoxy, an optionally substituted alkylthio, an optionally substituted (monoalkyl)amino, an optionally substituted (dialkyl)amino, an optionally substituted cycloalkyl, an optionally substituted cycloalkoxy, an optionally substituted cycloalkylthio, an optionally substituted (monocycloalkyl)amino, an optionally substituted (dicycloalkyl)amino, an optionally substituted heterocycloalkyl, an optionally substituted heterocycloalkoxy, an optionally substituted heterocycloalkylthio, an optionally substituted (monoheterocycloalkyl)amino, an optionally substituted (diheterocycloalkyl)amino, an optionally substituted aryl, an optionally substituted aryloxy, an optionally substituted arylthio, an optionally substituted (monoaryl)amino, an optionally substituted (diaryl)amino, an optionally substituted hetaryl, an optionally substituted hetaryloxy, an optionally substituted hetarylthio, an optionally substituted (monohetaryl)amino, or an optionally substituted (dihetaryl)amino;

a compound of formula (II.b)

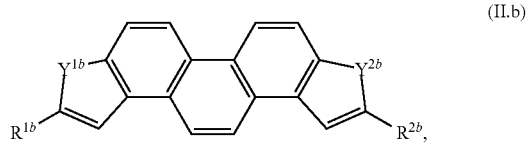

wherein:

R$^{1b}$ and R$^{2b}$ are independently hydrogen, an optionally substituted linear C$_1$-C$_{30}$-alkyl, an optionally substituted branched C$_3$-C$_{30}$-alkyl, an optionally substituted linear C$_2$-C$_{30}$-alkenyl, an optionally substituted branched C$_3$-C$_{30}$-alkenyl, an optionally substituted linear C$_2$-C$_{30}$-alkynyl, an optionally substituted branched C$_4$-C$_{30}$-alkynyl, an optionally substituted cycloalkyl, an optionally substituted aryl, or an optionally substituted hetaryl; and Y$^{1b}$ and Y$^{2b}$ are independently O, S, Se, or NR$^{3b}$ where R$^{3b}$ is independently hydrogen, an optionally substituted alkyl, an optionally substituted cycloalkyl, or an optionally substituted aryl;

a compound of formula (II.c):

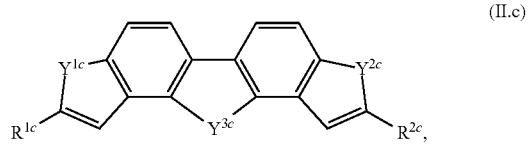

wherein:

R$^{1c}$ and R$^{2c}$ are independently hydrogen, an optionally substituted linear C$_1$-C$_{30}$-alkyl, an optionally substituted branched C$_3$-C$_{30}$-alkyl, an optionally substituted linear C$_2$-C$_{30}$-alkenyl, an optionally substituted branched C$_3$-C$_{30}$-alkenyl, an optionally substituted linear C$_2$-C$_{30}$-alkynyl, an optionally substituted branched C$_4$-C$_{30}$-alkynyl, an optionally substituted cycloalkyl, an optionally substituted aryl, or an optionally substituted hetaryl; and Y$^{1c}$, Y$^{2c}$ and Y$^{3c}$ are independently O, S, Se, or NR$^{3c}$, where R$^{3c}$ is independently hydrogen, an optionally substituted alkyl, an optionally substituted cycloalkyl, or an optionally substituted aryl;

a compound of formula (II.d):

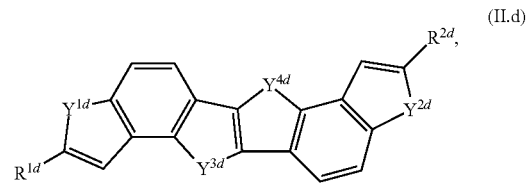

wherein:

R$^{1d}$ and R$^{2d}$ are independently hydrogen, an optionally substituted linear C$_1$-C$_{30}$-alkyl, an optionally substituted branched C$_3$-C$_{30}$-alkyl, an optionally substituted linear C$_2$-C$_{30}$-alkenyl, an optionally substituted branched C$_3$-C$_{30}$-alkenyl, an optionally substituted linear C$_2$-C$_{30}$-alkynyl, an optionally substituted branched $C_4$-$C_{30}$-alkynyl, an optionally substituted cycloalkyl, an optionally substituted aryl, or hetaryl; and $Y^{1d}$, $Y^{2d}$, $Y^{3d}$ and $Y^{4d}$ are independently O, S, Se, or $NR^{3d}$, where $R^{3d}$ is independently hydrogen, an optionally substituted alkyl, an optionally substituted cycloalkyl, or an optionally substituted aryl; and a compound of formula (II.e):

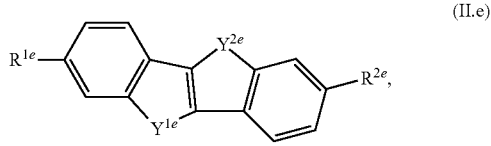

(II.e)

wherein:

$R^{1e}$ and $R^{2e}$ are independently hydrogen, an optionally substituted linear $C_1$-$C_{30}$-alkyl, an optionally substituted branched $C_3$-$C_{30}$-alkyl, an optionally substituted linear $C_2$-$C_{30}$-alkenyl, an optionally substituted branched $C_3$-$C_{30}$-alkenyl, an optionally substituted linear $C_2$-$C_{30}$-alkynyl, an optionally substituted branched $C_4$-$C_{30}$-alkynyl, an optionally substituted cycloalkyl, an optionally substituted aryl, or an optionally substituted hetaryl; and $Y^{1e}$ and $Y^{2e}$ are independently O, S, Se or $NR^{3e}$, where $R^{3e}$ is independently hydrogen, an optionally substituted alkyl, an optionally substituted cycloalkyl, or an optionally substituted aryl, wherein the solvent (L1) is at least one selected from the group consisting of a hydroxy benzoic ester, a compound of formula (I.1), a compound of formula (I.2), a compound of formula (I.3), a compound of formula (I.4), and a compound of formula (I.5):

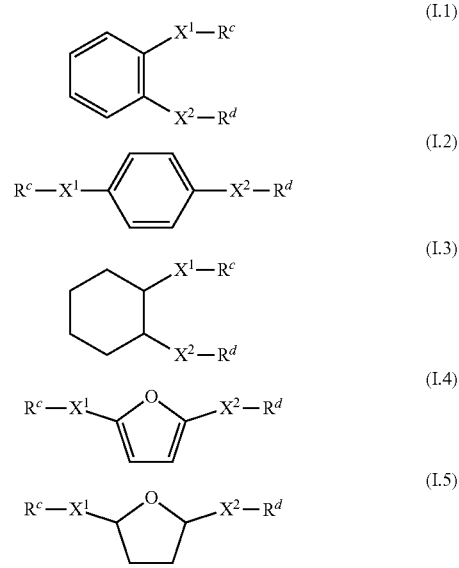

wherein:

$X^1$ and $X^2$ are independently *—(C=O)—O—, *—(CH$_2$)$_m$—O—, or *—(CH$_2$)$_m$—O—(C=O)—, where * is a point of linkage to the aliphatic or aromatic carbocycle or heterocycle, and m is 0, 1, or 2; and $R^c$ and $R^d$ are independently unbranched or branched $C_1$-$C_{12}$-alkyl or $C_2$-$C_{12}$-alkenyl, and wherein the solvent (L2) is at least one compound selected from the group consisting of:

an aliphatic, a cycloaliphatic, or an aromatic hydrocarbon other than a polycyclic hydrocarbon comprising a cycloaliphatic ring;

an aromatic ether;

an open chain aliphatic ether, a polyether, an ether alcohol, or a cyclic ether;

a ketone other than an aromatic aliphatic ketone;

an ester other than an alkyl benzoate, a hydroxybenzoic acid ester, and an alkylene carbonate;

an aliphatic or a cycloaliphatic alcohol;

a benzene based alcohol;

a halogenated aromatic compound;

a thiophenol or an alkylthio-substituted benzene;

an aromatic compound comprising a phenyl group fused to a 5-, 6-, or 7-membered cycloheteroalkyl group;

a 5-membered heteroaryl compound or a benzo-fused 5-membered heteroaryl compound;

an aromatic carboxylic acid;

an aromatic aldehyde;

a trifluoromethyl-substituted benzene compound;

a cyano-substituted or isocyano-substituted benzene compound;

a nitro-substituted benzene compound;

a phenyl sulfone;

a 6-membered heteroaryl compound or a benzofused 6-membered heteroaryl compound;

a 5-membered heteroaryl compound or a benzofused 5-membered heteroaryl compound; and an aprotic polar solvent other than dimethylsulfoxide and N-methylpyrrolidone.

23. The process according to claim 22, wherein (b) is performed by printing.

24. The process according to claim 22, wherein the device is an organic field-effect transistor, an electroluminescent arrangement, an organic solar cell or a photodetector.

25. The process according to claim 21, where $R^a$ and $R^b$ are identical and selected from a group consisting of a branched $C_{4-40}$ alkyl group, a branched $C_{4-40}$ alkenyl group and a branched $C_{4-40}$ haloalkyl group, wherein the branched $C_{4-40}$ alkyl group, the branched $C_{4-40}$ alkenyl group, or the branched $C_{4-40}$ haloalkyl group are selected from:

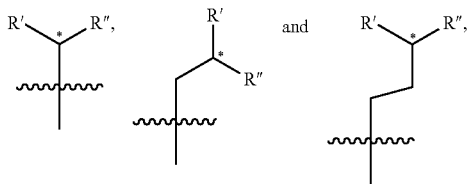

where

R' is a $C_{1-20}$ alkyl or haloalkyl group; and

R" is different from R' and selected from the group consisting of a $C_{1-20}$ alkyl group, a $C_{2-20}$ alkenyl group, and a $C_{1-20}$ haloalkyl group; and where the asterisk * denotes a stereogenic center.

26. The process according to claim 25, where the branched $C_{4-40}$ alkyl group, the branched $C_{4-40}$ alkenyl group, or the branched $C_{4-40}$ haloalkyl group are selected from

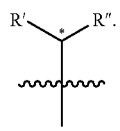

27. The process according to claim 26, where the semiconductor A of formula I.a2 comprises an excess of the (S,S)-stereoisomer in which both $R^a$ and $R^b$ have the (S)-configuration.

28. The process according to claim 26, where the semiconductor A of formula I.a2 comprises an excess of the (R,R)-stereoisomer in which both $R^a$ and $R^b$ have the (S)-configuration.

29. The process according to claim 26, where $R^a$ and $R^b$ are selected from the group consisting of (1S)-1-methylbutyl, (1S)-1-methylpentyl, (1S)-1-methylhexyl, (1S)-1-methylheptyl, (1S)-1-methyloctyl, (1S)-1-ethylpropyl, (1S)-1-ethylbutyl, (1S)-1-ethylpentyl, (1S)-1-propylbutyl, (1S)-1-propylpentyl, (1S)-1-propylhexyl, (1R)-1-methylbutyl, (1R)-1-methylpentyl, (1R)-1-methylhexyl, (1R)-1-methylheptyl, (1R)-1-methyloctyl, (1R)-1-ethylpropyl, (1R)-1-ethylbutyl, (1R)-1-ethylpentyl, (1R)-1-propylbutyl, (1R)-1-propylpentyl and (1R)-1-propylhexyl.

30. The process according to claim 26, where the semiconductor A of formula I.a2 is a compound of formula A1:

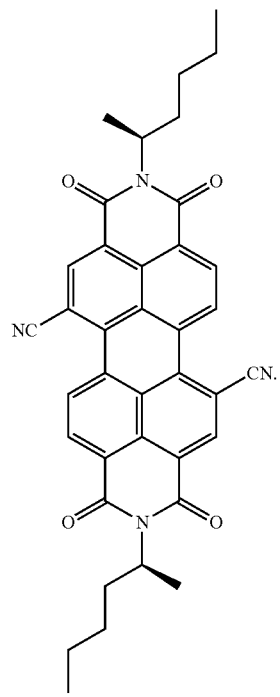 [SMILES: CCCC[C@H](C)N1C(=O)c2ccc3c4c(C#N)cc5c6c(ccc(c7c(C#N)cc(c2c37)C1=O)c64)C(=O)N([C@@H](C)CCCC)C5=O]

* * * * *

UNITED STATES PATENT AND TRADEMARK OFFICE
CERTIFICATE OF CORRECTION

PATENT NO. : 10,224,485 B2
APPLICATION NO. : 15/504463
DATED : March 5, 2019
INVENTOR(S) : Thomas Weitz et al.

It is certified that error appears in the above-identified patent and that said Letters Patent is hereby corrected as shown below:

In the Specification

Column 2, Line 35, "Cryst" should read -- Cryst. --;

Column 7, Line 4, "e.g" should read -- e.g. --;

Column 7, Line 53, "$C_2$-$C_3$-alkinyl," should read -- $C_2$-$C_{30}$-alkinyl, --;

Column 8, Lines 54-55, "2-undecyttridecyl, 2-decyttridecyl, 2-nonyttridecyl, 2-octyttridecyl," should read -- 2-undecyltridecyl, 2-decyltridecyl, 2-nonyltridecyl, 2-octyltridecyl, --;

Column 8, Line 57, "2-propyttridecyl, 2-ethytridecyl," should read -- 2-propyltridecyl, 2-ethyltridecyl, --;

Column 8, Lines 58-59, "2-nonyttetradecyl, 2-octyttetradecyl, 2-hetyttetradecyl, 2-hexyttetradecyl," should read -- 2-nonyltetradecyl, 2-octyltetradecyl, 2-hetyltetradecyl, 2-hexyltetradecyl, --;

Column 8, Lines 60-61, "2-pentyttetradecyl, 2-butyttetradecyl, 2-propyttetradecyl, 2-ethyttetradecyl, 2-methyttetradecyl," should read -- 2-pentyltetradecyl, 2-butyltetradecyl, 2-propyltetradecyl, 2-ethyltetradecyl, 2-methyltetradecyl, --;

Column 9, Lines 13-15, "2-docosanyttetracosanyl, 2-hexadecyttetracosanyl, 2-pentadecyttetracosanyl, 2-pentadecyttetracosanyl, 2-tetradecyttetracosanyl, 2-tridecyttetracosanyl," should read
-- 2-docosanyltetracosanyl, 2-hexadecyltetracosanyl, 2-pentadecyltetracosanyl, 2-pentadecyltetracosanyl, 2-tetradecyltetracosanyl, 2-tridecyltetracosanyl, --;

Signed and Sealed this
Seventh Day of January, 2020

Andrei Iancu
*Director of the United States Patent and Trademark Office*

CERTIFICATE OF CORRECTION (continued)

Column 9, Lines 16-18, "2-dodecyttetracosanyl, 2-undecyttetracosanyl, 2-decyttetracosanyl, 2-nonyttetracosanyl, 2-octyttetracosanyl, 2-heptyttetracosanyl, 2-hexyttetracosanyI, 2-pentyttetracosanyl," should read -- 2-dodecyltetracosanyl, 2-undecyltetracosanyl, 2-decyltetracosanyl, 2-nonyltetracosanyl, 2-octyltetracosanyl, 2-heptyltetracosanyl, 2-hexyltetracosanyl, 2-pentyltetracosanyl, --;

Column 9, Lines 19-20, "2-butyttetracosanyl, 2-propyttetracosanyl, 2-ethyttetracosanyl, 2-methyttetracosanyl," should read -- 2-butyltetracosanyl, 2-propyltetracosanyl, 2-ethyltetracosanyl, 2-methyltetracosanyl, --;

Column 10, Line 60, "sec-butythio," should read -- sec-butylthio, --;

Column 10, Lines 60-61, "neopentythio," should read -- neopentylthio, --;

Column 12, Line 45, "ring" should read -- 8 ring --;

Column 13, Lines 6-7, "heterocycloalkythio" should read -- heterocycloalkylthio --;

Column 14, Line 1, "2-propyiheptanoyl," should read -- 2-propylheptanoyl, --;

Column 15, Lines 25-30, " 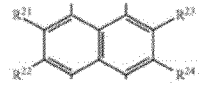 " should read -- 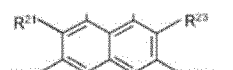 --;

Column 16, Lines 32-33, "$C_1$-$C_3$-alkyl," should read -- $C_1$-$C_{30}$-alkyl, --;

Column 16, Line 64, "perfluoro-$C_1$-$C_2$-alkyl." should read -- perfluoro-$C_1$-$C_{12}$-alkyl. --;

Column 19, Line 17, after "2-hexylnonyl," insert -- 2-pentylnonyl, 2-butylnonyl, 2-propylnonyl, 2-ethylnonyl, 2-methylnonyl, 2-octyldecyl, 2-heptyldecyl, 2-hexyldecyl, 2-pentyldecyl, 2-butyldecyl, 2-propyldecyl, 2-ethyldecyl, 2-methyldecyl, 2-nonylundecyl, 2-octylundecyl, 2-heptylundecyl, 2-hexylundecyl, --;

Column 19, Line 23, after "2-heptyltridecyl," insert -- 2-hexyltridecyl, 2-pentyltridecyl, 2-butyltridecyl, 2-propyltridecyl, 2-ethyltridecyl, --;

Column 19, Lines 24-25, "2-nonyttetradecyl," should read -- 2-nonyltetradecyl, --;

Column 19, Line 25, "2-hexyttetradecyl," should read -- 2-hexyltetradecyl, --;

Column 19, Lines 26-27, "2-propyttetradecyl, 2-ethyttetradecyl, 2-methyttetradecyl," should read -- 2-propyltetradecyl, 2-ethyltetradecyl, 2-methyltetradecyl, --;

Column 19, Line 35, "2 octyloctadecyl," should read -- 2 -octyloctadecyl, --;

CERTIFICATE OF CORRECTION (continued)
U.S. Pat. No. 10,224,485 B2

Column 19, Lines 53-55, "2-hexadecyttetracosanyl, 2-pentadecyttetracosanyl, 2-pentadecyttetracosanyl, 2-tetradecyttetracosanyl, 2-tridecyttetracosanyl, 2-dodecyttetracosanyl," should read -- 2-hexadecyltetracosanyl, 2 -pentadecyltetracosanyl, 2-pentadecyltetracosanyl, 2 -tetradecyltetracosanyl, 2-tridecyltetracosanyl, 2-dodecyltetracosanyl, --;

Column 19, Lines 56-57, "2-undecyttetracosanyl, 2-decyttetracosanyl, 2-nonyttetracosanyl, 2-octyttetracosanyl, 2-heptyttetracosanyl," should read -- 2-undecyltetracosanyl, 2-decyltetracosanyl, 2-nonyltetracosanyl, 2-octyltetracosanyl, 2 -heptyltetracosanyl, --;

Column 19, Lines 58-60, "2-hexyttetracosanyl, 2-pentyttetracosanyl, 2-butyttetracosanyl, 2-propyttetracosanyl, 2-ethyttetracosanyl, 2-methyttetracosanyl," should read -- 2-hexyltetracosanyl, 2-pentyltetracosanyl, 2-butyltetracosanyl, 2 -propyltetracosanyl, 2-ethyltetracosanyl, 2-methyltetracosanyl, --;

Column 20, Line 33, "1-propyttridecyl," should read -- 1-propyltridecyl, --;

Column 20, Line 35, "1-nonyttetradecyl, 1-octyttetradecyl," should read -- 1-nonyltetradecyl, 1-octyltetradecyl, --;

Column 20, Line 36-37, "1-hexyttetradecyl, 1-pentyttetradecyl, 1-butyttetradecyl, 1-propyttetradecy l, 1-ethyttetradecy l, 1-methyttetradecyl," should read -- 1-hexyltetradecyl, 1-pentyltetradecyl, 1-butyltetradecyl, 1-propyltetradecyl, 1-ethyltetradecyl, 1-methyltetradecyl, --;

Column 20, Lines 62-63, "1-tricosanytetracosanyl, 1-docosanyttetracosanyl," should read -- 1-tricosanyltetracosanyl, 1-docosanyltetracosanyl, --;

Column 20, Lines 64-67, "1-hexadecyttetracosanyl, 1-pentadecyttetracosanyl, 1-pentadecyttetracosanyl, 1-tetradecyttetracosanyl, 1-tridecyttetracosanyl, 1-dodecyttetracosanyl, 1-undecyttetracosanyl," should read -- 1-hexadecyltetracosanyl, 1-pentadecyltetracosanyl, 1-pentadecyltetracosanyl, 1-tetradecyltetracosanyl, 1-tridecyltetracosanyl, 1-dodecyltetracosanyl, 1-undecyltetracosanyl, --;

Column 21, Lines 1-4, "1-decyttetracosanyl, 1-nonyttetracosanyl, 1-octyttetracosanyl, 1-heptyttetracosanyl, 1-hexyttetracosanyl, 1-pentyttetracosanyl, 1-butyttetracosanyl, 1-propyttetracosanyl, 1-ethyttetracosanyl, 1-methyttetracosanyl," should read -- 1-decyltetracosanyl, 1-nonyltetracosanyl, 1-octyltetracosanyl, 1-heptyltetracosanyl, 1-hexyltetracosanyl, 1-pentyltetracosanyl, 1-butyltetracosanyl, 1-propyltetracosanyl, 1-ethyltetracosanyl, 1-methyltetracosanyl, --;

Column 22, Line 48, "Soc" should read -- Soc. --;

Column 24, Line 23, "(dicarboximide)" should read -- (dicarboximide), --;

Column 24, Line 25, "(dicarboximide)" should read -- (dicarboximide), --;

CERTIFICATE OF CORRECTION (continued)
U.S. Pat. No. 10,224,485 B2

Column 24, Line 27, "(dicarboximide)" should read -- (dicarboximide), --;

Column 24, Line 29, "(dicarboximide)" should read -- (dicarboximide), --;

Column 24, Line 66, "N,N'-bis(2-methyl hexyl)" should read -- N,N'-bis(2-methylhexyl) --;

Column 25, Line 1, "N,N'-bis(2-methyl hexyl)" should read -- N,N'-bis(2-methylhexyl) --;

Column 25, Line 3, "N,N'-bis(2-ethyl hexyl)" should read -- N,N'-bis(2-ethylhexyl) --;

Column 25, Line 5, "N,N'-bis(2-ethyl hexyl)" should read -- N,N'-bis(2-ethylhexyl) --;

Column 25, Line 11, "N,N'-bis( 4-n-hexyl phenyl)" should read -- N,N'-bis( 4-n-hexylphenyl) --;

Column 25, Line 17, "N,N'-bis( 4-n-dodecyl phenyl)" should read -- N,N'-bis( 4-n-dodecylphenyl) --;

Column 27, Line 7, "N,N'-bis( 4-n-dodecyl phenyl)" should read -- N,N'-bis( 4-n-dodecylphenyl) --;

Column 27, Line 9, "N,N'-bis( 4-n-dodecyl phenyl)" should read -- N,N'-bis( 4-n-dodecylphenyl) --;

Column 80, Line 57, "mandatory" should read -- mandatorily --;

Column 84, Line 39, "R" should read -- Rc --;

Column 85, Line 43, "2,5-furandicarboxylate" should read -- 2,5-furandicarboxylates --;

Column 85, Lines 44-45, "2,5-tetrahydrofurandicarboxylate" should read -- 2,5-tetrahydrofurandicarboxylates --;

Column 88, Line 56, "n-heptan," should read -- n-heptane, --;

Column 88, Line 60, "1-methyl naphthalene," should read -- 1-methylnaphthalene, --;

Column 88, Lines 60-61, "1- ethyl naphthalene," should read -- 1-ethylnaphthalene, --;

Column 88, Line 65, "1-methoxynaphthalen," should read -- 1-methoxynaphthalin, --;

Column 88, Line 66, "2-methoxynaphthalen," should read -- 2-methoxynaphthalin, --;

Column 89, Lines 11-12, "1-ethoxy-2-ethyl benzene," should read -- 1-ethoxy-2-ethylbenzene, --;

CERTIFICATE OF CORRECTION (continued)
U.S. Pat. No. 10,224,485 B2

Column 89, Line 39, "m-Cresol" should read -- m-cresol --;

Column 91, Lines 10-11, "methyl 2-trifluoromethyl benzoate, methyl 3-trifluoromethyl benzoate," should read -- methyl 2-trifluoromethylbenzoate, methyl 3-trifluoromethylbenzoate, --;

Column 91, Line 51, "methyl pyrazine-2-carboxylate," should read -- methylpyrazine-2-carboxylate, --;

Column 92, Line 37, "6-trifluoromethyquinoxaline," should read -- 6-trifluoromethylquinoxaline, --;

Column 96, Line 43, "n-octadecyltriethoxysi lane," should read -- -n-octadecyltriethoxysilane, --;

Column 100, Line 52, "bathocuproin" should read -- bathocuproine --;

Column 100, Line 62, "radioactively" should read -- radiatively --;

Column 101, Line 16, "benzidin," should read --benzidine, --;

Column 101, Lines 17-18, "spirobifluoren," should read -- spirobifluorene, --;

Column 101, Line 19, "-spirobifluoren," should read -- -spirobifluorene, --;

Column 101, Line 20, "benzidin," should read -- benzidine, --;

Column 101, Line 21, "benzidin," should read -- benzidine, --;

Column 101, Line 22, "benzidin," should read -- benzidine, --;

Column 101, Lines 25-26, "-spirobifluoren" should read -- -spirobifluorene, --;

Column 101, Line 28, "-spirobifluoren" should read -- -spirobifluorene, --;

Column 101, Lines 31-32, "-spirobifluoren" should read -- -spirobifluorene, --;

Column 101, Lines 33-34 "2,7-Bis[N,N-bis(9,9-spiro-bifluorene-2-yl)-amino]-9,9-spi-robifluoren," should read -- 2,7-Bis[N,N-bis(9,9-spirobifluorene-2-yl)-amino]-9,9-spirobifluorene, --;

Column 101, Line 35, "-spirobifluoren" should read -- -spirobifluorene, --;

Column 101, Line 36, "benzidin," should read -- benzidine, --;

Column 101, Line 37, "benzidin," should read -- benzidine, --;

CERTIFICATE OF CORRECTION (continued)
U.S. Pat. No. 10,224,485 B2

Column 101, Line 38, "-spirobifluoren" should read -- -spirobifluorene, --;

Column 101, Line 53, "benzidin," should read -- benzidine, --;

Column 101, Lines 54-55 "-spirobifluoren" should read -- -spirobifluorene, --;

Column 101, Lines 56-57, "-spirobifluoren" should read -- -spirobifluorene, --;

Column 101, Line 61, "benzidin," should read -- benzidine, --;

Column 101, Line 63, "benzidin," should read -- benzidine, --;

Column 103, Line 47, "fro a" should read -- for a --;

Column 106, Line 24, "fro a" should read -- for a --;

Column 106, Line 35, "on" should read -- one --;

Column 110, Line 67, "50 V" should read -- 50 V. --;

Column 111, Line 8, "20 V" should read -- 20 V. --;

Column 111, Line 28, "10 V" should read -- 10 V. --;

Column 114, Line approx. 5, "Kriss" should read -- Kruss --;

Column 120, Line 20, "DM P" should read -- DMP --;

Column 123, Line 21, "DM P/Acac" should read -- DMP/Acac --;

Column 123, Line 23, "crystalization" should read -- crystallization --;

In the Claims

Column 124, Line 37, Claim 1, "dig" should read -- the --;

Column 124, Line 38, Claim 1, "of the" should read -- the --;

Column 124, Line 38, Claim 1, "die" should read -- the --;

Column 124, Line 64, Claim 1, "alkadienyl" should read -- alkadienyl, --;

Column 129, Lines 1-4, Claim 15 "  " should read --  . --;

Column 129, Line 24, Claim 17, "n-heptan," should read -- n-heptane, --;

Column 129, Line 24, Claim 17, "heroin," should read -- ligroin, --;

Column 129, Lines 28-29, Claim 17, "2-methylnapthalene, 1-ethyl naphthalene, 2-ethylnapthalene," should read -- 2-methylnaphthalene, 1-ethylnaphthalene, 2-ethylnaphthalene, --;

Column 129, Line 42, Claim 17, "1,2-diethoxy benzene, 1,3-diethoxy benzene," should read -- 1,2-diethoxybenzene, 1,3-diethoxybenzene, --;

Column 130, Line 8, Claim 17, "m-Cresol" should read -- m-cresol --;

Column 130, Line 24, Claim 17, "isopropanol" should read -- isopropanol, --;

Column 130, Lines 38-39, Claim 17, "2-(4-methoxy phenoxy Methan-1-ol," should read -- 2-(4-methoxyphenoxy)ethan-1-ol, --;

Column 131, Line 56, Claim 17, "on" should read -- one --;

Column 132, Lines 65-66, Claim 17, "5 quinolinecarboxylate," should read -- 5-quinolinecarboxylate, --;

Column 133, Line 16, Claim 17, "6-trifluoromethyquinoxaline," should read -- 6-trifluoromethylquinoxaline, --;

Column 133, Line 42, Claim 17, "ethyl imidazole-2-carbaoxylate," should read -- ethyl imidazole-2-carboxylate, --;

Column 134, Line 15, Claim 17, "N-methyltetrazole," should read -- N-methyl-tetrazole, --;

Column 134, Line 56, Claim 17, "5-Acetylbenzothiazole," should read -- 5-acetylbenzothiazole, --;

Column 135, Line 30, Claim 18, "is" should read -- is a --;

Column 135, Line 40, Claim 18, "1,2," should read -- 1, 2, --;

Column 135, Line 64, Claim 19, "sited;" should read -- site; --;

Column 137, Line 24, Claim 22, "alkadienyl" should read -- alkadienyl, --;

Column 137, Line 43, Claim 22, "and," should read -- aryl, --; and

Column 139, Line 29, Claim 22, "arvi," should read -- aryl, --.